United States Patent
Garrity-Park et al.

(10) Patent No.: US 11,249,084 B2
(45) Date of Patent: *Feb. 15, 2022

(54) MATERIALS AND METHODS FOR DETERMINING CANCER RISK

(71) Applicant: Mayo Foundation for Medical Education and Research, Rochester, MN (US)

(72) Inventors: Megan Garrity-Park, Pine Island, MN (US); Thomas C. Smyrk, Rochester, MN (US); Edward V. Loftus, Jr., Rochester, MN (US); William J. Sandborn, La Jolla, CA (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 903 days.

This patent is subject to a terminal disclaimer.

(21) Appl. No.: 16/021,700

(22) Filed: Jun. 28, 2018

(65) Prior Publication Data

US 2018/0364239 A1 Dec. 20, 2018

Related U.S. Application Data

(63) Continuation of application No. 13/272,044, filed on Oct. 12, 2011, now Pat. No. 10,041,948.

(60) Provisional application No. 61/392,342, filed on Oct. 12, 2010.

(51) Int. Cl.
*G01N 33/574* (2006.01)
*C12Q 1/6886* (2018.01)

(52) U.S. Cl.
CPC ..... *G01N 33/57419* (2013.01); *C12Q 1/6886* (2013.01); *C12Q 2600/154* (2013.01); *C12Q 2600/156* (2013.01); *G01N 2800/065* (2013.01); *G01N 2800/50* (2013.01)

(58) Field of Classification Search
CPC ............................................... G01N 33/57419
See application file for complete search history.

(56) References Cited

U.S. PATENT DOCUMENTS

| | | | |
|---|---|---|---|
| 5,552,292 | A | 9/1996 | Uchida et al. |
| 10,041,948 | B2 | 8/2018 | Garrity-Park |
| 2003/0224040 | A1 | 12/2003 | Baylin et al. |
| 2009/0053706 | A1 | 2/2009 | Laird et al. |

FOREIGN PATENT DOCUMENTS

| WO | WO 99/57318 | 11/1999 |
|---|---|---|
| WO | WO 2008/150962 | 12/2008 |
| WO | WO 2009/037572 | 3/2009 |

OTHER PUBLICATIONS

Garrity-Park et al. (2008) Tumor Necrosis Factor-Alpha Polymorphisms in Ulcerative Colitis-Associated Colorectal Cancer. American Journal of Gastroenterology, 13(2):407-415 (Year: 2008).*
Garrity-Park et al. (2009) MHC Class II alleles in ulcerative colitis-associated colorectal cancer. Gut, 58:1226-1233 (Year: 2009).*
Vogel et al. (2007) Prospective study of interaction between alcohol, NSAID use and polymorphisms in genes involved in the inflammatory response in relation to risk of colorectal cancer. Mutation Research, 624:88-100 (Year: 2007).*
Tsilidis et al. (2009) Association of common polymorphisms in IL10, and in other genes related to inflammatory response and obesity with colorectal cancer. Cancer Causes Control, 20:1739-1751 (Year: 2009).*
The Cleveland Clinic ("How to Prevent Colon Cancer", publicly available on Jan. 5, 2009, obtained from <http://web.archive.org/web/20090105202118/http://my.clevelandclinic.org/disorders/Colorectal_Cancer/hic_How_to_Prevent_Colorectal_Cancer.aspx>, and obtained on Aug. 1, 2013, 4 pages (Year: 2009).*
"Laboratory Methods for the Detection of Mutations and Polymorphisms in DNA" (1997) G. R. Taylor, ed., CRC Press.
Agoff et al. "The Role of Cyclooxygenase 2 in Ulcerative Colitis-Associated Neoplasia," *Am J Pathol.*, 2000, 157(3):737-745.
Ahlquist et al., "Gene methylation profiles of normal mucosa, and benign and malignant colorectal tumors identify early onset markers," *Mol Cancer*, 2008,7:94-104.
Akhtar et al., "Promoter methylation regulates Helicobacter pylori-stimulated cyclooxygenase-2 expression in gastric epithelial cells," *Cancer Res*, Mar. 2001, 61:2399-2403.
Azarschab et al., "Epigenetic control of the E-cadherin gene (CDH1) by CpG methylation in colectomy samples of patients with ulcerative colitis," *Genes Chromosomes Cancer*, 2002, 35:121-126.
Azzoni et al., "Distinct molecular patterns based on proximal and distal sporadic colorectal cancer: arguments for different mechanisms in the tumorigenesis," *Int J Colorectal Dis.*, Feb. 2007, 22(2):115-126.
Bird, "CpG-rich islands and the function of DNA methylation," *Nature*, 1986, 321:209-213.
Brenner et al., "Loss of Runx3 function in leukocytes is associated with spontaneously developed colitis and gastric mucosal hyperplasia," *Proc Natl Acad Sci USA*, Nov. 2004, 101:16016-16021.
Chow et al., "Aberrant methylation of cyclooxygenase-2 in breast cancer patients," *Biomed Pharmacother*, 2005, 59(Suppl2):S264-267.
Cottrell and Laird, "Sensitive Detection of DNA Methylation," *Ann N Y Acad Sci*, Mar. 2003, 983:120-30.
Cuadrado et al., "Regulatory T cells in patients with inflammatory bowel diseases treated with adacolumn granulocytapheresis," *World J Gastroenterol*, Mar. 2008, 14(10):1521-1527.

(Continued)

*Primary Examiner* — Neil P Hammell
(74) *Attorney, Agent, or Firm* — Fish & Richardson P.C.

(57) ABSTRACT

This document relates to materials and methods involved in assessing inflammatory bowel disease patients at risk for developing cancer. For example, materials and methods for monitoring colorectal cancer risk in ulcerative colitis patients are provided.

1 Claim, 40 Drawing Sheets

Specification includes a Sequence Listing.

(56) References Cited

OTHER PUBLICATIONS

D'Incà et al., "Oxidative DNA damage in the mucosa of ulcerative colitis increases with disease duration and dysplasia," *Inflamm Bowel Dis.*, 2004, 10(1):23-27.
Eaden et al., "The risk of colorectal cancer in ulcerative colitis: a meta-analysis," *Gut*, 2001, 48(4):526-535.
Ekbom et al., "Ulcerative Colitis and Colorectal Cancer—A Population-Based Study," *N. Engl. J. Med.*, 1990, 323:1228-1233.
Erdman et al., "Nitric oxide and TNF-alpha trigger colonic inflammation and carcinogenesis in Helicobacter hepaticus infected, Rag2-deficient mice," *Proc Natl Acad Sci U S A*, Jan. 2009, 106(4):1027-32.
Esteller et al., "Cancer as an epigenetic disease: DNA methylation and chromatin alterations in human tumors," *J Pathol.*, 2002, 196:1-7.
Fainaru et al., "Runx3 regulates mouse TGF-β-mediated dendritic cell function and its absence results in airway inflammation," *EMBO J.*, 2004, 23(4):969-979.
Fantini et al., "Common immunologic mechanisms in inflammatory bowel disease and spondylarthropathies," *World J Gastroenterol.*, May 2009, 15(20):2472-2478.
Fujii et al., "Methylation of the oestrogen receptor gene in non-neoplastic epithelium as a marker of colorectal neoplasia risk in longstanding and extensive ulcerative colitis," *Gut*, 2005, 54: 1287-1292.
Gardiner-Garden and Frommer, "CpG Islands invertebrate genomes," *J. Mol. Biol.*, 1987, 196:261-282.
Garrity-Park et al., "Methylation Status of Genes in Non-Neoplastic Mucosa from Patients with Ulcerative Colitis-Associated Colorectal Cancer," *Am J Gastroenterol.*, 2010, 105:1610-1619.
Garrity-Park et al., "MHC Class II alleles in ulcerative colitis-associated colorectal cancer," *Gut*, 2009, 58:1226-1233.
Garrity-Park et al., "Myeloperoxidase Immunohistochemistry as a Measure of Disease Activity in Ulcerative Colitis: Association with Ulcerative Colitis-Colorectal Cancer, Tumor Necrosis Factor Polymorphism and RUNX3 Methylation," *Inflamm Bowel Dis.*, 2011, 9 pages.
Garrity-Park et al., "Tumor Necrosis Factor-Alpha Polymorphisms in Ulcerative Colitis-Associated Colorectal Cancer," *Am J Gastronenterol.*, 2008, 103:407-415.
Geboes et al., "A reproducible grading scale for histological assessment of inflammation in ulcerative colitis," *Gut*, Sep. 2000, 47(3):404-409.
Geboes, "Ulcerative colitis and malignancy," *Acta Gastroenterol Belg.*, 2000, 63:279-283.
GenBank Accession No. AB048818, GI No. 13365764, 2001, 1 page.
GenBank Accession No. AF044206; GI: 3282785, 2004, 3 pages.
GenBank Accession No. AF135501; GI No. 4914684, 1999, 1 page.
GenBank Accession No. AL023096; GI: 3900882, 2012, 21 pages.
Goel et al., "Epigenetic inactivation of RUNX3 in microsatellite unstable sporadic colon cancers," *Int J Cancer*, 2004, 112:754-759.
Gupta et al., "Histologic Inflammation is Risk Factor for Progression to Colorectal Neoplasia in Ulcerative Colitis: A Cohort Study," *Gastroenterol*, 2007, 133(4):1099-1105.
Harlow and Lane, eds. Antibodies: A Laboratory Manual (1988) Cold Spring Harbor Laboratory Press, Cold Spring Harbor, N.Y.
Hoang et al., "Epithelial cells bearing class II molecules stimulate allogeneic human colonic intraepithelial lymphocytes," *Gut*, 1992, 33(8):1089-1093.
Horii et al., "Age-related methylation in normal colon mucosa differs between the proximal and distal colon in patients who underwent colonoscopy," *Br J Cancer*, 2007, 97(10):1425-1431.
Hsieh et al., "Hypermethylation of the p16$^{INK4a}$ promoter in colectomy specimens of patients with long-standing and extensive ulcerative colitis," *Cancer Res.*, Sep. 1998, 58:3942-3945.
Iliopoulos et al., "Correlation of promoter hypermethylation in hTERT, DAPK and MGMT genes with cervical oncogenesis progression," *Oncol Rep.*, 2009, 22:199-204.
Imamura et al. (2005) RUNX3 Promoter Region is Specifically Methylated in Poorly-differentiated Colorectal Cancer. Anticancer Research,25:2627-2630.
Issa et al., "Accelerated age-related CpG island methylation in ulcerative colitis," *Cancer Res.*, May 2001, 61:3573-3577.
Itzkowitz and Present, "Consensus conference: Colorectal cancer screening and surveillance in inflammatoiy bowel disease," *Inflamm Bowel Dis.*, 2005, 11:314-321.
Itzkowitz et al., "Inflammation and Cancer IV. Colorectal cancer in inflammatory bowel disease: the role of inflammation," *Am. J Physiol Gastrointest Liver Physiol.*, 2004, 287:G7-G17, 11 pages.
Jin et al., "A multicenter, double-blinded validation study of methylation biomarkers for progression prediction in Barrett's esophagus," *Cancer Res.*, May 2009, 69:4112-4115.
Kamikozuru et al., "The expression profile of functional regulatory T cells, CD4+CD25$^{high+}$/forkhead box protein P3$^+$, in patients with ulcerative colitis during active and quiescent disease," *Clin. Exp. Immunol.*, 2009, 156(2):320-327.
Karray-Chouayekh et al., "Aberrant methylation of RASSF1A is associated with poor survival in Tunisian breast cancer patients," *J Cancer Res Clin Oncol.*, 2010, 136:203-2010.
Kazi and Qian, "Crocetin Reduces TNBS-Induced Experimental Colitis in Mice by Downregulation of NFkB," *Saudi J Gastronenterol.*, 2009, 15(3):181-187.
Kim et al., "Methylation of RUNX3 in various types of human cancers and premalignant stages of gastric carcinoma," *Lab Invest.*, 2004, 84:479-484.
Klimasauskas et al., "HhaI methyltransferase flips its target base out of the DNA helix," *Cell*, 1994, 76:357-369.
Konishi et al., "Rare CpG island methylator phenotype in ulcerative colitis-associated neoplasias," *Gastroenterol*, 2007, 132: 1254-1260.
Kononen et al., "Tissue microarrays for high-throughput molecular profiling of tumor specimens," *Nat. Med.*, 1998, 4:844-847.
Kundu and Surh, "Inflammation: gearing the journey to cancer," *Mutat Res*, 2008, 659(1-2):15-30.
Langholz et al., "Course of ulcerative colitis: Analysis of changes in disease activity over years," *Gastroenterol.*, 1994, 107:3-11.
Lau et al., "RUNX3 is frequently inactivated by dual mechanisms of protein mislocalization and promoter hypermethylation in breast cancer," *Cancer Res.*, 2006, 66:6512-6520.
Lee et al., "Differences in Immunophenotyping of Mucosal Lymphocytes between Ulcerative Colitis and Crohn's Disease," *Korean J Intern Med.*, Jan. 1997, 12(1):7-15.
Lengauer et al., "DNA methylation and genetic instability in colorectal cancer cells," *Proc. Natl. Acad. Sci. USA*, 1997, 94:2545-2550.
Li et al., "Causal relationship between the loss of RUNX3 expression and gastric cancer," *Cell*, 2002, 109:113-124.
Li et al., "Inflammation-associated cancer: NF-kappaB is the lynchpin," *Trends Immunol.*, 2005, 26:318-325.
Liu et al., "Potential role of Th17 cells in the pathogenesis of inflammatory bowel disease," *World J Gastroenterol.*, Dec. 2009, 15(46):5784-5788.
Loftus Jr, "Epidemiology and risk factors for colorectal dysplasia and cancer in ulcerative colitis," *Gastroenterol Clin North Am.*, 2006, 35:517-531.
MacDonald et al., "Recent developments in the immunology of inflammatory bowel disease," *Scand J Immunol.*, 2000, 51(1):2-9.
Maxwell et al., "Association of the tumour necrosis factor-308 variant with differential response to anti-TNF agents in the treatment of rheumatoid arthritis," *Human Molecular Genetics*, 2008, 17(22):3532-3538.
Monteleone et al., "Immunoregulation in the gut: success and failures in human disease," *Gut*, 2002, 50(Suppl III):iii60-iii64.
Noronha et al., "Hyperactivated B cells in human inflammatory bowel disease," *J Leukoc Biol.*, Oct. 2009, 86(4):1007-1016.
Olsen et al., "Tissue levels of tumor necrosis factor-alpha correlates with grade of inflammation in untreated ulcerative colitis," *Scand J Gastroenterol.*, 2007, 42(11):1312-1320.
Olson et al., "Genetic variants in SOD2, MPO, and NQO1, and risk of ovarian cancer," *Gynecol Oncol.*, 2004, 93(3):615-620.
Pepe et al., "Combining diagnostic test results to increase accuracy," *Biostatistics*, 2000, 1(2):123-140.

(56) References Cited

OTHER PUBLICATIONS

Piedrafita et al., "An Alu element in the myeloperoxidase promoter contains a composite SP1-thyroid hormone-retinoic acid response element," *J Biol Chem.*, 1996, 271(24):14412-14420.

Pohl et al., "Chronic inflammatory bowel disease and Cancer," *Hepatogastroenterology*, 2000, 47(31):57-70.

Provenzale and Onken, "Surveillance issues in inflammatory bowel disease:ulcerative colitis," *J Clin Gastroenterol*, 2001, 32(2): 99-105.

Roncucci et al., "Myeloperoxidase-positive cell infiltration in colorectal carcinogenesis as indicator of colorectal cancer risk," *Cancer Epidemiol Biomarkers Prev.*, 2008, 17(9):2291-2297.

Rutter et al., "Severity of inflammation is a risk factor for colorectal neoplasia in ulcerative colitis," *Gastroenterol.*, 2004, 126(2):451-459.

Sandborn et al., "Safety of celecoxib in patients with ulcerative colitis in remission: a randomized, placebo-controlled, pilot study," *Clin Gastroenterol Hepatol.*, 2006, 4(2):203-211.

Sato et al., "Hypermethylation of the p14$^{ARF}$ gene in ulcerative colitis-associated colorectal carcinogenesis," *Cancer Res*, 2002, 62:1148-1151.

Saygili et al., "Enzyme levels and G-463A polymorphism of myeloperoxidase in chronic lymphocytic leukemia and multiple myeloma," *Leuk Lymphoma.*, 2009, 50(12):2030-2037.

Schottenfeld and Beebe-Dimmer, "Chronic inflammation: a common and important factor in the pathogenesis of neoplasia," *CA Cancer J Clin.*, 2006, 56:69-83.

Schulmann et al., "Inactivation of *p16*, *RUNX3*, and *HPP1* occurs early in Barrett's-associated neoplastic progression and predicts progression risk," *Oncogene*, 2005, 24:4138-4148.

Seidal et al., "Interpretation and quantification of Immunostains," *Am J Surg Pathol.*, Sep. 2001, 25(9):1204-1207.

Shen et al., "Association between DNA methylation and shortened survival in patients with advanced colorectal cancer treated with 5-fluorouracil based chemotherapy," *Clin Cancer Res.*, 2007; 13:6093-6098.

Shimamoto et al., "Selective decrease in colonic CD56$^+$T and CD161$^+$T cells in the inflamed mucosa of patients with ulcerative colitis," *World J Gastroenterol.*, Dec. 2007, 13(45):5995-6002.

Silverberg et al., "Toward an integrated clinical, molecular and serological classification of inflammatory bowel disease: Report of a working party of the 2005 Montreal World Congress of Gastroenterology," *Can J Gasteroenterol.*, 2005, 19(Suppl A):5A-36A.

Solomon et al., "Cardiovascular risk associated with celecoxib in a clinical trial for colorectal adenoma prevention," *N Engl J Med.*, 2005, 352(11):1071-1080.

Soo et al., "Overexpression of cyclooxygenase-2 in nasopharyngeal carcinoma and association with epidermal growth factor receptor expression," *Arch Otolaryngol Head Neck Surg.*, 2005, 131:147-152.

Steenport et al., "Association of polymorphisms in myeloperoxidase and catalase genes with precancerous changes in the gastric mucosa of patients at inner-city hospitals in New York," *Oncol Rep.*, 2007, 18(1):235-240.

Subramaniam et al., "Molecular pathology of RUNX3 in human carcinogenesis," *Biochimica et Biophysica Acta*, 2009, 1796:315-331.

Subramaniam et al., "RUNX3 Inactivation in Colorectal Polyps Arising Through Different Pathways of Colonic Carcinogenesis," *Am J Gastroenterol.*, 2009, 104:426-436.

Suter et al., "CpG island methylation is a common finding in colorectal cancer cell lines," *Br J Cancer*, 2003, 88:413-419.

Tahara et al., "Risk prediction of gastric cancer by analysis of aberrant DNA methylation in non-neoplastic gastric epithelium," *Digestion*, 2007, 75:54-61.

Tanemura et al., "CpG island methylator phenotype predicts progression of malignant melanoma," *Clin Cancer Res.*, 2009, 15:1801-1807.

The Cleveland Clinic ("How to Prevent Colon Cancer", publicly available on Jan. 5, 2009, obtained from <http://web.archive.org/web/20090105202118/http://my.clevelandclinic.org/disorders/Colorectal_Cancer/hic_How_to_Prevent_Colorectal_Canceraspx>, and obtained on Aug. 1, 2013, 4 pages).

Tominaga et al., "Prediction of colorectal neoplasia by quantitative methylation analysis of estrogen receptor gene in nonneoplastic epithelium from patients with ulcerative colitis," *Clin Cancer Res.*, 2005, 11:8880-8885.

Toyota et al., "CpG island methylator phenotype in colorectal cancer," *Proc Natl Acad Sci USA*, Jul. 1999, 96:8681-8686.

Tucker et al., "Cyclooxygenase-2 expression is up-regulated in human pancreatic cancer," *Cancer Res.*, 1999, 59:987-990.

Ullman et al., "Diagnosis and management of dysplasia in patients with ulcerative colitis and Crohn's disease of the colon," *Inflamm Bowel Dis.*, Apr. 2009, 15(4):630-638.

Underhill et al., "Detection of Numerous Y Chromosome Biallelic Polymorphisms by Denaturing High-Performance Liquid Chromatography," *Genome Res.*, 1997, 7:996-1005.

Van Heel et al., "Inflammatory bowel disease susceptibility loci defined by genome scan meta-analysis of 1952 affected relative pairs," *Hum Mol Genet.*, 2004, 13(7):763-770.

Wang et al., "Aberrant DNA methylation in ulcerative colitis without neoplasia," *Hepatogastroenterology*, 2008, 55:62-65.

Wang et al., "Mechanism and clinical significance of cyclooxygenase-2 expression in gastric cancer," *World J Gastroenterol.*, 2005, 11:3240-3244.

Warren, "Genetic risk for colitis-associated colorectal cancer," *Gut*, 2009, 58(9):1177-1179.

Weber et al., "Distribution, silencing potential and evolutionary impact of promoter DNA methylation in the human genome," *Nature Genetics*, 2007, 39(4):457-466.

Whitehead et al., "Variation in tissue-specific gene expression among natural populations," *Genome Biol.*, 2005, 6:R13.1-R13.14, 14 pages.

Wolff et al., "Expression of cyclooxygenase-2 in human lung carcinoma," *Cancer Res.*, 1998, 58:4997-5001.

Xavier and Podolsky, "Unravelling the pathogenesis of inflammatory bowel disease," *Nature*, Jul. 2007, 448(7152):427-434.

Xie and Itzkowitz, "Cancer in inflammatory bowel disease," *World J Gastroenterol.*, Jan. 2008, 21:14(3):378-389.

Hegele, "SNP judgments and freedom of association," *Arterioscler Thromb Vasc Biol.*, 22(7):1058-1061, Jul. 1, 2002.

Vogel et al., "Prospective study of interaction between alcohol, NSAID use and polymorphisms in genes involved in the inflammatory response in relation to risk of colorectal cancer," *Mutat Res.*, 624(1-2):88-100, Epub Apr. 27, 2007.

Xu et al. "Methylation profile of the promoter CpG islands of 31 genes that may contribute to colorectal carcinogenesis," *World J Gastroenterol.*, 2004, 10(23):3441-3454.

Yu et al., "Expression and functional characterization of FOXP3+ CD4+ regulatory T cells in ulcerative colitis," *Inflamm. Bowel Dis.*, 2007, 13(2):191-199.

* cited by examiner

Figure 1

```
   1 gctgtctgct tgtgtgtgtg tgtctgggag tgagaacttc ccagtctatc taaggaatgg
  61 agggagggac agagggctca aagggagcaa gagctgtggg gagaacaaaa ggataagggc
 121 tcagagagct tcagggatat gtgatggact caccaggtga ggccgccaga ctgctgcagg
 181 ggaagcaaag gagaagctga gaagatgaag gaaaagtcag ggtctggagg ggcggggggtc
 241 agggagctcc tgggagatat ggccacatgt agcggctctg aggaatgggt tacaggagac
 301 ctctggggag atgtgaccac agcaatgggt aggagaatgt ccagggctat ggaagtcgag
 361 tatggggacc ccccttaac gaagacaggg ccatgtagag ggccccaggg agtgaaagag
 421 cctccaggac ctccaggtat ggaatacagg ggacgtttaa gaagatatgg ccacacactg
 481 gggccctgag aagtgagagc ttcatgaaaa aaatcaggga ccccagagtt ccttggaagc
 541 caagactgaa ccaagcatta tgagtctccg ggtcagaatg aaagaagagg gcctgcccca
 601 gtggggtctg tgaattcccg ggggtgattt cactccccgg ggctgtccca ggcttgtccc
 661 tgctacccgc acccagcctt tcctgaggcc tcaagcctgc caccaagccc ccagctcctt
 721 ctccccgcag ggcccaaaca caggcctcag gactcaacac agcttttccc tccaaccccg
 781 ttttctctcc ctcaacggac tcagctttct gaagcccctc ccagttctag ttctatcttt
 841 ttcctgcatc ctgtctggaa gttagaagga aacagaccac agacctggtc cccaaaagaa
 901 atggaggcaa taggttttga ggggcatggg gacggggttc agcctccagg gtcctacaca
 961 caaatcagtc agtggcccag aagaccccc tcggaatcag agcagggagg atggggagtg
1021 tgagggtat ccttgatgct tgtgtgtccc c   (SEQ ID NO:1)
```

Figure 2

```
  1 cccgggctgg gtacctggac ctataccttc atagctgcct taggctcaac ttttcggcgg
 61 ggatccctct gcagacgtgc aggtggcggg agagcagagg tagccgcagt aagtgctgag
121 agagcctgaa agaaacacca tgaattttca aactctccca catacattcc cgaagcgcct
181 gtctggcgtc taagagagag caagagaggg ctggagagca ggggagcccg cggggctgag
241 gctctttgtc agcgcctgca cttcctacgt tacaacgcct tcattcagca aaaaccttt
301 gggcgcctgc tgtgcgccag gccaggcgaa gnagaccgag gntgtgaagc tcagagggga
361 gagggaccaa tcgcagtaaa taagctaccg aggtaatctt agatggngat gagggcagga
421 aaagncatca gncgacctct gacctttctc ttagggggtt ttcccttcc gcctgggttc
481 tagaactggg aagantttc tccagagcgt cgcggggagc gccccggg (SEQ ID NO:51)
```

Figure 3

```
   1 ggtacccagg ctggagtgca ctggtgtgat catagctcac taacctcgaa ctcctgggct
  61 taggcaatcc tcttgccttg gcctcccaaa gtgccaggat tacaggcatg agccaccaca
 121 gtggagctct caattctgat actaataatt tgtgtcttct cttttttttcc ttagcctgac
 181 tagagtaatt aactttatgt cttttaaaag aaccacctttt ttggttttac ccatttttctt
 241 ttttgatttt ctgttttttga tttgattgat atctactcta atttttttatt atttcttttc
 301 ctctgcttac tttgaattta attacttttc ttttttgtag tctcctaaaa tagaagctta
 361 tattattgat tttagatctt tcttcttttc tattacagca ctcaatgcta taaatttccc
 421 tctaagcatt gctttcactg catcctacaa tatttcaact ctattgttat ttagctcaaa
 481 agaggttctt aatttctatt gggatttctc tttgacccat gtgttattca gaagtgttcc
 541 gtgtgatctc caaatatttg ggagttttttc agctatcttt ctattaatca tttcttgttt
 601 aattctattg tggcctgaga gcatatattg tatgatttat attcttgtaa atgtgttaag
 661 gtgtgtctta tggtgcagaa tgcggtttat cttgctatat gttccttaga gaataatgta
 721 tgttctgctg ttattggata aagtagtcta tagatgtcag ttacatctcg ttgattaatg
 781 gtgctgttga gttcagctat gtcctaaatg attttctgtc tgctgtatct gtctatttct
 841 gacacaaggc tgttgaagtc tccaaccata ataatgaatt aatctatttt tctttgcagt
 901 tttatcaatt ttgtcttata tatattgatg ctccattgtt tggcacatac acattaagaa
 961 ttgttatgtc ttcttggaga atttacccttt ccataacatg taacatttcc ctttattcct
1021 gataattttt cttgctcaaa agtttgccct gttggaaatt accagaacta ctctggcttt
1081 atttgattag tgttagcatg ctctctctttt ctctattctt acactttttaa tgtatacttg
1141 actttgtatt taaagtgggg ttcttataga aaacatatac ttggtagggt gggaagtaaa
1201 ataaaaagaa atacttgggt attggtttga tccactctaa caatctctat gttttaattg
1261 atgtatttag accattgata cttatttttt tatcctcatc cctgtgatta cccagagagc
1321 tgcttaaatt gattattgat atagacaaat taataattaa tatctaccgt ttgttactgt
1381 tttctatttt tcattgccct tactttctgc tcctatttttt tgctccttttt tctgttaatt
1441 taggttttga gttatttttat atcattctat tttctctccc ttctcagcat atgaattatc
1501 tttcttttttg acttttttag tggctgccct gaaggttgca atgtacatttt acaaccagtc
1561 ccaatctcct ttcaaaaaac acaatactgt ttcatggcta gtgcaagtac ctaataataa
1621 gaagtcactc ctaatttctt tctctcattc tttgtatctt tactgttatt catttcactt
1681 gtacataagc tgtaatcttt caatacatta ttgctattat tatttcaaaa catgttatct
1741 attatatcta tttaaaataa gaaaaatagg ccaggtgcag tggcttactc atgtaatccc
1801 agcactttgg gagaccgatg gattgctaga gctcaggaat tcgagaccag cctgggcaac
1861 atagtgaaac cctgtctcta ctaaaaatac aaaaaaaaaa attgctgggc atggtggcat
1921 gggcctgtgg tcacagctac tcgggaggct gaggtgagag gattgcttga gcctgggagg
1981 cagaggttgc agtgaaccaa aatcaagcta ctgcactcca gcctaagtga cagagtgaga
2041 ccctgtctca aaaaaaaaat gaaagaatta ttttttattta tcttcactta tttcttctct
2101 aatgctcttt gtttctttag tatgtagatc caagtttcta acctgtatca tttttcttat
2161 ctcaataact tcttttaaca tttctcacaa agcagatcta ctggccacag aatgcctcaa
2221 ttttcatttg tctgagaaaa ccttatttct ccttcacttt tgaaagataa ttttgtaggg
2281 tacagaattc taggttgtag gttttttccc ctcaaagtga aatatttcat tccactcttt
2341 tcttctttgt atggtatctg agaagaagtc agatgtaatt cttatcatta ttacttaaaa
2401 gattgcttct gttcctttct ctcttctcct tcccttctttt ccttctctgt atattacacc
2461 ttttatagtt gccccatatt tcttagatat tatgttttgg ttttcttctg tgttttttttc
2521 tttgattctc agttttagaa gtctctattt atatatctgc aatcgcaggg attctttcct
2581 ctgccatgtc cagtctacta ataagccctt acagacattg ttgacttctg ttccagtgtt
2641 tttgatctct agcatttctc tgattatttc ttggaattgc catctgtcta cttacattac
2701 caacctattc ttgtgtgttg tcttatcata gtaattgcag ttgttttaat ttcataggta
2761 ttgtaatttc aacatctcta ccatatttga cattgattct gatgcttgct ctgtcttatc
2821 aagctatgtt tttgtctttt agtgtgactt ctaatttttt gttgaaagcc aggcatgatg
2881 tactgagtga aagaaactca atacattgta atgtgacgat aagagttcag gggaagtgaa
```

Figure 3 (continued)

```
2941 gcattctata gtcctatagc aggtctcggc cttttagtga gcctgtgcct atgaacggtg
3001 actttcaaca agtgcttttc attccactct tttcctgtcc ttaagtggga caagatcact
3061 ggggggggc tagaattggg tatttccctt ctccaatgta gaagctaaag agagggctgg
3121 agttgggtat ttttcttccc ctgtatggaa agctagaggc agttaaattt ggatattttc
3181 cttcttctaa ttcagttagg ctgcgacaaa aatcccgaca gtttaggctc taatattata
3241 aaataatttc tcttgagtat aggccttatt aagaacacta tactctgatg gagctgaggg
3301 ggagttttct ctgatattca ctgcgagaac ctcgtagagc tccaggaagc aaaactcaca
3361 aaagtgtggg agtcttccag aattttcct ttgcagactt atctgcactg aacctccaga
3421 aattcatcaa ttacagttca ggttttccta cccaggtact ggttttcatg gaggtttctg
3481 cctgtgcatt tctgctccag taagttgttc ttcttgtatg gtctgtcttt caaattttt
3541 aagtagggtt atgacctgtc gcctcacttc tctgacagtt ctgagagtgt tgattttca
3601 gtttgcttag attttactt gttttagga tgaagtgaca atttccaagc tcctccctga
3661 catgccagat cagaaactga aagtcctaag cctcatattc tgtgcgtggg tatgttcaca
3721 tcctgcctgc tccagtgccc ccacctcaca ctctctttcc cttccttgtc ccttgtgag
3781 atttctaggt ccaatacaaa gactgtgttc aactcattca actacttggc tcatctgagt
3841 attataatga acaatcacaa aaaaaatga agtaaagaa aatccatca aagaattgag
3901 atatttgaga aaagaaagg agatcagtgt tttataaaac ttagaaatag attttttaag
3961 tgtttcttca ttgacttatg tgaaaggact tttcttaatt taacaaatta tgtgctttcg
4021 tttatagcct caaaacttct tgtgtagcta agaatgggta ataatcagg ctttactaaa
4081 ggactaacgt aaagatcttc tgtaagtaac atttctgcta ctcaaggaag agataaactt
4141 catggcataa ccttgccaaa gtatactaag aataaccctg acacaaagct cttttttcag
4201 ccaacatgcc atgaaagaaa gaagacaagg ggtgatctcc actctctaag tgaaccacta
4261 aacccaccaa agaagaaacg agggaaatag aaagaggacc cttgcctgag ataatggatc
4321 tgtatgtatg agtagtagaa ccctgctcaa agtacaagga agggaaaaaa aagttagttt
4381 atttggaatt ttggacatta agagtcttta ttgttcattt tcttttaact cacatgaatg
4441 gcttatcact tcaattaata aatatttcat ttcttttcaa tctatattca tgaaacaaat
4501 ctgaaatgaa cagtgcaaca tgtgaatgtt tagaacatta taaaattaaa cacaaaatct
4561 gtctggcaat cttcctagca tcttaggaaa aaagttgaca aaatttcaag cagcagaagg
4621 gggcagtaaa actcaacaga aagctctgga agatttttaa gattcttcct tattttcttt
4681 tcatgtagag tattccccaa caaatttcag acgctaatag aaattttgta caacagatcc
4741 atatatttgc ctaaaataga cacagaaaca ttgatatatg caaacatgag agctataagt
4801 tttacatgat caaaaccttt tttttatggt acacaatagt cacagtactt ttccatataa
4861 aacaggttta gtggtcttaa tttagtttgg cacatttaat acactcccat gaccagcatc
4921 ccaaatgtac ctatccgttt tattttattg tctcagaatt gtcagttatt taataaatta
4981 tgtaactttt ttccttatgc tcagatttgc acttctttct aaaactctgc ccatccttaa
5041 agtcccagat tctccttgaa cttttttttt tgactttcca agtacatgga actcttcact
5101 ctatcctgct ataagtga cagaatttcc actatgggat agatggagtt caattccttt
5161 gagtttaaaa taatctaaat ataattattc cttatgccct gttttccct cacttttgta
5221 tccaaatctc ttttcagaca acagaacaat taatgtctga taggaagac aatgatgatg
5281 atcacttcaa aataagcttg aattcaggat tgtaatgtaa aatttagta ctctctcaca
5341 gtatggattc taacatggct tctaacccaa actaacatta gtagctctaa ctataaactt
5401 caaatttcag tagatgcaac ctactccttt aaaatgaaac agaagattga aattattaaa
5461 ttatcaaaaa gaaaatgatc cacgctctta gttgaaattt catgtaagat tccatgcaat
5521 aaataggagt gccataaatg gaatgatgaa atatgactag aggaggagaa aggcttccta
5581 gatgagatgg aattttagtc atccgtgtct catgaagaat cagatgtgta cactaagcaa
5641 aacagttaaa aaaaaaacct ccaagtgagt ctcttattta ttttttttctt ataagacttc
5701 tacaaattga ggtacctggt gtagttttat ttcaggtttt atgctgtcat ttcctgtaa
5761 tgctaaggac ttaggacata actgaatttt ctattttcca cttcttttct ggtgtgtgtg
5821 tatatatata tgtatatata cacacacaca tatacatata tattttta gtatctcacc
5881 ctcacatgct cctccctgag cactacccat gatagatgtt aaacaaagc aagatgaaa
5941 ttccaactgt taaatctcc cttccatcta attaattcct catccaacta tgttccaaaa
6001 cgagaataga aaattagccc caataagccc aggcaactga aaagtaaatg ctatgttgta
6061 ctttgatcca tggtcacaac tcataatctt ggaaaagtgg acagaaaaga caaagagtg
```

Figure 3 (continued)

```
6121 aactttaaaa ctcgaattta ttttaccagt atctcctatg aagggctagt aaccaaaata
6181 atccacgcat cagggagaga aatgccttaa ggcatacgtt ttggacattt agcgtccctg
6241 caaattctgg ccatcgccgc ttcctttgtc catcagaagg caggaaactt tatattggtg
6301 acccgtggag ctcacattaa ctatttacag ggtaactgct taggaccagt attatgagga
6361 gaatttacct ttcccgcctc tctttccaag aaacaaggag ggggtgaagg tacggagaac
6421 agtatttctt ctgttgaaag caacttagct acaaagataa attacagcta tgtacactga
6481 aggtagctat ttcattccac aaaataagag ttttttaaaa agctatgtat gtatgtcctg
6541 catatagagc agatatacag cctattaagc gtcgtcacta aaacataaaa catgtcagcc
6601 tttcttaacc ttactcgccc cagtctgtcc cgacgtgact tcctcgaccc tctaaagacg
6661 tacagaccag acacggcggc ggcggcggga gaggggattc cctgcgcccc cggacctcag
6721 ggccgctcag attcctggag aggaagccaa gtgtccttct gccctccccc ggtatcccat
6781 ccaaggcgat cagtccagaa ctggctctcg gaagcgctcg gcaaagact gcgaagaaga
6841 aaagacatct ggcggaaacc tgtgcgcctg gggcggtgga actcggggag gagagggagg
6901 gatcagacag gagagtgggg actaccccct ctgctcccaa attggggcag cttcctgggt
6961 ttccgatttt ctcatttccg tgggtaaaaa accctgcccc caccgggctt acgcaatttt
7021 tttaagggga gaggagggaa aaatttgtgg ggggtacgaa aaggcggaaa gaaacagtca
7081 tttcgtcaca tgggcttggt tttcagtctt ataaaaagga aggttctctc ggttagcgac
7141 caattgtcat acgacttgca gtgagcgtca ggagcacgtc caggaactcc tcagcagcgc
7201 ctccttcagc tccacagcca gacgccctca gacagcaaag cctacccccc gcgccgcgcc
7261 ctgcccgaag ctt (SEQ ID NO: 52)
```

Figure 4

```
   1 gatcacctga ggtcaagagt tggagaccag cctggccatc atggcaaaac cctgtctcta
  61 ctaaaaatac aaaaattagg agggcatggt ggctcatgcc tgtaatccca gctacttggg
 121 aagcagagta ggagaatcac ttgaacctgg gaggtggagg ttgcaatgag ccgagatcgt
 181 gccactgcac tccagcctgg gcgacagagc aatctccatc tcaagaaaaa aaaaaaagaa
 241 aagaaaagaa atgaagattc tttctcccct ttcctcccag tgctctcccc acaggaacga
 301 gacctgcgtg gtgtggggag cagctgaaga cttctcatct gcctttgtga atgccaattg
 361 tacacagcca ctactggaat cttactcatc gcagcaggag gcctggcttc cggcacaggt
 421 ggaatgaatg aaggaaggaa cggatgaatg aaaacaatga agctgtacag agcagtctgt
 481 ctccgagtgg gcagtggatc ctggaaaaca catcttcagc catccagagt gggaagatct
 541 ggatttggga tgtagccgct tcctccctgt gtgacctttg gcagatgtca tttactttt
 601 ggaacttcag ttttttccatc cgcaaaaagg ggatgctgcc tgcccagttc atgtcacaga
 661 cctgtgaagg tcaaaacaga aggcaggagg gagcatattc cataaaaggt acagcagccg
 721 ggcagagtgg cccatgcctg gaatcccagc caaggcagga ggattgctgg agaccagaag
 781 tttgagacaa gtatgggcaa aatagcaata cctcatctct aaaaaaatt atttaaaaaa
 841 tcagctgggg ctgggtgcgg tggctcacct gtaatcccag tactttggga ggccaaggca
 901 ggcggatcac ttgaggccag gagttcaagc ccagcctagc caacatgatg aaacccatc
 961 tctcctaaaa atagaaaaat tagccaggtg tagtggtgca cacctgtagt accactgcac
1021 tccagcctgg gtgacaaagc gagactctgt ctcaacaaac aaacaaacaa acaaacaaaa
1081 aaccagcgga gcatggtggc acacactgta gtcccagata cttgggtggc tgagtgggga
1141 ggatggcttg agcccaggag gtccaggctg cagtgaacca cgatcgcacc actgcactcc
1201 ggcctgggcc acagagtgag actctgtctc tacaaaagaa aataagaaag gaaggaagga
1261 aggaaagaaa aaaaaaataa ataaaaatga aagataaagc ataggggacgt ctctgagaca
1321 aagagctgag tggaagaatc aagttaggac tcagcagcgc aggatggcga ggcttataat
1381 tttaatcccc tcctcgattt ctttcgatga ggcaaaaaac agtcttggaa attactcacc
1441 aaaccagcag tgggtgccag gagctcattc actttgtgtg tcattataat ttttgtaac
1501 tagaatggat ggagcaacca ctttggtagt gaaaatattt taatatccgc atgtgcataa
1561 agtgacacga ataacagttc ccgtttactg ggctctgatg ctgtagcagg ctgtggggat
1621 ggctactgtg ctcattttac agacaaggaa actgaaaccc aggcaggcga agtggcttgc
1681 ccaggctcac acagccagaa cgggatgaag caggttctga cctccaagca agactgactc
1741 cagtggggaa ttatgggttc ccaaatgaca ctgatcacag caacaacggg caggacagga
1801 caggtgactc agagcagact cctcatgcaa ggggagatgt tgcccagtgc cgagggcacc
1861 ggggcagggt tcatgccttc ccctgggaga gcaagaggtt cagagtcaga aagactgggg
1921 cttgtggtcc cagctctgcc actttctggt tgtgtaactt ctgccaaatc ccttcacccc
1981 tccgagcctc aatgtgctca tatgcaaaag gggcgagtaa ccacctacct gcaggcttg
2041 tgtggactga gtgtgttacg gccatgaaaa caccatgtgc tctataaggt gcgctttatt
2101 cattcctgaa gtgagcattt atcatgcacc cacgttcatg ccaagccctt ctctgggatc
2161 tggggagaca gcagcaaaca cagcagatga ggtcctggtc cctggagtta cttcaagtg
2221 gttggagcca gataatcaac cgagaaagcc tgacacagtt cagacggcgt tgagtgccgt
2281 ggagaaccca cgccggacag cgtgacggag cggcctcggg gctgggctac tgagcaaggg
2341 aggggcctct ctgactttgt gatgtctgca cagaggctga cggtgtggt gcaggtcagt
2401 gatggaaagc tgtttatggg aagtgtcaag ggatagcccc aaggaaggga ggagctacag
2461 cgggtgagga acagaaggct agggcaggga gaatgggcaa ggggcccacc gggcagtgcc
2521 tgtgcactag aggtggtctc tagaggtggg aatgtctttg tggacacgtg tcctttgctt
2581 aggacagcgg agagaggctt ccaggtctgg gtgggtgaga aagagggagg agctgtcagg
2641 cagaaccatg gaggtaggtg gtaggaggta ggaggtaggt gggagggtga ggcacctgct
2701 ctgagcccct tctccctggg caggaatggg gcatgtgggc agagcagagg gaagcagcgg
2761 tgcaggaatg gccctgacct gcacagatgt gggaggaggt ccgcacgccc agagagggc
2821 tgagatcata ccaccaggga cctggtgttg gttccacaag aggctcaggg acacacttcc
2881 agaattttga gagcacccct agcagaggca gggacttgga ctggttgacc tggctttccc
2941 acaccctcaa aacctcaaaa tgtccaatgt ccatccactg atcatgatgg gtctttctag
3001 aatgtcattt tctccccagt gcagttggtg agaggcattc tcacctcctc cctggagagt
```

Figure 4 (continued)

```
3061 ggggttcctc cttaccattg cctggtggtt gagctctagt ccttctgtct ggctggccgt
3121 gtagccttgg gcaagccgct ccatctctct gtgcctctgt tgcctgggct gtaaacagaa
3181 gtgagctaaa ggcaggcaga ccgaggtctg tgaccacgta ataactcata ctcagttcca
3241 gaaatattca cccacagaag tgtctggac aagcctggaa ggctgatcac accagccctc
3301 cgggtgctgc tcgtggctga gagaacagaa gggagccctg tccaccatgg gaagctgctg
3361 tttccatcac cagcctgggc tgtggtgcag aaagaaggaa ggggagtctg ggtggggcga
3421 gggaggcagc aaagggcctg gaccttcgtg ggagcacgga cacacaggac agccattgtc
3481 gagcttggac tgaccctact tggtgacgtt aagttctcaa gctccaagaa acagcatctg
3541 agttcttgag ctcaatcttc ccaccaaaga aaatcataca caagtcccgg cgcaggggct
3601 tcacagctca aagcatggtc tgtgtccaca tttcctgtgg tgggtcaggc cccactgcag
3661 tcctgagcca gctctgcatt cccaccagag ccccaggaga tcagatgcgg ggtgaactct
3721 gagaagcgct gctctagggc acaggtaggc tcattgcagc cttgtcccca gcgggaaaac
3781 gcggtggacc tgcagcagtc agaggcaagg cacactgcaa gctccaggaa caggcaggac
3841 ccgagaaacg taggtgggtg gaagcaggaa gaaggagaac ccagcgcaaa actgatgatg
3901 catattaaaa acatgcacat ggcggctggg cgtggtggct cacgcctgta atcccaggac
3961 tttgggaggc cgagatgggt ggatcatgag gtcaggattt cgagaccagc ctggccaaga
4021 tggtgaaacc ccatctctac taaaaattca aaaaattag ccgggcgcgg tggtgggcat
4081 agggagactg aggcaggaga atcacttgag cccaggaggt ggaggttgca gtgagctgag
4141 attgcaccat tgtactccag cctgggagac agagcaagac tcagtctcaa acaaaacaaa
4201 acaaaacaaa acaaaaaaac atgcacatgg caaaatgaca taaggagag tgttgggatg
4261 gtgggagccg tattgtgtca atgtgaactc tcctgaacgt ggttattgtt cctggttatg
4321 taagagcagc tccttgttct caggaggccc acggggaatg gtcctgacat gtgtaggtac
4381 ttctatatgg ctcagcaaac aaaatttatg cagatactca gagagaaccc ctggagcaaa
4441 atgttgacaa tctgtgagcc taggtaaagg ggatatggga ggtttgttgt tgttgttttt
4501 tgttttttga gacggagtct cgatctgtca ctgaggctgg agtgcagtgg tacaatctct
4561 gctcgctgca acctctgcct ctcaggttca gtaattctc gtgcctcaac ctcctgagca
4621 tctgggacta caggtgcacg ccactacacc tggctaattt ttgtatttt agtagagacg
4681 gggttttgct gtgttggcta ggttggtctt aaactcctga cctcaagtga tcctcctgct
4741 tcggcctccc aaagtgctgg gattacaggt gtgagccact gtgcctggct aattttata
4801 tttttagtag agatggggtt ttgccatgtt ggccagaact cctggcctca agtgatctgc
4861 ctgcctcggc ctcccaaaat gctgggatta caggcatgag ccactgcacc cagccggata
4921 tgggagttta ttgcactgtc cacagagtga aggtgtggct cctggacttc ctccctcgtc
4981 cagaggagag tcaggctgaa ccagccgggt cccaggagac caaaggagac ccccccccc
5041 ccgccgccac taacaaacca cagagatttt tactgaaaat aagttttctt cctctcttct
5101 tgtaattaca aagataaacc aagtttattg taaaaatgtg aaatgactaa gaagtgtata
5161 aagcaaaaag caaagcgttt tttcacctt gcccctcccc aattcttaac ctctgtggac
5221 agcttggcag ccccttctag gcattttct ttccaggtga aagttctgtc aatctttttt
5281 cctcccagag ggagtcctgc acaatttatt gttcatatat tggggacagg tttccatggc
5341 aaaactcaat ctgattcttt tttactttt ttttttttt tgagacagag tctcgctctg
5401 ttacccaggt tggaatgcag tgccatgatc tcggctcact gcaacctccg cctcccaggt
5461 tcaagcaatt ctccggcctc agcctcctga gtggttggga ttacaggcac tgccaccat
5521 gcctggctat ttttgtattt ttagtagaga tgaggtttca ccgtgttggt caggctggtc
5581 tagaactcct gatctcaagc aatccactca cctcggtctc ccaaagtgtt gggattaaag
5641 gcgtgagcca ccgcccctgg cccttctta cttttaaat caagaactga aaacgactt
5701 atttactctt cttgggacat ggccacgccc atggaagtcc ccaaagtagg ctggacaggc
5761 cacagcagca cccggagcag tggtggcagc tcctgttgag ctgccctcca gaagccagtt
5821 ctgatgcgcg gcctcgccgg gggcctgaga accctgttt cctgtgaggc tgggccaggg
5881 acaggataac aagggaggca gaaaagagtg ctggcgggga gccaggaggc ctgggttcca
5941 gccccggccc tgccgcttgc ctgctaggag cccttgagaa agtcagttcc cctgcctgaa
6001 cctcagtctc ctcaccttca gatggagatg ccggcccaga gggtaccaga ggcctttcct
6061 ggcttgcaaa caggatgcca gtccacaaag ccacagggtg agggtgcttc ccagttctct
6121 gtgcttcgga acagcgtgct gctccggggg accttggaaa ggtgactggg ctcttctggc
6181 ggtttggggt gggggttgta gtttgtgctc ccggatgttt gcccacgtgg gtggagcctg
6241 cctgtctgtt gccccttaga gggaagttgg cagtaggatg ggttgggggg ccgtggatgt
```

Figure 4 (continued)

```
6301 tgggaggccc taaagctgag cccagactct caggcttggg aaggaccttc ccgatcagcc
6361 ttctgtccat ggcttgaatt cctgtcttgt ggcatcagga aagacttatg tcttttaggg
6421 tccaaccaag aaagcagaaa aacactcagg tgttgcagac agagggcctt catacaggga
6481 gttagtcaca caggttatgg gagagccgag aagccgaaga gggtgtgatg agttaaccca
6541 gagattaaca actgcgagaa accaccaccg ccccaggatg gagaagccag ggaggtggtg
6601 gggttagcag atcctgggat cggggtcacc cagtaccagc caggggcttg tgcagagag
6661 ctggagcaca gaggagacat ggctgctgcc gctgagctca cgaaggaaga cagggaaggg
6721 gagggatacc cagcttctct catcacatgt gccccatctt cagtctcccc cagtgcctcg
6781 ctttggcaga actcgctgaa aaacgcagcc tgcaggtatc agccccacc ctgccctgaa
6841 cacagagagg aacatatttg aggtcagagg cccaggactg gcccagtgac tgtgtttaaa
6901 tgcttcgggc actggggagc tcactctcta actcttaact gtagaggtgg tggcaacagc
6961 ctgttttgct ggcggctgag catgagcatt tggttcagaa taaggaagaa acattggttt
7021 cctgtgactc cctacagaaa gatgaggggt ttgtcttggg agcagaagcc cccgtgtgtg
7081 ttgctttgtg ctgtcatgtc tgccaggaag gcccttcccg ccctcccatc gcttgagacc
7141 caattctccc agaaaacctt ccggcacctc catgtcgagg gatagtaccg tcatgtccgt
7201 ccacagcacc tgcgcttcct tctctattta gcagaatgta gcgaacatta tgttcaacgt
7261 ggacttctct gtttgttctg cctcattcat aggggcatg gagcttggag aacctgacgt
7321 tgcctaccca gagctggctc taggttaaag atgctcac taaggcacct atagtgtgcc
7381 aggtctgcca aatgtttggc atgcattatc tagtttaatg ctcccaacaa ctccggaggt
7441 tggtatgatt agcccatgcc tgctcagctg gagaatctga ggctcaaaag gagggtgtcc
7501 aaggccactt ggctagtaag ggcagagcta ggattcgaac acagcctctt aaaggccgcg
7561 ttccttagcc acggggccac gtggtcttgc cacagtgcag ctgggcccag ggtgggattg
7621 tgtgaagtcc ctcactggga atgtttccag ctcagctcct ggtgcctcct cccctgtcct
7681 ctgtccaaga ccacatgtca gccccttgaa ggcgaggcag ccattcccac agccacttct
7741 ctattctgac atgaccaaga agcctggctg gacagcagg tctgaccaca gattgacaga
7801 tgtttccaca tgtggaagtg aggtttgagc ctcgatgtgc tgtttctgtg gttccctttt
7861 cacgctttcc ttgggagatg tgtccagaca tggtctcatt gccctaatag gtttccatgt
7921 ctgttgtgca cagtctttag actgtttaac aatcctgttc actggtagag cactgcccag
7981 cttgcacaca gcactttctt atgcattggc tcagtggctc ttcccaacaa tcctgggact
8041 tgggttcatt tactggatgg aggctcagag aggctaagta acaacagtga caaccattag
8101 ttgccttttg cagatctgtc agcatgcctt gctcaaagag agacagaaac tgcccagtgc
8161 acagtgtctc acttgatctt cacaatagcc ctgcaaggta gatattatta caacctctca
8221 ttggaagtag ggaaactgag gctcagagag aataattgac ttacccaagg tcacacagcg
8281 tcaaatccac acctagaacc catctcttgg tcttgactcc tggttcagtg ttccaagcaa
8341 ctgttgagaa catccatcaa acttaaaaat atatatgact atatttcaac aaatctatga
8401 catcattgaa tatagataca ccactctttt atataccca ggaaatagaa atgctgtcag
8461 ctacagtaag acacagtatt tctcatcaca tagaattttt ttattttaga ctaattaaaa
8521 gagctctttc atatctgtat gcatcatata tataagca ttatatatgc atatatataa
8581 tgcatcatat atgcatcata tataagcata tatgcata tatataatgc atcatatata
8641 tgcatcatat atatgcttat atatgatgca tatataagca tatatatgca tatataagca
8701 tatatgcata tatatgta tctctctcag ttgtctgtac atagaaggaa aatttatctg
8761 aaaataaact tatatgacat gaaatggatt tatgtgaaaa taaacttctt catattcaaa
8821 atctaactga gtaactgggc gtggtggctc atgcctgtgt ccagcacttt gggaggtcaa
8881 ggcaggtgga tcacttgagg ccaggagttt gagaccagct tgggcaacat ggcgaaactc
8941 tgtctctaca aaaatacaa agttagcca ggtgtggtgg cagaggctgt agccccagct
9001 acttggagg ctggggcagg agagttgctt gaacccggga ggcggaggtt gcagtgagcc
9061 aagattgtgc cactgcactc cagtctgggt gacagagtga gactctgtct taagaaaaaa
9121 aaaaaaaaag acaaactctg agtgagcagt agaagcccag ctctttccca taagattgtt
9181 ctccgcacca gcaaatgctg gcgatgaaga tttctccctc tctcttcaaa aatatgttag
9241 agaggaaaag cgtgtttaca tataacaaag tacataaatt ataagtacac ttgatgaatt
9301 tttatccacg ttaatattca tctagactca ccagtgcgtt ggagctggct cacattagca
9361 ttgttaaaca ctcaggaatt ttgcaaactg gttttttaaat tgttggtcac ttaaaatcag
9421 ctgcgggcca ggcgcagtgg ctcacacctg taattccaac actttgggag gccaaggcag
9481 gaggactgct tgagcccagg agcttgagac cagcctgggc aacatagga gaccctgtct
```

Figure 4 (continued)

```
 9541 ctacaaaaat atatatattt ttaaattagc cagatgtggt ggtgtgtgcc tgttaagttc
 9601 cagttacttg ggaggattgc ttgagcccag gagattgagg ctgcagtagg ctatgatgga
 9661 gctgctgcac tccagcctgt gtgacagagc gagacgccgt ctcaaaaaac aaaaacaaaa
 9721 accaaaccct agctgcaatg ggagtatttt acatcatgga aattggcaaa tgctacataa
 9781 tccagggctg ttttttttccc ttcagaggtc tggtttactg gcccaccact gagtgtagct
 9841 actacccaga tggggagagc ttcccagcat cctagaagcc tcctttgtgg ctgtcccagc
 9901 cccttttccac caagggaaca actactggat gcggcatttc ctagaggtgg ctgagggcca
 9961 ctggcgctgg gctcctgcga ggggtttgcc attgtgcggg gctggcccac tttcgacgcc
10021 catgggagga atgctgctaa acacgtccga tttaccacct cctccatccc gtacccacag
10081 ccatttggtt cctagaggtt aaaagaacac tcctctattg tctccagggt ttccttccaa
10141 gccgcagaat cccattgtcg atgtgacggt gtaagcgggc tgtgaccact ccctggagag
10201 ggcctcctgc caacaattac tgtaagacac accctatttt cagagacact aaaatgtgaa
10261 aaatcaagcc tcttagagtc accaaaatac agtatattgc cttttgaaga tctttactga
10321 agcagtttcc tctgagaagc agcttgtctc catcattaag ccccggaaag cagatgagac
10381 tgcagttcct ccgggctagc tgtctcagtg gtcacttcgc ccccagacag gtagcttctg
10441 cccacttctc tcatggggca gccaagtgtt actacctctg gccccggcct ggaataagag
10501 gaccagcagg ccgtgggaaa cctcagctct aataccaggc tgcttctgga cagtcctttc
10561 tgggtgtgga taaagaccag gcttgtgccc tctggggacc gttcaaagca gtcttcaggg
10621 tcggacctca gactcatccc tgtgatgatt gtttcaggtc ctagcgagtt actttcccaa
10681 cctgtgagct tctgcaactg tgttttttttg ttttttgtta ttgttgtttg tttgttttaa
10741 tatttttttc ttttcttttt ttttgagac agagtcttgc tctgttgccc aggctggagt
10801 gcagtggtgc gatctcggct cactgcaacc tccacctcct gggttcaagc gattcttctg
10861 cctcagcctc gcgagtagct gggattacag acgtgtgcca ccacaccagc taatctttgt
10921 attttttagta gagacagggt ttcgccatgt tgcccagact agtctcaaac tcctgacctc
10981 aagtgatcca cccacctcga cctcccaaag tgttgggact acagggggtga gccactgtgc
11041 ctggccatgc aactgtgttt taatcacctt tgtgttccca aggccctgac atggaacaag
11101 cacccagtaa gtatttgaat gaatgagcaa atgaaaggcc aggaaggggag agcctttatt
11161 ttgaagcctg cccgccgggc tgcccttggg aaagccactt tctgcaaaag tcacaggagc
11221 aaatgagaca aagatgcaaa attgctctgc ctgagctgtg agggcttaac tgtgaatgtc
11281 tttaggtgac cttcttggag acctcaagac caccctctg tgacttggtt caggctgccc
11341 tgctgtgatg cctgctgggg ccaaggcctg gatccctggg tggggtgggg tggggtgggg
11401 cggggcgggg agggggcgggg cggggcgggg caggagtggc agcaggaagg atccggctga
11461 gacttgccct gggggggccag ggaaggaggg tggcaggagg cagaatccac aaatgaagta
11521 gatctggagc caggcagatc agcccttaga tataatctca gaagggggttg ggagaatgga
11581 aggatttttgt tgaggatgga gtgagagggt tggagggttg ggtatgttcc tgagcatatt
11641 tccctgtcta tgggggccatt cagagagaag cccacgtgct ccaggccagt ggtggagcct
11701 tcaacgtgga gctggaagac ctgggctcga gtcccacctc tgccatgtcc catcctccct
11761 catgactccc agtagttacc gccttctctg ggcctcagtt tccccaactg gaaattaaag
11821 aaaattaccc tgttcctgca tcagatggtt ggttgtggat atcactgaaa tctcctcacg
11881 tggtattgag ccgctgctct tggccagaca cagagcaatt tacatgaaat gatttttcgaa
11941 gtctggtccg ggaccagca gtgtcagcat cacttgggaa ctttgtcaga aatgcaaatt
12001 atcgggctcc accccaacta ctctagaccc aaaaacaatt tttattttta tttttattta
12061 cttttttagga tggagtcttg ctctgtcacc caggctggac tgcagtggtg caatctcagc
12121 tcactgaaac ctctgcctcc tgggttcaag cgattctcct gcctcagcct cctgaatagc
12181 tgggattaca ggcatgcacc acgacgccca gctaaattttt tttattttta gaagaggcag
12241 ggtttcacca tgttggccag gtggtctcgc actcctaacc tcaggtgatc cacctgtctc
12301 ggcctccaaa agtgctggga ttacaggcgt gagccacagc gccctgcccc aaggacaatt
12361 tttaaatgat ataattcata tcccataaaa ttaaccccttt aaagtgtgca gtgtggtggc
12421 ttttagtatt atccaccagg tcatacaacc tattatcact aattccagaa tattttcatt
12481 gctctcaaaa gaaaccttgt accatttagc agtgactccc cactcccctg tccctcagcc
12541 cctgcaatca caaacctact tttcatctct atggatttgc ctattctgga cacttcatat
12601 aaatggaatc atagaatatg tggtcttttc tttcacttag cataatgtct tcaaggttca
12661 tccatattgt aatatgtatt agtacatgtt gtactgatgg aacatgtatg ttgtagcatg
```

Figure 4 (continued)

```
12721 tttcacccttt ttaaaaaatc ttcttttttaa attaaaaaca tttttaaaat acattcaaag
12781 attttttttag agtcgtttta gtttcacagc aaaattggga ggcaggtatg gagatttccc
12841 tatgttccct gcccccacaa catacgcagc ctcccatcat taacatcccc caccagaatg
12901 gaacaatttt aacaaccgat gaactgacat tgacacatca ttatcactgc aaatccatag
12961 tttactttgg ggttcactgt taatgtagta cattctatgg gtttggacaa gcgtataatg
13021 acacgtatct gtcatgatgg tatcatacaa agtattttca ctgccataaa aatcctctgt
13081 gtgccaccta tttcttcctc ccatcccct aatccccggc aaccactgat cttctacca
13141 tctccacagt tttgccttt ccagaatgtc attctcttag tccatttct gctgctataa
13201 caaaatacca cagactgggt aatttataaa gaaagagac ttactaggct cgtggttggg
13261 gaaatccaag gttgagggt tgcatctggt gagggccttc ttgctgtgtc ataacacggc
13321 agagggcaag cgagctcacg gaacagagag aggaactcag actgaactca tctgtttatc
13381 aggagcccac tcctgcgata actaacccc tccctaata atggtattaa tccattcaag
13441 agagcagagc tctcatggcc taatcacctc tttttgttt gttttgttttt gttttcagac
13501 agggtctcac tctgttgctt aggctggagt gcagtggcac aaccatagct cattgcagcc
13561 ttgacctcgc aggctcaagt gatcctccta cctcaggctc caagtagtt gaaactatag
13621 gcatgtacca ccatgcttgg ctaattttga aatttttta gagatgaggg cttgctatgt
13681 ttcctaggct agtcttgaac tcctggactc aagtgatcct tctgcctcag cctcccaaag
13741 tgctgggatt acaggtgtga ggcattgcgc ctggccctaa tcacatccta aaggtcttgt
13801 ctctccacgc tgttacaatg gcaacgaaat ttcaacataa gttttggaaa agacattcaa
13861 gccatagcat tccacctctg gcccaccaaa actcttgtct tccttgcata caaaataaca
13921 ttcatcccat tccaatagcc ccaaagtttt aactcattcc agcaccgact caaaagactg
13981 aagtccagag tctcatctaa atcagatatg gatgagactc aaagcatgac tcatgctgtg
14041 gcaaattcct tccagttgtg agtctgcaaa atcaaaacaa gttatctact tccaaaatac
14101 aatagtggga caggcatagg atagatgttc ccattccgaa agggagcaac aggaaaggag
14161 aaaggagtaa caggccccaa agaagtgcaa aacccaaaag ggaaaacaag attaagtctt
14221 aaagctggag aacaatctcc tttgactcca cgaccagcca cctgggcaca ctgggcagcc
14281 ctgcctctac ggctttgcta ggctcagccc acacaatttt cacaggttgg gatctcatgc
14341 ctgcagcttt cccaggctgc catcactcac tggcagctca acagttctgt ggtctggaga
14401 gtggccccac ttccacggct gcagtaggca ttgccctagt gaggactctg tgcagtgcct
14461 ctgatcccac acttccactc ggcatttacc taatagggct ttctgtcatg gctttgcccc
14521 tgtggcaggt ttctgcctgg gccccctttt aaatctagtt gaaggtagcc atgcccccac
14581 agctcttgca ttctgtgagc ttgcagacct aacaccatgt ggatgctgct aaagtttaaa
14641 gcttgtacct cctggagcag caggttgagc tgcacctggg accacttaag ccacagccag
14701 ggaagtcaag aggtgctgca ctggaatgat gggggcagag tcctgagatg gctctgggca
14761 gtgagcctgt ggaggatgtc ccaggcatgt tccctgaaac cattctgctc tcctagagct
14821 ctgggcccgt aataagagaa acagcccgga agagctctga aatgtctttg gagtctttcc
14881 tccaaaggaa taacacctgg ctttcttcta tctagcctga tcttttaagt aaatggttgc
14941 ttggccacac ccttagtatt ctttttccgaa tgttattgct tttcactctt taggaggcca
15001 ggctgtgagt tttcctttgc ttctctttta attataaatt ctgtctttaa gtcattcctt
15061 tccttttgca tctcactgta tgtggttaaa aggagccatg cagcaacctg aatgctctgc
15121 tgcttagctg tttcttccat cagatatccc cgttcattgc tcttcagtcc tgcactctat
15181 aaagccctta gacataaaca cagttcagcc aaagtctttg ctactttgta acaaagatgg
15241 ccttttcctct tagtttccaa taccttgttc ctcatttctg tctgagacct cattagaatg
15301 gcctttactg ttcatatttc tacggacatt ctggtcatga ccacttaaat aatcttcaag
15361 aagatttagg ctgtccttag ttctagggcc ttcttttgag ccctcagcaa aattgctctt
15421 aatgctccat tcacaggaat ctaggctttt tctagcctgc tcctacaaac tcttccagct
15481 tctatccatt acccagttcc aaagcagctt ctacatgttc aagtatttgt catggcaaca
15541 gctcctcttc tgtgcaccaa ttttctgttg ctataacaca ataccacagg ctgggtaatt
15601 ttacgtatat atagaatata tatatagaat atatagaaaa aatatatatg tatgtatttt
15661 atataataat actgagcatt gactcatggt tctacaggct gggaagtcca aggttgagga
15721 actgcatctg gtgaggacct tcttgctgtg ccataacatg gcagaagggc caagagaaag
```

Figure 4 (continued)

```
15781 agaacagaaa tcaggctgaa ctcattcttt ttatcaggag cctacttcct agataactaa
15841 ccaactgtca caataacagc attaatccat tcatgagggc agagctctca taacctaatc
15901 acctttaaa  ggtcttgcct ctcaacagtt actatggcaa ctaaacttca acatcagttt
15961 tttgaggga  ctttcaaaca atagcagtca tatattggaa tcacacagta tgtagccttt
16021 tctgattggc ttctttcact tagtaatatg gatttaagtt tcctccattc ttttcatggc
16081 ttgatagctc atttctttt  agtgctgaat aatagttcat tgtctggatg taccacagtt
16141 aatccattta cctgctgaag gacatcctgg tttcttcttt tggcagcatg aaaaaagctg
16201 ctataaacat ctgtgtgcag attttttgtgt gaacataagt tttcaactct tttctgtaaa
16261 taccatggag tgtgattgct caatcatatg gtaaagtat  gtttagcttt atagaatgac
16321 aatttacctt tcaaagtgac tgtactatgt gctaagtggg tgtactattt tacatttacg
16381 tttacaacaa tgaaggaaag ttcctgttgc tccatatcct cctcagtgtt tggtgctgtt
16441 tgtattctgt attttggcca ttctaataga tatgtagtat cccgttattt tagttttcat
16501 tcccttgata acatgtgatg tagagtatct tttcttatgc ttatttgaca tctgtatatc
16561 ttttttggtg aggtgtctat taaggtacat ggcccatttt ttaattgggt tgttttttttt
16621 cttattgaga gctttaagag ttctttgtat attttggaca actgtctctt atcaaacatg
16681 tcttttgcaa atattttctc ccagtttgtt gcatgtctgg ttattccctt gacattggct
16741 ttcacaaaac agaagtttaa aaaattttt  taatgaattc cagctcattc attgtttatt
16801 tcagcaataa tgctttcggt gttatacctg acaagtcatc accataccta aggtcatcta
16861 gacttttttcc tatgttgtct tctcaagagt tttacagttt tgcattttta atttagattt
16921 atgaggtact ttgagttaac ttttgtggaa tgtataatgt ctgtgtctaa attcagtttt
16981 tttggtatat ggatgtccag ttattcatat tttttaaaag atggattttt gcatgatatt
17041 ttgaaaagac tgtctttgct ctattgcatt gtctttgctt ctttgtcaaa gattagttga
17101 ctacatttat gtgggcctat gttgggctct ctattctgtt tattaatcta cttgtttatt
17161 cttttgccaa taccacactg tcttgattag tatagcttta agtcttgaag attactatag
17221 ctttaagtct tgaagactac tatagctagt aagtcttgaa gtcaggtagt gtctgtcctc
17281 caactttgtt cttcctcagt attgtgttga ttattttgat cttttcctct tcatataaac
17341 tttagaatca ttttcaata  tccacaaaat aacatgctgg gattttgatt gggattgcac
17401 tgaatctata gatcaggttg gggaaaactt atatcatgac aattttgaat cttcctatct
17461 gtgaatatgg aatatctctt tatttattta gttcttcttt gattttgttc atcagagttt
17521 tgtagctttc ctcatataaa tcttatatat atttacttag atttatacct aagtactttc
17581 ttttattggg tgctaacgta aatggtattg tgttaaat   ttcaaatttc acttgcccat
17641 tgctggtata taggaaagtg acagacttgt acaacaacct tatatcctac aatcttacta
17701 taatcaccta ttagttccag agattttgt  gttgattat  ttggatttt  ctacatagat
17761 aatcatgtca tctacaaagg cagttttatt tcttccttcc caatcagtat aactttatt
17821 tcatttttctt gccttattga gttagcttgg acttccagta tgatgttgaa aaggagtggt
17881 gagaggaaac atccttgact tgttcctgat tttagtggga aagcttctag tttctcacca
17941 taagtatggt gtttgctgta agttttttgt agattttttc atcaaataga ggaagttctc
18001 ctcaattcct agtttactga gagttgttat atgaatgggt gttgaatttt gcgaaattat
18061 ttttcttcat ctattgatat aatcatgggg ttttctttt  ttagcttgtt catgtgatgg
18121 ttatattaat ttattttcaa atcttgaacc agccttatat acccaggata atctcactt
18181 gataatgagg tataattctt tttatacatg gttggatttg atttgctagt aatttgttga
18241 agattttgc  atctgtgttt atgagatata ttggtctgta gttttgtttt ttggtaatgt
18301 tttttttatct ggttttgtta gtgctggact cataggtgtga gttagaaagt atttgctctg
18361 cttctatcct ctgaaagtga ttgtagagaa ttggtataat ttcttcctta aatgtttggt
18421 tgaacttacc agtgaactct tctctgcctg gtgccttctg ttttggaagg ttattaacta
18481 ttgattcaat agatataggc ctattcagat tgtctatttc ttcttttatg agttttggca
18541 aattgtgtct ttcacagagt tggtccatt  cacccagatt atcaaatttc tgggcataga
18601 gttcatagta ttcctttctt atcctttcaa tgtccatagg atctgtagtg atgtcccttc
18661 tttaatttct gatattagta atttgtgttc cctctctttt tttcttagtc tgctataga
18721 cttattgatt taattgatct tttcaaagaa tcagcttttg atttcattga ttatttaatt
18781 ttcttttttc aatttcattg atttctgccc taattttac  tattcttttt ttcttctac
18841 ttactttggc cttcttttcc tagtctgtta aggtggaaac ttagattatt gatttagat
18901 ttttcttctt tcctaatata tgcatttgat gctataatct tccctcaaac cactgctttg
```

Figure 4 (continued)

```
18961 gcttatctta cacattttaa taagttgtgt tttaattttc atcaggtaaa aatattaaaa
19021 ttctttttga gatttcttct ttgacccatg tattatttag aagtgttttg tttaatctcc
19081 acatgttttg gaattttcta gttatctttc tgttattgat ttcttttaat tccattgttg
19141 tctgcgagca gaagttgtat gatttctact cctttaatt tgttaaggtg ggttttatgg
19201 cccaaaatgt ggtcaaattc tttctgtttt atggcccaat aatattccat tgtatagata
19261 tacaacattt tgtttatcta ctcatgagtt ggtggacatt ggggttgttt tcatttttg
19321 ttaattccat tgtacactga acatacaatt cagtggtatt ttgtatgctc acaatgttgt
19381 gcagccatca cctctatcta actccaaaac atttcatcaa ctcaaaggag atcttgaatc
19441 cattaagcag ccactcctca tgtccctgct ctcaacccct ggcaaccact aatctgcttt
19501 ctgtctccat gaatatagct attttggata cttcatttaa atggaatcat acaatatgtg
19561 atcttttgta tctgacttct tttacttttc ataatgtttt caatgttcat ccatgttgat
19621 agcattcctt tttagggctg aatactgttg tgttgcatgg atatactatg ttgtgtttat
19681 ccattcatct actgatggac gtttgagttg tttccacttt tgctgtgtga atagtgctgc
19741 tatgtatttg tactcattgt acacattgtg tacaaacatt tgttcgaata cctgttttca
19801 attcttttgg agaattattt tcaattctag gagcagaact gctgggttat atggtatcat
19861 tgtgaggaac tgccaagctg tttcccaaag tggctgaacc atttacatc cccaccagca
19921 acatatgaga gttctaattt ctccacattc tcaccagtgc ttgttttcct ttcctttcct
19981 ttcctttcct ttcctttcct ttcctttcct ttcctttcct ctctctctct ttctgtcttt
20041 taaattatag ccattctagt ggatatgaaa gagtatctca ttgtggtttt gatttggatt
20101 tttcaaatga ctaatgatgt tgagcatctt ttcatgtgct tcttggccat tgtatatctt
20161 ctttgaaaaa atgtctgttc aagcattttg accattttta aattgggtta ttttgtcttt
20221 ctgttgctga attgcaagag ttttttttat atgtcctgga ttctagatgc ttatcagata
20281 aatgatttac aaacattttc tcccattatt cattatttgc tgtcattcca ttttcctttt
20341 ttttttttt ctttcttaga cagggtctta ctctgtcacc caggctggag tgcagtggtg
20401 caatcttggc tcactgccac ctccacctcc ccagctcaag cagtcctccc acctcagcct
20461 ccccagtagc tgggactaca ggtgcacacc accatgctct gctaattttt atatttcttg
20521 tagagatgaa gtttcactat gctgcccagg ctggtctcga actcctgagc tcaagtgatc
20581 ctcctgcctc agcctctaaa agtgttggaa ttacaggcat gagccactgt gcccagcctc
20641 attttatttt cttgatagtg tctttttttt tttttgaga caaggtctca ctctgtcacc
20701 caggctggag tacagtgaca tgattatagc tcactgtaac cttgaactct gggctcaag
20761 caatcctcct gactcagcct ctcaagcagc tagtacaaca ggtgtgtgcc accacgtctg
20821 gctaactttt acatttttt gtagaggtgg agtcttgctg tgttgcccag gctggatctt
20881 gatagtgttt tgttttgttt ttttagatg gagtttcact tttgttgccc aggctgaagt
20941 gcaatgtgca attgcgcgat ctcggctcac agcaacctcc atctcccagg ttcaagtgat
21001 tcttctgcct cagcctccca gtagctgtg attacattta tgcaccacca cgcctagcta
21061 attttgcatt tttagtagag atggggtttc accatgttgg ccaggctagt caggtgatcc
21121 gcctgcctca gcctcccaaa gtgctaggat tataggcgtg agccactgtg cctgggtgcc
21181 tggccttgat agtgttttt gattaactat ctacttttat tttgatgaaa tccaagttac
21241 ccatctatgt atatactgag ctgaccctga gacatggcaa aatgtgtgaa gatggtactt
21301 gagtgagtga agtttgggca atgttgtttc tagtgaattc tttctccttg gtggtttcct
21361 ctggcctgtg gatatacttt attcagcaaa agatgccagg gctgagggga tatggcctct
21421 ggtctgccac ccagagggta aacttggcaa gaccccagcc aggctccccc tcctctgctg
21481 ttcctaaaca tgcattcatg gacaaggggt ctctggagca aaggagagtg actccttccc
21541 tctcccgcaa ccttgcccac ttaccttgta gccagccact ccctcctctt tctgtaactg
21601 ggcattggtc cagctgccag gcccaggacc tctcccattt agccagatgt agttccaaaa
21661 acaactgcag cagtatttgg atacattttc cagcctgaac tagtggtgtt cctgtccata
21721 gctggatcc aggtttgttg cctctgggtg gggctacagc tccttacctc ctggaaggtt
21781 gtggaagtgt ggtttccttt ttctcctttc tcttgtggaa cataagcatc tttccaagtc
21841 cttctggcca gatgatgatg gtgtgagcct gtccgtctcc catcagtgct gagggcctc
21901 agatgctgcc tcttacctat aacccagatg ctcccaggtg tgtttatttc ctagagctgc
21961 tgtgacacag agccacaaac tgggaggctc agaacaacag gcattgttcc ttgcacagtt
```

Figure 4 (continued)

```
22021 ctggaggctg gaagtccaaa atcaaggtgt tggcagggct ggttcctacg ggaggctctg
22081 aggaagaatc tgttccaggc gctctcctgg ctcctggtgg ttgctggcaa tccttggagc
22141 cccttgactt gtagatgcat cactccagtc tctgccttca tcttcacatg gcgttctccc
22201 tttccctctg tctctgtgtc ttcttctcct catcttattg tcatattgga ttaagggcct
22261 accctgcatc agtatggcct cgtcttagct aatttcatct gcagttaccc tatttccaaa
22321 ggtcacattc tcaggttcta agaagtacat gaattttgag caggataatg tatggcccag
22381 tgcaccaggc aatgccaagg gcatcactag gtaggaggct ggagatgact ccatttctgt
22441 gagctcctcc ttggctcctc tgtgtctttg cttctaacag cctgtgcctg ccactctctc
22501 tcgagggctc cccttgagct attagagggg ctttgtgtgc acaaaattca gacacacaca
22561 cacacacacg cacatgcaca tgcacacaca catgcacaca tgcacacaca cacacatata
22621 cacacacaca cagagccaga gtgcctggat attcgtgacc cctggagctg tcttaccatg
22681 gtgatgactg acaggtgggc agggcacggt ggctcacacc tgtaattcca gcactttggg
22741 aggccaaggc aggtggacca cctgaggtta ggagttcaag accagcctaa ccaacatggt
22801 gaaaccttgt ctctactaaa aatagaaaaa aattagttgg gcatggtggc gcatgactgt
22861 aacccagcta cttgggaggc tgaggcagga gaatcacttc aacctgggag gcggaggttg
22921 caatgaaccg agatcacgcc attgcactca agcttgggca acaagagtga aactccatct
22981 caaaaaaaaa aaaaaaaaaa aaaaaaagga atgactgaca ggtgcacatg cagaagcata
23041 gaagcccaga tccctggcct gcagttgggc acaaactctg aggtgtaact tatactccgg
23101 agcccccccac aggtcagttt caactggcct caccctccat gtctagctcc ccctactctg
23161 acactggctt gtcctgggag tacttcctta agaaatcact ttcatgtgaa ttctcttctc
23221 aaagtctgct tctgggcagc ccaagctgaa acagatcccc atacctggag cctgctgcag
23281 ccaggactga tatgcaggaa cccagcccag ggagccacaa agggatccac ctccccggat
23341 ccaggggttc atgattcatg ggcgatggtg ctctgtaaat gggaaggccc tctgtgaaca
23401 ctggggtgtt tgccacgcat tgtgctcaat tgtcccctct atgggcgggc cttccccaac
23461 cacaccatcc aagatattct aatcttgtcc tttcaggctg ctgatcaact agttcaggag
23521 tcactgtgga catgtcacac ttcttcctcc atgagatgga gatgaccaaa tctattcata
23581 gttctgtgtg ccaacctatg aaccagacct gagccccttta ccctctgac agtcggcttc
23641 aggaaatcgc catgaggcta caggtgtgtg ttgaggggtg ggtagagaca caacataagt
23701 gggtggcgtg gggtctggca cacttcttca tgtaacccac ttgtacctgc tggacctgcc
23761 agtctcaatc ccaaatatca ctgtagcatt tctcttttt ttatattatg acaaatactt
23821 atttattat ttatttattt atttatttat ttattttta attttatttt aagttccagg
23881 gtacatgtgc agaatgtgca ggtttgttac gtaggtaaat gtgtgccatg gtggcttgct
23941 gcacctatca acccatcatc taagcattaa gcccagcatg cattagctat ttatcctgat
24001 gctctccctc cccacgcacc tcctgaaagg ccccagtgtg tgttgttccc ccaccgtgtc
24061 cttgtgttct cattgttcag ctcccactta tgagtgaaaa cacgtggtgt ttggttttct
24121 gttcctgcat tagtttgctg agaataatgg ctcccagttc catccatgtc cctgcaaagg
24181 acataatatc gttccttttt atggttgtat agtattccat ggtgtatgtg taccacattt
24241 tctttatcca gtctatcatt gatgggtatt tggattgatt tcatgtcttt gctattgtga
24301 atagtgcatt gtagcatttc cattgtacag tgggttactg ctgtgcctgc ctcacattag
24361 gatttggtgg atctggtcat agccagctca cagagggaaa ctcagccagc atagttgctt
24421 gatgtctcat ggtcaggctc tgagtctctg tagggttcag tagcatgcca gcaattgttt
24481 ttcaaaagga gagtagttct ccactgcaga aaattttaga ggtctgtact gggactcttc
24541 tactggggtt tgttaaaggc tccacccaag ttctttatct agcaccataa atcttctcag
24601 tctcatggct agcagagcag ctcacactgc agcttggacc tatgcagcgt tctcttttgc
24661 tttgtctcag aactgaaagc tttctgaatt gcctaataaa taggtcagag tagcattccc
24721 aagtgtggta tatgctgctt tgaaattcaa ggagaacaaa gaaggtgggc ataaaacaac
24781 agaaggacag tttctcgcag ctggggagat cagaagtctg aaaccaagat gttggcaggg
24841 ctgacacggg caatacacga ggcccgtgta ttgcctcttc ctgcttctct tggctccaga
24901 cattccttgg cttgtggctg catcactcca atctgcgtct gtggtcacat ggcctcctcc
24961 tcttccctat gtgcctctgt tctgtatgtc tcttataagg acatttgcca ttacatttag
25021 gacctgcctg catcatccaa gattacctcc ccatcttgag atccttaact gaattacatc
```

Figure 4 (continued)

```
25081 tgcaaagatc tgttttccaa ataaggtaat atccccatag gttctggaaa ttaggacatg
25141 gacatatctt cgtggtgggg tgggggggtg cttttttcatc ctactgtatg gtagaggtgc
25201 aaatgcagca acttgtcttt ttttctgaga ggggatggct tggcatgcct cagatcacag
25261 gttccttaag atcttcatca atacggggga ccctgaattt tcagaggctt tatcttccac
25321 tctctggtgt gcatacattt ttgttttgtt ttgttttgag atggagtctc actctgtcac
25381 ccaggctgga gtgcagtggc acgatcttgg ctcactgaaa cctccaactc ctgggttcaa
25441 accattctcc tgcctcagcc tcccaagtag ctgggatgac aggtgcccgc caccatgcat
25501 ggctaatttt tgtattttta gtagagacag ggtttcacca tgttgaccag gctggcctcg
25561 aacgcctcac ctcaggtgat ccacccacct cagcctccca aagtgctggg attacaagcg
25621 taagccactg tgcccagcca tatattttat taaagcatct tgggttcttg ccattttttcc
25681 tccttaggtt tagagcagca ggagcatggg agcaactgtc cagtgaaggg ggtctgttga
25741 gaggctcacc cacagcatcc actgcagtgt ccttgatcat cttgacaccc cacgctacca
25801 cccaggtccg tcatgttaac attgtgtgag cattggctgc aaactgctca catctgcccc
25861 cttctctgga gaattgctct ctgccaaaca gtagacatct caccgtggag gttatgctcc
25921 tttggggggtg tggcaagtct tgccaactga cttacctgag gacacaaaaa gtctgctatc
25981 tggaggggac aagtcagtgc tgtaattaat gctccaaagg ccctcatgag accagaatga
26041 ggctggcctc cagcccaggg atgtcataga ttaactttct ttctctgctg tgtcctgctt
26101 ccctctttcc acttcccctg aaagtcctcc ccacaaaaat ccccacctct tgatctgctt
26161 ctagggaaac ctgacctaag agattccttg ggtgtattag tctattctca cgctgctaat
26221 aaaggcatac tcgagactgg gtaatttata aaggaaagag gtttaattga ctcacagttc
26281 ccatggcagg ggaggcctca caatcatggt agaagagcaa ggaatgtctt acatggtggc
26341 aggcaagaga ggatgagagc taagttaaag gggaaactcc ttataaaatc tcgtgagatt
26401 tattcaatat cacaagaaca gtatgaggga aaccacctcc atgattcaat tagctcccac
26461 tgggtccctc ccacaacgta tgggaattat gggagctaca attcaagatg agatttgggt
26521 gaggatacag ccaaaacata tcattccctc cctagcccct cccaaatctt atgtcatcac
26581 atttcaaaat caatcatgcc attccaacag tccctcaaag tcttaactca tttcagcatg
26641 aactcaaaag ttcacagtcc aaagtctcat ctgaaacaag gtaaatccct tctgcctatg
26701 cacctgtaaa atcaaaagca agttagttac ttcctggata aaatgggggt acagggattg
26761 ggtaaataca gctgttccaa atgggagaaa ttggccaaaa caagggact acaggcccca
26821 tgcaagtcca aaatccagtg gggcagtcaa atattaaagt tccaaaatga tctcctttga
26881 ctccatgtct cacatccagg tcacactgat gcaagaggtg ggttcccatg gtcttgggca
26941 gctctgcccc tgtggcttca tggggtagag cctccctcct ggctaatttc acaggctggc
27001 gttgagtatc tatggctttt ccagatgcac agtgcaacct gttggtgggt ctaccattct
27061 gaggtctgga ggatgatggc cctttctcac agctccacta ggcagcaccc cagtggggac
27121 tctatgtggg ggcttcaacc ccacatttct tttctgcact gccctagcag aggttctcca
27181 tgagggcctc accccctgcag caaacttctg cctagacatc cagttacatc ctctgaaatc
27241 taagcagagg ttcccaaacc tcaattcttg acttctgtgc acccacaggc acaataccac
27301 atggaagctg ccaaggcttg ggcttccac ctctgaagcc acagcctgag ctgtaccttg
27361 gcccctttta gatatgacta gagcaactgg gatgcagggc accaagtccc taggctgcac
27421 agagcagtgg ggctctggac cccagcccat gaagccattt tgtccttcta agcctctggg
27481 cctgtgatgg gaggggctgc cacaaagtct ctgttatgcc ctggagacat ttcccccatt
27541 gtcttggcga ttaacatttg gctcctcatt acttatgcaa atttctgcag caggcttgaa
27601 tttctcctca gaatatggat ttttcttatc tattgcatca tcaggctgca acttttccaa
27661 acttttatgc tctgcttccc cattaaacat aagttccaat tccaaaccat atctttgtga
27721 atgaataaaa ctgaatgctt taacagtac ccaagtcacc tcttgaacac tttgctgcct
27781 agaaatttct cccaccagat gccctaaatc atctctctca agttcaaaat gccaccagtc
27841 tcttttggtaa aacatagcaa cagtcacctt tgctcttcct ttgtcttctg ccatgactgt
27901 gaggcctccc cagccatgtg aacagagag tcaattaaat gataccatga tggaggatgg
27961 agtgagggag tcctgaggct ggaccatgaa ggtgctctgc tgtccctgcc atgtaaactg
28021 ctctagtgcc tctctgctgt tggatatcag gaagaaagga tttaccaaat tggtagctgc
28081 ataccaaatt ccagagacag tgttgatctg ctgtagtcaa gatgccacaa ctggtacagt
```

Figure 4 (continued)

```
28141 gggtgaaact ggactatgcc tggctatgtt tatgtagtcc acagtcagct cctctgagag
28201 accttccctg accatcttat ctaatgatgc cttccaactc ccagtcttcc tccatcatat
28261 tctcctgttt tattttttg tgtactgatt actgtctgta gccatgtgat ctatttattc
28321 gtttatggcc tttctcccca attagggtgt aggctccagg ggaataagga cattgtgtga
28381 cttgtttgca gctgcatccc aagcacccgc cactgtagta gatgcctaac caatgtgtgt
28441 tgaatgaata aaagagcagg ccaatgttct tttgctcaaa gtagagggga agaaataggg
28501 ttttctgtgg agattccaag gcagaggcca tttctggggg tcactggagt gggagaaggc
28561 aggtcaaggt gggttgtctt ccaggcagtg caaaccccct ggcctctgcc agctgctcac
28621 tggccagtct gcttgttggg tctggcacag gcctcaagga aacataacat ttttaataaa
28681 acctcagagt caataaaggc gaatggtcct gggtgcctct cctgccggcc ccagctgttg
28741 actttagaag tcaagagagt ggggcgttgc ccaattctca tgtagtacag ggagatataa
28801 gctggaaggg cctagcccat tttatatgaa acaaaacaa aacaaaacaa aactcaccag
28861 gccctggaaa gagtccacca ccagccagaa tcaaggtcc attcagagcg acagagctcc
28921 tcacattcgc cgctaatgaa aaccaaattt ctcatccctc tgagcatttc caggggctac
28981 aaatggaagg ggctgcagag tctttggcca ccgctcccac caccgaaggg gccccactgt
29041 gttaaaatag ttttatgata atataggcct tgtattttcc taatttcagg cgtcagtgat
29101 ttaggacgga gttgttttca tggaaaaaga aatagaacct gtttgtggcg gggcaagact
29161 gatgcctggg cagatattcc cactgtgggc atatttgggt agggggtga gcctgccatg
29221 aagaggctca gacctagctc cggggaggcc tcgttcatga agttcccgc cttgggcggg
29281 gaagaatggg ctgggggttt ccagacagat tcagagacag tcacagtgac ttctgttttt
29341 tgatttcatg ctttgtgaaa tcttagaatc acaactcaga aaggtagagg catccctctc
29401 agacgcagag aaagggcctc tgttttttta aaaagacatt ttctcatttc ttttctttt
29461 tttcctcccc cttgatcaat ctttataagc aagtatgtgt agaaatgtca tattttttt
29521 ttcttaaagt caacttgatt cttactttga gcctccaata cttttagttg gtaggaaact
29581 taatattttc agcgactgct ctgccttcgt caggatcagg tggaattctg tccttgtttc
29641 tcagttttgt tttgttttgt tttcagatgg aatctcactc tgttgtccag gctggagtgc
29701 agtggcacaa actcagctca ctgcaacctc tgcctcctgg attcaagtga ttctcctgcc
29761 tcagcctctt gagtagctgg gattacaggc atgtgccacc atgcctggct aattttgta
29821 tttttagtag agatggggtt tcactatgtt ggccaggctg gtctcgaact cctgacctca
29881 ggtgatcctc ctgcctcagc ctcccaaagt gctgggatta caggcaggag ctaccgcacc
29941 caacctgttt ctcagttttt tttcatctgt aagatgggga gaatgataat acatacctca
30001 atgggctggg ttaaaaaatg gtgaaatatt tagaatagtg cctggcacag agtaagtatt
30061 aactattatt attattattt ttattattcc agagataaag agaaggcatc aaacctagta
30121 tgagggtatc agggaaggct acctggaaga ggtggtgttt cagctaatga cagatgaggt
30181 agtccttgca tgattttgaa ctcctctgct tggacattta tgtctagaat tgatatgct
30241 ataccctgaa caagtgtgct aatttttagaa aactgtaaag aagaaaacag aaaacagcca
30301 taatcccatc tttgcattga tttcattctg gattaatttt atctctattt ttaactatat
30361 taattgataa cctgtatacg cagtgtgtgt ctggctagaa aaatgtttat ttctaaaaag
30421 tatttatata tttataggaa ataaagatct gaatggggga gaaaagccta aaaatattaa
30481 cagtggttat ctttggaggg ggggattatg gctcattttt ctcgtgtgtt tgttggtaat
30541 ccggactgtc tactttccct ctcatgatta tatattagtt tgtgtcattt aaaaatgtca
30601 tttagtctgg gcatggtggc tcatcctgta atcccgacac tttgggaggc caaggtggaa
30661 ggtttgcttg aggccaagag tttgaggcca gcctgggaaa cgtaacgagg ccctgcctct
30721 aaaaaaaaaa ttagccaggt gtggtggtgc acacctgtag ttctagctcc ttgagaggcc
30781 aaggcaggag ggaggatcac ttgagcccag gagttggagg ctgcaatgca ctccagtctg
30841 ggtgacagag tgagaccctg tctaaaaata aaactaaaa atattactta aaatgtaata
30901 tatagaactc aggaaccgca gatggagagt ctcataatct ttatattttc agaccatgaa
30961 ggagagtggg gtagcttggc cggactctga gcgtcctgga cccacaagtc tgagaggaga
31021 ggctgcatgt ggcctctggt atggtcacat ggttctataa ggaaactgag gcaggacata
31081 aggcttcact tgtgaagtgg tggagaggga ggggcaatt gccaactggg tgataataaa
31141 gactattgtt aagaccttgc ccccagtggc acatgaaatg ccactaaccc tgagagattg
```

Figure 4 (continued)

```
31201 agagacattc aaacctgagg tttggggcat ggtgcccttc ctgtgacttt ggtgctaatg
31261 atgtctaaga tacctcttag ctcctccctc tgtcattctg cacaggcttc tcctttgcct
31321 ggactatttt agtagcctgt gaacaggtct ctggaccctc atccccagtc cgcaccatga
31381 tggtgctccc atccaacaca tacatctccg cttggctccc ccgtgccact gacccctgac
31441 atggatcctc tcccacctcc catcaccatt gcgccacttg ccccaccatc ctcccagctc
31501 agcgacacct ggttctccag gcctttgcac atgggattcc ctcctgccac atctctgctt
31561 gatccattcc tactcatctt tccatctgat ctcggggggag agacattttc tctgaggagc
31621 ttggcttgtt tgccctgatc cacactgggc tggcacaacc tgctttcctg tctgtctgcc
31681 ctgtgagatc cctgaggcca tggctgtgac ttgttcacct tgttcttggt gtctggcacc
31741 tgagggtggg gtggggctct gtgtctggtg aatgagtgaa tgaattctgg ccaaggcctc
31801 aaagacaccc agcccaatga gctgagtggg gtggtgtggc ccaaatggtg tgtttggaca
31861 ccagagagcc cacattgctg ccagccgtca gggtgggcac aaaggagggg agtccaggcc
31921 ggctccaggg ctgccgcact cccccttccca tgataggtcc cctgggccag gcccagggca
31981 ggccctttct gtgggtgaat ataaatatat aaaacacaca gcgcactctt agctgcaaaa
32041 ctaaaaatag gaagcgcggg atccggctcc ccaggcttcc ccagccactg daccacacag
32101 gtgtggctgc ggatgtcggg gcgatgtggc ccctcacccc tcccagctct ggagccctca
32161 tggggaggaa tgagggcat tttggatttc tgccaggaac agttcattct ttcactctgg
32221 cctccctcct gccccgtcc catttgacag ctcatttcat ttacgacccc aaaatgaacc
32281 gacccactga ggtgtattct ctactcacgt ggccaggctg ggttgtttgg tgcagctgag
32341 agctgccctc tgggccatgc tgggggggctg catttatgcg ggggtgcagt ctggagcaga
32401 ggagaggccg gggctgagga gggaggcagg gctgggtctg catccagccc tgccctcccc
32461 tacccacggc actggcccca ccccgcgcca tctcctcaag ccctcaccag gccctaacgt
32521 gggaatgtgt catctctggc ctgtagcctc actgccagga catccattgc tcagtgtaaa
32581 agccaaagcc atccccatgg ccacagccca acagtggcag ggctgctcct aggggccggc
32641 aaggcgggtc catctgggcc acttcacccc acaggaggcc acttctggga gccccaggc
32701 cacagccggc tctctgggtc catcattggg cccatctggg ccaacctcaa gctgtggggg
32761 ctgaagaaac tggagggact caaagtccag cccagatcaa caggactcct agagcctcca
32821 aagcggaatt ctggagtcca ggggctccca ggctgtggaa ctaaatggct tcctcaatct
32881 gaactggctt ctacatgacc taagctcttg ctggtggctc aggggacatg ggtggggctg
32941 ggcccagggt ccaggaggcc agggttgtaa aactatgaaa gtcaaccctg ccttcaagcc
33001 aggtacaccc tgtcccaaag cagacgatta tggggtgtgg ggtcctactc cacacctggc
33061 acacggccgg tgctcattca gcgtatgacc aaaaagggag actcagagag ggacagggac
33121 ctcccactgc cacacggctc gggaagggaa aaccttcccc acatcaagac ctttagctgg
33181 ccctttcggg aatgagtcac ctgaggttgg gaagttcttc ttaataccttt acctgaattc
33241 ttgctgtaac caaggcagcc tctcctcacc cttgtccaaa ggggatgatg tccactctct
33301 ccacctgctg cccagggatg ccgcccccta ttgccacctg caggctgctg tggctactgc
33361 agcacttcct cccgcagccc tgggacctca ggcaagctga gacttctcgg gaccttgagt
33421 ttccccttgg caagctgggt gtgctggttc gtgcctgcta gggtgcaggt gatggagatt
33481 tgagtcagga actctggagg gcacagctcc tctccgatct gctgtggcac caaagtgtgc
33541 ctggtgagga gtgctaccat ccctacaaa gtgaccccaa ataatagaa acagttttgg
33601 ccatgtagat gccgtttcag gaccaaccct ggcagaggct gcccagagca gaccaacaga
33661 gaagttctgt agccacggct gaggtcctgt ccagagatgg acctgctgtc ttttgggtaa
33721 aaggggatgc cgggctaggg aaatggaagc ttcttgttgg gagctgagtt tcaggcagac
33781 caaccaaact gagcagggca aagctttggg agtggttttt gaagtcggtg ggcatcactc
33841 aaaaataagg tctgtttttgt aaaaatttcc cttcacaaat cccaactggc caggctctgg
33901 gctgtgtgtt ggtacaaatc ccaagtggac caggcctcct tgctggcaag gtgggagggg
33961 ggctgtcaag ccaggtcccc acaccatcac acccatgcta ccattgttgg gctgtggtcc
34021 cagttcagcc atggacaacc ccagggagac atggaccttg atgacactcc ttctttgcac
34081 cgcagttgtc tcatctgcaa aatgggggca ctgaagttgc cgcttactcc caatccccac
34141 tgctgctagc ttgccacaga tcttgaaaca cgagcctcag aggggggttc tcaccaaggc
34201 acttggactc tccctctgcc tctgccccct cccgaaatgt gaatctgagg aacaggcata
```

Figure 4 (continued)

```
34261 ggaattcctc ccaacacggc tgggaagact cacagcccgc tcatgattgg tggaagggtt
34321 gtggcacttt gaagacctat ttgatgctct cctggggtcc cagccataca ggagcaggcc
34381 tcaccggctg tcctgtggcc agggtggtct ctgcggccat tcctgaagaa gttggaagca
34441 aggagatgaa ggtgctgggt gtctctgttc ctgttcctcc tgggcaacag caggaggtct
34501 ccatcctctc ccccacccca ccccacctcc atgcatagcc ctagaaaccg ggcactggac
34561 tccttccaca catctcagag ttatattatt gtaacaaatc agtcaaaatt ccattttaca
34621 gttaaatagt acagaagaca gtttactgta caagcaagtt gtgcgttaaa aacaaacacc
34681 aagcaaacga tagtgcaaag cagtttccac ccagctccat cctctcgcca gctctggat
34741 ggttttacat cagatgagtg cagcaggtgt cacacctcag catgacaata tgtcacaaaa
34801 gattggtacc cactactgac aggctcacag taacactata tcaaaacgtc ttcctttcct
34861 cgtgcttcct acatcagtgt gtttgcctag tacaacttta acgcagcctt gtaaataagg
34921 acctactttt accagcccag gctgtctgta cccactttgg gccttacaga ctcagtacgg
34981 ctgccgtcac tttttgtcag gggatggggg atggggtagg aagagcaatt tatttactat
35041 ccctgcctct ccaggatcag gaagggttag taatctggga tgagactaca aagtgctggg
35101 cactgggaac ccaaaggtgc ctcccacgct gacctgggac cagctataac cagagaacag
35161 gagggaagaa actacaagga caatggattc atagctgctt cctaagaagg catggagagg
35221 cccttgggt gcaggagtc agcaactatt ttgaggagat ggagactgtt tttccagtga
35281 ggacaggcca agagaaaccg cagcaggagg gaatggaata ggatcaccag aaggactgcc
35341 taacctgcca gtgtgtctct ggtgtatggt tctggccgtt gtgacaggtt gggtggggac
35401 agtgctctca cagagacaac caatgaagag catttgtag ggcagatttc tgcatccaca
35461 gaggccgagg cagaaagtta aaataccgca tgctgctagc ctttatgagt tcccttacgc
35521 cttttctaag cctttctagg gccagagaac tctgatgtga aatccatgc agcctggccc
35581 ttgggcaagc gcccactttc ccattttgca aaattcaggg gcaagacttc acctcggaac
35641 gcagtgcagc tgagctgcgg ctggagagcc ctttacagtg cttctgtcct gccacgcaca
35701 gccagtactc cccacctctc acatcctgcc cacctccgcc cagcctcctg gacagatgtc
35761 ctagagccac agaggagaga tgcccagcgt ctcatcagcg tttccctcgt cctcccaggg
35821 gagcctgtgg tgcaggctgg tgggatgctg cctgatgggg agtgtagccc cttgagaaag
35881 tattgagacc ctaataaccc cacaccctca ggaggcagct gggggtccgc ggggggggaga
35941 ggggcgggg atgttgctta taatcacaga gctatcataa tcacggaact atacctgtaa
36001 gagaccttgt gtttgaaaac gttagattaa gcttcttttt ctaaaatcag ttttaaaaac
36061 tgttttgttt tttttttgtt ttttgtttt ttttttttt ttgctcagga ctatttgctt
36121 tcagagcaca aaacaggtta cagacaggtg tgtgccagga gtcgcaagat ttggctggat
36181 cctcccagga ggcttggggg atggggcaca gcttggctgg acccaggggg gacagggaca
36241 ttgatgtctg acccaaaatg atccctcacc tcaatgcctt ctgctaggac ctatctatct
36301 ggccctcctg ttctctccac aaatggaatt atgagaccac ctaggggaaa ggggacctcc
36361 tatccccct ccccgccct gccaagagaa cagagagtgg atgcgttgag ctggtaaagt
36421 gcatggagga gccggtctgt aggtgctttc ctgggtttaa gaacctgatg ccatagactc
36481 atcttctctg ggcctgggga cccgtgcggc tggggggaaag ccaacagtta ggaacggagg
36541 ggaagctggg ctgggggggac tggcttggat gtgttctcaa accatctctg ccagcagcgt
36601 gctgggtcct gccccatctg tacaatgagg ggaaccccgc tcgagggtgg tggggtggg
36661 ggacactttc cagttctgac tcaaatctgt gtaaatgcag aggggggctgg acccagggga
36721 tgcagggct ccaacgaagg tgcagggtc gggaggtttc ccaggcctg aggcttatcc
36781 tgtgggccaa tgctgcctct ctctggaaga gagatggcct ctgtcccagg agacatgggt
36841 cccatgcagc actgggcata gctggagaca gtgaggtcct tccgggggg tggcaggagg
36901 ctgattcccc acagaagtat gggatgagac ggccaggatc tgggccgggg gcagtatccc
36961 gggccggggt ggggtggta acctatgcct ctgtacaagg atgtggctgc acagatgcag
37021 ccagaggctc ccaccagctg ggaccaccct gggaccgaga ccaccctgga gcgcaggtcc
37081 cattcccgcc cggagcctcg gagccggccc atcactggtc ttgaaggttg ttagggtccc
37141 cgcctccagc gggaggagtc caccagggcg gtcagtaggg ccgccacacg gcctcatcca
37201 tgcggcctgg cgtgctcagg gccgtgggtg agttgctgtg gctgccgtcg gcctccacgc
37261 catcactctg gccgcccagg ctggggttca tgaggttgcc ggcggcgaca gaggcagcgc
```

Figure 4 (continued)

```
37321 tgctggtgca agaggccagc atgcgggtag gtgagcggtc gcccccactg ctgctgccgg
37381 ccaccatgga gaactggtag gagccagagg atgtcccgta gtagaggtgg taggggacg
37441 ggttggcctg aagggcccg ctctggttct gcggggcccc cgggtagggt ggcgggaggt
37501 aggtatggtg gaagcggctg gtggccggca tgcccgccac gctgaggctg ctgatgctcg
37561 tgcccgaggg cgtggcgctg taggggaagg cagctgacat ggccccggga taatgcatcc
37621 tggggtctgg gaagcggctc tccgtgaggg ttggcagcgt ggggaaggag cggtcaaact
37681 ggcggggtc ggagaatggg ttcagttccg aggtgcctgg aggacagcag ggaagaggtc
37741 agttccagct cgagacaacc ccaggagggc ttcctgaaga atgaccttgg gctctggttc
37801 ccaaggccca tctgggggac ccctagttct agacctggct ctcctcttcc tgccctaggc
37861 tgcccggggc ctcccccgcc aggactccga acacagacct gccgggaagc tggttggagc
37921 gtgccccggg ccaagagggg ccatgggagc cccccacag cagcaacaga acagaggagg
37981 gggtctattc ttcttttaa atcctccttc ccagcctcgc agaggagagg cctaggatgc
38041 ggtggtgggg ctgagggcag agtcagctca ggcctcccag cagccctgcc caggcaggtt
38101 cctctcccca ccggcccatg ttaacagctg ggaaggccgt ggatgtgtaa agggctccaa
38161 tgaccgtgtg agactgggag ttggaacccg cttttgaaga caagaaaatg gaggcagaga
38221 gagagcaaga ctgagtctct gtggcagaga aaggactggt tctcatcaca aggcctctgc
38281 tggggacaca cgtgcctctc ctgcccaggt gcagcacgcg gaggttctgt gcgctcacac
38341 ctggggttgtg ggcactgagt tcacaggagc tctggcctcc acctcaccct gggcctgtgt
38401 ctctggagcc gactcgtggc cacacagtga ctggatgcca ccctaacctg ccttggcagc
38461 aaagtgagac agcagtcaga caaacttggg gacccagacc ccaacctggt cacagtgtcc
38521 agcccagact ctgccctgc tccccagga atgtggcttc tcaatgggct ccaaggcaag
38581 ggtgttccat cctctgtccc caacttttgt catcacagac ccccaaaacc tcagcattca
38641 aagggctca gggattgagt ctaacaccct tgatggggaa actgaggccc agacagggtg
38701 aggcacttcc ctcagggtca cagcacat tggacctggc acacaatcct agggcctctg
38761 gtcctgagcc ccaacacgta cttgagaggg agctgtcccg tctttgaggc agcacaggat
38821 caaggcttac tgtgtggctt ctggagccgg acagttatcc tggtttggac acttactagc
38881 tttgtgtcct tgggcaagtc acttaacctc tctgcgcatc agtttcccca tataaaacat
38941 gagacgataa cagttcatca ggattcagtt aattcacatc gagtacttag aatggcactg
39001 ggcacagagc aggggtccat gaggctttgc aaggccactg tggctgtggt gtctcttact
39061 ctgggtaccc aggagaactg gctcattcag ggccctgcca agttgaggcc ctggtgcagg
39121 gcctcccttc tactctggca gccgggggag gtggatgagc ccccagcagt ggtccagagg
39181 tgcagtctgt ccagcccagc aacccctctg tgtcacccac caaaggataa gggccggtgc
39241 tagccggagt gggctctgcc tgccacgccg aggcttggct gaggacggag agctatgagc
39301 ctgaggtgtg tgtgacttcg gctgggactt ggaacttctc ggggctttgg ggtcttccca
39361 agtcagctgg ggtatgtttc cctcagcagc gtactctggc cctgggcgtg gatccgaacg
39421 gagtgatgct cctggcttaa ggtaagaaga tgtggggaca gcagtctggg tggcgggggc
39481 cttctgggac atctgggatg ttccctagta ggtcacttgg ctgtcccggc cccttgaggc
39541 cgagagcctc cgaggcacct ggctgccagt tttcatctgg ggagcccctc ggggggagag
39601 gtcctgttgc aggtgctggg cacgtcagca cagctgagat gggtggggtg gaagtgggtg
39661 ctggccgcct gatgggaacc ccattctcaa gacgaaggaa acaaatgggg accgcaggat
39721 acaacggcag gactgtgccc ctcagagctc acgcgggctg cagggcgctg ggctgggcct
39781 ccctggacct gccaccatcc cctccagcct cttcctcag gccaccacc cctcctccgg
39841 ggtggtgggg gaagtacctg ccctcagcac tccctcagac ccccagcag cttccttgga
39901 gctcctgtac ccccaccctg cggcctcgca gccccaggaa acccgagctg cccggggcac
39961 tgtcgagtgg ccaatcccaa cagtggaaag aaatgtttat ttcttctcc agattgtccg
40021 ggctgctgca tggtggctga atgagccctt tcagctgtga gaagccccca ttgtgggcgg
40081 ctgcggctgg gggctggggc tggggtatgg gaggtgctgg ggtctctgca ctgcttgcca
40141 gtgaccaata ttggagggtc aaagcactta acaggcaccg agggaagtgg tggtggggtg
40201 tcccaagggg gatccccagg agggagtccg agggcagagg gaggagggcc tgtgagagtg
40261 acttcccaag cctaggtctg ccagcaaccc ctctttgtca gggacctcct tctccccact
40321 tcacagatga gaaaactgag gctgagttta agtgacttgt ctaagatcat acagccaatg
40381 cctggcagag cctgaattcc tagcctggtc cagctgactg cagagttcat gctcgccctg
```

Figure 4 (continued)

```
40441 tcctggtcat ccgaggccct ttctctcacc caaaggggat gggcctgagg atggagatgc
40501 ctggctgcct gtggcccagt gctgtggggg gctagcgagg gactgggcca ggcctcagga
40561 gggagcaggc agagaagcag aagtcagcca ctgccccaca caggctgggc tcctttcctc
40621 ccagcccagg atggaagcag cagctgtgcc tgccgtgggg ccaggcattg attcccaagc
40681 tgtgcccacc cagcagtgga tgggcagatg tgggctctcc ttccatgggg gctggtggac
40741 aggaagccac tgttcacccc acctcctgga ttctggctcc cccgctgagc cccgatcccc
40801 tggcctggct ctgtccatgg cagagaaagg ctggctctca ggctactgca cctcgacaga
40861 tgctggccca tgggtagcag aagcagaggc agctacgcgg caggggtggg cgtgagcaca
40921 gcgtgcaggg ctccttccgc tacctcttga gagcagacct ccaactcctg ggctcgagag
40981 ctgagagtct caaatgcact agctcctggg ctcagagagg ctgggcctgg ggcttctccc
41041 aaccttggcg tctcagcagg accaaggcca aaagtcctga gcccaggcca gaaggggagg
41101 ggtcctctct tcacactgaa ggcctgcatc cagcccctgg ctgcagcact atgcctggaa
41161 caatgtcagt agagagaccc agtcggcccc cacctcagcg tggcaccgga aaaggggtg
41221 gggcaggcag accggttggc agccctgttc caggccccctt tatctgtccc ctcagaagta
41281 cagaaagttc ttgggagcag gtactgtgga gactgtggac ctggtcacag atgggctgtg
41341 tgacccgagg gtggctctga acctcttagg cctctcaatt cattcatctg ccaagggtt
41401 ctaaccaggc tctggggaat tgagaaagaa tgggcacagt ccgtgacggc agccagctgc
41461 ctgcctctgt ccaccccggcc accaagcacc cttggcaccc cacttagccc aagggccggc
41521 tgtgcacaca gcctcccatg tccccagctc actgactgag agaacagagg agagatgcag
41581 ccggcagccg tttagtgagc ggctactatg cgccaggcac ctcgatactc cagaagacct
41641 gcctgaggcc tggctgcaac tgtgcttgct gtatccgtct aggcagtgga gatggagacc
41701 ccagctcggt cttcccttcc acctcagctc ctcctgtttg ggaggatgct ctgggcaggg
41761 tgggagacct ttcccaggaa tgctatgtgc ctctctaggg ttggaatgtc acttaacagt
41821 gtgcaaagtt tgtgtgagta cagtaatgtc atttgaatgt catcccagcc ctgggtggag
41881 gcatccgccc caatccactt tcagatgaaa aatcgcaggc tgtggggcag gggtggggaa
41941 actgtacatg gcaggggcga gtctgtcacg gctccttgga caagtcatgc cccaatttta
42001 ataggggcac tatggggtta accccatttc cccaggcaca gtgaactcct ggtatgcaga
42061 tccctggggc caggcaccag gcatgtgtca gtaatgtcag tgtttgctga gtgaacgaat
42121 gatggctagc acacagaaag cccacaggaa ccgtctgcag gtgccaatga gcaccagcag
42181 ctcctctaca aacaagggg gtgcagtgac tgatcttcgg acaggctttt ggtctggggc
42241 agattggacc acatcgaggc cctccacccc cacctcaccc cgctgcagcc cctccctccg
42301 tgccgtacct tggattgggg tctggggctg gctgctgaag tggcttgtgg tgctgagtga
42361 gcctcggggg ctgggtgtgc tcggtgtcac ccgcatgcgc agccgttcca ggtccccaaa
42421 gcggtcaggg aacggcttgg tctggtcctc cagcttctgc cggtgccctg cagagcacag
42481 gaagcccatc agccgttgct tccccagagt ctcagtggag acagaaatgc ctcactctgc
42541 tgggaagttc ttcctgaggt ctgaccttag gcctctgctg ggagaaccct gaggtcaccg
42601 ccagcctctt cacagaggtt ttcaaaagac tttctgaaca gagaatggtc gttatgtgcc
42661 accccacata tctaaacctc tacaacacac ggtgatccaa acctctacaa cacgcggtga
42721 tctaaacctc tacaacacgc ggtgatctaa acctctacaa cacgcggtga tctaaacctc
42781 tacaacacac tgtgatgtaa acctctacaa cacgcggtga tctaaacctc tacaacacac
42841 ggtgatccaa acctctacaa cacggtga tctaaacctc tacaacacac ggtgatctaa
42901 acctctacaa cacactgtga tgtaaacctc tacaacacgc ggtgatctaa acctctacaa
42961 cacactgtga tgtaaacctc tacaacacgc ggtgatctaa acctcaacca cacgcggtga
43021 tctaaacctc tacaacacgc ggtgatctaa acctctacaa cacgcggtga tccgaacctc
43081 aaccacacgc ggtgatccga acctctacga cacggtga tccgaacctc tacgacacgc
43141 ggtgatccga acctctacga cacgcggtga tccaaacctc tatgacacgc ggtgatccga
43201 acctctacga cacgcggtga tccgaagctc tacgacacgc ggtgatccga acctctacga
43261 cacgcggtga tctgaacctc tatgacacgc ggtgatctga acctctacga cacgcggtga
43321 tccaaacctc tacgacatgt ggtgatccaa acctctacga cacggtga tccaaacctc
43381 tacaacacac tgtttggcag aagaggaaac tgagggccag gtgcagtggc ttacgcctat
43441 aatctcagca ctttgggaga ctgagatggg aggatcagtt gaacccagga gtttgagatc
```

Figure 4 (continued)

```
43501 agcctgggca actatcgaga cccctgtctg tacaaaaatt aaaaaaaaaa aagaaaaaag
43561 aaaaacttag ccaggtgggg tggcacaagc ctgtagtccc agctactggg atgactgagg
43621 caggaggatc acttgagccc aggaggtgga ggctgcagtg agctgattgt accactgcat
43681 cccagtctgg gcaacggaac aaggaccta gatctaaaaa aaggaaactg aggcaacaga
43741 catgagaaag tggctcatgc ccccaaggga ggcagggaga taacccagga gcactgccac
43801 cctctgcctc ccagcatccc agcctgcctt gcacactgtc tcccatgtct acaagaacaa
43861 tgggaggtgg ccccaggagg ggactgcagg cttttccagc cctaagtcac tctgggatcc
43921 ccagaacatg ccttcttctc tctgggcctc aggcagaaaa ataactccac caggatgctg
43981 ggcagaggtg tagggggctt gcatgaggga ctagacagcc atctctgcct ggaagctggg
44041 gtcagggac gagatgtcac acctggagaa aactgccagc attttccact ccctatctgc
44101 cagagcccac acaggaagaa tcccagcctc acatccgagg actcagaggt gctgggaggg
44161 tcaaggtggc caggctccca ccctcctgcg gcctgctgag gccgagggac acttctggag
44221 tgatatcaag cttgcaggga cctcccccgc cacacacact tttttaatta ctaattttac
44281 atttcacaag caacacgtga atatttacaa aaataaaagc attacagata aggctctgtc
44341 caccgctcta agctcctctc cagagtcccc accgtgacca gtttctttcc agacattttt
44401 catcttccat gaatggaaaa cgcaaagtag gcttctcatg gaactctctt gaacagcctc
44461 agtccgggtg tgtcattctg taacttgctt tcttagtagc acaccttgga gctcaaactc
44521 agtttcccta tctgcaaaat ggggacagta atccagcccc acagaaatga cggagttccc
44581 ataaaacct ggggatcctc cctgctacgg aagggattca acaagcatgg cgagaatgac
44641 gctgctctcc ctcttttcctg ctggccactg gaggcacagt tcactccgca gtcctctcca
44701 cccacatttc agtccttctc aagcttcccc tttagttccc ttacatgcaa cactcccggg
44761 aacgtccctg ttcgcacccc ctagtggctg cagcttctcc agggctgacc cgaggaaagg
44821 acggctccct tggaggactg tgcactccag ggttcggctg atcaaccta cacggtcac
44881 ggccattcta cctcacgtga cttggtggga ggctgccagt caggcagggt ggccaggccc
44941 tcttttacaa gtaagagaac tgcaactgcg gagaggcgag gaagcttgtt ggaggccaca
45001 cgccgaacaa ggggtgggat ttcctggacc tgggacccctt tagaaaagat ggaggctagg
45061 catggtggct acgcctgtaa tcccagcgct ttgggaagcc gaggcgggcg gatcacctga
45121 gtgaggtcag gagtttgaaa ccagcctgac caatatggtg aaaccccgtc tctactaaaa
45181 gtacaaaaat tagccggggcg tggtggcggg cgcctatgat cccaactact tgggaggctg
45241 aggcaggaga atcgcttgaa cccgggaggc ggaggttgca gtgagccaag atcacaccac
45301 tgcactccag cctaggtgac agagcaagat tccatctcaa aaaaaaaaaa aaaaaaaat
45361 gtgggagggg gtaagggga ggagaaggtt tgcctaaggc cttgggtcta gaatgacatg
45421 tgcgttttct agtttggcag agggagaaga ggcaagatgt aggtgggagg taaaacagaa
45481 ctcactgcgc ttcttggggc ctgaacaagt gattgctggg gactcgaaaa gtgggaaaag
45541 cctgtcgacc actgtagggc atgaggggac agagcccgag gcctcgcatg ggcctgattt
45601 ctgattttca gaatgggaac gcaatggatt ctggtacttg taggccccca agctccctac
45661 gcatccctgt tggaagctca acaggtatc tgggagcctc agaaagaaag caggggggcct
45721 gggagccaca ggggctcagc cagtcaccaa gaaccaggga gccccacctt ctcctccaat
45781 gaggccccag accaggaatc catgggacac ttggtggcag gaataagacc atttggtctc
45841 tggccaggcc cccactgctg cctcccaggg cccttggcaa caaggggaa aacatgggct
45901 ggggggcgagt ttagctggag ctggggctgc aaactcagat gcccatgggg atggggcaag
45961 tcacgtgaac gaggcaagtg ggatggtgg ggcctggagc ggatggggag gagatgcctt
46021 gtggaaagca cctgactgct accctgagga gggcaggccc agtacggcca gagcttccaa
46081 ttccagaccg agtcctcagc cctaacaggc cttggaggaa atgttgtcct tgctcctgag
46141 gccactggaa atggcaggga gatgtggatg agctggggga caagtgagca gaagaatctt
46201 aacaggcatg aagcctgccg ggtggacgtg gggaccacag actgatccga caacagcctg
46261 agtgcaaagg atctgggtgt tttagtcagc cacaagcttg aagggagcca ataggctgg
46321 tgcaaaacct caggccttgt tactttcgtc acaggagaat aaagtcccct gtttctgagt
46381 cacaccatgt acaaagagtg tttacagtta ctcctgcggc ctggcggaag agggcggggt
46441 tgacagccag cctgggttcg aggacgggtc ctgtcacttg cagtctggtg gcctcactca
```

Figure 4 (continued)

```
46501 agtcacactc ctttccccca ccccgagctg cggtgtcccc atcacactgt ctttgtgggt
46561 tgaggtgctg gcctaaggtg tggacacttt ccagtcacgt gggtcaccac catcatgacc
46621 atcgctttta tctctgctca tgcccaaagg aagcagaact atcatcccca tgctggagac
46681 cggggtgtgg aggccaggat gctgaagtcg tgtgaggaac acagagcctg agcagcaagg
46741 caggattcac acccggatcc cccgactcca agcccagggc tcttttcctg acactttccc
46801 ttttgttccc attgtttaga cggggccacc gaggcttcac catgagaccg acgctgagcg
46861 cctgttccgg gacccaggct gtgggtcagg taatctgacc ccggaaccca cgctcccacc
46921 acatgctccc ttgccctccg tagggcagac ttcccggagg aggggagtcc aacagcactt
46981 cggaaatagc ttccttgtta ctgtggaacg ctggagccac tgccagggag gggagagggg
47041 agccaaggcg gccccacgtg gccagggcgc cagagagtct cagagccaca gggccagggc
47101 tctcacactg ggaataggac agaagttcca gtgcctgagg aaagaagatg gtcttcagaa
47161 aaagcctctt tcattcggtt acccagagca agagctgcgt ggggagctct ggctctaacc
47221 cactccgtca ccttgggccc agtcctgcta cgcctcagtt tcccctctgc acagtctgct
47281 cactgaggcc ccttcctttt gaaagtccct gatttaaggt agcaaagatc agccgctggt
47341 cagaggggcc ccagaaagaa aagaaggcag ggctgctggc cccagggccc acccactacc
47401 acttcttcct gctgctgctg ttcccagtat ttcttgaata ttctctgccc cccactcttc
47461 agagcctcag ctcaggacag cctctgccag caatgctttc tgtcctgtga agcccagtcc
47521 aggagcccct cctccaggaa gccccccttc tcccacagta gatccccatc acacctctgc
47581 aggctagggc tgtcctttaa agcagtcgcc agcaggagtg gaaatcatca aaacggcagc
47641 agatgcttgc tgggtgcttc ctccacggca gcgtctaagc agctgacaag caccatcttg
47701 tttcgcctgg cagcatcccc ttgagtaatg tctgccacca tcctatcata tgggtgaaaa
47761 aactgaggct ctggacagcc agtgagctca aggtcaagca gaagacacac agccacctgc
47821 tctccctaga gcctgtgaaa acacatctat tgtggcggaa gagggcgggg ttcacagcca
47881 gcctgggttc gatacatcaa tagatgtatc gggactccac aatagatgtt agggccccgt
47941 ccagccccag gcccagagct gctatctgca gcccaggag gataggactt gggagaggaa
48001 gatgagaagg tctcagtgga ctccaccagg ggcccttccc tgctctgaag ctcagggttg
48061 agagtgcaat ttccaatcat accctgctct agaccaccaa gtcactctct gcctctgggc
48121 cacagtttcc acatctgtaa agtggttatc atactgtcta accctgagg gtgccgatga
48181 gctggaggac aggccacatg cttttaaaag cagaggactg agatggctgg ggaaagcccc
48241 gcgttggccc tcagggcctg tcctggctgc tgtcagcctc cagctgctgg gctcagatca
48301 gacagctcct ccagcatggc ctggattagt gtctatgacc ctcacttatg ggagggcaga
48361 tcccagcctg cccctcccaa gggcccagtg gccccaagct cataccaggc agctctcacc
48421 caccagtggt cactgtcttg ggcaagccac tcttgccttc tgggcctcag ctgtcttatc
48481 tgcaaaatgg ggatcacacc tctaaccccc gagggtcagg aaaggtttca agaattacac
48541 agcccaccag gccttggcct ttgaggaagg tgttctgggt tcccattctg acttggccat
48601 ctgctcctag gcaaacagct cctctctgat gcgtctgtgc agtggggtg acccacctca
48661 caggcatatg ataaaggcca aagtgggagc aggaatgctg gccccagcc agtctgggga
48721 ctcaccaggg tcacgcagtg tgggagctag aggaccaggg ctggattctg ggttggcagc
48781 tcctttacca ctgtccccag ggaatccttc ccaccacca gcctggcag cctggggtcc
48841 taccccgcc aggtacctga tgcttctggg ggaaccaaga gaccatcagg gttacccct
48901 tgcctccatg caggcccaac acaagcccct gtcataggag tggcaaccat tttagcaggc
48961 atccatgatg tgccgggcac tgtgcaaggg gggccatgca tgtcgtctcc aagggtcata
49021 tccctctgac aggctgtgac tatcaccccc gttttacaga tggaaaagtg gaggcacacg
49081 gtcaaggtca cacggtgtgt ggcacccctg agattcaaac ctggaaaggt cacacatgga
49141 gctcagctgc taaggtcatc gcttcccaag acctccatga gagaagagct gggtcacctg
49201 gccgtaaggt ccagctggca agaggccagc tcagtgttca gcctcttggg aaaagcagag
49261 tcgggcaggg ccacaggaac agcatcgtct gctggggaca gtgtgggctc caatgaccag
49321 gcccgtcacc catctgaagc cactcggcag ccttcttggc cgcctggtgc ggctgtgacc
49381 cagacacagc agccactgtc tacccagcag cagggtgggg cgccgggccc gaggccggct
49441 ctgcggcctg tcaggagatt tacacccgac tcttaacagc ctcgcggaat cgcaggcggg
49501 tgccgggcct ggggtggtct gctgtgaatc ggcccctgt gagcagatga agccgggtc
49561 ggtggctggg cagggaaacg ggctggccgg gggccagcgg gcagggaggc gagcggttcc
```

Figure 4 (continued)

```
49621 ctcccagggc tgcaagtggg gcttccagag gcctggggtt gattaggaga acccaggagg
49681 tctgtggtta accccttccc tcctgctggg cagactccgc tagccctgcc cctagcgcag
49741 gagacactcc tgggggttgt ggggatcttg ggagccaggg acctggagca gctgcctctc
49801 ctcagcccag gaagaaacta cagaaactct aaggccttca aaggcccaac tgcgggctca
49861 gggtcacttc tcctgcccac gccaaaccct cggcagccac actctgctgg ctgctcactt
49921 caggcccctg ctcaaaggtc acctcttcag gaggcctccc cgccccatcc cttgttccat
49981 cccttgcacg ctccactcct tctcccagct ttgtttttct tcataggact tcctactacc
50041 cgaaatgaca ttaatgaatc atttgcttat tcatcaacga tttatggagc agctgtgaag
50101 ggctcctgcc cacattctca gggtctagct ataccagggc ctggcaaacc agagcaaaga
50161 actctgccct tgtagagcat aaacaacagg gggccgggtg cggtggctca cgcctgtagt
50221 cccagcactt tgggaggctg aggtgggcgg atcacttgag gtcgggagtt caagactagc
50281 ctggccaaca tggtgaaacc ctgtctctat taaaaataca aaaattagct gggtgtggtg
50341 gcgtgtgcct gtaatcccag ctcctaggga ggctgaggca agagaatctc ctgaacctgg
50401 gaggcggagg ttgctgtgag ccgagatctt gccactgcac tccagcctgg gcaacagagc
50461 aagactccat ctcaaaaaac aaaacaaaac aaaatgggag aaatgaataa caaatgaaac
50521 aaactatcgg actagatagc accttagaag gtggtagtgg taagtgctcg gggtaacctt
50581 aaagccagga aggaaagggg ggagaggtga ggaaggctgt gtgtgtgcca cttgaaacag
50641 gcgggctgct gagaagtgca gaggctttag ggtgtgaagg agtgtgccat gcatctgggg
50701 gtgtccgggg aggagtgttc cagatagaaa aaagagcagt gcaaaggccc ccgaggcagg
50761 agtgtccctg gcaagttcaa agaccagcca ggataccagg gtggccagag caggatgtgg
50821 gagggagggc aggggtaac gggcacaggc tagggggcg tgagggcctt tcccccaccg
50881 tggtccatgc cagacttgcc aggtgtcacc gcccctcctg ctgggatcct ggacctggct
50941 cagcaacctg cttcttaacc agcccccagt gactctgagg gacaccagca ctgagaacct
51001 cagaaaccga ggccacacag gcaggaagcc accaagccag ccttcaaacc cagctggcca
51061 cctggctgca ggccgggcac gctctgcagg gcaccagagg ggaacgaccc ggccacagaa
51121 cccacagccg gcctcaggga tctacagatt cccagtcctt ggctcccagg accagcccct
51181 actccactt caccccacag cgggctcaga tttcagaggg tcggaggtgg caaaacagga
51241 aaaaagccgg gaaggaagt ccaggagcac aaaaggcctg taacaacctg tgaaggttgt
51301 ggggggcactt cctgggggcca ggccccggta aactcagtca accttcacag cgactcccct
51361 aggcagacac caataccatc catttgacag ctgagcacac tgaggtgaaa aggcccttcc
51421 aagtggccct cacttcccgc agcccccggg tcggagcccc cagggtgtgc tgacagtcac
51481 cttgggcaaa aggttttgcg ccctggcctc tatcctctcc tggggttgcc caagagatca
51541 gttactgggg actttgcaca gggcctgacg caagggaggg ggttgctcag tgaccaggag
51601 ccgctgagct ggtcccttca ctcttacaga tggggacgct gaggacccga aaggccaagg
51661 atttgtccag ggccaaagac aaaggagtgg ggctgcaacc cagggtatgg gggggacct
51721 gatctcaggg ccaggatatg ccagggacag gaacaggcag gtcctaagga tgggggacct
51781 agtagactgc cccccgactc catctctgct ctgttctgta aataaaacca ctgatccagc
51841 cgctgccggg gcccagagag ggaggtcacc tgtctcaggt ggtgcagcaa gcctggcttc
51901 tgacgccgtg ggtctccagg cccagcctct gtccctccct cttgttgcct cgtcctgagc
51961 cacgcattta ccttccagct caccccagaa ggggccatct caggtctggg agacccaggc
52021 agggaagagc aggcagggga ttctgctgga atctcccaca ggcagggctg agtctccatg
52081 ctcatccagg ggtcccagca gggcagagtg ggcggctctg gggtgggctg ggctgagcat
52141 ggagggctct cagaggggcc aaccttgccc ggtcccttgg atcttccac caagcgtcaa
52201 gaccccgtcc cgtgcctccc tctttctgga gtggctcccc tctttctgga gtggcttctg
52261 agtgccgcat ccccacccag agcccaactg aggctcctgt ccatgctgac cctgcccctg
52321 gagacatagg gcagggctgc cacctccttc aatggagact tgatacctgc acctctatta
52381 ccaaggcagc cacccagctg ctgcccatga gagagctcac cgttgactaa tggtggtggt
52441 gggagtgcag gaagggggct gggtactgag gacgacaaaa cgctgcggac ccagtgactc
52501 atgggacccc tctgtgctac ggccacgtgc tgtccacatg tcgcccctga tctccaggtc
52561 cgcagggtgg gtggcatcat cacacttcat ggaggaggga gctgaggccc agagaggtca
52621 gtgacttgcc ctaggtcaca ctgcagataa cagccctggc taaagtgacg gatcccttgc
```

Figure 4 (continued)

```
52681 taacccccac cgctaagtgc tttctataga ttaagccact gtttcctcgc aatagcatca
52741 tgaggtagct gcttgtgcga atatcatttt tcagttcagg aaactgaggc acggagatga
52801 ctagcccaag gacccacagc caggaaggct ggcttggaaa ctgctctcta caccatggtg
52861 gtctatggct catgagggct tcccagccat caccaccttg agactcctgg agtcactgat
52921 ccagttctca gatgacaaaa ctgaggccac aaagaagaca tgacttgcct agggtcatga
52981 agcccaaggc caagggcatg ggctggtcta tgtctgatct cagcaggagg gaaccagcag
53041 gagtgtggcc agggcaagtg ctggctggga gctgacggtg caggcctgag gatgcgtgcc
53101 ggggctcagg gctggcagag gtgaccctga gagccctgga gggaaactct tccagggctg
53161 ctggactcag ctccaagcct ttcccaagtg gccagatgct gggatgggcc caggaattgg
53221 atgatggggt gtcaggccca gctgactccc aagaagggag gggccagccc agggctaggc
53281 ctcctgcccc aggcctcctg cccaggcct gctcagccta gaatcttgcc tctgggaaga
53341 ctgaagcctg ggcgccttc ctgctccttg cacagcatta ggtcctattc aggtacccaa
53401 ctccctcagg cctggattct ctcctcactg gaacttgggt gaccctctg gctctgctgt
53461 catcaagatc ccattcaata gtgactgcta aaggtcttc taaactacaa agggtcacat
53521 ttctgagaaa gagagggtg ggccaacctt cagtgcacca agctgaaaat gccttgggga
53581 ggtgggatgg agctcaggaa gctggctggc tctatttcat tcattcattc attcattcag
53641 tcagtcagtc agtcagtcat tcattcattc tgtggacaca gagcctcagc ctaccctccc
53701 acttccccag ccttaatctg accttcagca agcagagaga attaaacaca aactcgcttt
53761 gatggaccag aactccctgc tcatagggtc tgggtgcccg gactctgggt gacctgagca
53821 agtcacatgc taagattcaa agactcagtt tccaaggaag aggcctggcc tcacagccag
53881 accagcccct gacttttgat cactcctgcc ctccatgcat ccctcagcca cccgcagaga
53941 agctgggggc agagtaaagc aagcctggct caacctccac ccagaaacac acaagcaccc
54001 gacaaatgcc atatctgaaa gctttctcca tccttttcct ttccttgact ccctcagtag
54061 tctccatgga cagtcatctc cactcccagc ctcctcgctg gcctccacg gtctcaggct
54121 aagcccagag ggtttagggg tttgccagca ggcacgcagt gtgtggggc acagagccaa
54181 ggactgcaac cccccgagga gggctccatc tgtctgacct agctgctgtc cttcccgcac
54241 tggaccctcc tcccccgcgc aggggctcag ggggctcggt ggcacttacg tctgggctcc
54301 cggggtccgt ccacggtcac cttgatggct cggtggtagg tcgccacttg ggtggggttg
54361 gtgaacacag tgatggtcag ggtgaaactc ttccctgggg agagtgggga atagaggcag
54421 gtggttggca cctggagctt ccacaatacc ctgctctccc acctgtatct accccctggaa
54481 gcccctaact gtcaagaagg ggcactctgt cctctttgaa catgggcaga agatagggct
54541 ctgggtgaag ttcaagctct tgggcttggc attcaaggcc cctgggggtc tgacgccaac
54601 tttgtcaacc ccccgcccca tgccgtgacc accctggctc atgttcccct cttcttggcc
54661 tttctgctgt ctcttctatt cagagaccca cacgattttg tggtggggag caggatgggt
54721 atattctatt ttctgaaagt aattggtgat ctttgtagaa aaattcaaga acatacaaaa
54781 tataaataaa gaagaaaaga cacccccccc ccacggttcc actagctgga gatagacacc
54841 gttaccattt ggtgttttcc ctttcagctc ttttttgtatg ggtttgtata tttacacagt
54901 cgcagtggta ctaaaataca gattttcata ctgttttttt tttcatttaa cctcacatca
54961 gaagcacttt cccacgtcat taaaactcca taaacttcgt ttttaatggc tgcaaaatat
55021 ttcaactcaa ggaagcctcc tcatctttta tttatctacc tccttactct cgggtattta
55081 catcgttgct aatttcttat tgatgtgtgc agctggagct gaaaaaggac tgatttggga
55141 gctgcagaca tttcttctgt agacacaact gttatttcca gaatgttcta tttttagata
55201 gacatttggc tccaaagtct ccattcaaaa ttcctgagag gggaaaaaac ttttaaaata
55261 ctactttttt tttttttac catttaaaat aaaatgaaag tgaccttctg tttataaaaa
55321 tcttttgtctg catctctgct tatttcctta gaagagattc caagaagcgg tgagtgattt
55381 cacggcagca gagggttggg acatattacg ggcgcggatc cctcttggag tgagatgact
55441 ctccggagag atttagtcgt caccctcgcg tgtgaggctg cgtcacaccc cagggatgtg
55501 tctatcaaga tggaagatct tttacacgct cttgattttg tttgccttt tttctattac
55561 tagtgagaat gaaacttttt atatgattat tatccatcat aatccaacac aaattactgc
55621 ttcatgttct tttactttcc tgtgaaggtt ttagtgcctt taaaaattg ctatatatta
55681 agcttgttaa tactttccat gctgtatttg tggccatcag tttccccggg cacaggcctg
```

Figure 4 (continued)

```
55741 cacattttgc cttcacacgc tgggtggttt ttcattttca cttctatttc tcgttcttct
55801 atcgttttat gttcagacgg gtttctccgt gtagaaagca gtttatgaag atttactttc
55861 gacagtcttc tctctacttt ctacagtgaa ttctctgatg tgtctgggag tttgggggtc
55921 tgggtaagag tcctcctctc accctattct ctattacgat ccacagcctc atgctttatg
55981 agattggtgg ccgggagcgg gggagatttg cggatccccc aagccagact ttatcccct
56041 atccctgcct ctggatccca cgtacaggcc tgggaactcc ctgtgggtag ggccaatgg
56101 tctcgcactc tcacctgtac cccagggctg gcacaggatg gtcaaggaga gaggctgccc
56161 aagcgcatcc ctctggtgtc cccctgacac gcctccaaag tgagcaggta ggtttcaaca
56221 gccccacgtt gcaggtggga gatgaagctc agggtggaga ccagtatctc acagttctct
56281 ttgcatggcc gggtacttgt tagtcaactg atcaagtgaa aattctagcc cagaggcag
56341 gagaatccgg aacaaaatta aaccagccag gctgccagga gccatgccac aggacccaag
56401 gccctctgag acaccagggg gaatttaaag ctcaagaccc actgagtgtc actccagctg
56461 ggaaatgagg ggcttctctg gaagccttt cctaagccag tcggctgagg cagggataga
56521 aattctgact gcacttgccc ccggagcccc aggtcagaac agacctggtc tcccactctc
56581 aggtcacagg gccactttg tatgatttct ggaagcagaa gtgcagatgg tctagggaag
56641 tgccaggcag atgcctcggg ctccctgccc gaccctcct actgccttc ctcactctga
56701 ggtcatttct ctgctggacc tctttctcct ccaaccagcc cagcactctc ctggggtccc
56761 tgagcctctg accctgccag cattgtccag caccttcttg gttatgacgg ggagtttagg
56821 cagacagccc agagccctag gggccagact ggagacacgg aggactaatg ggtcccagtg
56881 ccctgccaca gggccccggg cccacagcag catttgaaag cttactaaaa ccctccttca
56941 ggtcgcccac cttctcagtc aggccttccc tggtcacttt atctgaagta ggcatttta
57001 attttaatta attttttga acaaggtct tgctctgtca cccaggttgg agtgcagtgg
57061 catgatcata gctcactgca gcctggacct cccgggctca agtgatcctc ctgtctcagc
57121 ctcctgagta gctgggacaa caggtgagcg ccaccatgcc cggctatttc ttttttcc
57181 ttccttcttt tccttccctc ccttccttcc ttccttct ttcttttctt tctttccttt
57241 ctttctttt ttttttc aagcttttac tatgtgccca ggctggtctt gaactcctgg
57301 gctcaagtga tcctcctgcc ttggcctccc aaagtgttgg gattacagtc gtaaaccact
57361 acacctggaa ggcattttta acttggctcc gtagagttga atgagcctga gaactagggt
57421 aggaaaaaat tacaattgta ttgtccctaa cctctaactg aaatttagca tcactctcaa
57481 gtacgagcgt aggcaacaaa ccacagaggt attatcagcc gtacctgtga ccttgtcacc
57541 aacagacgtc acagatactt acatatcaca ttacagttgc tgcagattgc tctaaatatc
57601 ttttatgctc atcacaactt caaaaccatg gttgtcatta ggcccaatgc tagatcttat
57661 ttaatacatt gaataaagca gcacatttac cacaattt aaagtatt gctatgttt
57721 aatagaaatg gtttctattg taatactttg tatttgattt tataccttaa aaatatcatt
57781 gttctgagaa aggtgtgcgg gcttccag ctatcagagg ggcccacagg gcaaaaaaa
57841 aaaaaaaaa aaaaaagcg ctaagcagct caacctgaag tatcacaggc cctaccactc
57901 cctttctcta ttccctgcac ctgctggaat tttctcacaa tgcatatgct tttaataatc
57961 catctactca ttttgtctcc ttctactaga ttataacctc cccaggggcc caagttttg
58021 tcttgttcat gcagtgtctc cagcccctag gacggcatcc ggcacagagt aggtgctcaa
58081 caacatttgt taaataaatt aagggcagag ataatggctc ccatttgca cacaggtact
58141 aacgtcccgc tcctgagaag tgagaagccc ccacccatac caggtagcaa accacatgcc
58201 accctgagg tcaccagcac tcctcggccg cttccaccag cttccacgcc tgtcaccacc
58261 cctccaggt acaaggaga ggagtgtggg gcctaagagg aggagtgaga gggaggggca
58321 ggagtcctgg acctcgggag acagggagcc tggggagcag gggtgggaga aagctgtctc
58381 cctgagtgcc cctcagctac cccggccctg cccagctctc tctctgcctg gcagtggcaa
58441 acccatccat ccctctctct cagcctctag atataactct gtgcaggagt cccaggcaaa
58501 cctgcaatcc atcaggagcc caggaagtgt aaacccaggc tctctgaggg ctggccctgg
58561 ttgcagggga gaagtcttgg tctgggaaat gggtttcctt tagggctcca gaaactcctc
58621 caggacccat catcaaccag ccggggtggc agcagggcct caggcaagtc cttgagcatt
58681 ctctgcctgg gttcctatgt gtataaggtc cccgccccac ccacaggagc tgcatgggtg
```

Figure 4 (continued)

```
58741 gggggagggg acgtgtctca gtctcagggg acctcggggt tttctcagct tcagccaaga
58801 agccattcat ctctccccca accagcggtt ccctcagcc tgcaccggca cactgcaccc
58861 cgaatctctg tcgacacaca gttgctttt aaccagttga tcacagctcg agagctcatg
58921 tgcttttcat tttcacttag gccagtggcc gcctgctaga ggggcatttt tgggatttgt
58981 ggtggcgtgt ggtcaacata tgttgggt ggcactgcca gcgttagggg tgggtgcgt
59041 gtatgtggtg ggggatgcca gcacccaacg ctgcccaggg tggtgaagat tcaattcttc
59101 ctgggaggga aaaacttgct tataaaagtt ctctggctgg tcgcagtggc tcatgcctgt
59161 aatcccaaca ctttgagagg ctgaggcagg aggatcgctt gagtccagga gttcaagacc
59221 agcctgagca acacagtgaa caacacccc atctctacaa caataattt taaaaatca
59281 gctgagcatg gtggcgcatg cctatagtcc cagctattga ggtgggagga ctgcttgaga
59341 ccaggaggtt gagactgcag tgatcgcacc actgcaccct ggcctgggcg acagagcgag
59401 accttgtccc aaaaaaagt aaaagaaaaa aaattatct gagtcatgaa cctaactcag
59461 ttttacataa acaaggggtt ttttttgtac ttttaatatc tactgaattt tccagaagga
59521 aagacagttc ttttttttt tttaattttg ttcagcgctt tgccaacagg tgttgacaac
59581 ttcagaaagt catggtattg gcagcaaggc caggttcaga ttgagccctg ccaccctgcc
59641 tgttccctct gctgtgggct tctgcatgga gggcattcgt ccacctcatg gagtcctgtg
59701 gccccaacgt ttacatattc aaatcagtgt tttattataa attactttcc ctttttttct
59761 ccatcatagc tatggaataa catagtttgc aactgcatgt aaataggtag gtttcattat
59821 ttatacattt caacgtagaa tagtaaggct tgatataaaa tatgtattgt aagaaaggct
59881 cctcgtgtct ggcagggcag ggacctcagc cctaatcact gcaggagaca gcaatgacct
59941 ggttttcctc ccttccttt cttggttcac accttcagcc tgttgttaa gagctctgtg
60001 gtgttactgg gtgcgtgtct ttcatgaaa gccatcttcc tggaattcag acagaatgta
60061 gaactaaaaa ttgaggcaac aagcagaggt ttccatcaga cttcttagtt ctggcagaag
60121 tcaagagacc caggcaaggg ttctgggtcc caacccccag tcttaactcc caaagtgtcc
60181 catctcctaa agtggcccag attgtcactg tcaaccactg actgttctct caggtgggaa
60241 tttcccagtc agcaggatgg gcactgcaga tgtgtgtctg catgccagcg gacccggcac
60301 cctccttcct ccctgccaac cgcctccacc tctcccactc agcagttcac accttctggg
60361 tttcccccac ccccgcccaa accacacagt aatcagagaa tcagtggctg tcaccgctca
60421 aagggacctc aaagtcctcc tccagtccca ggcatttgaa gtaacaaaat ctctaacatg
60481 tatccagctc tcaatatgcg ccagctgata cacttgtgtc aatttcccta accttcccaa
60541 aatctcatga ggtaggtacc attatcatcc ccatctcaca gatgaggaaa ctgaggcaca
60601 gagtggttaa gtcatttgcc caatgtcatc cagcaagtca ttagcagagc tgggactcaa
60661 acgcagggtg gctgatacta gaatgcaggc tctcaaagac ctcgagcctc tgaaggctga
60721 acgccttagc cacagttcct cagacatcgg aactcctcct cagatcactt cctgcctccc
60781 aggaccactg agactggtta tggacctctg agaggagatg gatgagagaa tggtttataa
60841 actcagcctc ttgcatctcc cagagccaca gtcccagcct cggccattcc tgctacaagg
60901 acaagctccc aaccaacgcc ttggaaaccc atttccctcc ctgcaggcct ggggaggggg
60961 gctcaaggtc tgtgggcatg aaaaccccta aaaaaatcat tctcagtgtg cagaatggcc
61021 agacaaggtc tcggtaactc agaaaatcgt cgtctcttct ctttctctcg cttcccagga
61081 gagagagtgg gaagggagaa tcaagttcct gatgccttgc tgggctccca gatcgacagc
61141 accttctgcc cgcctcgcaa caggcagcag ctatagtgct cctgacacat acctgggcta
61201 gcagacctgg ccactgcccc gcagtcagca gagctcatca gccttgtctg ccaccgacca
61261 aggaccagtg actgtcctct cagggttggg attaagtcgc aaagggtttg agagattggg
61321 gatgacaaaa gggacttgga gactaattag gagcagcaat gaaagcttaa ttcataaaag
61381 caaacatttt ccatccatca acctgcaacc agttaagggc accgtttgaa agaaatctgt
61441 gtgtggggaa gggagccaac aggaacagga aatgtttgaa agaatgtaaa ctatttcagt
61501 ttcataaaaa gtaacaagta aacagttatt acatgcaaat aatgtcctgg ttttaattaa
61561 tgctgaaaag tcaaaatatg gctgacattt gtatgtatac atcgaacggc tggaaaggaa
61621 aaaatggtgc ccagatgcct gtttcagagc ggggctggca gctcagaggg aactagaacc
61681 ttgagaaggt cctgtttatt ggtgatgaaa agcacggttc tgcttcagcc acttcagcct
61741 gctgtggagt tggggagcag agggaaccca gcttacttct taacaaagct agaggcgggc
61801 ctggtgcttg ggaagggcga ctcccacttc agccacttct cgtaggcagg ctggtcttaa
```

Figure 4 (continued)

```
61861 agggccagtg gaccctcagg cctccgttcc acaggggcag ggtttccagg actttcccat
61921 ccaggagtta agtgatgatg ggtttcaggt cccagaagcc tcccattcaa cagcccccca
61981 cccccgtccc gccttccttc tgctgctcaa ggtcggtcag acaggcaggg tggcacaccc
62041 gccttgactc tggggcagga gatggcagcc ttcgagctgt gctttccaac attcagctgc
62101 gttagcttcc gttctagacc acctagggct caaaggcgct gggaaactgg gtctgggaga
62161 ccacagctgg agacagcc tcagagtgtg ggggatattc tgcccctat ggagagagtg
62221 gctggggtgc ttgggcccca cagatcaggg acttgtcctg caaccgcctt gctgaaagac
62281 ctataagctc cctttttgag cttgttaatc caccatctcc tgccagcatt ttttgtgaga
62341 ccaggtgtgc ttaaccggga aagaggggt ggcatgaacg gtttcaggag ttggtaaacc
62401 ctagaaactg ggagaaaatt gtctttttct ggcaagagac cataactttc ctcacctcct
62461 caaagcgatc tgtaatatcc tacaggatta caaattgctg ttttagaca gagctgcatc
62521 tggagacctg tttttcggga ttctaaggcc cctctttcaa cctccttccc tgctgcccct
62581 gccattgcca atgctgaaat ggcgaggcct cccttccact tacctcgccc actgcggccc
62641 acgaagcgaa ggtcgttgaa cctggccacc tggttcttca tgacggccga ggcattgcgc
62701 agctcagcgg agtagttctc gtcattgcct gccatcacag tcaccaccgt accatccggc
62761 acgtccccca atgccaccac ctgaagacac ggggcggggg gatgcagggg acagcttag
62821 aaaggaagag ggtgaccagg gaaaggaggg gaggggctgg gctgggcagc tcccccaggt
62881 cccaggcaca ctgagtattt ctccaatgca gggtggagaa gaggcttaaa acaataaag
62941 accttccccc aaatatcacg aaaacaagaa gatggaatct cgagcttcca caccaaaatc
63001 ctagatcaac tgcttacata aactgtgtcc caagaaatca tccttcaat gaaatctaag
63061 ccagagctgt gaatcagctc agtcactatg atgtggggtg cagttcccct gttgtcttcg
63121 gctgcagcga aagaggaatc aacatgctcc tagcaacgaa gtctccaaat gagaaagagt
63181 aacaacaata ataacaacag ggctgctacc cccactcaat ttatgcaaga gctgtttagg
63241 gcatgaaatt tggccctgaa atgtggacca ggcccagttt attggcctct gcagagccta
63301 aattcgttat gcagagaaaa tgcagaatgc aaaactcact ggtgttttga aaaaggccac
63361 cagaaaaccc ctttaaagtg agagtggggc ttttgataat ggaaggatgc acctgccggg
63421 aattgcagga tgggggtggc gatgtccccc taaacaccat ctcccccaaa tcccccaccc
63481 ccaggagcac ggagaggcgg atgccttttg aaaaagaatc agactttaaa cagagtcaca
63541 actatttaaa cgtggccgcc gcgtgcaggg actggggatc catatggtaa aaatttcaag
63601 gagaaaatgt ttgggatctg attaagaaga ccagatttcc tgtcaacatc ctgtcttctt
63661 ttaatttcaa agactccttt taagctccaa gtgacagtaa aacctccgat ctgacgatta
63721 aagtcacacg ggcctcccgc ccctcccggc gagatttccc ccactggtat tttaagatgt
63781 caccccggag acctcaaaga gccactcttc cttttttcc catttagagt cgtcttaatg
63841 ggagcaggga cggcctcagc ttccagccac ctcgggcagc accacccca gccgccggcc
63901 cttcctgccc tgcccttttc tcacggcagc tgtgagaggt ttaggggaaa accgaggcgt
63961 tttcgtttca tctcgctgcc cccttaaaaa aatgaaaatg aaacagtcgc ctactccctg
64021 gcataaagaa aaggtcctc taaatggctg ggggctgcca gggttagggg tcccccaatc
64081 tcaactcgcc attcgggacg cataatatcc ccgagcaaac gtctggagag cagtgccccg
64141 atcccggcct agcgccgtcc ggtaaaattt cggaagcccg agggtgtgag caggaagctt
64201 ttgcgaagcg gcgcgggagg aggggtgctg gaggcggagg gtaggcccctt tcaccgttcg
64261 caccccaccc gcggtgtcct tgcccctgtc ccgggatcct cttctccgtt acccgcaggg
64321 ctgtatctga gcgatccggg ttaggggggc gcaaaacccc atccgccat ttccgcacca
64381 acgtctctac gcaaggcgcc ccaaaaccca ggtggagcgg gcaaccccg ttaaaagtca
64441 ttcctgcagg gcgcatccaa aacggaacgc cgaggtcccg gagccgagcg cgcagccaga
64501 ctgaaccggg tgcccggtg tcgccgcggc gtctcgggca cctcccatcc ccactgctcc
64561 cgaggctctg gctcccgcag ctcagacgcc cggagccca gggccggcgc cctcccgccc
64621 cgggtcccgc actcaccttg aaggcgacgg gcagcgtctt gttgcagcgc cagtgcgagg
64681 gcagcacgga gcagaggaag ttggggctgt cggtgcgcac gagctcgcct gcgtggtccg
64741 ccagcacgtc caccatcgag cgcacctcgg gccgggcgcg cctccgggc ccacggccg
64801 cctgcgcgct cagcgcgccg ctgttctcgc ccatcttgcc gccgccgccg ccgcagggga
64861 aggccgggga gggaggtgtg aagcggcggc tggtgcttgg gtctacggga atacgcataa
```

Figure 4 (continued)

```
64921 cagcggccgt cagggcgccg ggcaggcgga gacggcgcgg cttccccgg gggcggccgg
64981 cgcgggcgcc tcctcggccg ccgctgccgc gagaagcggg aaagcagaag cggcggggcc
65041 cgggcctcag ggcgcagggg gcggcgcccg gccactactc gccagggccc gcccgctgcg
65101 aggcctcgct ggcccgacgg ccgcccgcag cctgcccggc tagtcccgca tcctcggcgc
65161 gcggccccgc gtgcggccgc ccctcgtggc tgtcccggct gcctgggccg cggcggggcc
65221 cgcgcggggc tgtgccgctg ccgccgcctc ccgcccgaa gctcgcccgc ggccgccccg
65281 actccgcggc cgcagcccca gaacaaatcc tccagaatca agtggcgggg ccgcggccgc
65341 ccgcgcgggg ttagtacccc cggggcccgc ggggcggggc tggcggagcg acgcgtcgca
65401 cagccaatcg gcggagcccc catcgcgggc acctcggtgg cgttcgcggg gaggaacggg
65461 gcctgccgga ggccgcccaa cggggagggg cggaaggcgc caccccgcgg aggaggcccc
65521 agtgccacag cccagggccc ccgagagctc tgggagcccg gggcaaatgc tagaaatttg
65581 cttagaacgt ccgggtccca cggaaggcgc ccttgccgcc ctctctcggg tcgtagctcc
65641 ctgacgctgg ggcgcaaccc cttcgctcct cctcccgct ggccgcggcc gggcttcccc
65701 agctcttgct gcttcgggcc tgtgacttct gcaaccccgg gctggggcc gcggggtctc
65761 agggccggtg acgccgcact gggagccgcc ccaaagaggt tactcacctc cctcgtcccg
65821 cacattattc tgacccaaga gcctccaccc cacacgggat tttgcgcgtc gtccacgccc
65881 ggccggcggc ctttgctgct cccagccctg cgcggctttg gtcccagcct cggtggcccc
65941 tgtgccaaac cggggacagg cggaagggag tcctctaggg accctaagta gcctggggcc
66001 aacaacccct ttcctctctg ctctcccctc aaaacaagtt tcaggatctt gcaggcctcg
66061 cggcgtcgtt cttcgttgtg gcggcctgtg gctcttttgaa aaacacgacg aggcctgcaa
66121 aatgcgtttt tctttttttc ctttacgcat gtaaccacgg tcctgcatcg tgaaacggta
66181 cgcgcgtcgg tggcaaaaga aaaacagcag tggctgcaaa gctaagggcc ctcgctttca
66241 gaggagagaa ttttcttct ccatgcgggt ggaaagtggc tctgcgggt ccaaccccac
66301 ttcttcttgg gcccgtgcgc tccggctgcg ccgcagggac cgcggacagc ttcgccaagg
66361 cactgcctgc ccgcccggct ccgggtcccc gctcccactc ccagccgcgt ggcccaacct
66421 ctcctgggct tcactgcaaa tcacccttc ctctcccgcc tcctaagtct gtcgagcaga
66481 cctaggggcc ggctacagtt gggagggcaa cgggaaagat caagccacaa tcattccgaa
66541 ttatcgcccc agacacctcc ctagactctg gggaacgaac gcgtgctgag cctcccccgcc
66601 gcttttggaga cggggctaga ttttcgttgc ctccggctct cgacaggtgc aaaacaatga
66661 attccaagcc tcggaagcaa agaagcttag gatccgacgg tggccgcaag atctcatcat
66721 ggatctgacc cctgctcagc gcgcgccatt tcgtcgttgc caaacgaaat caagcccgc
66781 gtgcgctcca ggggcgaagg actctggact caccccgacc accgggagag ctggcccctaa
66841 cccacctcgg gacctcacag cacgccctca ggccgtgtcg aaaggaagga cggcaaaggt
66901 cccttactga acctttaag agagcctgcg cctggcagtt gtcgattgcg gacccaggcc
66961 cgcgcgccct cggacgcgct ggcacgagca gcagaactag aggaaagcga gtgatccagc
67021 ctgggcgctc ccacctccgg gaacgtctcc gagaaggcgc agcgcgtcgt ggccaggtag
67081 ggccctggcc gggggcgggc aacacgtgct gccctcgagc aggttgcggg accatgaccc
67141 gctgtttcag gtggtggtaa attccatttg tcgaatggtt tcggtttgca ccgtgccctt
67201 tgcttgttcc tccgcctgat ttctccctct ccgcttacga tgggttcaca gacaagtttc
67261 cagagaatga gggactcttg tgggccctgg cacctggcgc agggcccggc acggctccgg
67321 ctctccgtag ggcgctggct ccccgtgggc accagatcca agggaccagg gcggcggggg
67381 gagggggggc gggtgcaggc ccttgggtcc ccagaccaag gtcgcggggc cgcctggcag
67441 gcacagtggc gggagccgcc gctagttggc gcccgcgccc tgccagccgc ggaggtgcgg
67501 gcccggccgg gctacagatg cgcgccagct gcggcccggg gtgcaggcgc ggcgaccgcc
67561 cccgaggagc tgccctttcc ttgccatcca tgcggccagg tctcagacaa accgatggct
67621 ttgtgtcaaa ccaaggccgc cttcctcacc tctgataaga tggacgcctt ctgtcttcgc
67681 gttttcaggc acccggggaa gacccacaga acaggctagc ttgttcccaa tttccacctg
67741 cttcctcccc atcccggacc gacaaaaatt gtcgtctgtt tgatgggagg agaactccg
67801 actcccccac ctggggcatg cagacaccct cgcccttccc cagttggcat ggaccgtcgt
67861 cttttctccc tcttccatca gatcgatgga caaacaggcc agtttctccc cagtggcccc
67921 cacctaagag caccctaagt tgtccacagc agggctagga agcagaaggt caggacactc
```

Figure 4 (continued)

```
67981 ccctacccta ccttgactta gagctgggta aacccagaac ccatccccgg gcaaatagag
68041 ccagctcctt tgccccagga aggggattcg tctccctctg gcatttagga gtgctctcta
68101 agtgcgttct tggcagtgag ggtgccgcct tcccagggca ggtgtgattc atgtggactc
68161 tgtggcgcct gggcagggat ccccaggtat accagacaag gggcaggtgt gccctgggaa
68221 accgcctaag aggtccatgg gctatggaag gagctggggt ccacagtccc tctgcctgag
68281 cgtgtctttt tccctcaccc acagcgctct agggaaagtt gcctaaacct ctctgagcct
68341 catttctttc atttgtaaag tggggcactc atagtggccc ttcatagaat tgtgtgtaaa
68401 gtgcttagca caggcctggc acatggaggg tgctccagcc tccgggagcc atcactgtca
68461 tgaaaaaata agacctctca atccttgctg ggggcctttg acccacccct cctctctctg
68521 ggcctcacac ttccatctgt gaaatgtcca gttctcatat tcaaagctta ctaggactcc
68581 aagccagtcc atgctgtcct gatccctcaa ttcgcccaca ggctgcctgg gggaggtaag
68641 gactggctgt gacctacctc cacgtggagt cagctcatag cggggtttcc agcaaccatc
68701 acagggcggc cagagctggg tctcgatgat tgcctgtctg accattcctc tcagaacctc
68761 actttcgccc ccagccggcc gcctcctgt gggcagaccc tttcctgagt agcaactggg
68821 cctcagcgga cactgccagg gaccccgttt ccttcccagg aggcctctgt tccccatatc
68881 ccgaatcaca caggagccta gtccagcgaa gagagcagag gactctcttc tagaactgaa
68941 aatttctccc agcctggccc taaatcccct gtccagaggg acccgtggtg aaacctatct
69001 cctgcccagt gccctagaac tcaaagggga cattcatgcc cctcactgag cctcaatttc
69061 ctcttctgtc aatggaggtc attctaacca ctccatttca cgggaggggg attaaggatt
69121 ccctctagga ggggaggggc atcattgtga ttgatgatcg attgtttgaa gaaacagaaa
69181 gaaaatgctg ctgagtaaac taggactcat ctgcatcctg atttcagata atgatctctg
69241 aatatataag cgagaaatgt taatgaaaaa tggcaatata tctgggttga ggggttgtct
69301 cctgtaggcc gggggtccag ctccagagag tccagctctg gggtcatcta tcctgggcag
69361 cctctctgga aggattcaga atgtgtggga gcacaaatgt gcttctcaaa ttacagagat
69421 ctttcttcct ttttggaaag ttccagactt ggaggggagg gagaaggagc aagggagagc
69481 agggtggtga gggtgttagg acccagatgc tgcctgtgcg gtctgagact tttgcctggt
69541 gtccacgctc ccctgagcct tggtccccga gggtaaaatg ggaagaacag taacagctgg
69601 gggtgctgag gctttacctt gtgccaggcg ccgcacatgg gcattgctca tggtattcaa
69661 tccccacggc gtcatatgtg gtaggtgtta tgcccatgta agcaaagagg aacgttgtcc
69721 gaggtcagcc aggctagaga gggccagacc cgggttaaaa gtctgctctg gttcaaaatg
69781 tggggcatga acgcatcacc tggccaagca tgtcagcact ctcctcctag tggctgagta
69841 atgggaagag ctagcatcta gatacagagg aaagagctat tgtgatgggg agagggagct
69901 gggtttggta aatcctgcta agcagccctg ggcttggaaa tcagtaaact cttcaaatct
69961 gcagggagtc aggaaggact tgccagggtc attcgggagg gtcctgtgat agtcaaggtg
70021 cacccaccac ctgctctcct ttggcctcag aaccagtctg cgaggaggca ggactggcag
70081 tagtccccag tttacagatg ggaacactga ggcccagaaa ggggaaaggg cgtgatcagg
70141 atctggaatg agctccagca aggccaggag caagcacctc gaggcaaaac gcagttggac
70201 aggacctttg ccttgcagga gactgcagcc cagtcctggg cctcatacac tagcaccctg
70261 atgccacatt cagtgcctct cgcccagggg aagtgctaat cagacgtgtt tccctctggg
70321 cctcagtgtt tgcatctgaa tgcggggtg cactttcaag gcccctctac atgccatgcg
70381 ggttccatag accccaggg tttggttgtg acccgaggcc cctcctcccc acccacctcc
70441 tctccacctc ccgcggggcg ccagctccct tgcgtccaca tgacctcgga tccttccacg
70501 cccatcccca ccctgttctg caggtgggtg gtcagagggt gctctgcttt gaggatggga
70561 gagagaaagg gaggcaagga cggagaaaag agacttcttt tgcgggagcg cagagcagaa
70621 aaaccgtctc catcggttac cagggaaggg gtttctggtt tcagatccca tcacttggtg
70681 gggccttcct accaccctcc ctgctactcg ctcttgtcat ctgtaaatca gggaaatact
70741 tctggaagac agttatctgg tctgtgactt tgatcattgg tctatgacta ataattgccc
70801 taattttttg aacacctgcc gcatgctggg agttttccgc caattgtcgc tcaccctcag
70861 gtgcctctga agggcagaga ttttattctt tccatttcac agatgggaa acccaagctc
70921 cgaaagtaaa gagcttttcc tctgtgggcc tcagaatctg agaagttcaa acaggttctc
70981 aggagcccctt ccagcacccc actcctcgat cagggagggg ctgtctgcac tctgaccgct
```

Figure 4 (continued)

```
71041 gctctcagcg cagagctctc catccaaagc agcaggtgcg tgcagagcta cctgccagca
71101 gagccatcaa acacggactc ttctactggg agccatggag tggtgagaga gacctgggca
71161 gcttggagcc aaggggggctt ctgggaaaca tgtgcccttc ccccagggtg gggttcagct
71221 ctggcgggca gggagagaaa gggctcttct gagtggctgt tgctttacac acattttgc
71281 ttcacagtat tcttagggag tagcgacagt tatcactccc attttacagg aaagaaaact
71341 gaggcttaga gagctcaagt aacttgtcca agttggcacc actgggaaac cacaggggta
71401 ggattccaac gaggcagcct ggccccagag cccatgttgc tgcccactac actctactct
71461 tgtggactaa accagatgc tcagagttac agtcatggaa tagaattaga atcctggcag
71521 aagaactgtg ggcaggattc ggaattttac aatgtcagac tcgaaagggc tctgagatat
71581 caaatccaaa tccccatttc tcaaatgaca gaactgaggc ctaggaagga agagtctcac
71641 tcaaggtcac agccagtgcc agggacagag tctgcacccc ctgcctctcc agctacctcc
71701 cgctgactcc gcaccttcct ctctcgcagg ccctcctctc cccactgccc acccagcagc
71761 ttctgggccc agccaggccc attagggatt ttccacctcc ccaaaaaggt cctgatgact
71821 gtcagtcctt gtgaagcctt aattaatctc agaggccgat ggctcggagg agactggggg
71881 ctttggcctt acgcagatga agattgcggc tctatttcat gtggtggtga aagaacgcct
71941 cagacattcc tgccagcaat aaaagccaca tggcttttcca gcatcgccct tggaaaagaa
72001 aaaaaagtgc agcccttttgc ggaaataaat caactatgtg ctgtacgcat ggcatgagat
72061 acaaatgggc atacggaggt gggcaacagt cggtctttta tgccgcctct gatgtccact
72121 gacagtggca gggccagcgg tcatggtccc agctgcaatc ctggggagag ggagtgaccc
72181 ccagtgtggt ggggggaagcc tcagcttctc cacctgaact ggatttgagc caccctagat
72241 atcccagagg cagggccggc tttctggcct gtgacccatg cagtcgcaca gggccctggt
72301 ctcagaaggg tcctgagctt gttttaatgc cctgccacca ctgccttgaa cttctgaata
72361 cttgctcaac aaaggtcctg cgttttcatt ttgtactggg ccccccaaat tatatagcca
72421 gtcctgacca caaatccacc cctcatcacc aattgtcacg tctctcctgg cccctgccat
72481 gtacccaatc ccggggagta gggtttcttg agtgcctact agccagtttg cttatatcac
72541 ctgagatgaa cttcagaatg actttgtgaa ttgggcagat gtggaaaatt gaggctcaga
72601 gaggcttcca tatggcaagg aagcctagac ttgaactcag gtctccctga ctccaaagtg
72661 agtgctctta gcagctctac attctgcatt atttcatctt caccatgccc aggggggatgg
72721 ggatacacac agttaggctg ctctattccc agataacaga aggcataact gaggccagag
72781 aagtgaaggt tctcaagtca gtgtcaaacc gagggcctgg gcaacagtgg acctgggcct
72841 ggatccatag ggctggggat ggagtctcag ttttatagtt gtttgtgcca cttgtaaatt
72901 tattagctct ttccatgcag gtcactgcct tgagtctggt ctggaatgtg gctggagccc
72961 taccctgtcc ccctccccca cagctctcca ttctaaacat ctggaagtcc ttccttgtgt
73021 cttcttccac tctttcacgc tgcagttttc ctctgccacc ctcactggtt gggaagcagt
73081 tggatctggc accttgataa actcaaaaga gtccaaattc ttgatgaaag ttggggctga
73141 acagagccca tagattgcca tgtcctataa ccaggcctgg gcctaaggct catagagcca
73201 actgctagat ccagggcagc catttccttg ttccttgctg ggtaaccttg agcaagtccc
73261 ttccctctct ggccctcaga ctccccttca gggagataaa tgcattggac cacacctgag
73321 ccccaggagg cctctctgtc ttcaacattc tagaattcca tattaatcta caacaggtct
73381 gttcatttcc gcatctaata gctggggaaa ccgaggccca ggaaggatca gagatttgcc
73441 caccgtcaca gaaggtgctt attgacaagt ggacttgact ctgaggctcc tgtcagctgg
73501 cccggttgcc tctgcacaaa cttttcggagg atctggcctc agcatcagct cagcttgccc
73561 ttgtcccgcc gcctttagcc caggtggtct gtcaggcacc ctcagtgtcc aggcctggaa
73621 atcacagcta agagtccttg gcaggcaata aagttcctct tctatggctt gaatgtctcc
73681 caaaagtcat acattaaaac ttcaccccca ttgtgatggt attaagaggc agtgggggggc
73741 ctttcgggaa gtgattaagt ggtgaaggct ctgccctcat gaatggatta ggccctcttt
73801 gcccttctga cttcaggaca caatgttctg tgtcctccgg aggacacagc cagaagacac
73861 tgccttggaa acagggagtc caggacctca ccagatgcgg aacctgccag agccttgatc
73921 ttggacttcc cagtctccag aaccatgtgt agtaagtttc tatttctcta tttataaatt
73981 atcccgtctc aggtattttg ttacagcgac acagagtgaa ctaagacact ctctttagac
74041 aaaagtgggc caggggatgg cagcaaccct tttctcccca atcgcatttg ggctgtgtca
```

Figure 4 (continued)

```
74101 gtgtttccgt aataaaggcc ccttttccag gggttataat ttggctggaa aatgaggagg
74161 aaagaccaga ctccaggact ggaggggcac atgaagtagg aggctaggat gggaaaagtc
74221 tccactggac cctgggcacg cagagtgcac acacacacgc acacacatct atacccctaca
74281 tgtgtgcact cacacacagc acccacgctc atgggcacag tctctcacac attcactggc
74341 agctcacacc cacatggaca agccctcatg gaggacagca ttgttacagt gcagccacag
74401 gtgcaaacag ttaagtgcag gtgtgtgcaa agatgctcct aggagatgcc tctgtctgca
74461 tcatcatgca tggacctatt ggtatagatg cgcagataga tgcacagata ggccccatta
74521 tatgagtggt gtggacacac acatgggcag aaacccacat cacagctgtg taaacagcag
74581 accattgtgt ggacaaatct ttacacacag aggcaggcat ggaatcaggg ctcagagctt
74641 tggatttgtt ctacagagca gctctgggag gagtcgaacc ctggctctgg aagtttctgc
74701 ttctcctcaa ttcagaggca tggactttct gggtggtttg ccccctggg gcttccaaac
74761 cattccccag catctgagtt taacccgctc cctcattgtt cgatggggac aaggagagcc
74821 tgtcttcctg gtccagagaa aggcagtggg aggggagaag tgggagggtt gcagctaggg
74881 tgccccacgg cagcatgggt ggaagggcag ggcactagcc taggggccca gagacctgag
74941 tttgggttta ggttgagatg ccctaggcca acacatggcc tctctgggct tcatcctgag
75001 cccctctgt tagggccatg tgacaccccc aggggcctca gcatgggaa gagcactgaa
75061 accatgtcac atgatgaact attaaagcaa ctggagactt tgccctggag gagagcaggc
75121 ttgggggggta agagctcctc tggcagatct atgaagagct cccaggtggc agggaccata
75181 tggatgctgg gggctccata ccaggaatag aaatattgag agctggcttg gaatagggac
75241 acgtccctc agaggtagag atcaagttga gaccaggata ttgtgcaggg agttcgagtg
75301 ttagatgggg caggggccgg accagatact agtgtctcaa acgctcagct catagcaaac
75361 acgtattgaa caaatgagag agcgactgca gagctccatt tctgagccaa tcatccgtga
75421 ttcagagcat accagctctg ggttcccacc ttgccatctg catgaccttg gccctctcca
75481 aacctcagtt tcctcatcta tgaaatgggg agaacaaatt atttccaaga gctccagcaa
75541 gtcacatccc ctattgttgg tctttcaggt catcccagaa tttctgctct tataaataga
75601 aaatgacatt gaaggtgaaa agcagacaga caagcaagag aatagttaat acaaaaatca
75661 tagctaggcg tggtaacttg tgtctgtaat ctcagctact tggaagggtg aggtggggg
75721 atctacttga ggcctagagt tcaagactag cctgggcaac aaagtgagac tctgtatcta
75781 ccaaaaaaaa aaaaaaaat caggagagtg gtccccacca cttgccacct gtgatgagta
75841 gggagaggga tgcagtcagg gaagggacac tggtgggagc cctaaggtcc cattagtgct
75901 ttgttttta aagccaggtg gtaggtagat agatgtctgc tttattcttc ttctttaaac
75961 aatacttata ttttatacat tcttctgtac atgtatttta catgtttaaa aatattttaa
76021 aggaaagcaa aagataaaat atagaaaaag ttcccctgcc ccaaacctct gaaaaatgg
76081 acaatatgct caaatgtgca taatatcgta caattattca tgatgcagca aagctgcact
76141 gtttcatccg gatggtcctg tgtaccatca cactctcagt tgaatctctg caggcccttg
76201 cagctgtcct catcatggca acccccacct aggtaagcac ttctaggtaa cagcccctgc
76261 tgagcacgct ccccaagcac tcctcatggc cgaccagtag cccttcaggt atgtgtcagt
76321 gggcccactt tacaggcaag gaagtccctt gcacctacat aggaaggggc agagctggga
76381 tttgaaccag ctctgtcaat gccaagttg tgcagcaacc tcacccgagg agccaggccc
76441 cttgattata gtaactagcg ttatgtacac tcacacatgc tgttgaatcc ccggagccac
76501 ttttgtatta ggtacattta tcatcatccc cattgtaaca gtaggacaac ggaggcatag
76561 caaggtcagg aacgtgttca agttcacacc ctaggtgagt atcagagctg agccttgaac
76621 ctcagcagcc tgatcccaga ttgtgtttcc tggcctggct gtgtggggag ctcagacttc
76681 atggaaacaa aagacagaac ggtggctcca gggtccacag cggatcccaa gggaccagag
76741 gccagcaggg gggttggctg gggttggagg atgctgccta ggagatctgc tcccagagtg
76801 atgctagccc tgtgtgatga cctgagtccc cgcctcctta cagggtcatg gctgctgggg
76861 aggtgctgag gctgtgggta cagccaaacg gagctagagc aggctttgga ctccctgcct
76921 ggcaagtcca ggtgacaggc tcagacactg gcactctgt catttgctgt tggcataagt
76981 ttccactggc aggaatgtga catttatcac ctgagtgggc ttccagaagc ccactgaatg
77041 tcctcagacc tggggtgggg ggccctctca ctgcctcacc tctgagcctt aatcaaatcc
77101 agggtggctg gatgatctga aggcccttt agctcacgga ggcctgggct tgccctgcc
```

Figure 4 (continued)

```
77161 cccatccgtg tcctcagggg aaaaggttcc cagtcctgcc cttagcagct ctgagcttag
77221 atgaggggggg gagatgagat ggaaaggaaa aggagaagta agaaacagac agaggaaaag
77281 gagttggcac tagattgaag cagtcaacac acacttatta ggcacctagg gctattttag
77341 gtgctgggga tacaagcaat ggaccagaaa gccatggagc tccttggggg ctttgattcc
77401 agcagggcag acagaagaca gacaaggagg caaataaata agcacgccaa tatttgatag
77461 tgtcttggga cactcaagaa aacagatggg ggtaaagtca gagagagtga ctgggtggat
77521 ggggagagag gggctcttgg caatacttta gacagggtgg tcagggaagg tctgtcggag
77581 caggtgacat gcgagctgag accagagggt tgagagggac ccaggaaggg agaaggggc
77641 tggtaggagg gcccactgca cagtggaact ggctttaccc acctgccttc tccccactcc
77701 tctgcactgc tagtatcccc agttcctaaa actcttactg cccttctct ctgttgcttc
77761 tcccacaaca gccctgagag ccagatgggg tgagcctaag tagcctgacc tgcagtgcag
77821 gaaactgagg ctagagtggg gagggtcagc atcagcggtg ccctaatgcc aggacctgac
77881 ccggctcccc gcctcccagc ctggtgctcc tcggagcctg cccattgcct ggcatgttat
77941 tcaaccaccc cagtccaggc aggctgcagc cactgtggag ccagcccgtg ggcaccgctc
78001 ctgagaggtc acaggctgga aatgtgggca gctgggtagg gtctaggagg gggcagcggc
78061 tcaggactgg gcggggggtcc ggagcggaag gcgcccagcc ctgattggaa caaggtggca
78121 gcaccgggag ccgagccggg tgtcattgat cttgcccggt gttccagcca ccaggcggga
78181 ccagcgccgg gcagactgcc ggttttccca ggtgtgggga cccctgagg gaatgacttt
78241 tcatgtggtt gtggggcagg catgccaccc agcacgtggg ggaggccagg gctttgggag
78301 catgctggca gcagggtgga ggggggtgtc tggagactca gaatcccaca gccagcaaat
78361 gtgaggctcc tggagacagg gtcatggact tgaggctctg agaccctgag gatgttagaa
78421 tcttcatcgc agtagctccc actgatggtg tgctcacggt gccaggcacg gttctgagaa
78481 ctcacacagc ttaactcttc atccttgctc catcctaaga gggggttctg tgatcatccc
78541 cacttacagt tggggaaact gaggctcggc aaggttaagt agcctgccaa acacacagct
78601 accaggtttt tgtcttagga aataagagcc ctggaacagt tggccagtgc ggagaggacc
78661 cccgaagatc tctgaggcta gtcccttgt gtcggaaaaa caggtctgga gaggggatgt
78721 gacgtgctgg ggcccagggg agtccaaagt caggactcat tcttccccca ggtcatcgtg
78781 ggacctccgc tggtccctga atgtcaggcc ccctgagggc agggtcctca gccaggacct
78841 aggctcccag atgttaccaa ccttaactga cagttttctg ctagcacaca ggaagttctt
78901 ttgaacatct aacctgaatc cctcgtttgc agggaaagcc tcttccttct catcttgcag
78961 tactctaaga agagtttggc ctttgatgtt agggaagatc accagttccc tggtgttgtg
79021 ggaggtgaga ctgtgcccct ctctgccata aaatatctct ttactgtcca tcgctgggcc
79081 taaacattag cgacttagcc cttggggcct tacagagttt cttattaaaa tgtgagtact
79141 cctggaatgg gtgtcagctt agcaggacag ggtggtactt caggggcagg gcttggggc
79201 cgttgagggg caggagagag ctgattctcc ccttctagcc aggcttgatg gggtctacat
79261 gacctgccac cctccacctc tctgacctca tctgcttcca ctctgccct ccctcaccct
79321 gctccagcca ccctgccttc aaatatgccc atcatactcc caccacaggg cctttgtctg
79381 tgctgccctt tacctggaaa acccttccca ttctgtctgc ctggctcagc tacccacttc
79441 attcaggtcc ctgctgcctc ctccaagagg ccttctctgg tctcctgtgg taggcagaat
79501 aatggccaca gagatgtcca catcctaatc cccaaacctg tggctatgtt accttatatg
79561 gcaaaaggga cttcgcagat gtgatgaagg ataaagactt tcagatggga gattatcctg
79621 gattccccag gtgggcccca tatgatcaca aggatcctca cacatggaat agggaggcag
79681 aaaaggacag tcggagggag atggggtgtg gaaactgatt agggaacctg agagatggca
79741 gcgtgggaaa aacatggctc aaagctgtgg gctttgaagg tggaggaagg ggctatgagc
79801 catggaaagc agacagcctt taggagctgg acaagacaag gaaacaaatt ctccaccaga
79861 gcctccagca aggaacacag ccctgccctg accttgatct tggccaaggg agactcatag
79921 agaatttctg atccctggaa ctgtaagatt ataaatgcat gttttttta aggcactaaa
79981 agtgggttaa tttatgatgg caggcatagg aaacgaatat gtctcccttc cttgattgac
80041 agttcctcag cacatttatt agtgcctgat acacaatagc ttgacttatg aattgtctct
80101 tttctctcac agaaggtcag ctgcaggagg gcagggattt tttgcttgct tggtgttaca
80161 ttcgcagata gagttgtcac atttaacaaa tggaaatata aaacacccag ttaaattgaa
80221 tttcagataa ataatgaact ccttttagt ataaagttgc cccaaatatt gcaattattt
```

Figure 4 (continued)

```
80281 atcgtttatc tgaaattaaa ataatttagg agtcttgtat tttatctggc gaattcatcc
80341 ccaacacata aaaccattcc tgggtatgta ttaggatctc aataaatgtc tgttgaatga
80401 gtgaaataga taagcaaatg aattcacatt aacttctagc ttaaaaaccc tctttggctc
80461 ccagaatgcc tacagggtaa agtgtaaatc atagcaaatg ataaaagcag acagtttcat
80521 agccgcttca atatgccaga cccgggctga gtgctttaca cttattaact cactcggttc
80581 ttgcaataac ccaatgaggt ggttagccca ttttccagat gaggaaactg aggcccagga
80641 ggcttagtaa cttgttcaaa gtcacataac cattgagcag cagagccagg caattccagg
80701 cctttgaaaa cttggctcat ggaatgttct aatgttatct ccctacccat tcccctgaac
80761 actgtggatc ctctctctct aacagccccc ggttccttttt cagggtatgt gcttccgcat
80821 tctctgactg ctgaactcct cctcatacat caaagccctg tcctacttttt ctctctttgt
80881 gagaccatct ctaaaactcc caggaggact tggccccctc tctttccccct cccaccatg
80941 gccccttgtc tgaatgcgtt gtaaggactt gctattgtgt cctttacgtt ccctgactgt
81001 gacctccctg agaacggaga tgggccccttt tcagctcttt ggcatggggc ttcaaactga
81061 gtctggctttt aggggggttc ccagaagcat tgagaatga atgaatgaat gaatgaatga
81121 gtgagtgaat gaatggctga gtgaatgaac gaatgctgtt tgtttccact ctgggcctca
81181 gtttcagagt ctataaaagg ggaagaacaa tcctgaaccg cccccattc cttaaaacaa
81241 aacacatttt tttctgatta taaaaataat acacattcat taaagaaaaa ttggaaaata
81301 ataaaattat gaagaagaaa attaaaacca tccataatcc tgccacccag aacaatggtt
81361 cccactgggt gttcagcctt ctgctcttct tactgtatgt atagatttat tatcttcttc
81421 tcttccccgc cctccctccc ttctctcctt cctttttttt ttgagtgttg ggaacataca
81481 gtatggggtc ctttaaacct gcttttgaaa tcccccaaca tgtgtgtatg tgtgttctcc
81541 tgtttttctta aagcctccct gatggcaggg gacaagtggc tgctagacaa gcctggtagg
81601 ggccaggtg tggaaagccc attccccccc tactcatgga ccaccatagt tcccttgtga
81661 tgggctgttt aggggtttc cagatttctg tcagggaaca ccctgcgtgg atgtcttagc
81721 tgcatccctg gttccttcct taggacagat tctgggactg gggttgctga ccagtata
81781 gacactgaga ggctccggac accgccccac atcctcccca cagctgctct ccagccccac
81841 tcccactggc agcctggact tctcagcttg gcagaaagcc gggggcagta ttccacctcc
81901 tccagagaaa agccttgtct acacccaagg cctcactgat tccatccaac gctgaaaata
81961 cccatttact cagctatttc tccacgttat ggtctaaggc ccagatgctt agttccaacc
82021 aaaatagcca cagaggtcac tgtggtctga gggtcctctg acctcaggc tgtgtagac
82081 atcatacttg gtaataatta acccacggag ctcaccacgt gccagaccct ctgcgtctct
82141 gtgtgtcctc acggtaaccc tgaagctagg gatggctgtc tcccatctta caggtgagaa
82201 cactgagggt gctccagaga gctgtgggcc ctaggccttg tcacctgggg gtgcaaaggc
82261 gctgccccag tagtccggct gcctgctacc tggctgcctg ctacccaatg gggcaaagtc
82321 ccagcactac cccgaaacaa ggacaagctt tggcctagaa gctgggcagc caggtcctgt
82381 gcctgttttt tctccatatg tgccctgggc agctcaccct ctccgtctgt gaaatgggag
82441 agcagggagt cagagacagc ctcctaggcc tgtggcggct ctgagcacag tgggtgcaga
82501 tactcagtgc tgagtcaaag agagagagaa ccctgccaga tgggccagct caccacaagc
82561 agccaagccc ggtctttgag gggttggagt gggcaggcct ttgaccaagg ctgagctagg
82621 agggacctga cggccccaga tggaggctgg cccaccctgc cccagcagat gggaggctat
82681 tttttaaccc cacaggaaga agaggacaga aatgattgca ggggttaac ctaggcccct
82741 ggggacgctc cctgtttgca tcctcctttc cccacaaccc agagagctat gtgggcttca
82801 cctggagttc cctgaatcct tctggagctc cccgcagatc acagccggag ctggcagggc
82861 ctgagtggcc cctgtctgcc aggcgaggga cccagagccc agagaagttt gaccaggact
82921 ggcttcctct gccctctctg ctgtgtgctt ccaccaggtg aggctgcctc ctccgcttct
82981 acctttcttc ctggggtgac ctggggaggc cccaccttct cccgggccag tttccccatc
83041 tgtcagacaa tgggaccctc cagacatcac tgaggcttct cccagctggg aaacctcctt
83101 ctgagctggg gccctgactc tgtcacatca gtcctggatt ctggaggcc tcagccctcc
83161 agaagcatcc acccagtgga caggagctcg tgcaggtgt ctggggaccc ccaggaagag
83221 gaaggatttc ctggccagag ataagaagag cagcgtgggt aggggttaag catcctcccc
83281 ctgcagcctc cctcagacca cgccaccagg tggcccttgg tccccccaaa aggagttcct
```

Figure 4 (continued)

```
83341 gaaaagtctg tgtctgttgc agcaggtgcg gcctgtgaag tgtgtgtatg cttgtgtgag
83401 ggtggtgtgt gttcacatgc acatggtggg ggtgggcaca caaggcggga ggcctaacat
83461 ggtggcaggg acagactttg gttgctgagc tgggacagcc tgtgacagag gccccagcac
83521 acccgcaggt cttaccagaa accctcagat ggtgctggtc tgacctgaag gtgggcacat
83581 gcagggaagg ggtacatgca ggacagggt gcatgtgggg gagggccatg tacagggcag
83641 gggtgcatgt ggaggagggg tacatgcagg atgggtgcat gtcggggagg gtcatgtgca
83701 ggacggggtg catgtggggg gtgcgtgcaa gacagaggtg catgggagag aagggtttgt
83761 acatggcagg ggtgcattgg gggtgcatgc agggcaggtg tgcatgtggg ggagggcat
83821 atccaggaca agggtacatg tggggaggcc acagggctca aatgctgtca gggcctctgg
83881 gaagctggga ccccagtgaa tgcttgaggg gagccaactc tgcctgacct cctcttatga
83941 ttgtctattt aaacaatact gtaaattaat cacattaatc gaacccacct ccctgcctcc
84001 tgctgcttgc ccctgtgata caaataatat gagcacaatg aaaatcttg gaaatacag
84061 aaaacacata aaaatgtta aagcctgaag tcttataacc acagtgaaca ctgcgagtgt
84121 ctttgagggg atgggggtct gcaggtcttc ttgatacaat cacattcatt cccacatact
84181 ggagcatttc ccacgggcgg ctgtggagct gagcacttca ggtttgtctt agtgaattct
84241 ctaacagcct gagagggagg tactgttatt ctccccattg tatggctgaa gaaacagcaa
84301 aaaggaggtt aaatatcccc ctcagggtgt aagaagcaga gccaagattt gaatccaagt
84361 ctggctaaat ggaaagtgca aatcgtccag cgtccaggc tgcactccag ccatgccccg
84421 ccccccgtga gcagaccact catttattca ttcctccagg agcatttact gagcacctcc
84481 tgtgactcag accctgccca gcacccacac caaggacttg gcggatgtga acgagacaga
84541 gagaggcccc aacctgactc cccaagcggc cacaaactga gtcccaacct tgaccacagc
84601 ttgatttcta gtccaagttg tcactgaccc ccactggcct tcatcactga ctgaactgtg
84661 acctggcctc ctgcactctg cagtggcctc tgtgagcttt tcattccccg tgatgtgtgt
84721 gaaagccaag gccagcagcc cacctcaccc agccatcat ccacgcggcc tgggccaggg
84781 aggccgtcag gagcccaccc accacctctg gcctgccact ctgggccagg cctctctgga
84841 gcgggggttt ggccttggcc cttggcaccc tgcttggcag aagggtgggc cttggctcag
84901 agcatggggc caccccagga ggggtcagca tagctgagct cagggtacct gtgggcgggg
84961 cttccatgtc ccaggtcct cacactgcag cctcctcttt ttgcctgggc cctggaaccc
85021 caggagaccc caggagccgt tgctccctcc tctcacttgc agaaactcaa cagggcagct
85081 catctgagct cccccgatgc ctgcactgta tttctggggg tcctgcatgt ctctccaatc
85141 ctcaggcagg gccagttacc tactttatag gacccagtgc aaaaagaaaa tacaggaccc
85201 cttttcaaaa tgcaggaaca aaagttttc cttcttctg tggactctca acccacggtg
85261 gtgttttta tttgctgttc aatgtcacac gtacttggac ctggggagac ttgtgcagaa
85321 agtgcagacc ctcacagatg ctcaggggcc accccaaaac ttggtgtgca gattccaacc
85381 cctttctcct ccccatgcct gcctcagtgg agggcggcag tgcaggtagt gggctgctga
85441 gaacccatcc ctggaggcag caggaggcag actggacccg ggcccaagt ccccaggcat
85501 gctgcactag cccatcaggc ttcatttaca acacactaat tcagagcgaa aatgatccag
85561 catttcaata tggcaactgc tgagcgttaa attcaagcac aggaggtggg ggggccaggt
85621 agccctggaa catagcagtc tcacaggtgg ctgggcgtgg ggtggatctc tgttcttgga
85681 gtagagggat gtggagtacc tccctctgct tggagtatct ggggtacctg acaagcaca
85741 ggggccatg aacagggcca tgcctgtgtg cctgcccctc gctcagaaga gggcacctga
85801 cgggaatacc agggcatatc tgcaccatgc ccgggcagta ggcctgggca tgaccctgga
85861 tcaggcagac ctgtagtagg tggaagggcc ccaggagagc tgaggagcct aggggagagg
85921 aacccagagg tccctgccaa agtgcttgat gtgctgccgt aagaagggca gcataggccg
85981 ggcgtggtgg ctcacgcctg taatcctagc accttgggag gctgaggtgg gtggatcacg
86041 aggtcaggag attgagaccc tcctggataa catggggaaa ccctgtctct actaaaaata
86101 caaaaattag ccggttgtgg tggtgcgtgc ctgtaatccc agctactcgg aaggctgagg
86161 tagaagaatt gcttgaacca gggagttgga ggttgcagtg agccaagatc atgccactgc
86221 actccagtct ggcaacagag agagactcca tctcaaaaaa aaaaaaaaaa aaataaggca
86281 gcatgggtgc ctgctgagag agagagaaag aagctctttc cctgcatgtg ttgccatggg
```

Figure 4 (continued)

```
86341 attctggccc agctccctgg ggtgctctct gagctcagct ttggccctgt ccctctctct
86401 ctgtgcctca atttctctaa ctatgcactg agcaaggaga agaccaccac acctcaagta
86461 ccttctgcat gggccataca ctgagtttta tgaatctccc ctctcttgtt ccacaaatga
86521 ttactggccc atttctcaga cgaggaaact gaagcccaga ggaggcaatg actcacccag
86581 taagaaggtg gtggagctgg ttctgcctgg cttcccttca ccccttgagt cgctccagcc
86641 tctctaggtt tgggtggagg acgtgggaac caagctcgtg ggggcaccac cagctcttgc
86701 cagaaatggg gccaagagaa gaccaaggat gctccttgac ctgaggaaac gtccattaat
86761 tcatagctac tgtgctttgg cgagccacgc aggctctgga tgcaggctgc ctgggtgggt
86821 gacctgagca gatgccttaa tctctctggg gttcagtttt ctcatctgta aaataggcct
86881 cataagagct tttgtcttat agggttgtga ggattaaatg agctaaggta tatcacttga
86941 gcctgggagg cagagacttt agtgagcaag attatgccac tgcactccag cctggaagac
87001 agagccagaa cctgtctcaa atacatatat aaacaaaatg agcaaggta tggaaaacac
87061 ttagacagtg gctgacatag agttaagagc tatgtaaatg tttactgcta atggaactat
87121 ttaaaagttg agtcataatt tatattttct agactgtcaa ttacgaattg attcatttca
87181 atgttgtgct tttccctttt gtatttagga tccagcaaat tttcctttga aatctcaata
87241 caatttccta ggtccttgag aagataattt ccccgccccc acagtgctta tagcccatgg
87301 tggatccaat agctctctct agagcagctt ttccaaaagt ggactttgca cacaccagcc
87361 ccttccagat gcatcatctc accccaagag ataactcaat aaacagttga gcatacacta
87421 ttttagatct ccatggccca acaaggtagc cattagcata tcaaagactc tgacaagtcc
87481 tgcagcaaaa caccattgaa cattgtttga acaaccaat cccaatcttg tttgaccaca
87541 gagttccatt atttctgctc aacagctgat aacatctgaa cacacgttgg gagatgccac
87601 cctcatttcc tgctttctag gaaatggcaa ggggagtcag agctgtgagg aacaccctct
87661 cgcagggatg agtggctcca cctctacaga aatcatctcc agtcatgtgc accatcgcta
87721 ggccattcct cctgttctca ccttccttgt ctgattcagc ccccacagcg gcctggagag
87781 gtcactagca tcaatgtctc catcatacag atgaggaaat tgaggttcac aaaggttaag
87841 tgggcacata gccagtaagt ggcagatccg gtagacaaac ccacagcttc tgattctaaa
87901 ccccacattc gttcttctgt atgttgactg gaaaagtaaa aatagatcct attctaacag
87961 gatcaatctt cccccatcat aggcttttaa aaaactcagg tattttttttt ttccggtagc
88021 attgaatgct ttaaaaactt aaaattttta ctatctttct tttgattact aaagcagtac
88081 gtgcttgtta tgtataaaac ttttcaaaca ttttgagttg aaaaatgaaa aaaaggcagg
88141 gcgcggtggc tcaagcctgc aatcccatca ctttgggagg ctgaggcggg cggatcacga
88201 ggtcaggaga tcgagaccat cctggctaac acagtgaaac cccgtctcta ctaaaaatac
88261 aaaaattagc caggcgtagt ggcgggcacc tgtagtccca gctactcgag aggctgaggc
88321 aggagaatgg cgtgaaccca ggaggcggag cttcagtga gtgcgattgc gccactgcac
88381 gccagcctgg gcgacagagc cagactccgt ctgaaaaaaa aaaaaaag aaaagaaaag
88441 aaaagaaaaa tgaaaaaaaa aaaaaacag atctgcatag ccctacaaag tagccattag
88501 cttttaaatg aaaatactta aatgctatct aaatgaaaat agttaaaatg aaataagata
88561 aaaaattcag ttcctcagtt acagtagcca cgtttcaagc gctcgggatt cacgtgcccc
88621 tggtggctac tgtgttgggc agcacagaca tgggacatta ctatcatcac agagaatcct
88681 acgggacggt gccgttctag attcttctta gacatatcct aacacctata caggttgatt
88741 atccctaatt caaaaatcta aaatctgaaa tgctccaaaa tccaaaactt ttttagggcc
88801 aacatggtac tcaaggaaa tgctcattgg agaattttgg attttggact gaagtataat
88861 ccaactattc cgaaatctga caaaatcaga agtcctaaat ttgaatgctt ctggtcccag
88921 ccatcttggg taagggatgt tcaacctgta atgactgtta atgtgtggtt ttttttttttg
88981 gagaccaggt cttgctctgt cgcccaagct agagtgcagt ggcacgatca tagttcactg
89041 cagccttcac ctcttgagct caagttatcc tcctgcctca gcctcccaaa gtgttgggat
89101 tacaggcggg agccgccatg cccagcccta ttgatattct tgttgaggtt ctcagacata
89161 tctgcatggc ctcacacatg gaggaaagag acccacagag gcaaaacaa gacatggggt
89221 aaaatagac tggaaggaaa cacaccgaat gatagtggtt ttttctgggt gttgagatta
89281 ccgagcttat ttttaaattt cttagatcct tcaggtgttc tacaacgtaa aatgcagaca
89341 gggtggggac gttggttgga gtcatgtttt ccctaatgtt cttactggtt ctaaaatctt
89401 caagctatgc tctcacccaa ggcttcactt attattattt taacactgtg gattcataaa
```

Figure 4 (continued)

```
89461 gaatggaagc ccacacaagt ccagggaagg aaggaaaggc agacagaggc ttattttcag
89521 gcctgggcag ttgcacaggg tcccttgctt agaagggcct catgcttggt ttcgtgttct
89581 gtggtcgctg tcctgaaatt cttactgatt tttgaacaag ggatcctgta ttttcatttt
89641 gcactgtgcc ctgaaaatca tgccgccgtc actagccctg ggattctccc caggacaggt
89701 ttcccttcag ctgctctaag ccttcgccct tgtccttgtc caaccacgga cgtggccatc
89761 cacggagccc tctacgtgcc tcagagcaag tgtgcttcgg ctgctcaggt gtgtgtctag
89821 agactgataa aaacagggct cgtgagtggg tgcgggaggc ccctgtggtc tctgttcaca
89881 cacgtaccta ccctcaaggc catgtctaca ctggccatt tcagagaacc gccctgtgca
89941 tcatgggatg ctttgcccca catcacggcc cagcttggtt cagtcctgga gccctgtgtc
90001 ctgaagccat gaccaacccc aggcctggcc caccttcttc ctcagtctcc tctccctcaa
90061 gccctccaca ggacccataa accttccatc tccatgtaat cctttgtgt gatccttctt
90121 ccatacctt gcccatgctg ttcactctgc ttgtaccagc aaggttcctt cctccccaga
90181 tctgcccttt ctagacccat ctcagattcc acccttcta gaaagacttc aggaagtatt
90241 tgagaagggc ctgaagatgc tgtggttgca tagaggagga tatgaatcac ctcgcttaga
90301 ggtatcgggg agggctccat ggaggtggtg ccctcaggcc aaggaagaga agatatcttc
90361 cgggcagaag ggagagtttg acgggctggt ttgatgtcag acagaccaca ggatgactca
90421 aggtcctctt tcctcttctt aaacattagt tgcagcaagt cccaccatct gcctgagtct
90481 gttttcatct ccacaatgga ggtggtgatg cccagcacac ggagctgtga tgaggattta
90541 atggggaatc cagagcattt atggaagtgc caggaggcca agattctgca taggtaggaa
90601 ggacctaagc cagaggggtg tgggtggcca gaggagagag cctaccttag tagggcttgg
90661 taggctaagg tctgggctga atctcgaggc tctggagctt agaacagcat ctgcaactcc
90721 ctggctgtcg gggttcaggc aaggactgcc tcctctctga gtgtcagttt ccccatctat
90781 aaatggaaag ctgggacact gaaaaacact ggggggagg gtggttcctg aggcagtctc
90841 tctccacaca tcacaggaat gtggcgcccc agggagaagg catctttgtc cattgtgttc
90901 acttctgcat ctccagtgcc cagaacagtg cttgcatgca gtagatgctc aataaatgtt
90961 cattgaatga atcagcagca accaattcgc ccacctcaca tcctaagtcc gctggggacg
91021 taggcccacc tctccaggga aactgtctgc agattgggac cacacctcag gtcacaagca
91081 tttcctgagc acctactgta tgcatggctc tgcgcagccc ggggcagacc cttgctccac
91141 agcccgacag ggcagagcca aggaggcagg tgacagacac agtgatttgg gaagaagaac
91201 agagagcagg gtggccagca gggccttgcc tgggtgggag caggccgttc ccaggctgga
91261 gctcaggctg atgggagccc cagcttgcct gttcctggga gggtgggact gcctcttcct
91321 ctttctttct ctgaaaacaa aaattgtttt cccttaaatt tacaagtatt aaaagtttgg
91381 aaaatacaca ataatcaaaa gaatataaaa taaggttac ctgccatcat ggcggaccac
91441 acagtattaa ctactatgga cttttcagtg tttccctcta gtctttttc tgaggtggct
91501 ttgctctcag aggtggcttt ctctcccct gggaagggat atagctgctc tgtaggagat
91561 gtggggcac caggctctct ccatgggctc tttatcactt ctgacttgga ggtccttcct
91621 ccacccccc tggacctagc acctcttccc gagacacagg ggtgcgaaga gctggggag
91681 gtacgtcagc aggcctcccc tcctgcccct gcttacccca cggaggtggg gtgggacaga
91741 actcaggctt gaggaaggag cactggaggc caagccacag gtgctggtcc tcagccctgg
91801 tgcccaggca agttgggttt gggaataggg gcatgaccaa aatggacccc tcctttcctc
91861 cccaccctt tccactccat ccgcctttcc ctttgcgttc tccaagcgtt ccgtccccca
91921 gatgccctct gtttcctctg ctccagcctt ttaactcctc tcaacaaagg ccaaggaatc
91981 aggcagactg tggacactca ggtgtgcatg atgggaaggg acctgcattt acaaaagctc
92041 cccccacag ggactgcatg tgctggtgga atctcagtca ccatgtccca cgttgaagga
92101 tgtttggagg gggctgactt tggtcaccct tcaaatcata agttatatgc gtctgccctt
92161 tccgcccaca cgtaagtctg aaccttttgc caaaaacact tttcccagac tcgaaagaaa
92221 accccaaaga ggaacctaaa ccttcacgct gcctgcaccg attggaccgg agtgctcagg
92281 ctcgcgccaa caagtgtttc aaagaagaag ccagacagtg aaggggaag tgagggagaa
92341 gctggaaaac tctcaggctg accaatcgtc agccattca ttcgttcatc catccatcca
92401 tccatccatc catccatcca tccatccatc cattctttct ttctttcctc tatccattca
92461 gtgagaaggg ctgaatatca cctgtgagcc tgccctgct cccaagaaca ccctttggac
92521 acctgtgggg tgagtagtga ggggcagcaa tggcagagca ccccaccgc ctggaggga
```

Figure 4 (continued)

```
92581 gaaagggaag ggctgggaag gctccccaag ggggcggcca tgaagctggg ccttgagaag
92641 acaggccagg gtttctcacc ttccacatcc tgcttagagt cagacagaag gcttttgcag
92701 aggaggagga acattaaata gtagtaattt ctggcattcc atgagggctt gtctgtgccg
92761 ggccctgtgc tgtgcacgtg atacacacta cctcattaaa cctacccaac atgccttgag
92821 ggggtgctat tcattttctc cattttacag gtaagaaaat gaaacacaga gaggtgaggc
92881 acctctccca acgccacaca gcgaggaagt ggcagagcct ggctgcagct gaggcttata
92941 gccgcatttt acattgcttt ctctccgaag agtgccttcc tttatccctg ggagccattg
93001 acaaggggtc tgacagtccc tctagtcttg tgcctgctca gccctctcta gccctgaaaa
93061 aaccagggct tggcgctgga gaaagagcag gagggtgaga tgtggaaaca tctgttgagt
93121 ggcagggat cacgctggcg cagagggcc cgagccgatc aggaggccgg cctgtgccag
93181 gccagtgctc cctgtgtacc aggtgccaca tgcggggctc agggtagggc cacagttgct
93241 cctcccaacc acccttttgag gtcagtgtta ctagcccatt ttacagagga ggaaactgag
93301 accttaagag gtgaattaac atgtcaggtc acccagctac catgcagttt aagcctagat
93361 tgttctgact cctaaactgt gtgcaaggcg gatgattgga ccccagggag gcaaggaaag
93421 tcagttttcc tgctgctgaa ttcaatgttt tacaagacca cacacctctt tagacctcag
93481 tttcgtcatg tatgaaatga ggaggggaac tctctgcctc cgggctctga tatgctcctg
93541 gactgattca ctgttccttg ttcttgtgac ttctcaaagc aagaccagag tcccactccc
93601 agccctaggc ccgagattcc catcccact gtgtccaggg gcttcaggag gtgctatttt
93661 agggcagatg gcaaaggcct gggctgtaga tccactgagg gctaaaggca atctttcttc
93721 cctccacccc tcccttcctt ccttccttct ctttacttcc actaagcaag gtagggaact
93781 actcgctgag tctcagggca ggcccacgga ctgaagctca ggaggacagg gctccccagt
93841 ggctgcaggt gtcccagcac tgactcctag cagaggggt gtttggttc agtctggaag
93901 attgggtgag attccccaac tacggggggt ggggcacac tctgggtggc agatttgagg
93961 aagagtctgc agataaggca tccccaggag atggcaataa gagctggtgt tggggctgcc
94021 ccactgaacc cagagcccag gcctgtttcc ccacccatgg aggagtccgg actggctcag
94081 tggcaaggcc ggggtcagag gctgccactc tcctcctgcc tctcacagcc cgctggaagg
94141 tcaggttttc aggctctgct tatccgtctc ccggcctcct ccctccaggt aaccgaggga
94201 gcctccgctt tgatgcggcc acctccaggc ccaggcgtca atgagccctc tatatgacca
94261 gtggggctgc tgggggcctc cagcccgcca gagtgggtgc ggtgaggcct ggacacacag
94321 tcccgctgtg tggggtcggc tcatgcctgc ctagaccctg tgggcagtgg ggggctccta
94381 ggaatgcttt tccagcctgg ggggcacttt ggacaggcag ggtggtctgg ggagacgggt
94441 gtgtgcaggg cagcctcaga agccgccatc aaagggacct agcagacgtg gcgccaggca
94501 agcgccatag tgggcacgga agggctggcg gtcagtctgt tcctctccca gggatggcgg
94561 ggagggggag gccccatgga cacatgtgct cagggtgacc agccatcagg ggttgcctgg
94621 gatgaagggg tttcctggga cgtggagctt tcagtgctaa aacagagagt cccctgttat
94681 tggaacttcc tggaccttcg gaaaggatac agtgactgac ctctctggtc tgggcagcct
94741 cctccctgtc cggtgacctc tgagtcagac catctcggcc agacctgccc agggccattt
94801 tgtccacccc ctgcctccac acaggcctgc ctcataccca agagtccact ttccatttct
94861 cccaggcatc ttcaggggag gagctgccgg ccaactccaa ccactgctag ggggacctcg
94921 gccagaccca caccacgctc ccagccctcc ctgtggctcc cgagccagct catactttcc
94981 tgcttccaca cctttgccca ggacgttcct tctgcctgga acatcctttc cctgtctttg
95041 ttacctcttt acccttaggg acccagtttc caagtcactc ctccagagga cttgttctct
95101 cttttcccaag gctgggctag taccctctt tgaactcaca gccctggttc ttctcccaaa
95161 aaacctttgt cacgccccag ggcaattttc tgttgaccca tcttttttcta caccagatgg
95221 tgagctctta ggatggagat c (SEQ ID NO:53)
```

ACCTGGTCCCCAAAAGAAATGGAGGCAATAGGTTTTGAGGGGCATG(G)GGACGGGGTTCAGCCT
CCAGGGTCCTACACACAAATCAGTCAGTGGCCCAGAAGACCCCCCTCGGAATCA(G)AGCAGGGA
GGATGGGGAGTGTGAGGGGTATCCTTGATGCTTGTGTGTCCCCAACTTTCCAAATCCCCG
(SEQ ID NO:4)

Receiver Operating Characteristic Curves for Combined Marker Analysis

MATERIALS AND METHODS FOR DETERMINING CANCER RISK

CROSS-REFERENCE TO RELATED APPLICATIONS

This application is a continuation of U.S. application Ser. No. 13/272,044, filed Oct. 12, 2011 (now U.S. Pat. No. 10,041,948), which claims the benefit of U.S. Provisional Application Ser. No. 61/392,342, filed Oct. 12, 2010. The disclosures of the prior applications are considered part of (and are incorporated by reference in) the disclosure of this application.

BACKGROUND

1. Technical Field

This document relates to materials and methods involved in assessing inflammatory bowel disease patients at risk for developing cancer. For example, this document relates to materials and methods for monitoring colorectal cancer risk in ulcerative colitis patients.

2. Background Information

Inflammatory bowel disease (IBD) refers to chronic diseases that cause inflammation in the intestine. The major types of IBD are Crohn's disease and ulcerative colitis (UC). Crohn's disease and UC differ in the location and nature of the inflammation. Crohn's disease can affect any part of the gastrointestinal tract, though it most commonly affects the terminal ileum and parts of the large intestine. Ulcerative colitis is an idiopathic inflammatory bowel disease characterized by chronic, relapsing mucosal inflammation primarily limited to the colon and rectum. Patients with longstanding and extensive IBD are at increased risk to develop colorectal cancer (CRC). Because of this, patients with IBD are advised to undergo surveillance colonoscopy and biopsy, every one to two years, wherein biopsy samples are histologically evaluated for the presence of pre-cancerous changes (colorectal dysplasia) or CRC.

SUMMARY

This document provides methods and materials for assessing inflammatory bowel disease patients at risk for developing cancer. For example, this document provides materials and methods that can be used to monitor colorectal cancer risk in ulcerative colitis patients. As described herein, markers (e.g., nucleic acid markers, polypeptide markers, epigenetic markers, or combinations thereof) can be used to screen UC patients to determine risk for developing CRC. Detection of such markers may allow a physician to more closely monitor those patients deemed to be at a higher risk of developing CRC.

Patients with UC have an increased risk of developing CRC as compared with the general population (Ekbom et al., *N. Engl. J. Med.*, 323:1228-1233 (1990)). The exact mechanism by which the extent and duration of UC contribute to the pathogenesis of CRC is unclear, but studies measuring colonic inflammation and CRC risk have found a correlation between increased severity of histologic inflammation and risk for CRC (Rutter et al., *Gastroenterology*, 126(2):451-459 (2004) and Gupta et al., *Gastroenterology*, 133(4):1099-1105 (2007)). Rutter et al. assessed disease activity using a four-point grading scale ranging from 0 (inactive) to 3 (severely active) to quantify levels of neutrophil infiltration on hematoxylin and eosin-stained tissue sections (H&E).

This document is based, in part, on the discovery that hemotoxylin and eosin-stained tissue section (H&E) examinations alone may underestimate the level of disease activity present in the colonic tissue of patients with UC, and that patients with UC-CRC may have higher levels of disease activity at the tissue level even when they have what would currently be defined as inactive disease. For example, nucleic acid markers, epigenetic markers, polypeptide markers, or combinations of markers can be used to identify patients with higher levels of immune cell infiltrate associated with UC-CRC and can be detected even during what is currently defined as inactive disease (e.g., no neutrophil infiltration seen on H&E stained tissue slides). Measuring polypeptide levels of MPO (myeloperoxidase), and/or the methylation status of MINT1, COX-2, and/or RUNX3 nucleic acids in patient samples can provide useful information about the risk of developing colorectal cancer in inflammatory bowel disease patients. In some cases, genetic associations in TNF-alpha nucleic acids or in other biomolecules regulated by NFκB can provide additional useful information about cancer risk.

In general, one aspect of this document features a method for assessing a mammal diagnosed with inflammatory bowel disease for the presence of or an increased risk of developing colorectal cancer. The method comprises, or consists essentially of, determining whether or not the mammal comprises at least two markers from the group consisting of elevated MPO polypeptide levels, elevated RUNX3 methylation status, elevated MINT1 methylation status, and reduced COX-2 methylation status as compared to a normal control, wherein the presence of the at least two markers is indicative of an increased risk of developing colorectal cancer. The method can further comprise determining whether or not the mammal comprises at least one polymorphism in a TNF alpha nucleic acid, wherein the presence of the polymorphism is indicative of an increased risk of developing colorectal cancer. The inflammatory bowel disease can be ulcerative colitis. The determining step can comprise performing an immunoassay. The determining step can comprise performing methylation-specific PCR. The mammal can be a human.

In another aspect, this document features a method for assessing a mammal with histologically inactive inflammatory bowel disease for the presence of colorectal cancer or an increased risk of developing colorectal cancer. The method comprises, or consists essentially of, determining whether or not the mammal comprises the presence of at least two markers selected from a group consisting of the presence of at least one polymorphism in a TNF alpha nucleic acid, an elevated MPO polypeptide level, an elevated methylation level of a RUNX3 nucleic acid, an elevated methylation level of a MINT1 nucleic acid, and a reduced methylation level of a COX-2 nucleic acid as compared to a normal control, wherein the presence of the at least two markers is indicative of the presence of colorectal cancer or an increased risk of developing the colorectal cancer. The mammal can be assessed as having the increased risk of developing colorectal cancer and can be categorized as a mammal needing more frequent monitoring than a mammal assessed as not having the increased risk of developing colorectal cancer.

In another aspect, this document features a method for assessing a mammal diagnosed with inflammatory bowel disease for the presence of or an increased risk of developing colorectal cancer. The method comprises, or consists essentially of, (a) determining the methylation status in a RUNX3 nucleic acid and a COX-2 nucleic acid in the human, (b) classifying the human as having or as having an increased risk of developing the colorectal cancer if the RUNX3 nucleic acid methylation status is elevated and the COX-2 nucleic acid methylation status is reduced as compared to a normal control, and (c) classifying the human as not having or as not having at an increased risk of developing the colorectal cancer if the RUNX3 nucleic acid methylation status is not elevated and the COX-2 nucleic acid methylation status is not reduced. The inflammatory bowel disease can be histologically inactive. The method can further comprise determining the level of an MPO polypeptide in the mammal, wherein an elevated level of the MPO polypeptide is indicative of the presence of or an increased risk of developing colorectal cancer. The method can further comprise determining the methylation status of a MINT1 nucleic acid in the mammal, wherein an elevated level of the MINT1 nucleic acid methylation status is indicative of the presence of or an increased risk of developing the colorectal cancer. The method can further comprise determining whether or not the mammal contains a polymorphism in a nucleic acid encoding a TNF-alpha protein, wherein the presence of the polymorphism is associated with the presence of or an increased risk of the colorectal cancer. The polymorphism can be rs1800629.

In another aspect, this document features a method for assessing a biopsy sample from an ulcerative colitis patient having the presence of a polymorphism in a TNF-alpha nucleic acid. The method comprises, or consists essentially of, analyzing the biopsy sample for at least two markers selected from the group consisting of an MPO polypeptide level, methylation status of a RUNX3 nucleic acid, methylation status of a MINT1 nucleic acid, and methylation status of a COX-2 nucleic acid.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIG. 1 contains a sequence listing of human TNF-alpha nucleic acid promoter region (GenBank Accession No. AB048818; GI No. 13365764; SEQ ID NO: 1).

FIG. 2 contains a sequence listing of a human clone MINT1 colon cancer differentially methylated CpG island genomic sequence (GenBank Accession No. AF135501; GI No: 4914684; SEQ ID NO: 51).

FIG. 3 contains a sequence listing of human cyclooxygenase nucleic acid, promoter region and exon 1 (GenBank Accession No. AF044206; GI: 3282785; SEQ ID NO: 52).

FIG. 4 contains the 3' end of human runt-related transcription factor 3 coding and non-coding regions and a CpG island, complete sequence. (GenBank Accession No. AL023096; GI: 3900882; SEQ ID NO: 53).

DETAILED DESCRIPTION

Figures 5, 6:
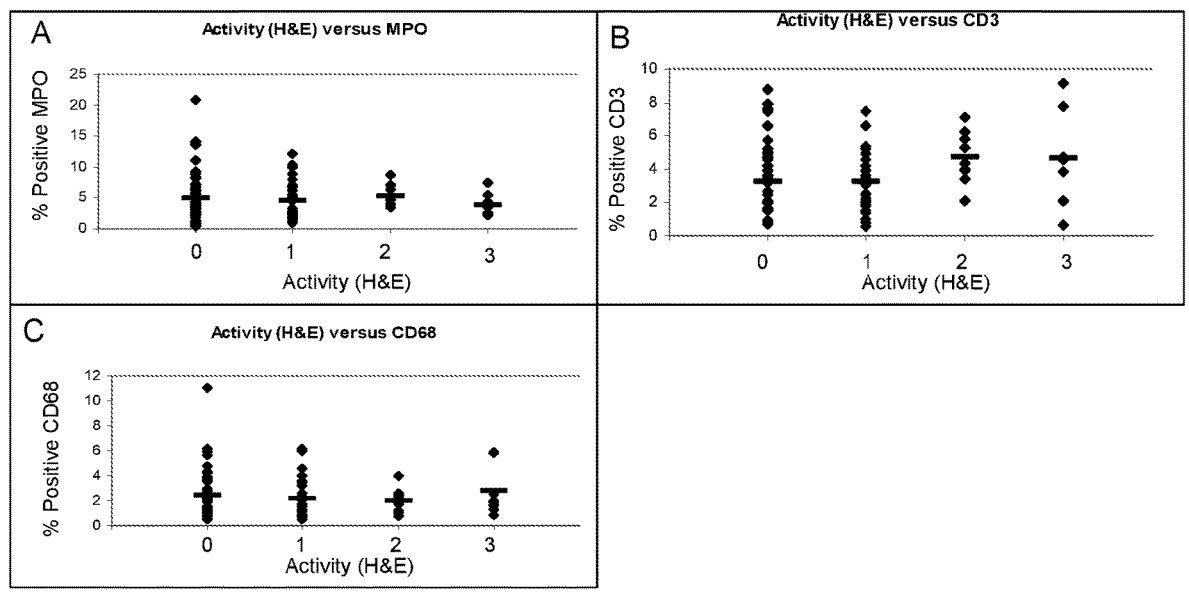
FIG. 5 contains a sequence listing of a human TNF-alpha nucleic acid promoter region (SEQ ID NO: 4). The underlined regions represent the area of the −308 and −238 SNP, respectively, and the parenthetic bases indicate the polymorphism sites.
FIG. 6 is a graph of histologic disease activity and cell surface marker levels.

This document provides materials and methods related to assessing inflammatory bowel disease patients at risk for developing cancer. For example, this document relates to materials and methods for monitoring colorectal cancer risk in ulcerative colitis patients.

In general, this document provides methods for determining the risk of inflammatory bowel disease patients of developing a cancer by determining the methylation status, genetic polymorphism status, or level of one or more biomolecules in a test sample from a mammal. The methylation status, genetic polymorphism status, or level of one or more biomolecules can be correlated with the presence of or the risk of developing cancer. Identifying cancers at an early stage can help a physician properly diagnose and treat a cancer patient. Typically, a properly diagnosed and treated cancer patient can experience an improvement in general health and survival.

As described herein, methods and materials to stratify risk of inflammatory bowel disease patients developing CRC have been identified that may identify patients at risk of developing CRC even in patients deemed to have histologically inactive disease (0 neutrophils on H&E). Patients found to have an increased risk of developing colorectal cancer may benefit from more intensive surveillance and/or different treatment strategies.

The term "biomolecule" as used herein refers to DNA, RNA, or polypeptides. This document provides methods for measuring biomolecules related to, without limitation, markers of immune cell infiltration into gastrointestinal tissue such as markers of neutrophil granulocytes (e.g., myeloperoxidase; MPO), T-cells (e.g., CD3), natural killer cells (e.g., CD16, CD56, CD8), B-cells (e.g., CD19, CD20), and macrophages (e.g., CD68). This document also provides methods for measuring biomolecules related to inflammatory markers (e.g., tumor necrosis factor alpha; TNF-alpha, cyclooxygenase 2; COX-2), runt-related transcription factors (e.g., RUNX3), and other factors such as Methylated-in-tumor 1 (MINT1). In some cases, this document provides methods for measuring biomolecules that are regulated by nuclear factor kappa beta (NFκB).

The term "marker level" as used herein refers to a test level of a biomolecule that is either altered or normal compared to a control level. The level of a particular biomolecule can be measured in a test sample from a mammal. The resulting test level then can be compared to a control level of the corresponding biomolecule. If a test level is altered compared to a control level, then the potential for the presence of or the risk of developing cancer in the mammal corresponding to that test sample can be classified as increased. For example, if the level of an MPO polypeptide measured in a colorectal biopsy sample from a patient is elevated compared to a control level of MPO polypeptide, then that patient can be classified as having an increased risk of developing colorectal cancer. In another example, if the methylation status of a MINT1 or RUNX3 nucleic acid measured in a colorectal tissue biopsy is elevated compared to a control level of MINT1 or RUNX3 methylation, then that patient can be classified as having an increased risk of developing colorectal cancer. In yet another example, if the methylation status of a COX-2 nucleic acid measured in a colorectal tissue biopsy is reduced compared to a control level of COX-2 methylation, then that patient can be classified as having an increased risk of developing colorectal cancer.

In some cases, if a test level is normal compared to a control level, then the risk of developing cancer in a patient corresponding to that test sample can be classified as decreased. For example, if the level of an MPO polypeptide measured in a colorectal biopsy sample is normal compared to a control level of MPO polypeptide, then the patient corresponding to that tissue biopsy sample can be classified as having a decreased risk of developing colorectal cancer.

In another embodiment, detecting the presence, absence, levels, or status of multiple biomarkers can be used to determine the risk for developing a cancer. In some cases, the presence of one or more polymorphisms in the promoter region of a TNF-alpha nucleic acid can be determined in combination with determining the methylation levels of one or more MINT1, COX-2, and RUNX3 nucleic acids and/or polypeptide levels of biomarkers associated with immune cell infiltration (e.g., MPO).

In some cases, a combination of biomarkers that do not include TNF-alpha polymorphism detection can be used as described herein. For example, the presence of a polymorphism (e.g., −308G>A, −301G>A, −293C>T) in a TNF-alpha nucleic acid, an elevated level of an MPO polypeptide, and an elevated level of methylation in a RUNX3 nucleic acid in a sample or samples from a mammal can indicate that that mammal has an increased risk of developing colorectal cancer. In some cases, determining the presence or absence of a polymorphism in a nucleic acid of a biomolecule regulated by NFκB (e.g., IL1B) in combination with determining the methylation status of one or more MINT1, COX-2, and RUNX3 nucleic acids can be used to determine the risk for developing cancer. Other non-limiting examples of suitable combinations of markers include determining an MPO polypeptide level in a patient sample in combination with determining the methylation status of one or more RUNX3, MINT1, or COX-2 nucleic acids.

In some cases, the presence, absence, level, or status of one or more biomarkers can be determined prior to testing for the presence, absence, level, or status of additional biomarkers. For example, the presence of one or more polymorphisms in a promoter region of a TNF-alpha nucleic acid (or other biomarkers regulated by NFκB) can be determined in an initial screening assay from a patient with UC. Genomic screening tools such as single nucleotide polymorphism (SNP) analysis are particularly useful in inflammatory disease settings because these markers are not affected by disease activity and thus do not change over time. Patients determined to have a SNP present in a TNF alpha nucleic acid could then undergo additional testing to determine the status or levels of other biomarkers. For example, MPO polypeptide levels could be determined in a biopsy sample. In another example, methylation levels of one or more RUNX3, MINT1, and COX-2 nucleic acids can be determined in patients with a SNP present in a TNF alpha nucleic acid. Other non-limiting examples of suitable screening/reflex tests include determining MPO polypeptide levels in a blood or biopsy tissue sample followed by determining methylation status of one or more RUNX3, MINT1, and COX-2 nucleic acids in biopsy samples from patients with increased MPO polypeptide levels.

In some cases, it may be useful to determine the presence, absence, level, or status of one or more biomarkers in a patient that has previously been deemed to have histologically inactive disease (e.g., 0 neutrophils on H&E). For example, determining the presence or absence of a polymorphism in a nucleic acid of a biomolecule (e.g., TNF-alpha, IL1B), optionally in combination with determining the methylation status of one or more MINT1, COX-2, and RUNX3 nucleic acids in a biopsy sample from an inactive area of the colon (e.g., 0 neutrophils on H&E), can be used to determine the risk for developing cancer in a patient previously found to have histologically inactive disease. Other non-limiting examples of suitable combinations of markers include determining an MPO polypeptide level in a patient sample in combination with determining the methylation status of one or more RUNX3, MINT1, or COX-2 nucleic acids in a patient previously found to have histologically inactive disease.

Various types of samples can be used when measuring a biomolecule. Such samples include, without limitation, tissue samples, neoplastic tissue biopsies, non-neoplastic tissue biopsies, blood, plasma, serum, surgical waste, and whole organs. Biopsy specimens can be frozen, embedded, sectioned, and stained to identify regions of cellular infiltration. Samples can also include those that have been manipulated in any way after their procurement, such as by treatment with reagents, solubilization, or enrichment for certain components, such as polynucleotides or polypeptides.

Various appropriate methods can be used to measure a biomolecule level in a sample. Such methods can vary depending on the type of biomolecule measured. For example, methods for measuring polypeptide levels include, without limitation, ELISA, immunohistochemistry, and immunofluorescence-based techniques. Such methods typically involve using antibodies having specific binding affinity for a particular polypeptide.

The term "antibody" as used herein refers to intact antibodies as well as antibody fragments that retain some ability to bind an epitope. Such fragments include, without limitation, Fab, F(ab')2, and Fv antibody fragments. The term "epitope" refers to an antigenic determinant on an antigen to which the paratope of an antibody binds. Epitopic determinants usually consist of chemically active surface groupings of molecules (e.g., amino acid residues, amino acid-nucleic linkages) and usually have specific three dimensional structural characteristics as well as specific charge characteristics.

The antibodies provided herein can be any monoclonal or polyclonal antibody having specific binding affinity for an MPO polypeptide. "Specific binding affinity" refers to an antibody's ability to interact specifically with a particular polypeptide without significantly cross-reacting with other different polypeptides in the same environment. An antibody having specific binding affinity for MPO can interact with MPO polypeptides specifically in the presence of multiple different polypeptides, for example, multiple different markers expressed by neutrophils. MPO antibodies can have specific binding affinity for full-length or fragments of an MPO polypeptide from any suitable species, including, without limitation, mouse, rat, chimpanzee, and human. For example, MPO antibodies can have specific binding affinity for a full-length human MPO polypeptide or fragments of a human MPO polypeptide including.

Antibodies used for measuring polypeptide levels can include a detectable label. A detectably labeled antibody can refer to an antibody (or antibody fragment which retains binding specificity for a target polypeptide or epitope), having an attached detectable label. The detectable label is normally attached by-chemical conjugation, but where the label is a polypeptide, it could alternatively be attached by genetic engineering techniques. Methods for production of detectably labeled proteins are well known in the art. Detectable labels may be selected from a variety of such labels known in the art, including, but not limited to, radioisotopes, fluorophores, paramagnetic labels, enzymes (e.g., horseradish peroxidase), or other moieties or compounds which either emit a detectable signal (e.g., radioactivity, fluorescence, color) or emit a detectable signal after exposure of the label to its substrate. Various detectable label/substrate pairs (e.g., horseradish peroxidase/diaminobenzidine, avidin/streptavidin, luciferase/luciferin), methods for labeling antibodies, and methods for using labeled antibodies are well known in the art (see, for example, Harlow and Lane, eds. Antibodies: A Laboratory Manual (1988) Cold Spring Harbor Laboratory Press, Cold Spring Harbor, N.Y.).

MPO polypeptide levels in a colon tissue biopsy sample can, for example, be measured using a quantitative or semi-quantitative immunohistochemistry technique. For example, a section of a colorectal tissue biopsy sample can be treated with anti-MPO primary antibodies. Negative control sections can be incubated with pre-immune rabbit or mouse serum in lieu of primary antibodies. After antibody binding and subsequent washing, the primary antibodies can be detected with appropriate label-conjugated secondary antibodies (e.g., gold-conjugated or enzyme-conjugated antibodies). The label is then developed and quantitated using an image analysis system such as a computer-aided imaging system.

The resulting quantitated polypeptide levels can be correlated with the risk of having or developing colorectal cancer. Although samples can be processed individually, samples from different tissues or from a population of different patients can be processed simultaneously. Such processing methods include, without limitation, tissue microarrays as described elsewhere (Kononen et al., *Nat. Med.*, 4:844-847 (1998)).

Immunofluorescence techniques represent another approach to measuring the level of a polypeptide. For example, MPO and CD68 polypeptides can be localized in the same colon biopsy sample section using polyclonal and monoclonal antibodies against MPO and CD68. The bound antibodies can be detected using different fluorescently conjugated antibodies. The levels of MPO and CD68 fluorescence can be quantitated using an image analysis system, and the resulting quantitated levels correlated with the risk of having or developing cancer.

Suitable antibodies for ELISA-, immunohistochemistry- and immunofluorescence-based methods can be obtained using standard techniques. In addition, commercially available antibodies to polypeptides associated with immune cell infiltration can be used.

As used herein, a "methylated nucleic acid marker" is a mammalian nucleic acid sequence that is methylated (e.g., hypermethylated or hypomethylated) in certain conditions (e.g., pre-cancer, cancer) as compared to the methylation status of the same mammalian nucleic acid under normal conditions (e.g., in an individual that does not have pre-cancer or cancer). In some cases, hypermethylated DNA markers can be particularly useful for detecting colorectal dysplasia or colorectal cancer. Such hypermethylated DNA markers can include, for example, CpG sequences from a methylated-in-tumor 1 (MINT1) nucleic acid and a runt-related transcript factor 3 (RUNX3) nucleic acid. In some cases, hypomethylated DNA markers can be particularly useful for detecting colorectal dysplasia or colon cancer. Such hypomethylated DNA markers can include, for example, CpG sequences from a cyclooxygenase 2 (COX-2) nucleic acid.

DNA methylation does not alter the coding function of a DNA, but has the potential to alter gene expression and thus can have profound developmental and genetic consequences. DNA methylation occurs at target cytosine residues that are found within CpG dinucleotides. The methylation reaction involves flipping a target cytosine out of an intact double helix to allow the transfer of a methyl group from S-adenosylmethionine to form 5-methylcytosine (Klimasauskas et al., *Cell* 76:357-369 (1994)). Areas of the genome containing long repeats of CpG dinucleotides are referred to as "CpG islands" (Bird, *Nature* 321:209-213 (1986) and Gardiner-Garden et al., *J. Mol. Biol.*, 196:261-282 (1987)). CpG islands typically are between 0.2 to about 1 kb in length and are located upstream of many genes, but may also extend into gene coding regions.

Methylation of cytosine residues contained within CpG islands of certain genes typically correlates inversely with gene activity. For example, CpG islands of promotors are unmethylated if genes are expressed. Methylation can lead to decreased gene expression by a variety of mechanisms including, without limitation, disruption of local chromatin structure, inhibition of DNA binding by transcription factors, or by recruitment of proteins that interact specifically with methylated sequences and thus indirectly prevent transcription factor binding. Hypermethylation of CpG islands within tumor suppressor genes therefore can lead to progressive reduction of normal tumor suppressor expression, resulting in the selection of a population of cells having a selective growth advantage (i.e., neoplasm). Alterations in normal methylation processes also can be associated with genomic instability (see, e.g., Lengauer et al., *Proc. Natl. Acad. Sci. USA*, 94:2545-2550 (1997)). Such abnormal epigenetic changes may be found in many types of cancer and can therefore serve as potential markers for oncogenic transformation.

Any appropriate method can be used to detect a DNA methylation marker in a sample. Such methods can include isolating DNA from the sample, separating out one or more particular regions from the total DNA (e.g., CpG islands), subjecting the DNAs to bisulfite treatment, and determining whether the separated DNAs are abnormally methylated (e.g., hypermethylated). To analyze which residues within a DNA sample are methylated, the sequences of PCR products corresponding to samples treated with and without sodium bisulfite can be compared. The sequence from the untreated DNA will reveal the positions of all cytosine residues within the PCR product. Cytosines that were methylated will be converted to thymidine residues in the sequence of the bisulfite-treated DNA, while residues that were not methylated will be unaffected by bisulfite treatment.

In some cases, a test nucleic acid sample can be amplified with primers which amplify a sequence region known to include a CpG island region of interest. For example, primers specific for unmethylated and methylated nucleic acids such as those described in Example 1 can be used to amplify the sample DNA and determine the methylation status of the tested residues. In some cases, oligonucleotide primers can amplify a region of interest in a RUNX3, MINT 1, or COX-2 nucleic acid. For example, the methylated primers of SEQ ID NO: 37 and SEQ ID NO: 38 amplify a 129 base pair fragment (SEQ ID NO: 45) and unmethylated primers of SEQ ID NO: 39 and SEQ ID NO: 40 can be used to amplify a 159 base pair fragment (SEQ ID NO 46) in the promoter region of a RUNX3 nucleic acid (Table 1). In some cases, alternate oligonucleotide primer sequences could be used to amplify all or part of the RUNX3 nucleic acid fragment of SEQ ID NO: 45 or SEQ ID NO: 46 or any fragment of SEQ ID NO: 53 (FIG. 4) that when amplified, can be analyzed to determine the methylation status of a RUNX3 nucleic acid. A patient diagnosed with IBD and containing a hypermethlated RUNX3 nucleic acid (e.g. elevated methylation status) can be classified as being at a higher risk of having or developing colorectal cancer as compared to a corresponding patient not containing a hypermethylated RUNX3 nucleic acid.

In another example, the methylated primers of SEQ ID NO: 29 and SEQ ID NO: 30 amplify a 81 base pair fragment (SEQ ID NO: 47) and unmethylated primers of SEQ ID NO: 32 and SEQ ID NO: 33 can be used to amplify a 112 base pair fragment (SEQ ID NO 48) in the promoter region of a MINT1 nucleic acid. In some cases, alternate oligonucleotide primer sequences could be used to amplify all or part of the MINT1 nucleic acid fragment of SEQ ID NO: 47 or SEQ ID NO: 48 or any fragment of SEQ ID NO: 51 (FIG. 2) that when amplified, can be analyzed to determine the methylation status of a MINT1 nucleic acid. A patient diagnosed with IBD and containing a hypermethlated MINT1 nucleic acid (e.g. elevated methylation status) can be classified as being at a higher risk of having or developing colorectal cancer as compared to a corresponding patient not containing a hypermethylated MINT1 nucleic acid.

In yet another example, the methylated primers of SEQ ID NO: 13 and SEQ ID NO: 14 amplify a 142 base pair fragment (SEQ ID NO: 49) and the unmethylated primers of SEQ ID NO: 15 and SEQ ID NO: 16 can be used to amplify a 138 base pair fragment (SEQ ID NO 50) in the promoter region of a COX-2 nucleic acid. In some cases, alternate oligonucleotide primer sequences could be used to amplify all or part of the COX-2 nucleic acid fragment of SEQ ID NO: 49 or SEQ ID NO: 50 or any fragment of SEQ ID NO: 52 (FIG. 3) that when amplified, can be analyzed to determine the methylation status of a COX-2 nucleic acid. In some cases, a patient diagnosed with IBD and containing a hypomethylated COX-2 nucleic acid (e.g. reduced methylation status) can be classified as being at a higher risk of having or developing colorectal cancer as compared to a corresponding patient not containing a hypomethylated COX-2 nucleic acid.

Other non-limiting examples of nucleic acids where analyzing the methylation status may be useful in determining the risk of developing colorectal cancer in IBD patients include p16, p14, e-cadherin, estrogen receptor and HPP1.

TABLE 1

Methylation Assay Amplification Products

| SEQ ID | Gene | Status | Nucleotide Sequence |
|---|---|---|---|
| 45 | RUNX3 | Methylated | CGTTTGCGTGGTTCGTTAGTACGTTTATTA TCGAGCGTATTTCGGGTCGGGCGCGTTTTT CGGGTTTTACGGTCGTTTGCGCGTTTAGCG CGTCGTTGTTTTCGTTTATTTTGTCGTCGT CGTCGTCGT |
| 46 | RUNX3 | Unmethylated | TTGGGTTTTATGGTTGTTTGTGTGTTTAGT GTGTTGTTGTTTTTGTTTATTTTGTTGTTG TTGTTGTTGTAGGGGAAGGTTGGGGAGGGA GGTGTGAAGTGGTGGTTGGTGTTTGGGTTT ATGGGAATATGTATAATAGTGGTTGTTAGG GTGTTGGGT |
| 47 | MINT1 | Methylated | TTTCGAAGCGTTTGTTTGGCGTTTAAGAGA GAGTAAGAGAGGGTTGGAGAGTAGGGGAGT TCGCGGGGTTGAGGTTT |
| 48 | MINT1 | Unmethylated | TGGAGAGTAGGGGAGTTTGTGGGGTTGAGG TTTTTTGTTAGTGTTTGTATTTTTTATGTT ATAATGTTTTTATTTAGTAAAAATTTTTTG GGTGTTTGTTGTGTGTTAGGTT |
| 49 | COX-2 | Methylated | AGGGGATTTTTTGCGTTTTCGGATTTTAGG GTCGTTTAGATTTTTGGAGAGGAAGTTAAG TGTTTTTTGTTTTTTTTCGGTATTTTATT TAAGGCGATTAGTTTAGAATTGGTTTTCGG AAGCGTTCGGGTAAAGATTGCG |
| 50 | COX-2 | Unmethylated | GAGGGGATTTTTTGTGTTTTTGGATTTTAG GGTTGTTTAGATTTTTGGAGAGGAAGTTAA GTGTTTTTTGTTTTTTTTTGGTATTTTAT TTAAGGTGATTAGTTTAGAATTGGTTTTTG GAAGTGTTTGGGTAAAGA |

It is noted that a single sample can be analyzed for one DNA methylation marker or for multiple DNA methylation markers. For example, a sample can be analyzed using assays that detect a panel of different DNA methylation markers. In addition, multiple samples can be collected from a single mammal and analyzed as described herein. In some cases, PCR techniques can be used to detect the presence or absence of a methylated mammalian nucleic acid marker. Cottrell et al describe appropriate methods of methylation-specific PCR (MSP) and other DNA methylation techniques (*Ann N Y Acad Sci* 2003 March; 983:120-30).

Purified nucleic acid fragments from a sample or samples can be analyzed to determine the presence or absence of one or more polymorphisms, such as single nucleotide polymorphisms (SNPs). For example, a sample can be analyzed to determine the presence or absence of a polymorphism identified as rs1800629 (−308G>A) which can be viewed in the single nucleotide polymorphism section of the NCBI website and the TNF-alpha sequences carrying the major alleles disclosed as SEQ ID NO: 1 in the present document. It is noted that the minor allele (e.g. A) of this SNP is associated with higher risk of having or developing colorectal cancer, whereas the major allele (e.g. G) is associated with lower risk of developing colorectal cancer. In some cases, a test sample can be analyzed to determine the presence or absence of one or more polymorphisms such as −301G>A, and −293C>T in a TNF-alpha nucleic acid. The exact position of the aforementioned variants may vary from individual to individual or from species to species, e.g., by from 1 to about 10 base pairs. Further description of these and other TNF-alpha polymorphisms are provided elsewhere (Garrity-Park et al., *Am. J. Gastroenterol.*, 103:407-415 (2008)). In some cases, polymorphisms may occur in the promoter region of a TNF-alpha nucleic acid. In some cases, polymorphisms may occur in the coding or non-coding regions of a TNF-alpha nucleic acid.

A mammal diagnosed with IBD and containing one or more polymorphisms in a TNF-alpha nucleic acid can be classified as being at a higher risk of having or developing colorectal cancer as compared to a corresponding mammal containing wild-type TNF-alpha nucleic acid at one or both alleles. For example, detection of the rs1800629 polymorphism in a sample from an IBD patient indicates that the patient is at a higher risk of having or developing colorectal cancer. Detection of this polymorphism allows selection of a monitoring schedule or treatment plan that is most likely to be effective in early diagnosis and prevention of CRC.

In some embodiments, genomic DNA or mRNA can be used to detect polymorphisms. If mRNA is used, a cDNA copy may first be made. Genomic DNA or mRNA is typically extracted from a biological sample, such as a peripheral blood sample or a tissue sample. Standard methods can be used to extract genomic DNA or mRNA from a biological sample, such as phenol extraction. In some cases, genomic DNA or mRNA can be extracted using a commercially available kit (e.g., from Qiagen, Chatsworth, Calif.; Promega, Madison, Wis.; or Gentra Systems, Minneapolis, Minn.).

Any appropriate method of analysis can be used to detect a polymorphism in a nucleic acid. Methods of analysis can include conventional Sanger based sequencing, pyrosequencing, next generation sequencing, allele specific PCR, allele-specific restriction digests, microarrays, single molecule sequencing, sequencing by synthesis, single strand conformation polymorphism (SSCP) detection, restriction length polymorphism (RFLP) analysis, denaturing high performance liquid chromatography (DHPLC), and the like. The aforementioned techniques are well known in the art. Detailed description of these techniques can be found in a variety of publications, including, e.g., "Laboratory Methods for the Detection of Mutations and Polymorphisms in DNA" (1997) G. R. Taylor, ed., CRC Press, and references cited therein.

In some cases, a test nucleic acid sample can be amplified with primers which amplify a sequence region known to comprise the polymorphism(s) of interest. For example, oligonucleotide primers such as SEQ ID NO: 2 (ACCTGGTCCCCA-AAAGA) and SEQ ID NO: 3 (CGGGGATTTGGAAAGTTG) can be used to amplify a region of interest in a TNF-alpha nucleic acid. The primers of SEQ ID NO: 2 and SEQ ID NO: 3 amplify a 186 base pair fragment (SEQ ID NO: 4) in the promoter region of a TNF-alpha nucleic acid. In some cases, alternate oligonucleotide primer sequences could be used to amplify all or part of the TNF-alpha nucleic acid fragment of SEQ ID NO: 4 (FIG. 5) or any fragment of SEQ ID NO: 1 that when amplified, can be analyzed for association with increased TNF-alpha expression levels. The reference TNF-alpha promoter region nucleic acid sequence is provided in GenBank (Accession No. AB048818; GI No. 13365764); a portion of this sequence is provided in FIG. 1 and SEQ ID NO: 1.

In another example, commercially available kits can be used to amplify a region of interest. For example, a commercially available kit, such as a SNP genotyping kit from Applied Biosystems, can be used to amplify of region of interest in an Interleukin 1B (IL1B) nucleic acid. In some cases alternate kits or methods could be used to amplify all or part of an IL1B nucleic acid fragment that when amplified, can be analyzed for the presence or absence of a polymorphism identified as rs1143627 (−31T>C) which can be viewed in the single nucleotide polymorphism section of the NCBI website. It is noted that the T allele of this SNP is associated with higher risk of having or developing ulcerative colitis associated-colorectal cancer, whereas the C allele is associated with lower risk of developing ulcerative colitis associated-colorectal cancer. The exact position of the aforementioned variants may vary from individual to individual or from species to species, e.g., by from 1 to about 10 base pairs. In some cases, polymorphisms may occur in the promoter region of an IL1B nucleic acid. In some cases, polymorphisms may occur in the coding or non-coding regions of an IL1B nucleic acid.

A mammal diagnosed with IBD and containing one or more polymorphisms in an IL1B nucleic acid can be classified as being at a higher risk of having or developing colorectal cancer as compared to a corresponding mammal containing wild-type IL1B nucleic acid at one or both alleles. For example, detection of the rs1143627 polymorphism in a sample from an IBD patient indicates that the patient is at a higher risk of developing colorectal cancer. Detection of this polymorphism allows selection of a monitoring schedule or treatment plan that is most likely to be effective in early diagnosis and treatment of CRC. Other non-limiting examples of polymorphisms associated with a higher risk of developing colorectal cancer include SNP's found in an Interleukin-23 Receptor (IL-23R) nucleic acid such as rs10889677 (2284C>A) and rs1884444 (94G>T).

Polymorphisms in promoter sequences may affect gene expression. In some cases, serum levels of one or more of a TNF-alpha, IL1B, or IL-23R polypeptide can be measured to determine whether or not an IBD patient has an increased risk of developing CRC. For example, an IBD patient with an increased serum level of a TNF-alpha polypeptide as compared to a normal control may have an increased likelihood of developing CRC. Detection of an increased level of a TNF-alpha polypeptide allows selection of a monitoring schedule or treatment plan that is most likely to be effective in early diagnosis and treatment of CRC. Any known method for measuring polypeptide levels can be used, such as denaturing high performance liquid chromatography (DHPLC, Underhill et al. (1997) *Genome Res.* 7:996-1005), infrared matrix-assisted laser desorption/ionization (IR-MALDI) mass spectrometry (WO 99/57318), and combinations of such methods. Other useful detection techniques include, but are not limited to surface-enhanced laser desorption/ionization (SELDI) mass spectrometry, immunoassays, and array-based technologies. Other non-limiting examples of increased polypeptide levels associated with a higher risk of developing CRC include increased IL-23R and IL1B polypeptide levels.

It is understood that the term "specifically amplifies" refers to the ability of an oligonucleotide primer to interact specifically with a particular nucleic acid without significantly cross-reacting with other different nucleic acids in the same environment and facilitate or promote the amplification of that particular nucleic acid. Likewise, the term "specifically hybridizes" refers to the ability of an oligonucleotide probe to interact specifically with a particular nucleic acid without significantly cross-reacting with other different nucleic acids in the same environment and facilitate or promote the detection of that particular nucleic acid.

The term "elevated level" as used herein with respect to the level of an MPO polypeptide is any level that is above a median polypeptide level in a sample from a random population of mammals (e.g., a random population of 10, 20, 30, 40, 50, 100, or 500 mammals) that do not have UC-CRC. Elevated MPO polypeptide levels can be any level provided that the level is greater than a corresponding reference level.

For example, an elevated level of MPO polypeptide can be 0.5, 1, 2, 3, 4, 5, 6, 7, 8, 9, 10, or more fold greater than the reference level MPO polypeptide observed in a normal colon biopsy or blood sample. It is noted that a reference level can be any amount. For example, a reference level can be zero. In some cases, an elevated level of an MPO polypeptide can be any detectable level of an MPO polypeptide in a tissue biopsy sample.

The term "elevated level" as used herein with respect to the methylation status of MINT1 or RUNX3 nucleic acid is any methylation level that is above a median methylation level in a sample from a random population of mammals (e.g., a random population of 10, 20, 30, 40, 50, 100, or 500 mammals) that do not have UC-CRC. Elevated MINT1 or RUNX3 methylation levels can be any level provided that the level is greater than a corresponding reference level. For example, an elevated level of MINT1 or RUNX3 methylation can be 0.5, 1, 2, 3, 4, 5, 6, 7, 8, 9, 10, or more fold greater than the reference level methylation observed in a normal colon biopsy sample. It is noted that a reference level can be any amount.

The term "reduced level" as used herein with respect to the level of COX-2 methylation status is any level that is below a median methylation level in a sample from a random population of mammals (e.g., a random population of 10, 20, 30, 40, 50, 100, or 500 mammals) that do not have UC-CRC. Reduced COX-2 methylation levels can be any level provided that the level is lesser than a corresponding reference level. For example, a reduced level of COX-2 methylation can be 0.5, 1, 2, 3, 4, 5, 6, 7, 8, 9, 10, or more fold lesser than the reference level methylation observed in a normal colon biopsy sample. It is noted that a reference level can be any amount.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment," as used herein, includes any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

This document provides kits that can be used to determine the level of one or more biomolecules in a sample. Kits can contain an oligonucleotide primer pair that specifically amplifies all or a portion of a target region of a nucleic acid. For example, kits can contain oligonucleotide primers that specifically amplify a TNF-alpha, COX-2, MINT1, or a RUNX3 nucleic acid. Target regions can be defined at any place along a TNF-alpha, COX-2, MINT1, or RUNX3 nucleic acid. For example, a target region can be defined by nucleotides 1-500 of the 5' portion of a TNF-alpha nucleic acid. In this case, a kit of the invention can contain an oligonucleotide primer pair that specifically amplifies all 500 nucleotides defining that target region, or a portion (e.g., nucleotides 80-188) of that target region.

Components and methods for producing kits are well known. Kits can contain multiple oligonucleotide primer pairs that specifically amplify TNF-alpha, COX-2, MINT1, or RUNX3-related nucleic acids, or probes that specifically hybridize TNF-alpha, COX-2, MINT1, or RUNX3-related nucleic acids. In addition, kits can contain antibodies for detecting MPO-related polypeptides. The kits provided herein also can contain a reference chart that indicates a reference level or baseline for MPO polypeptides or TNF-alpha, COX-2, MINT1, or RUNX3 nucleic acids. Kits can be configured in any type of design (e.g., microtiter plate design) and can be made of any type of material (e.g., plastic).

In some cases, a human may have a family history of primary sclerosing cholangitis (PSC) or CRC. Family history or relatives with PSC or CRC can be identified by examining medical records or family tree history. The methods provided in this document can also be used to identify CRC risk in relatives of affected mammals likely to have IBD or UC. Thus, these methods can facilitate decisions regarding the course of evaluation and treatment in humans with and without altered methylation in MINT1, COX-2, or RUNX3 nucleic acids, with and without polymorphisms in a TNF-alpha nucleic acid, or with and without increased MPO polypeptide levels.

This document also provides materials and methods to assist a medical professional in determining the risk of having or developing colorectal cancer in a mammal. Such a medical professional can be, for example, a physician, a nurse, a medical laboratory technologist, or a pharmacist. A person can be assisted by (1) determining the presence or absence of a nucleic acid polymorphism in a nucleic acid such as a TNF-alpha nucleic acid, determining the methylation status of a nucleic acids such as a RUNX3 nucleic acid in a test sample, and/or determining the level of a polypeptide such as an MPO polypeptide, and (2) communicating information about the presence, absence, or level of that marker to that medical professional.

After the presence, absence, level, or status of a particular biomolecule or biomolecules is reported, a medical professional can take one or more actions that can affect patient care. For example, a medical professional can record the results in a patient's medical record. In some cases, a medical professional can record that a patient is at an increased risk of developing colorectal cancer, or otherwise transform the patient's medical record to reflect the patient's medical condition. In some cases, a medical professional can review and evaluate a patient's entire medical record and assess multiple strategies for clinical intervention of a patient's condition. In some cases, a medical professional can recommend a change in therapy or a change in frequency or type of surveillance.

Any appropriate method can be used to communicate information to another person. For example, information can be given directly or indirectly to a person. In addition, any type of communication can be used to communicate the information. For example, mail, e mail, telephone, and face-to-face interactions can be used. The information also can be communicated to a person by making that information electronically available to the person. For example, the information can be communicated to a person by placing the information on a computer database such that the person can access the information. In addition, the information can be communicated to a hospital, clinic, or research facility at which the person is located.

The invention will be further described in the following examples, which do not limit the scope of the invention described in the claims.

EXAMPLES

Example 1—Methylation Status of Genes in Non-Neoplastic Mucosa from Patients with Ulcerative Colitis-Associated Colorectal Cancer Patient Selection The Mayo Clinic Institutional Review Board approved this work. The UC-CRC cases and UC controls analyzed herein were described elsewhere (Garrity-Park et al., *Am. J. Gastroenterol*, (2008) and Garrity-Park et al., *Gut* (2009)). UC-CRC cases were selected from a review of 274 patients identified from the Mayo Clinic centralized diagnostic index of medical records (1976-2006). These patients had inflammatory bowel disease (either Crohn's or UC) and CRC. Patients with Crohn's disease were excluded. Medical records for the remaining UC-CRC patients were reviewed to establish a date of disease onset. For each case, pathology slides from the surgical resection were also recalled to confirm the diagnosis of UC and identify the best tumor and non-adjacent, non-neoplastic block for DNA extraction. Patients who did not have UC confirmed by review of the pathology or whose duration of disease was less than 10 years were excluded. After these exclusions, 114 UC-CRC cases were included.

Potential UC controls were identified through the Mayo pathology index (1994-2006), which indicated the patient age, gender, and extent of UC as well as the presence of other confounding pathologies such as dysplasia. The final pool of potential UC controls for this work included UC patients who did not develop CRC, who underwent either colectomy or colonoscopy with biopsy at the Mayo Clinic, and who did not have prior dysplasia. The Mayo Clinic centralized diagnostic index of medical records was used with these remaining controls to establish a date of diagnosis. Patients with less than ten years between the date of UC diagnosis and either colectomy or date of last biopsy were excluded as were patients with a prior dysplasia diagnosis. From the remaining list, 181 controls were selected that were most closely matched to the UC-CRC cases with regard to gender, age, ethnicity, duration, and extent of UC. The surgical resection or biopsy specimens from these 181 controls were re-reviewed to confirm histologically the diagnosis of UC. After final review, 114 UC controls were included.

DNA Extraction

All formalin-fixed, paraffin-embedded (FFPE) blocks and hematoxylin and eosin-stained (H&E) slides were reviewed on all cases and controls to determine the inflammatory activity level (as assessed by neutrophil infiltrates) for all non-neoplastic sections. Each section was scored as normal, inactive (0), mildly active (1), moderate (2), or severe (3). A total of three different DNA extractions were then completed: 1) UC control, 2) UC-CRC non-neoplastic, non-adjacent, and 3) UC-CRC tumor. For non-adjacent, non-neoplastic UC-CRC cases and UC controls, DNA was extracted from all non-neoplastic paraffin tissue sections that showed evidence of chronic disease (scores 0-3; n=1-6 blocks/patient). For the tumor DNA extraction, only the section with confirmed CRC was used. Any sections scored as "normal colon" or any dysplastic lesions located away from the CRC in UC-CRC cases were excluded from all extractions. DNA was extracted using Gentra Puregene Tissue kit (Qiagen, Valencia, Calif.). DNA pellets were suspended in TE (10 mM Tris, pH=7.5, 0.1 mM EDTA, Integrated DNA Technologies, Coralville, Iowa) and quantified using Quant-iT™ PicoGreen® (Invitrogen, Carlsbad, Calif.).

Bisulfite Treatment/Methylation Specific Polymerase Chain Reaction (MSP)

Methylation status of each gene was determined using MSP after bisulfite treatment of 500 ng of DNA using the EZ DNA Methylation-Gold Kit™ (Zymo Research, Orange, Calif.) following standard protocols. Primers were designed using Methyl Primer Express v1.0 software (Applied Biosystems, Foster City, Calif.) (Table 2). Most of the proposed genes have multiple methylation sites. Therefore, whenever possible, sites chosen for evaluation were selected based on published studies that indicated that methylation in that area altered protein expression in situ. Primers were designed for the following genes: p16, p14, cyclooxygenase-2 (COX-2), e-cadherin, estrogen receptor (ER), HPP1, methylated-in-tumor 1 (MINT1), MINT31, RUNX3, and sodium solute symporter family 5 member 8 protein (SLC5A8). Unmethylated and methylated PCR reactions were carried out in separate, 25 µL reactions.

Amplicons were run through ethidium-stained agarose gels and visualized using the BioRad Gel Doc™ (Bio-Rad, Hercules, Calif.). Positive and negative controls were included in each experimental set-up. A sample was considered positive if amplicon was produced using the methylated primer set. A sample was negative for methylation if amplicon was produced using only the unmethylated primer set. Samples that did not produce amplicons for either reaction were excluded from analyses. To ensure the specificity of each reaction and to validate the adequacy of the bisulfite modification, 25 methylated and 25 unmethylated amplicons were sequenced for each gene using the ABI PRISM™ (Applied Biosystems) after shrimp alkaline phosphatase (USB, Cleveland, Ohio) and exonuclease (USB) treatment of the amplicon. All of the MSP products demonstrated methylation of CpG sites. To test the sensitivity of each methylated/unmethylated assay, serial dilutions of positive control DNA (100% to 0%) were tested for each gene. All assays could detect a positive result with 5% positive control DNA.

TABLE 2

Methylation-specific PCR primers.

| Gene | Forward (5'→3') | Reverse (5'→3') | Size (bp) | Temp |
|---|---|---|---|---|
| p16 | | | | |
| Methylated | TGGGGCGGATCGCGT GCGTT (SEQ ID NO: 5) | CGACCCCGAACCGC GACGGT (SEQ ID NO: 6) | 140 | 60 |
| Unmethylated | TGGGGTGGATTGTGT GTGTTTGGT (SEQ ID NO: 7) | CCACCTCCAACAATA CCCATACCT (SEQ ID NO: 8) | 172 | 60 |

TABLE 2-continued

Methylation-specific PCR primers.

| Gene | Forward (5'→3') | Reverse (5'→3') | Size (bp) | Temp |
|---|---|---|---|---|
| p14 | | | | |
| Methylated | GGCGGCGAGAATATGGTGC (SEQ ID NO: 9) | ACGACGAACGGCCCTAACG (SEQ ID NO: 10) | 137 | 60 |
| Unmethylated | TTGGTGTTAAAGGGTGGT (SEQ ID NO: 11) | AAAAACCCTCACTCACAA (SEQ ID NO: 12) | 126 | 60 |
| COX-2 | | | | |
| Methylated | AGGGGATTTTTGCGTTTTC (SEQ ID NO: 13) | CGCAATCTTTACCCGAACGC (SEQ ID NO: 14) | 142 | 55 |
| Unmethylated | GAGGGGATTTTTGTGTTTTT (SEQ ID NO: 15) | TCTTTACCCAAACACTTCCAA (SEQ ID NO: 16) | 138 | 60 |
| E-cadherin | | | | |
| Methylated | TTAGAGGGTTATCGCGTTTATGC (SEQ ID NO: 17) | ACCAAATAAACCCCGAAACACGG (SEQ ID NO: 18) | 150 | 50 |
| Unmethylated | TAATTTTAGGTTAGAGGGTTATTGT (SEQ ID NO: 19) | CACAACCAATCAACAACACA (SEQ ID NO: 20) | 97 | 63 |
| Estrogen receptor | | | | |
| Methylated | CGTTCGGTTTTATCGGATTC (SEQ ID NO: 21) | AAAAACTCAAAAACCGACGA (SEQ ID NO: 22) | 138 | 55 |
| Unmethylated | TGAGTTGGAGTTTTTGAATTGTTT (SEQ ID NO: 23) | ACACATTAACAACAACCACA (SEQ ID NO: 24) | 149 | 60 |
| HPP1 | | | | |
| Methylated | TTTCGGCGTAGTTTTTTAGC (SEQ ID NO: 25) | ACTAAACATCCCGCGAACG (SEQ ID NO: 26) | 167 | 60 |
| Unmethylated | TGGTGTAGTTTTTTAGTGGATG (SEQ ID NO: 27) | ACAATAACAATAACACCCAACA (SEQ ID NO: 28) | 127 | 60 |
| MINT1 | | | | |
| Methylated | TTTCGAAGCGTTTGTTTGGC (SEQ ID NO: 29) | CAAAAAACCTCAACCCCGGG (SEQ ID NO: 30) | 81 | 55 |
| Unmethylated | TGGAGAGTAGGGGAGTTTGT (SEQ ID NO: 31) | AACCTAACACACAACAAACA (SEQ ID NO: 32) | 112 | 60 |
| MINT31 | | | | |
| Methylated | TATTCGATTTATTTCGTC (SEQ ID NO: 33) | CTACGAAAAATAAACACG (SEQ ID NO: 34) | 105 | 55 |
| Unmethylated | GATTTTAATTTTTGTGGTGGT (SEQ ID NO: 35) | CTAAAACCATCACCCCTAAACA (SEQ ID NO: 36) | 95 | 60 |
| RUNX3 | | | | |
| Methylated | CGTTTGCGTGGTTCGTAGTAC (SEQ ID NO: 37) | ACGACGACGACGACGACA (SEQ ID NO: 38) | 129 | 60 |
| Unmethylated | TTGGGTTTTATGGTTGTTTGTGT (SEQ ID NO: 39) | ACCCAACACCCTAACAACCAC (SEQ ID NO: 40) | 159 | 60 |
| SLC5A8 | | | | |
| Methylated | ACGGGGTATCGGTATTTTC (SEQ ID NO: 41) | TACGATCATTCTACGACCG (SEQ ID NO: 42) | 151 | 55 |
| Unmethylated | GGTTATTTTGGTTGTTATT (SEQ ID NO: 43) | CAAACACTACAATCATTCTACA (SEQ ID NO: 44) | 104 | 55 | bp, base pairs (bases in bold indicate methylation sites); COX, cyclooxygenase; HPP, hyperplastic polyposis gene; MINT, methylated-in-tumor; RUNX, runt-related transcript factor; SLC5A8, sodium solute symporter family-5 member-8.

Inflammation Scoring

All H&E slides from each case or control were reviewed by a pathologist, and the histologic disease activity was scored as inactive, mild, moderate, or severe based on the percentage of neutrophils. Each histologic activity level was given a corresponding number, such that inactive sections were scored as 0 and mildly active, moderate, or severe sections were scored as 1, 2, or 3, respectively. To obtain the final inflammation score for each case or control extracted, the values for all sections included in the extraction were summed and then divided by the total number of sections used. For instance, if a non-adjacent, non-neoplastic extraction for a case had four sections that were inactive and two sections that were mildly active, the inflammation score would be 0.33. Scores were obtained for all non-adjacent, non-neoplastic extractions for cases and for all extractions for controls.

Statistics

For initial identification of potential genes, a univariate analysis using the Fisher's exact test was done to compare the prevalence of methylation for each gene in UC-CRC cases versus UC controls. For genes identified as significant, another Fisher's Exact test was performed to determine its significance when comparing non-neoplastic DNA from UC-CRC cases versus UC controls. A multivariable analysis was then done to test for interactions between the genes found to be significant in the non-neoplastic comparison. Finally, logistic regression modeling was performed to determine the additive effect of these significant genes.

Results

Patient Selection

The summary of patient characteristics is given in Table 3. There were no significant differences between cases and controls with regard to age, gender, family history of CRC, or duration n/extent of UC. Because there were no significant differences in distribution of disease extent between cases and controls (p=0.07), all subsequent analyses involving extent therefore used the broad categorization of extensive versus non-extensive (left-sided and proctitis) disease for cases and controls. Primary sclerosing cholangitis (PSC) was more prevalent in UC-CRC cases (p<0.0001). All cases and controls were Caucasian.

TABLE 3

Demographic and clinical features of 114 UC-CRC cases and 114 UC controls.

| Demographic/clinical information | UC-CRC (n = 114) | UC, no CRC (n = 114) | P value |
|---|---|---|---|
| Mean age at index date, years (range)[a] | 47.8 (26-82) | 48.8 (24-77) | 0.35 |
| Gender, n (%) | | | |
| Female | 36 (32) | 36 (32) | |
| Male | 78 (68) | 78 (68) | 1.00 |
| Mean duration of UC at index date, years (range) | 20.3 (10-49) | 19.5 (10-45) | 0.37 |
| Maximal extent, n (%)[b] | | | |
| Proctitis | 8 (7.0) | 7 (6) | |
| Left-sided | 12 (10.5) | 25 (22) | |
| Extensive | 94 (82.5) | 82 (72) | 0.07[c] |
| PSC, n (% yes) | 31 (27.2) | 4 (3.5) | <0.0001 |
| Family history of CRC, n (%) | 19 (17) | 15 (13) | 0.58 |

[a]Index date for UC-CRC was the age at CRC and for UC controls was the age at colectomy or most recent biopsy.
[b]Extent based on histological assessment of involvement.
[c]$\chi^2$-Test, P value represents the comparison between cases and controls with extensive colitis vs. left-sided vs. proctitis.
Values in bold are significant.

DNA Extraction and Location

Sixty percent of UC-CRC non-adjacent, non-neoplastic DNA extractions included a tissue section that was from the same segment of the colon in which the tumor arose, i.e. the tumor was in the ascending colon, and a different block without neoplasia was also available from the ascending colon. The majority of UC-CRC non-neoplastic and UC control DNA extractions included tissues obtained from both the left and right side of the colon (69% versus 74%, p=0.57). Three cases and two controls had tissue available from the rectum only. The majority of tissues used for UC-CRC case and UC control (218/228) extractions were obtained from resected colons. The remaining 10 patients had only biopsy samples available.

UC-CRC DNA Versus UC Control DNA

Univariate Analyses

To identify targets to investigate in non-adjacent, non-neoplastic regions of the UC-CRC colon, initial univariate analyses focused on the level of gene methylation in DNA extracted from tumor sections only as compared to UC controls. The majority of DNA from UC controls (between 96 to 109) and UC-CRC tumors (between 83 to 100) were successfully amplified for each target. Table 4 summarizes the results of these analyses for all 10 genes included in this study. The prevalence of gene methylation for p16, RUNX3, MINT1, MINT31, and HPP1 was significantly increased in UC-CRC cases versus controls. Conversely, COX-2 and e-cadherin were more frequently methylated in controls as compared to cases. The difference in methylation for ER, p14, and SLC5A8 was not significantly different between cases and controls.

TABLE 4

Univariate analyses of gene methylation status in UC-CRC cases (tumor sections) vs. UC controls

| Gene (±for methylation) | UC-CRC (%) | UC controls (%) | P value[a] |
|---|---|---|---|
| (a) Methylated in UC-CRC cases | | | |
| p16 | | | |
| Negative | 72 (84.7) | 107 (100) | |
| Positive | 13 (15.3) | 0 (0) | <0.0001 |
| RUNX3 | | | |
| Negative | 46 (55.4) | 97 (93.3) | |
| Positive | 37 (44.6) | 7 (6.7) | <0.0001 |
| MINT1 | | | |
| Negative | 46 (49.5) | 87 (85.3) | |
| Positive | 47 (50.5) | 15 (14.7) | <0.0001 |
| MINT31 | | | |
| Negative | 39 (40.6) | 76 (79.2) | |
| Positive | 57 (59.4) | 20 (20.8) | <0.0001 |
| HPP1 | | | |
| Negative | 19 (21.3) | 53 (49.5) | |
| Positive | 70 (78.7) | 54 (50.5) | 0.0001 |
| ESR1 | | | |
| Negative | 10 (10.8) | 17 (15.9) | |
| Positive | 83 (89.2) | 90 (84.1) | 0.31 |
| p14 | | | |
| Negative | 75 (81.5) | 95 (88.0) | |
| Positive | 17 (18.5) | 13 (12.0) | 0.24 |

TABLE 4-continued

Univariate analyses of gene methylation status
in UC-CRC cases (tumor sections) vs. UC controls

| Gene (± for methylation) | UC-CRC (%) | UC controls (%) | P value[a] |
|---|---|---|---|
| SLC5A8 | | | |
| Negative | 14 (14.7) | 6 (5.8) | |
| Positive | 81 (85.3) | 97 (94.2) | 0.06 |
| (b) Methylated in UC controls | | | |
| COX-2 | | | |
| Negative | 64 (66.7) | 43 (39.4) | |
| Positive | 32 (33.3) | 66 (60.6) | 0.0001 |
| E-cadherin | | | |
| Negative | 64 (64.0) | 42 (38.9) | |
| Positive | 36 (36.0) | 66 (61.1) | 0.0003 |

COX, cyclooxygenase;
CRC, colorectal cancer;
HPP, hyperplastic polyposis gene;
MINT, methylated-in-tumor;
RUNX, runt-related transcript factor;
SLC5A8, sodium solute symporter family-5 member-8;
UC, ulcerative colitis.
[a]Calculated using Fisher's exact test.
Values in bold are significant.

UC-CRC Non-Neoplastic DNA Versus UC-Control DNA

Univariate Analyses

Only genes that were significantly different between tumor and UC controls were tested for significance in non-adjacent, non-neoplastic normal tissue. The majority of DNA from UC controls (between 96 to 109) and non-adjacent, non-neoplastic areas from UC-CRC patients (between 66 to 88) were successfully amplified for each target. RUNX3, p16, MINT1, MINT31, e-cadherin, and COX-2 remained significantly associated with UC-CRC. The association involving HPP1 was no longer significant (Table 5).

TABLE 5

Univariate analyses of gene methylation status in UC-CRC
cases (non-adjacent, non-neoplastic sections) vs. UC controls.

| Gene (± for methylation) | UC-CRC (%) | UC controls (%) | P value[a] |
|---|---|---|---|
| (a) Methylated in UC-CRC cases | | | |
| p16 | | | |
| Negative | 53 (80.3) | 107 (100) | |
| Positive | 13 (19.7) | 0 (0) | <0.0001 |
| RUNX3 | | | |
| Negative | 37 (49.3) | 97 (93.3) | |
| Positive | 38 (50.7) | 7 (6.7) | <0.0001 |
| MINT1 | | | |
| Negative | 48 (54.5) | 87 (85.3) | |
| Positive | 40 (45.5) | 15 (14.7) | <0.0001 |
| MINT31 | | | |
| Negative | 47 (54.7) | 76 (79.2) | |
| Positive | 39 (45.3) | 20 (20.8) | 0.0005 |
| HPP1 | | | |
| Negative | 27 (36.0) | 53 (49.5) | |
| Positive | 48 (64.0) | 54 (50.5) | 0.09 |

TABLE 5-continued

Univariate analyses of gene methylation status in UC-CRC
cases (non-adjacent, non-neoplastic sections) vs. UC controls.

| Gene (± for methylation) | UC-CRC (%) | UC controls (%) | P value[a] |
|---|---|---|---|
| (b) Methylated in UC controls | | | |
| COX-2 | | | |
| Negative | 54 (61.4) | 43 (39.4) | |
| Positive | 34 (38.6) | 66 (60.6) | 0.003 |
| E-cadherin | | | |
| Negative | 46 (55.4) | 42 (38.9) | |
| Positive | 37 (44.6) | 66 (61.1) | 0.03 |

COX, cyclooxygenase;
CRC, colorectal cancer;
HPP, hyperplastic polyposis gene;
MINT, methylated-in-tumor;
RUNX, runt-related transcript factor;
SLC5A8, sodium solute symporter family-5 member-8;
UC, ulcerative colitis.
[a] Calculated using Fisher's exact test.
Values in bold are significant.

Multivariable Analyses

Multivariable logistic regression was performed with the univariately significant genes (p16, RUNX3, MINT1, MINT31, e-cadherin, and COX-2) to determine if each gene was independently significant for UC-CRC. Table 6 indicates p-values and odds ratios for the three genes that remained significant in this analysis. Methylation of RUNX3 and MINT1 in non-neoplastic sections remained strongly associated with the presence of CRC. Conversely, unmethylated COX-2 was an indication of CRC.

TABLE 6

Multivariate analyses of UC-CRC (non-adjacent,
non-neoplastic sections) vs. UC controls.

| Gene | Logistic regression | | |
|---|---|---|---|
| (± for methylation) | Odds ratio | CI | P value |
| (a) Significantly methylated in UC-CRC cases | | | |
| RUNX3 | 12.6 | 4.4, 35.7 | <0.0001 |
| MINT1 | 9.0 | 3.4, 23.7 | <0.0001 |
| (b) Significantly methylated in UC controls | | | |
| COX-2 | 0.2 | 0.07, 0.4 | 0.0002 |

CI, confidence interval;
COX, cyclooxygenase;
CRC, colorectal cancer;
HPP, hyperplastic polyposis gene;
MINT, methylated-in-tumor;
RUNX, runt-related transcript factor;
UC, ulcerative colitis.
Values in bold are significant.

Given the association of methylation with inflammation (Kundu et al., *Mutat Res* (2008)), a multivariable logistic regression also was performed that included RUNX3, MINT1, COX-2, and the inflammation score to determine if the increased incidence of methylation merely reflected a higher inflammation score in cases versus controls. Table 7A summarizes these findings. The p-values and odds ratios all remained highly significant even when the degree of inflammation, as determined by H&E, was incorporated into the logistic regression. Interestingly, greater inflammation as determined by neutrophils on H&E was not associated with UC-CRC.

Because cases and controls varied with regard to the presence of PSC, logistic regression also was performed to ensure that the significance of RUNX3, MINT1, and COX-2 was independent of PSC (Table 7B). Although PSC remained highly associated with UC-CRC, the methylation status of these three genes was still significant in this analysis.

Given that for the majority of the UC-CRC cases (60%) the non-adjacent, non-neoplastic DNA sample included tissue procured from the same region in which the tumor arose, analysis was performed to determine whether proximity to the tumor affected methylation status. The presence or absence of a non-neoplastic section from within the corresponding tumor region did not affect the prevalence of methylation for RUNX3, COX-2, or MINT1 (P=0.17, 0.69, and 0.23, respectively).

Although there was no significant difference between the UC-CRC non-neoplastic and UC controls with regard to inclusion of tissue from both the right and the left colon (P=0.57), tests were performed to determine whether this could have affected the methylation status of a given gene. It was found that the prevalence of altered methylation was not significantly different between DNA samples containing tissue sections from both the left and the right side of the colon and those that did not (P=0.24, 0.87, and 0.48 for COX-2, MINT1, and RUNX3, respectively).

Finally, to interrogate whether these alterations in methylation were specific to UC, the prevalence of altered gene methylation in a cohort of non-UC patients described elsewhere (Garrity-Park et al., *Gut*, 58:1226-1233 (2009)) was assessed. In brief, this cohort included biopsies taken from 60 non-UC normal patients that are a part of the average risk CRC screening population at the Mayo Clinic. These were frequency matched for age to the UC patients (both CRC and non-CRC controls) in this study (average age for UC group, 48 years, vs. 49 years for non-UC patients). For RUNX3, COX-2, and MINT1, there was no significant difference between the UC controls and non-UC patients (P=0.53, 0.21, and 0.70, respectively), but there was a significance between the UC-CRC cases and non-UC patients (P<0.0001, 0.001, and <0.001, respectively).

TABLE 7

Effect of inclusion of inflammation and PSC in the multivariable model of UC-CRC risk

|  | Odds ratio | CI | P value |
|---|---|---|---|
| (a) Inflammation | | | |
| Inflammation score | 0.3 | 0.1, 0.6 | 0.001 |
| RUNX3 | 11.9 | 3.9, 36.0 | <0.0001 |
| MINT1 | 9.7 | 3.4, 27.7 | <0.0001 |
| COX-2 | 0.2 | 0.1, 0.5 | 0.002 |
| (b) PSC | | | |
| PSC | 9 | 2.2, 37.8 | 0.003 |
| RUNX3 | 11.7 | 3.9, 35.3 | <0.0001 |
| MINT1 | 10.4 | 3.7, 28.8 | <0.0001 |
| COX-2 | 0.2 | 0.06, 0.4 | 0.0002 |

CI, confidence interval;
COX, cyclooxygenase;
CRC, colorectal cancer;
MINT, methylated-in-tumor;
PSC, primary sclerosing cholangitis;
RUNX, runt-related transcript factor;
UC, ulcerative colitis.
Values in bold are significant.

Diagnostic Modeling

Logistic regression modeling was undertaken to determine if RUNX3, MINT1, and COX-2 interacted to have an additive effect, i.e. did the odds of having a synchronous CRC increase as the number of genes altered increased (Table 8). These analyses indicated that having both RUNX3 methylated and COX-2 unmethylated greatly increased the likelihood of a CRC elsewhere in the colon. This also was true of the concurrent presence of MINT1 methylation and COX-2 unmethylation, although the increase was not as dramatic. Although informative, it is important to note that the number of samples available for this analysis was small, as reflected by the wide confidence intervals.

TABLE 8

Logistic regression model of gene methylation on UC-CRC.

| Gene combination | Logistic regression | | Exact odds ratio CI estimation method (StatExact)$^a$ | |
|---|---|---|---|---|
| (M = methylated; U = unmethylated) | Odds Ratio | 95% CI | Exact | 95% CI |
| RUNX3 (M) + MINT1 (U) + COX-2 (M) | 1.0 | Referent | 1.0 | Referent |
| RUNX3 (M) + COX-2 (M) | 4.4 | 0.8, 23.2 | 4.2 | 0.5, 29.6 |
| MINT1 (M) + COX-2 (M) | 6.1 | 1.7, 21.4 | 5.9 | 1.5, 26.8 |
| RUNX3 (U) + MINT1 (U) + COX-2 (U) | 4.7 | 1.6, 14.0 | 4.6 | 1.4, 17.7 |
| RUNX3 (M) + MINT1 (M) + COX-2 (M) | $b$ | $b$ | $b$ | 29.5,$^b$ |
| RUNX3 (M) + COX-2 (U) | 61.2 | 6.2, 608.5 | 53.5 | 5.4, 2,833.0 |
| MINT1 (M) + COX-2 (U) | 17.6 | 2.5, 121.6 | 16.0 | 1.8, 219.4 |
| RUNX3 (M) + MINT1 (M) + COX-2 (U) | $b$ | $b$ | $b$ | 19.6,$^b$ |

$^a$Used to establish the lower confidence interval of the effect.
$^b$Unable to calculate because there is a 0 in the control group.

Example 2—Myeloperoxidase as a Measure of Disease Activity in UC: Association with UC-CRC, TNF Polymorphism, and RUNX3

Patient Selection

The Mayo Clinic Institutional Review Board approved this work. Patients with UC for >10 years who developed CRC were identified from the Mayo Clinic centralized diagnostic index of medical records (1986-2006). For each case, pathology slides from the surgical resection were recalled to confirm the diagnosis of UC and to identify the best non-adjacent, non-neoplastic block for immunostaining. Complete patient chart reviews were completed on all UC-CRC cases. Patients who did not have UC confirmed by review of the pathology or whose duration of disease was less than 10 years as documented in the clinical chart were excluded. A total of 50 UC-CRC cases, representing a subset of the UC-CRC cases described elsewhere (Garrity-Park et al., *Gut.*, 58:1226-1233 (2009); Garrity-Park et al., *Am. J. Gastroenterol.*, 103(2):407-15 (2008); and Garrity-Park et al., *Am. J Gastroenterol.*, 107(7):1610-9 (2010)), were examined in this study. UC controls were identified through the Mayo pathology index (1994-2006), which indicated the patient age, gender, and extent of UC as well as any other confounding pathologies such as dysplasia. Complete patient chart reviews were completed on all potential UC-controls. All potential UC-controls included UC patients who did not develop CRC, who had greater than 10 years of disease, who underwent either colectomy or colonoscopy with biopsy at the Mayo Clinic, and who did not have prior dysplasia. The final selection of UC-controls was based on frequency matching to UC-CRC cases for age, gender, extent, and duration of UC. A representative non-neoplastic section for each control was selected for analyses. A total of 50 UC-controls, a subset of the UC-control group described elsewhere (Garrity-Park et al., *Gut.*, 58:1226-1233 (2009); Garrity-Park et al., *Am. J. Gastroenterol.*, 103(2):407-15 (2008); and Garrity-Park et al., *Am. J. Gastroenterol.*, 107 (7): 1610-9 (2010)), were analyzed in this study.

H&E Scoring

A board certified pathologist reviewed and scored all sections. Histologic disease activity level was determined for the entire resection specimen using standard clinical methodologies utilizing H&E-stained sections. A disease activity score was assigned to each case or control using the following cut offs: 0 (inactive)—no neutrophils; 1 (mild)—rare neutrophils in crypt or surface epithelium; 2 (moderate)-neutrophils in up to 25% of crypts; and 3 (severe)—neutrophils in more than 25% of crypts.

For cases, slides from all available sections were examined to identify the best non-adjacent, non-neoplastic section for immunostaining. Whenever possible, this section was from an area distinct from where the tumor arose. Selection criteria also included 1) a well-oriented, full thickness section with generous amounts of mucosa for improved likelihood of informative IHC scoring and 2) a section reflective of overall disease state, i.e. if the patient had colitis to the hepatic flexure, sections were not chosen from the cecum.

For controls, slides from all available sections were examined to represent the best normal section for immunostaining. This included a well-oriented, full thickness section with generous amounts of mucosa that was reflective of the overall disease state.

Immunohistochemistry

Serial 4-micron sections were cut from each selected block. CD3 (DAKO, Carpinteria, Calif.), CD68 (DAKO), and MPO (Abcam, Cambridge, Mass.) antibodies were applied and developed using the DAKO Envision+ system (DAKO) after heated antigen retrieval. Whole sections were then digitally scanned using the NanoZoomer (Hamamatsu, Bridgewater, N.J.). Scans were downloaded and analyzed using ImageJ software (available at http://rsbweb.nih.gov/ij/). Using 15 different tissue sections, optimal thresholding was established that accurately distinguished positive cellular area (stained brown) from negative area (stained purple). Once established, this threshold was used for all subsequent slides to avoid biasing results. A total of four to six areas of mucosa were measured to determine the % area positive (scans were analyzed at 5× magnification). The average of the areas was recorded and used for statistical analyses.

TNF-α Polymorphism and RUNX3 Data

Prior studies included runt-related transcription factor 3 (RUNX3) methylation status and single nucleotide polymorphism testing for TNF-α (Garrity-Park et al., *Am. J. Gastroenterol.*, 103(2):407-15 (2008); and Garrity-Park et al., *Am. J Gastroenterol.*, 107(7):1610-9 (2010)). These previously derived data were used for associations in the current study. Cases and controls were selected without knowledge of TNF-α or RUNX3 status.

Statistical Analyses

Four statistical analyses were performed: 1) a Fisher exact test or Chi-square test was used to determine if the demographic/clinical selection criteria between UC-CRC and UC-control groups were appropriately matched; 2) a Fisher exact test was used to test for significant differences in % area between UC-CRC cases and UC-controls for CD3, CD68, and MPO, and for the association between the % area and the presence/absence of TNF-α SNP and RUNX3; 3) a Chi-square test was used to determine the association between case/control status and TNF-α SNP and RUNX3 methylation; and 4) logistic regression and receiver operating characteristic (ROC) analyses were performed to determine if the combination of any significant variables improved the prediction of case/control status.

Results

Patient and Sample Characteristics

UC-CRC cases and controls did not have any significant differences with regard to clinical characteristics (Table 9). Similarly, the UC-CRC or UC-control tissue sections selected for analyses were matched for location. However, UC-controls demonstrated significantly higher levels of histologic disease activity as determined by H&E than UC-CRC cases (Table 10).

TABLE 9

Characteristics of UC-CRC cases versus UC-controls.

| Characteristic | Cases (n = 50) | Controls (n = 50) | p-value |
|---|---|---|---|
| Average age, years (range) | 49.4 (26-80) | 50.8 (28-77) | 0.55 |
| Average duration of UC, years (range) | 20.6 (10-49) | 20.9 (10-45) | 0.86 |
| Extent of UC | | | |
| Extensive/pancolitis | 82% | 68% | 0.11 |
| Left-sided | 18% | 32% | |
| Gender | | | |
| Male | 68% | 66% | 0.83 |
| Female | 32% | 34% | |
| Ethnicity | | | |
| Caucasian | 100% | 100% | 1.00 |

TABLE 10

Pathological characteristics of UC-CRC cases versus UC-controls.

| | Cases (n = 50) | Controls (n = 50) | p-value* |
|---|---|---|---|
| Non-neoplastic tissue location | | | |
| Rectum | 21% | 26% | 0.12 |
| Sigmoid | 32% | 19% | |
| Descending | 15% | 33% | |
| Transverse | 9% | 14% | |
| Ascending | 9% | 5% | |
| Cecum | 15% | 2% | |
| Histologic disease activity level of non-neoplastic tissue section | | | |
| 0 | 66% | 41% | 0.01 |
| 1 | 26% | 35% | |
| 2 | 8% | 10% | |
| 3 | 0% | 14% | |

*p-value calculated using chi-square test.

Activity Level Determined Using Cell Surface Markers

Analysis of all cases and controls indicated detectable staining of all three cell surface markers, demonstrating that current H&E scoring, in general, underestimates cellular infiltrate (FIG. 6). Determination of the possible significance of a given cell surface marker in discriminating between UC-CRC cases and UC-controls is summarized in Table 11. For cases, MPO staining was significantly higher than that of UC-controls regardless of H&E activity level (p<0.0001). There were limited UC-CRC cases with active disease as measured by H&E so to facilitate subgroup analyses, cases and controls were pooled and categorized as either inactive (H&E=0) or active (H&E=1, 2 or 3). The significance of MPO was maintained in subgroup analyses of inactive cases and controls (H&E score of 0, p=0.002) as well as those classified as active (H&E score of 1-3, p=0.02). CD68 staining was slightly elevated in the overall analysis of UC-CRC cases versus controls (p=0.04), but this finding did not persist in subgroup analyses. CD3 staining did not vary between UC-CRC cases and UC-controls. The % area of positive staining for FOXP3, a marker of T-regulatory cells ($T_{reg}$) involved in suppression of inflammation (Kamikozuru et al., *Clin. Exp. Immunol.*, 156(2):320-327 (2009); Yu et al., *Inflamm. Bowel Dis.*, 13(2):191-199 (2007)), on a subset of cases and controls (n=25 for both) was subsequently investigated to see if this could account for the lack of difference in CD3. Analysis indicated that there was no significant difference (p=0.624, data not shown).

TABLE 11

Disease activity level versus cell surface markers in cases and controls.

| Activity | CD68 | | | MPO | | | CD3 | | |
|---|---|---|---|---|---|---|---|---|---|
| Level | Cases | Controls | p-value | Cases | Controls | p-value | Cases | Controls | p-value |
| All | 2.668 | 2.031 | 0.04 | 6.06 | 3.41 | <0.0001 | 3.58 | 3.44 | 0.70 |
| 0 | 2.76 | 1.95 | 0.14 | 6.44 | 2.77 | 0.002 | 3.65 | 2.69 | 0.07 |
| 1-3 | 2.49 | 2.09 | 0.25 | 5.74 | 3.85 | 0.02 | 3.45 | 3.94 | 0.43 |

Values in bold are significant.

MPO Expression Associated with Genetic and Epigenetic Changes

Figure 7A:
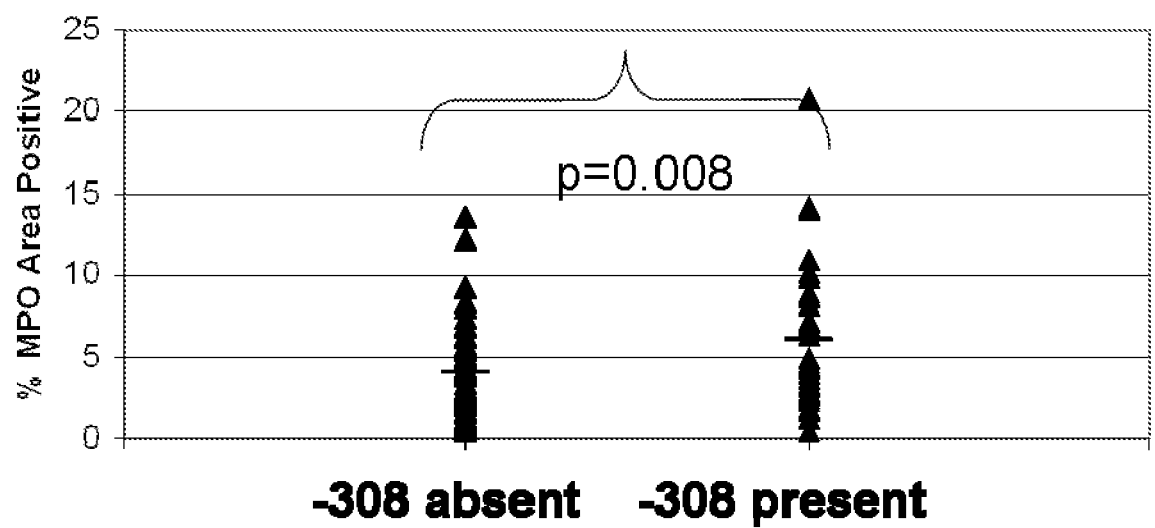
FIGS. 7A-7B contain data showing the association of MPO expression levels with a TNF-alpha polymorphism (FIG. 7A) and RUNX3 methylation status (FIG. 7B).
Figure 7B:
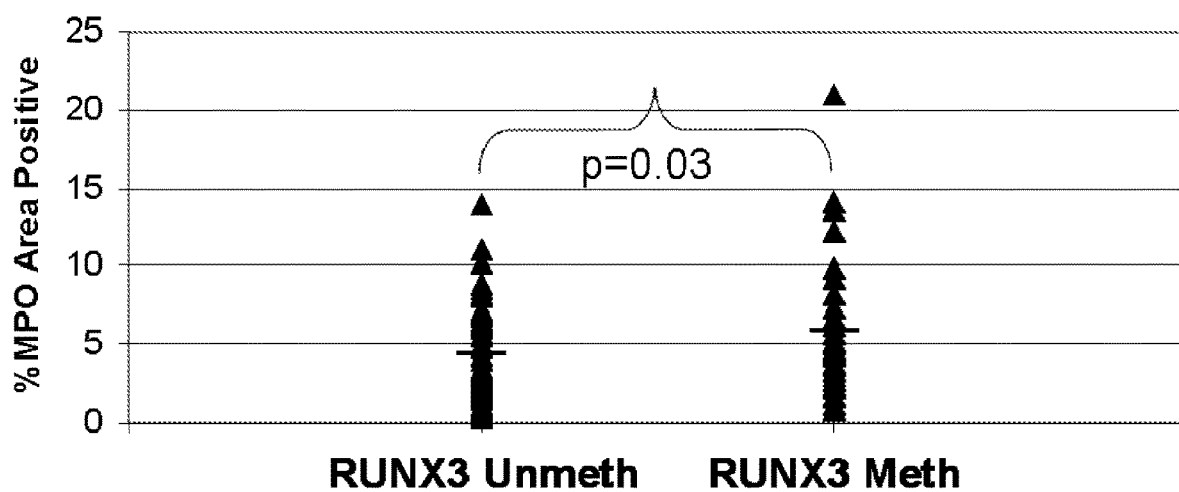
Figure 8A:
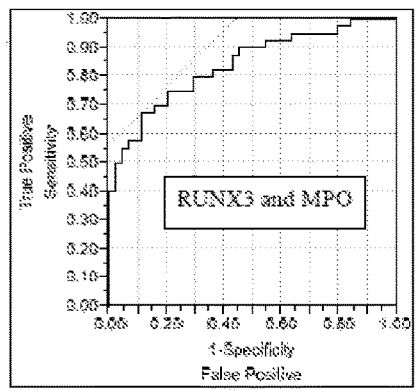
FIGS. 8A-8C contain Receiver operating characteristic (ROC) curves for combined markers. The area under the curve (AUC) for any combination of markers was higher than for TNF-α (72.0%), MPO (72.3%) or RUNX3 (66.9%) alone. The AUC for RUNX3 & MPO was 84.1, for TNF-α & MPO was 82.2% and for TNF-α, MPO & RUNX3 was 88.1%.
Figure 8B:
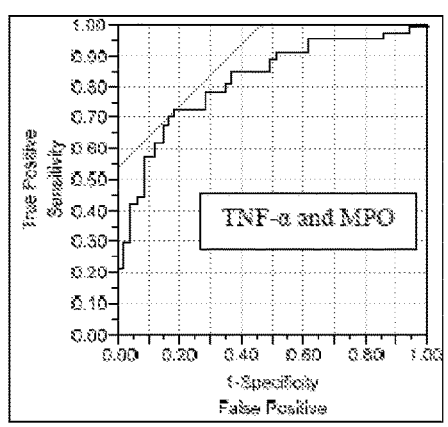
Figure 8C:
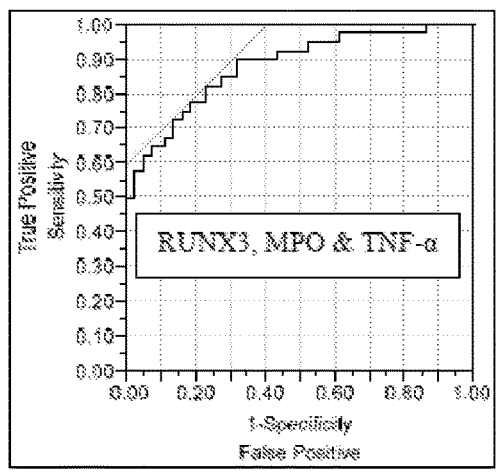

Increased MPO expression was significantly associated with the presence of the TNF-α-308 G>A SNP (5.95 vs 4.02, p=0.008) (FIG. 7A) as well as RUNX3 methylation (5.90 vs 4.30, p=0.03) (FIG. 7B). It is important to note that the RUNX3 methylation was detected in DNA extracted from non-adjacent, non-neoplastic of UC-CRC cases. Receiver operating characteristic (ROC) curves indicated that an analysis with combined markers was more informative than individual marker assessment (FIG. 7). The area under the curve (AUC) was higher for MPO combined with TNF-α and/or RUNX3. To further interrogate this association, logistic regression was performed. Odds ratios and p-values were either improved or remained highly significant in the presence of other variables (Table 12).

TABLE 12

Univariate and Multivariate analyses of variables.

| | Odds Ratio | CI* | p-value |
|---|---|---|---|
| Univariate | | | |
| MPO | 1.38 | 1.17, 1.67 | <0.0001 |
| RUNX3 methylated | 8.07 | 2.47, 36.58 | 0.0003 |
| TNF-α | 7.87 | 3.18, 21.36 | <0.0001 |
| Multivariate | | | |
| MPO&TNF-α | | | |
| MPO | 1.36 | 1.13, 1.69 | 0.0005 |
| TNF-α | 7.15 | 2.66, 21.06 | <0.0001 |

TABLE 12-continued

Univariate and Multivariate analyses of variables.

| | Odds Ratio | CI* | p-value |
|---|---|---|---|
| MPO&RUNX3 | | | |
| MPO | 1.51 | 1.25, 1.90 | <0.0001 |
| RUNX3 | 15.90 | 4.20, 81.78 | <0.0001 |
| MPO, RUNX3 & TNF-α | | | |
| MPO | 1.46 | 1.19, 1.87 | <0.0001 |
| RUNX3 | 14.29 | 3.46, 80.00 | 0.0001 |
| TNF-α | 6.60 | 2.22, 21.63 | 0.0006 |

*Confidence interval
P-values in bold are significant.

Example 3—Nucleic Acid Markers and UC-CRC

Patient Selection

The Mayo Clinic Institutional Review Board approved this work. The UC-CRC cases and UC controls analyzed in this study have been described elsewhere (Garrity-Park et al., *Am. J. Gastroenterol.*, 103(2):407-15 (2008); and Garrity-Park et al., *Gut.*, 58:1226-1233 (2009)). UC-CRC cases were selected from a review of 274 patients identified from the Mayo Clinic centralized diagnostic index of medical records (1976-2006). These patients had inflammatory bowel disease (either Crohn's or UC) and CRC. Patients with Crohn's disease were excluded. Medical records for the remaining UC-CRC patients were reviewed to establish a date of disease onset. For each case, pathology slides from the surgical resection also were recalled to confirm the diagnosis of UC and identify the best block for DNA extraction. Patients who did not have UC confirmed by review of the pathology or whose duration of disease was less than 10 years were excluded. After these exclusions, 114 UC-CRC cases were included in the study. Potential UC controls were identified through the Mayo pathology index (1994-2006), which indicated the patient age, gender, and extent of UC as well as the presence of other confounding pathologies such as dysplasia. The final pool of potential UC controls for this study included UC patients who did not develop CRC, who underwent either colectomy or colonoscopy with biopsy at the Mayo Clinic, and who did not have prior dysplasia. The Mayo Clinic centralized diagnostic index of medical records was used with these remaining controls to establish a date of diagnosis. Patients with less than ten years between the date of UC diagnosis and either colectomy or date of last biopsy were excluded as were patients with a prior dysplasia diagnosis. From the remaining list, 181 controls were selected that were most closely matched to the UC-CRC cases with regard to gender, age, ethnicity, duration, and extent of UC. The surgical resection or biopsy specimens from these 181 controls were re-reviewed to histologically confirm the diagnosis of UC. After final review, 114 UC controls were included in this study.

DNA Extraction

DNA was extracted from formalin-fixed, paraffin-embedded tissues using a modified Gentra (Gentra Systems Inc., Minneapolis, Minn.) protocol, and DNA was suspended in TE (10 mM Tris/0.1 mM EDTA, Integrated DNA Technologies, Coralville, Iowa). Quantification of total DNA was performed using the Picogreen assay (Invitrogen, Portland, Oreg.).

Genotyping

Samples are interrogated for the presence of additional SNP's in the nucleic acid sequences outlined in Table 13 below. If possible, testing is completed using Taqman genotyping kits (Applied Biosystems; ABI) after optimization for use with formalin fixed, paraffin embedded DNA samples. The 7900HT real-time PCR system is used for evaluating each sample. If a kit is not available for a given SNP, testing is then completed using traditional PCR followed by sequencing as described elsewhere (Garrity-Park et al., *Am. J. Gastroenterol.*, 103(2):407-15 (2008)).

Statistical Analysis

The ability of a SNP to delineate a case from a control is determined using either a Fisher Exact test or chi-square, as appropriate. Any significant SNP is further interrogated using logistic regression with all other significant SNPs and previously known clinical risk factors (i.e., PSC). Modeling is then performed to determine the best diagnostic paradigm for predicting CRC.

TABLE 13

Analysis of nucleic acid polymorphisms in UC-CRC cases vs. UC controls
(SEQ ID NOS 54-87, respectively, in order of appearance)

| Target | SNP(s) Identified | p-value | Context sequence (ABI) |
|---|---|---|---|
| IL-1 | | | |
| IL-6 | -174G > C (1800925) | | |
| IL-6 | -6337T > C | | |
| IL-10 | -1082G > A (1800896) | | TCCTCTTACCTATCCCTACTTCCCC[T/C]TCCC AAAGAAGCCTTAGTAGTGTTG |
| IL-10 | -819C.T (1800871) | | AGTGAGCAAACTGAGGCACAGAGAT[A/G]T TACATCACCTGTACAAGGGTACAC |
| IL-10 | -592 C > A (1800872) | | CTTTCCAGAGACTGGCTTCCTACAG[T/G]AC AGGCGGGGTCACAGGATGTGTTC |
| IL-10 | -627C > A | | |
| IL-15 | | | |
| IL-18 | | | |
| TGFB | | | |
| TNF-α | -308G > A (G19) | | |
| TNF-α | -238G > A (673) | | |
| TNF-α | -863C > A (1800630); | | |
| TNF-α | -857C > T | | |
| TNF-α | -301G > A | | |
| TNF-α | -293C > T | | |
| IL-12 | | | |
| IL-15 | | | |
| IL-23 | | | |
| IL-23R | 2284C > A (10889677) | >0.0001 | TTTAATTTTAGCCATTCTTCTGCCT[A/C]AT TTCTTAAAATTAGAGAATTAAGG |
| IL-23R | 94G > T (1884444) | =0.02 | TTTTCCTGCTTCCAGACATGAATCA[G/T]GT CACTATTCAATGGGATGCAGTAA |

TABLE 13-continued

Analysis of nucleic acid polymorphisms in
UC-CRC cases vs. UC controls
(SEQ ID NOS 54-87, respectively, in order of appearance)

| Target | SNP(s) Identified | p-value | Context sequence (ABI) |
|---|---|---|---|
| IL-23R | 1142G > A (11209026) | | ATTGGGATATTTAACAGATCATTCC[A/G]AA CTGGGTAGGTTTTTGCAGAATTT |
| IL-7 | | | |
| NFKB | DelATTG | | |
| TLR1-10 | | | |
| IL-8 | -251T > A (4073) | | TTATCTAGAAATAAAAAAGCATACA[A/T]T TGATAATTCACCAAATTGTGGAGC |
| IL-8 | 2767A > T | | |
| IL-8 | 781C > T (2227306) | | AACTCTAACTCTTTATATAGGAAGT[C/T]G TTCAATGTTGTCAGTTATGACTGT |
| IFNG | | | |
| IL-4 | -168C > T (2070874) | | TTAGCTTCTCCTGATAAACTAATTG[C/T]CT CACATTGTCACTGCAAATCGACA |
| IL-4 | -590C > T | | |
| IL-4 | -34C > T | | |
| IL-4 | -588C > T (2243250) | | ACACCTAAACTTGGGAGAACATTGT[C/T]C CCCAGTGCTGGGGTAGGAGAGTCT |
| IL-1β | -31T > C (1143627) | >0.0001 | CCAGTTTCTCCCTCGCTGTTTTTAT[G/A]GC TTTCAAAAGCAGAAGTAGGAGGC |
| IL-1β | -571C > T | | |
| IL-1β | 3953C > T (114634) | | CATAAGCCTCGTTATCCCATGTGTC[G/A]A AGAAGATAGGTTCTGAAATGTGGA |
| IL-1β | -511 C > T (3087258) | | |
| IL-21 | | | |
| IL-17 | -197G > A (2275913) | | TGCCCTTCCCATTTTCCTTCAGAAG[A/G]A GAGATTCTTCTATGACCTCATTGG |
| TREM1 | | | |
| MPO | | | |
| MIP-1α | | | |
| MDR1 | | | |
| P16 | | | |
| RUNX3 | | | |
| COX2 | | | |
| MINT1 | | | |
| HPP1 | | | |
| MINT31 | | | |
| PPARγ | 34C > G | | |
| PPARγ | 161C > T | | |
| IL-1RA | 86 bp repeat (Intron 2) | | |

TABLE 13-continued

Analysis of nucleic acid polymorphisms in
UC-CRC cases vs. UC controls
(SEQ ID NOS 54-87, respectively, in order of appearance)

| Target | SNP(s) Identified | p-value | Context sequence (ABI) |
|---|---|---|---|
| IL-13 | 2044 G > A (20541) | | TTAAAGAAACTTTTTCGCGAGGGAC[A/G]GT TCAACTGAAACTTCGAAAGCATC |
| IL-13 | -1112 C > T (1800925); | | GGTTTCTGGAGGACTTCTAGGAAAA[C/T]GA GGGAAGAGCAGGAAAAGGCGACA |
| IL-13 | -1512 A > C | | |
| TLR1 | R80T (5743611) | | AACACTGATATCAAGATACTGGATT[C/G]TA TTATGAGAAATTATCAAAATCCT |
| TLR1 | I602S (5743618) | | |
| TLR2 | R753Q (5743708); | | |
| TLR2 | GT repeat (Intron2); | | |
| TLR2 | P631H (5743704) | | GCCTGGCTCCAGGCCAAAAGGAAGC[A/C]C AGGAAAGCTCCCAGCAGGAACATC |
| TLR3 | N284I (5743316); | | CTCACTATGCTCGATCTTTCCTACA[A/T]CA ACTTAAATGTGGTTGGTAACGAT |
| TLR3 | L412F (3775291); | | ACTTGCTCATTCTCCCTTACACATA[T/C]TC AACCTAACCAAGAATAAAATCTC |
| TLR3 | 908 T > C | | |
| TLR4 | D299G (4986790) | | GCATACTTAGACTACTACCTCGATG[A/G]TA TTATTGACTTATTTAATTGTTTG |
| TLR4 | T399I (4986791) | | TGTTCTCAAAGTGATTTTGGGACAA[C/T]C AGCCTAAAGTATTTAGATCTGAGC |
| TLR5 | R392* | | |
| TLR6 | S249P (5743810) | | TTGAGGGTAAAATTCAGTAAGGTTG[A/G]A CCTCTGGTGAGTTCTGATAAAAAT |
| TLR6 | -1401 A > G (5743795) | | |
| TLR7 | Q11L (179008); | | TTTCCAATGTGGACACTGAAGAGAC[A/T]A ATTCTTATCCTTTTTAACATAATC |
| TLR7 | A448V (5743781) | | AGTGAAGTTGGCTTCTGCTCAAATG[C/T]C AGAACTTCTGTAGAAAGTTATGAA |
| TLR7 | T801T (864058) | | GGTTTGTCTGGTGGGTTAACCATAC[A/G]G AGGTGACTATTCCTTACCTGGCCA |
| TLR8 | M1V (3764880); | | AATGAAAAATTAGAACAACAGAAAC[A/G]TG GTAAGCCACTTCTATTTCTTTAG |
| TLR8 | D118D (2159377) | | AATCAAATGGCTTGAATATCACAGA[C/T]G GGGCATTCCTCAACCTAAAAAACC |
| TLR8 | L651L (2407992) | | GTCTGGATTTATCCCTTAATAGGCT[C/G]A AGCACATCCCAAATGAAGCATTCC |
| TLR9 | 1174 G > A (352139); | | TGTGTGAGTGGCCGGCCCCCAGCTC[C/T]A CCTCCACCCACTCCACTTCATGGG |
| TLR9 | 1635 G > A (352140); | | AGCTGAGGTCCAGGGCCTCCAGTCG[C/T]G GTAGCTCCGTGAATGAGTGCTCGT |
| TLR9 | -1237 T > C (5743836) | | |

TABLE 13-continued

Analysis of nucleic acid polymorphisms in
UC-CRC cases vs. UC controls
(SEQ ID NOS 54-87, respectively, in order of appearance)

| Target | SNP(s) Identified | p-value | Context sequence (ABI) |
|---|---|---|---|
| TLR10 | N241H (11096957); | | AGCAATAGAACCGATGTCTTAGCAT[T/G]TT CTAAACTAAGATTTCGTTGCATT |
| TLR10 | I369L (11096955) | | AGAGTTTTCAAGTGAGGCAGTTGGAA GTTCTTTTAAACAACTCGTCTGTT |
| TLR10 | I473T (11466657); | | GAGATCAGTTAGAAAATTAAATGCA[A/G]TA TTTAGTTCTCGTAAGGCCATCAG |
| TLR10 | R525W (11466658) | | AAATTTTTTAATTCACAGGTACACC[A/G]GA ATGGATTTCTTCCCGCATTTAGA |

Example 4—Early Appearance of Nucleic Acid Markers in UC-CRC Pateints

Biopsies from 10 UC-CRC cases and 10 UC-controls obtained between 10 and 24 months prior to the index date analyzed in the work described in the above Examples were tested for methylation of RUNX3 and MINT1. RUNX3 was more frequently methylated in UC-CRC cases than controls (80% versus 10%). MINT1 was also more frequently methylated in UC-CRC cases than controls (60% versus 0%). These results demonstrate that the methylation changes apparent at the time of CRC (index date) actually occurred prior to overt neoplasm.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for conducting a beneficial colonoscopy and biopsy surveillance regimen on a human diagnosed with inflammatory bowel disease, wherein said method comprises:
   (a) detecting the presence of a thymine at the polymorphic position of rs1143627 in an IL-1 beta nucleic acid of said human, and
   (b) conducting more frequent colonoscopy and biopsy surveillance on said human than surveillance colonoscopy and biopsy every year based at least in part on said presence of said rs1143627 polymorphism.

* * * * *

SEQUENCE LISTING

<160> NUMBER OF SEQ ID NOS: 87

<210> SEQ ID NO 1
<211> LENGTH: 1051
<212> TYPE: DNA
<213> ORGANISM: Homo sapiens

<400> SEQUENCE: 1

```
gctgtctgct tgtgtgtgtg tgtctgggag tgagaacttc ccagtctatc taaggaatgg     60
agggagggac agagggctca aagggagcaa gagctgtggg gagaacaaaa ggataagggc    120
tcagagagct tcagggatat gtgatggact caccaggtga ggccgccaga ctgctgcagg    180
ggaagcaaag gagaagctga gaagatgaag gaaaagtcag ggtctggagg ggcggggggtc   240 agggagctcc tgggagatat ggccacatgt agcggctctg aggaatgggt tacaggagac    300
ctctggggag atgtgaccac agcaatgggt aggagaatgt ccagggctat ggaagtcgag    360
tatggggacc ccccttaac gaagacaggg ccatgtagag ggcccaggg agtgaaagag      420 cctccaggac ctccaggtat ggaatacagg ggacgtttaa gaagatatgg ccacacactg    480
gggccctgag aagtgagagc ttcatgaaaa aaatcaggga ccccagagtt ccttggaagc    540
caagactgaa ccaagcatta tgagtctccg ggtcagaatg aaagaagagg gcctgcccca    600
gtggggtctg tgaattcccg ggggtgattt cactccccgg ggctgtccca ggcttgtccc    660
tgctacccgc acccagcctt tcctgaggcc tcaagcctgc caccaagccc ccagctcctt    720
ctccccgcag ggcccaaaca caggcctcag gactcaacac agcttttccc tccaaccccg    780
ttttctctcc ctcaacggac tcagctttct gaagcccctc ccagttctag ttctatcttt    840
ttcctgcatc ctgtctggaa gttagaagga aacagaccac agacctggtc cccaaaagaa    900
```

```
atggaggcaa taggttttga ggggcatggg gacggggttc agcctccagg gtcctacaca    960
caaatcagtc agtggcccag aagaccccc tcggaatcag agcagggagg atggggagtg   1020 tgagggtat ccttgatgct tgtgtgtccc c                                   1051
```

<210> SEQ ID NO 2
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 2

```
acctggtccc caaaaga                                                    17
```

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 3

```
cggggatttg gaaagttg                                                   18
```

<210> SEQ ID NO 4
<211> LENGTH: 186
<212> TYPE: DNA
<213> ORGANISM: Homo sapiens

<400> SEQUENCE: 4

```
acctggtccc caaagaaat ggaggcaata ggttttgagg ggcatgggga cggggttcag     60
cctccagggt cctacacaca aatcagtcag tggcccagaa gacccccctc ggaatcagag   120 caggaggat ggggagtgtg aggggtatcc ttgatgcttg tgtgtcccca actttccaaa    180
tccccg                                                              186
```

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 5

```
tggggcggat cgcgtgcgtt                                                 20
```

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 6

```
cgaccccgaa ccgcgacggt                                                 20
```

<210> SEQ ID NO 7
<211> LENGTH: 24
<212> TYPE: DNA

<213> ORGANISM: Artificial Sequence
<220> FEATURE:
<223> OTHER INFORMATION: Description of Artificial Sequence: Synthetic
      primer

<400> SEQUENCE: 7
tggggtggat tgtgtgtgtt tggt                                            24

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ccacctccaa caatacccat acct                                            24

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ggcggcgaga atatggtgc                                                  19

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
acgacgaacg gccctaacg                                                  19

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ttggtgttaa agggtggt                                                   18

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
aaaaaccctc actcacaa                                                   18

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13 aggggattttt ttgcgttttc                                              20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cgcaatcttt acccgaacgc                                               20

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gagggatttt tttgtgtttt t                                             21

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
tctttaccca aacacttcca a                                             21

<210> SEQ ID NO 17
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ttagagggtt atcgcgttta tgc                                           23

<210> SEQ ID NO 18
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
accaaataaa ccccgaaaca cgg                                           23

<210> SEQ ID NO 19
<211> LENGTH: 25
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 19
taattttagg ttagagggtt attgt                                          25

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
cacaaccaat caacaacaca                                                20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
cgttcggttt tatcggattc                                                20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
aaaaactcaa aaaccgacga                                                20

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
tgagttggag tttttgaatt gttt                                           24

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
acacattaac aacaaccaca                                                20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 25
tttcggcgta gtttttttagc                                          20

<210> SEQ ID NO 26
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
actaaacatc ccgcgaacg                                            19

<210> SEQ ID NO 27
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
tggtgtagtt ttttagtgga tg                                        22

<210> SEQ ID NO 28
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
acaataacaa taacacccaa ca                                        22

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
tttcgaagcg tttgtttggc                                           20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
caaaaaacct caaccccggg                                           20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 31
tggagagtag gggagtttgt                                              20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
aacctaacac acaacaaaca                                              20

<210> SEQ ID NO 33
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
tattcgattt atttcgtc                                                18

<210> SEQ ID NO 34
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
ctacgaaaaa taaacacg                                                18

<210> SEQ ID NO 35
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
gattttaatt ttttgtggtg gt                                           22

<210> SEQ ID NO 36
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
ctaaaaccat cacccctaaa ca                                           22

<210> SEQ ID NO 37
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 37
cgtttgcgtg gttcgttagt ac                                              22

<210> SEQ ID NO 38
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
acgacgacga cgacgaca                                                   18

<210> SEQ ID NO 39
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
ttgggtttta tggttgtttg tgt                                             23

<210> SEQ ID NO 40
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
acccaacacc ctaacaacca c                                               21

<210> SEQ ID NO 41
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
acggggtatc ggtattttc                                                  19

<210> SEQ ID NO 42
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
tacgatcatt ctacgaccg                                                  19

<210> SEQ ID NO 43
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
```
ggttattttg gttgttatt                                                  19

<210> SEQ ID NO 44
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
caaacactac aatcattcta ca                                              22

<210> SEQ ID NO 45
<211> LENGTH: 129
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 45
cgtttgcgtg gttcgttagt acgtttatta tcgagcgtat ttcgggtcgg gcgcgttttt     60
cgggttttac ggtcgtttgc gcgtttagcg cgtcgttgtt ttcgtttatt ttgtcgtcgt    120
cgtcgtcgt                                                            129

<210> SEQ ID NO 46
<211> LENGTH: 159
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 46
ttgggtttta tggttgtttg tgtgtttagt gtgttgttgt ttttgtttat tttgttgttg     60
ttgttgttgt aggggaaggt tggggaggga ggtgtgaagt ggtggttggt gtttgggttt    120
atgggaatat gtataatagt ggttgttagg gtgttgggt                           159

<210> SEQ ID NO 47
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
tttcgaagcg tttgtttggc gtttaagaga gagtaagaga gggttggaga gtagggagt      60 tcgcggggtt gaggttt                                                   77

<210> SEQ ID NO 48
<211> LENGTH: 112
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 48
tggagagtag gggagtttgt ggggttgagg ttttttgtta gtgtttgtat ttttatgtt      60 ataatgtttt tatttagtaa aaattttttg ggtgtttgtt gtgtgttagg tt            112

```
<210> SEQ ID NO 49
<211> LENGTH: 142
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 49
aggggatttt ttgcgttttc ggattttagg gtcgtttaga ttttggaga ggaagttaag      60 tgttttttg ttttttttcg gtattttatt taaggcgatt agtttagaat tggttttcgg     120
aagcgttcgg gtaaagattg cg                                             142

<210> SEQ ID NO 50
<211> LENGTH: 138
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 50
gagggatttt tttgtgtttt tggattttag ggttgtttag attttggag aggaagttaa     60 gtgttttttt gtttttttt ggtatttat ttaaggtgat tagtttagaa ttggttttg      120 gaagtgtttg ggtaaaga                                                  138

<210> SEQ ID NO 51
<211> LENGTH: 528
<212> TYPE: DNA
<213> ORGANISM: Homo sapiens
<220> FEATURE:
<221> NAME/KEY: modified_base
<222> LOCATION: (332)..(332)
<223> OTHER INFORMATION: a, c, t, g, unknown or other
<220> FEATURE:
<221> NAME/KEY: modified_base
<222> LOCATION: (342)..(342)
<223> OTHER INFORMATION: a, c, t, g, unknown or other
<220> FEATURE:
<221> NAME/KEY: modified_base
<222> LOCATION: (407)..(407)
<223> OTHER INFORMATION: a, c, t, g, unknown or other
<220> FEATURE:
<221> NAME/KEY: modified_base
<222> LOCATION: (425)..(425)
<223> OTHER INFORMATION: a, c, t, g, unknown or other
<220> FEATURE:
<221> NAME/KEY: modified_base
<222> LOCATION: (432)..(432)
<223> OTHER INFORMATION: a, c, t, g, unknown or other
<220> FEATURE:
<221> NAME/KEY: modified_base
<222> LOCATION: (495)..(495)
<223> OTHER INFORMATION: a, c, t, g, unknown or other

<400> SEQUENCE: 51
cccgggctgg gtacctggac ctataccttc atagctgcct taggctcaac ttttcggcgg    60
ggatccctct gcagacgtgc aggtggcggg agagcagagg tagccgcagt aagtgctgag   120
agagcctgaa agaaacacca tgaattttca aactctccca catacattcc cgaagcgcct   180
gtctggcgtc taagagagag caagagaggg ctggagagca ggggagcccg cggggctgag   240
gctctttgtc agcgcctgca cttcctacgt tacaacgcct tcattcagca aaaaccttt    300 gggcgcctgc tgtgcgccag gccaggcgaa gnagaccgag gntgtgaagc tcagagggga   360
```

```
gagggaccaa tcgcagtaaa taagctaccg aggtaatctt agatggngat gagggcagga    420
aaagncatca gncgacctct gacctttctc ttaggggggtt ttcccccttcc gcctgggttc    480 tagaactggg aagantttttc tccagagcgt cgcggggagc gccccggg                528
```

<210> SEQ ID NO 52
<211> LENGTH: 7273
<212> TYPE: DNA
<213> ORGANISM: Homo sapiens

<400> SEQUENCE: 52

```
ggtacccagg ctggagtgca ctggtgtgat catagctcac taacctcgaa ctcctgggct     60
taggcaatcc tcttgccttg gcctcccaaa gtgccaggat tacaggcatg agccaccaca    120
gtggagctct caattctgat actaataatt tgtgtcttct cttttttttcc ttagcctgac    180 tagagtaatt aactttatgt cttttaaaag aaccaccttt ttggttttac ccattttctt    240
ttttgatttt ctgttttttga tttgattgat atctactcta attttttatt atttcttttc    300
ctctgcttac tttgaattta attacttttc ttttttgtag tctcctaaaa tagaagctta    360
tattattgat tttagatctt tcttcttttc tattacagca ctcaatgcta taaatttccc    420
tctaagcatt gctttcactg catcctacaa tatttcaact ctattgttat ttagctcaaa    480
agaggttctt aatttctatt gggatttctc tttgacccat gtgttattca gaagtgttcc    540
gtgtgatctc caaatatttg ggagttttttc agctatcttt ctattaatca tttcttgttt    600
aattctattg tggcctgaga gcatatattg tatgatttat attcttgtaa atgtgttaag    660
gtgtgtctta tggtgcagaa tgcggtttat cttgctatat gttccttaga gaataatgta    720
tgttctgctg ttattggata aagtagtcta tagatgtcag ttacatctcg ttgattaatg    780
gtgctgttga gttcagctat gtcctaaatg atttttctgtc tgctgtatct gtctatttct    840
gacacaaggc tgttgaagtc tccaaccata ataatgaatt aatctatttt tctttgcagt    900
tttatcaatt ttgtcttata tatattgatg ctccattgtt tggcacatac acattaagaa    960
ttgttatgtc ttcttggaga atttaccttt ccataacatg taacatttcc ctttattcct   1020
gataattttt cttgctcaaa agtttgccct gttggaaatt accagaacta ctctggcttt   1080
atttgattag tgttagcatg ctctctcttt ctctattctt acactttttaa tgtatacttg   1140 actttgtatt taaagtgggg ttcttataga aaacatatac ttggtagggt gggaagtaaa   1200
ataaaaagaa atacttgggt attggtttga tccactctaa caatctctat gttttaattg   1260
atgtatttag accattgata cttattttttt tatcctcatc cctgtgatta cccagagagc   1320
tgcttaaatt gattattgat atagacaaat taataattaa tatctaccgt ttgttactgt   1380
tttctatttt tcattgccct tactttctgc tcctattttt tgctccttttt tctgttaatt   1440 taggttttga gttatttttat atcattctat tttctctccc ttctcagcat atgaattatc   1500 tttcttttttg acttttttag tggctgccct gaaggttgca atgtacattt acaaccagtc   1560
ccaatctcct ttcaaaaaac acaatactgt ttcatggcta gtgcaagtac ctaataataa   1620
gaagtcactc ctaatttctt tctctcattc tttgtatctt tactgttatt catttcactt   1680
gtacataagc tgtaatcttt caatacatta ttgctattat tatttcaaaa catgttatct   1740
attatatcta tttaaaataa gaaaaatagg ccaggtgcag tggcttactc atgtaatccc   1800
agcactttgg gagaccgatg gattgctaga gctcaggaat tcgagaccag cctgggcaac   1860
atagtgaaac cctgtctcta ctaaaaatac aaaaaaaaaa attgctgggc atggtggcat   1920
gggcctgtgg tcacagctac tcgggaggct gaggtgagag gattgcttga gcctggggagg   1980
```

```
cagaggttgc agtgaaccaa aatcaagcta ctgcactcca gcctaagtga cagagtgaga      2040
ccctgtctca aaaaaaaaat gaaagaatta tttttattta tcttcactta tttcttctct      2100
aatgctcttt gtttctttag tatgtagatc caagtttcta acctgtatca tttttcttat      2160
ctcaataact tcttttaaca tttctcacaa agcagatca ctggccacag aatgcctcaa       2220
ttttcatttg tctgagaaaa ccttatttct ccttcacttt tgaaagataa ttttgtaggg      2280
tacagaattc taggttgtag gtttttttccc ctcaaagtga aatatttcat tccactcttt    2340
tcttctttgt atggtatctg agaagaagtc agatgtaatt cttatcatta ttacttaaaa     2400
gattgcttct gttcctttct ctcttctcct tcccttcttt ccttctctgt atattacacc     2460
ttttatagtt gccccatatt tcttagatat tatgttttgg ttttcttctg tgttttttc      2520 tttgattctc agttttagaa gtctctattt atatatctgc aatcgcaggg attctttcct     2580
ctgccatgtc cagtctacta ataagcccctt acagacattg ttgacttctg ttccagtgtt    2640
tttgatctct agcatttctc tgattatttc ttggaattgc catctgtcta cttacattac    2700
caacctattc ttgtgtgttg tcttatcata gtaattgcag ttgttttaat ttcataggta    2760
ttgtaatttc aacatctcta ccatatttga cattgattct gatgcttgct ctgtcttatc    2820
aagctatgtt tttgtctttt agtgtgactt ctaattttt gttgaaagcc aggcatgatg     2880
tactgagtga aagaaactca atacattgta atgtgacgat aagagttcag gggaagtgaa    2940
gcattctata gtcctatagc aggtctcggc cttttagtga gcctgtgcct atgaacggtg    3000
actttcaaca agtgcttttc attccactct tttcctgtcc ttaagtggga caagatcact   3060
gggggggggc tagaattggg tatttcccctt ctccaatgta gaagctaaag agagggctgg   3120
agttgggtat ttttcttccc ctgtatggaa agctagaggc agttaaattt ggatatttttc   3180 cttcttctaa ttcagttagg ctgcgacaaa atcccgaca gtttaggctc taatattata     3240
aaataatttc tcttgagtat aggccttatt aagaacacta tactctgatg gagctgaggg   3300
ggagttttct ctgatattca ctgcgagaac ctcgtagagc tccaggaagc aaaactcaca   3360
aaagtgtggg agtcttccag aattttttcct ttgcagactt atctgcactg aacctccaga   3420
aattcatcaa ttacagttca ggttttccta cccaggtact ggttttcatg gaggtttctg    3480
cctgtgcatt tctgctccag taagttgttc ttcttgtatg gtctgtcttt caaattttttt  3540 aagtagggtt atgacctgtc gcctcacttc tctgacagtt ctgagagtgt tgattttca    3600 gtttgcttag atttttactt gttttttagga tgaagtgaca atttccaagc tcctccctga   3660
catgccagat cagaaactga aagtcctaag cctcatattc tgtgcgtggg tatgttcaca   3720
tcctgcctgc tccagtgccc ccacctcaca ctctctttcc cttccttgtc cccttgtgag   3780
atttctaggt ccaatacaaa gactgtgttc aactcattca actacttggc tcatctgagt   3840
attataatga acaatcacaa aaaaaatga agtaaaagaa aaatccatca aagaattgag    3900
atatttgaga aaagaaagg agatcagtgt tttataaaac ttagaaatag attttttaag    3960
tgtttcttca ttgacttatg tgaaaggact tttcttaatt taacaaatta tgtgctttcg    4020
tttatagcct caaaacttct tgtgtagcta agaatgggta aataatcagg ctttactaaa    4080
ggactaacgt aaagatcttc tgtaagtaac atttctgcta ctcaaggaag agataaactt   4140
catggcataa ccttgccaaa gtatactaag aataaccctg acacaaagct ctttttttcag   4200 ccaacatgcc atgaaagaaa gaagacaagg ggtgatctcc actctctaag tgaaccacta    4260
aacccaccaa agaagaaacg agggaaatag aaagaggacc cttgcctgag ataatggatc    4320
```

```
tgtatgtatg agtagtagaa ccctgctcaa agtacaagga agggaaaaaa aagttagttt    4380
atttggaatt ttggacatta agagtcttta ttgttcattt tcttttaact cacatgaatg    4440
gcttatcact tcaattaata aatatttcat ttcttttcaa tctatattca tgaaacaaat    4500
ctgaaatgaa cagtgcaaca tgtgaatgtt tagaacatta taaaattaaa cacaaaatct    4560
gtctggcaat cttcctagca tcttaggaaa aaagttgaca aaatttcaag cagcagaagg    4620
gggcagtaaa actcaacaga aagctctgga agattttttaa gattcttcct tattttcttt    4680
tcatgtagag tatttcccaa caaatttcag acgctaatag aaattttgta caacagatcc    4740
atatatttgc ctaaaataga cacagaaaca ttgatatatg caaacatgag agctataagt    4800
tttacatgat caaaaccttt tttttatggt acacaatagt cacagtactt ttccatataa    4860
aacaggttta gtggtcttaa tttagtttgg cacatttaat acactcccat gaccagcatc    4920
ccaaatgtac ctatccgttt tatttttattg tctcagaatt gtcagttatt taataaatta    4980
tgtaactttt ttccttatgc tcagatttgc acttctttct aaaactctgc ccatccttaa    5040
agtcccagat tctccttgaa cttttttttt tgactttcca agtacatgga actcttcact    5100
ctatcctgct atataagtga cagaattttcc actatgggat agatggagtt caattccttt    5160
gagtttaaaa taatctaaat ataattattc cttatgccct gttttttccct cacttttgta    5220 tccaaatctc ttttcagaca acagaacaat taatgtctga taaggaagac aatgatgatg    5280
atcacttcaa aataagcttg aattcaggat tgtaatgtaa aattttagta ctctctcaca    5340
gtatggattc taacatggct tctaacccaa actaacatta gtagctctaa ctataaactt    5400
caaatttcag tagatgcaac ctactccttt aaaatgaaac agaagattga aattattaaa    5460
ttatcaaaaa gaaaatgatc cacgctctta gttgaaattt catgtaagat tccatgcaat    5520
aaataggagt gccataaatg gaatgatgaa atatgactag aggaggagaa aggcttccta    5580
gatgagatgg aattttagtc atccgtgtct catgaagaat cagatgtgta cactaagcaa    5640
aacagttaaa aaaaaaacct ccaagtgagt ctcttattta ttttttttctt ataagacttc    5700 tacaaattga ggtacctggt gtagttttat ttcaggtttt atgctgtcat tttcctgtaa    5760
tgctaaggac ttaggacata actgaatttt ctatttttcca cttcttttct ggtgtgtgtg    5820
tatatatata tgtatatata cacacacaca tatacatata tatattttta gtatctcacc    5880
ctcacatgct cctccctgag cactacccat gatagatgt aaacaaaagc aaagatgaaa    5940
ttccaactgt taaaatctcc cttccatcta attaattcct catccaacta tgttccaaaa    6000
cgagaataga aaattagccc caataagccc aggcaactga aaagtaaatg ctatgttgta    6060
ctttgatcca tggtcacaac tcataatctt ggaaaagtgg acagaaaaga caaaagagtg    6120
aactttaaaa ctcgaatta ttttaccagt atctcctatg aagggctagt aaccaaaata    6180
atccacgcat cagggagaga aatgccttaa ggcatacgtt ttggacattt agcgtccctg    6240
caaattctgg ccatcgccgc ttcctttgtc catcagaagg caggaaactt tatattggtg    6300
acccgtggag ctcacattaa ctatttacag ggtaactgct taggaccagt attatgagga    6360
gaatttacct ttcccgcctc tctttccaag aaacaaggag ggggtgaagg tacggagaac    6420
agtatttctt ctgttgaaag caacttagct acaaagataa attacagcta tgtacactga    6480
aggtagctat ttcattccac aaaataagag ttttttaaaa agctatgtat gtatgtcctg    6540
catatagagc agatatacag cctattaagc gtcgtcacta aaacataaaa catgtcagcc    6600
tttcttaacc ttactcgccc cagtctgtcc cgacgtgact tcctcgaccc tctaaagacg    6660
tacagaccag acacggcggc ggcggcggga gagggggattc cctgcgcccc cggacctcag    6720
```

```
ggccgctcag attcctggag aggaagccaa gtgtccttct gccctccccc ggtatcccat      6780
ccaaggcgat cagtccagaa ctggctctcg gaagcgctcg ggcaaagact gcgaagaaga      6840
aaagacatct ggcggaaacc tgtgcgcctg ggcggtgga  actcggggag gagagggagg      6900
gatcagacag gagagtgggg actaccccct ctgctcccaa attggggcag cttcctgggt      6960
ttccgatttt ctcatttccg tgggtaaaaa accctgcccc caccgggctt acgcaatttt      7020
tttaagggga gaggagggaa aaatttgtgg ggggtacgaa aaggcggaaa gaaacagtca      7080
tttcgtcaca tgggcttggt tttcagtctt ataaaaagga aggttctctc ggttagcgac      7140
caattgtcat acgacttgca gtgagcgtca ggagcacgtc caggaactcc tcagcagcgc      7200
ctccttcagc tccacagcca gacgccctca gacagcaaag cctacccccc gcgccgcgcc      7260
ctgcccgaag ctt                                                         7273
```

```
<210> SEQ ID NO 53
<211> LENGTH: 95241
<212> TYPE: DNA
<213> ORGANISM: Homo sapiens

<400> SEQUENCE: 53
gatcacctga ggtcaagagt tggagaccag cctggccatc atggcaaaac cctgtctcta        60
ctaaaaatac aaaaattagg agggcatggt ggctcatgcc tgtaatccca gctacttggg       120
aagcagagta ggagaatcac ttgaacctgg gaggtggagg ttgcaatgag ccgagatcgt       180
gccactgcac tccagcctgg gcgacagagc aatctccatc tcaagaaaaa aaaaaaagaa       240
aagaaaagaa atgaagattc tttctcccct ttcctcccag tgctctcccc acaggaacga       300
gacctgcgtg gtgtggggag cagctgaaga cttctcatct gcctttgtga atgccaattg       360
tacacagcca ctactggaat cttactcatc gcagcaggag gcctggcttc cggcacaggt       420
ggaatgaatg aaggaaggaa cggatgaatg aaaacaatga agctgtacag agcagtctgt       480
ctccgagtgg gcagtggatc ctggaaaaca catcttcagc catccagagt gggaagatct       540
ggatttggga tgtagccgct tcctccctgt gtgacctttg gcagatgtca ттттасттттт       600 ggaacttcag tttttccatc cgcaaaaagg ggatgctgcc tgcccagttc atgtcacaga       660
cctgtgaagg tcaaaacaga aggcaggagg gagcatattc cataaaaggt acagcagccg       720
ggcagagtgg cccatgcctg gaatcccagc caaggcagga ggattgctgg agaccagaag       780

tttgagacaa gtatgggcaa atagcaata  cctcatctct aaaaaaaatt atttaaaaaa       840

tcagctgggg ctgggtgcgg tggctcacct gtaatcccag tactttggga ggccaaggca       900
ggcggatcac ttgaggccag gagttcaagc ccagcctagc caacatgatg aaaccccatc       960

tctcctaaaa atgaaaaat  tagccaggtg tagtggtgca cacctgtagt accactgcac      1020
tccagcctgg gtgacaaagc gagactctgt ctcaacaaac aaacaaacaa acaaacaaaa      1080
aaccagcgga gcatggtggc acacactgta gtcccagata cttgggtggc tgagtgggga      1140
ggatggcttg agcccaggag gtccaggctg cagtgaacca cgatcgcacc actgcactcc      1200
ggcctgggcc acagagtgag actctgtctc tacaaaagaa aataagaaag gaaggaagga      1260
aggaaagaaa aaaaaataa ataaaaatga agataaagc  atagggacgt ctctgagaca      1320
aagagctgag tggaagaatc aagttaggac tcagcagcgc aggatggcga ggcttataat      1380

ttaatccccc tcctcgattt сттттсgaтga ggcaaaaaac agtcttggaa attactcacc      1440
aaaccagcag tgggtgccag gagctcattc actttgtgtg tcattataat tttttgtaac      1500
```

-continued

```
tagaatggat ggagcaacca ctttggtagt gaaaatattt taatatccgc atgtgcataa    1560
agtgacacga ataacagttc ccgtttactg ggctctgatg ctgtagcagg ctgtggggat    1620
ggctactgtg ctcattttac agacaaggaa actgaaaccc aggcaggcga agtggcttgc    1680
ccaggctcac acagccagaa cgggatgaag caggttctga cctccaagca agactgactc    1740
cagtggggaa ttatgggttc ccaaatgaca ctgatcacag caacaacggg caggacagga    1800
caggtgactc agagcagact cctcatgcaa ggggagatgt tgcccagtgc cgagggcacc    1860
ggggcagggt tcatgccttc ccctgggaga gcaagaggtt cagagtcaga aagactgggg    1920
cttgtggtcc cagctctgcc actttctggt tgtgtaactt ctgccaaatc ccttcacccc    1980
tccgagcctc aatgtgctca tatgcaaaag gggcgagtaa ccacctacct tgcaggcttg    2040
tgtggactga gtgtgttacg gccatgaaaa caccatgtgc tctataaggt gcgctttatt    2100
cattcctgaa gtgagcattt atcatgcacc cacgttcatg ccaagccctt ctctgggatc    2160 tgggagaca gcagcaaaca cagcagatga ggtcctggtc cctggagtta ctttcaagtg    2220
gttggagcca gataatcaac cgagaaagcc tgacacagtt cagacggcgt tgagtgccgt    2280
ggagaaccca cgccggacag cgtgacggag cggcctcggg gctgggctac tgagcaaggg    2340
aggggcctct ctgactttgt gatgtctgca cagaggctga gcggtgtggt gcaggtcagt    2400 gatgaaagc tgtttatggg aagtgtcaag ggatagcccc aaggaaggga ggagctacag    2460
cgggtgagga acagaaggct agggcaggga gaatgggcaa ggggcccacc gggcagtgcc    2520
tgtgcactag aggtggtctc tagaggtggg aatgtctttg tggacacgtg tcctttgctt    2580
aggacagcgg agagaggctt ccaggtctgg gtgggtgaga agagggagg agctgtcagg    2640 cagaaccatg gaggtaggtg gtaggaggta ggaggtaggt gggagggtga ggcacctgct    2700
ctgagcccct tctccctggg caggaatggg gcatgtgggc agagcagagg gaagcagcgg    2760
tgcaggaatg gccctgacct gcacagatgt gggaggaggt ccgcacgccc agagaggggc    2820
tgagatcata ccaccaggga cctggtgttg gttccacaag aggctcaggg acacacttcc    2880
agaattttga gagcacccct agcagaggca gggacttgga ctggttgacc tggctttccc    2940
acaccctcaa aacctcaaaa tgtccaatgt ccatccactg atcatgatgg gtcttttctag    3000 aatgtcattt tctccccagt gcagttggtg agaggcattc tcacctcctc cctggagagt    3060
ggggttcctc cttaccattg cctggtggtt gagctctagt ccttctgtct ggctggccgt    3120
gtagccttgg gcaagccgct ccatctctct gtgcctctgt tgcctgggct gtaaacagaa    3180
gtgagctaaa gcaggcaga ccgaggtctg tgaccacgta ataactcata ctcagttcca    3240
gaaatattca cccacagaag tgtctgggac aagcctggaa ggctgatcac accagccctc    3300
cgggtgctgc tcgtggctga gagaacagaa gggagccctg tccaccatgg gaagctgctg    3360
tttccatcac cagcctgggc tgtggtgcag aaagaaggaa ggggagtctg ggtggggcga    3420
gggaggcagc aaagggcctg gaccttcgtg ggagcacgga cacacaggac agccattgtc    3480
gagcttggac tgaccctact tggtgacgtt aagttctcaa gctccaagaa acagcatctg    3540
agttcttgag ctcaatcttc ccaccaaaga aaatcataca caagtcccgg cgcaggggct    3600
tcacagctca aagcatggtc tgtgtccaca tttcctgtgg tgggtcaggc cccactgcag    3660
tcctgagcca gctctgcatt cccaccagag ccccaggaga tcagatgcgg ggtgaactct    3720
gagaagcgct gctctagggc acaggtaggc tcattgcagc cttgtcccca gcgggaaaac    3780
gcggtggacc tgcagcagtc agaggcaagg cacactgcaa gctccaggaa caggcaggac    3840
ccgagaaacg taggtgggtg aagcaggaa gaaggagaac ccagcgcaaa actgatgatg    3900
```

```
catattaaaa acatgcacat ggcggctggg cgtggtggct cacgcctgta atcccaggac   3960
tttgggaggc cgagatgggt ggatcatgag gtcaggattt cgagaccagc ctggccaaga   4020
tggtgaaacc ccatctctac taaaaattca aaaaattag ccgggcgcgg tggtgggcat    4080
agggagactg aggcaggaga atcacttgag cccaggaggt ggaggttgca gtgagctgag   4140
attgcaccat tgtactccag cctgggagac agagcaagac tcagtctcaa acaaaacaaa   4200
acaaaacaaa acaaaaaaac atgcacatgg caaaatgaca taaggagag tgttgggatg    4260
gtgggagccg tattgtgtca atgtgaactc tcctgaacgt ggttattgtt cctggttatg   4320
taagagcagc tccttgttct caggaggccc acggggaatg gtcctgacat gtgtaggtac   4380
ttctatatgg ctcagcaaac aaaatttatg cagatactca gagagaaccc ctggagcaaa   4440
atgttgacaa tctgtgagcc taggtaaagg ggatatggga ggtttgttgt tgttgttttt   4500
tgttttttga gacggagtct cgatctgtca ctgaggctgg agtgcagtgg tacaatctct   4560
gctcgctgca acctctgcct ctcaggttca agtaattctc gtgcctcaac ctcctgagca   4620
tctgggacta caggtgcacg ccactacacc tggctaattt ttgtattttt agtagagacg   4680
gggttttgct gtgttggcta ggttggtctt aaactcctga cctcaagtga tcctcctgct   4740
tcggcctccc aaagtgctgg gattacaggt gtgagccact gtgcctggct aattttttata  4800
tttttagtag agatggggtt ttgccatgtt ggccagaact cctggcctca agtgatctgc   4860
ctgcctcggc ctcccaaaat gctgggatta caggcatgag ccactgcacc cagccggata   4920
tgggagttta ttgcactgtc cacagagtga aggtgtggct cctggacttc ctccctcgtc   4980
cagaggagag tcaggctgaa ccagccgggt cccaggagac caaaggagac ccccccccc   5040
ccgccgccac taacaaacca cagagatttt tactgaaaat aagttttctt cctctcttct   5100
tgtaattaca aagataaacc aagtttattg taaaaatgtg aaatgactaa gaagtgtata   5160
aagcaaaaag caaagcgttt tttcacctttt gcccctcccc aattcttaac ctctgtggac   5220
agcttggcag ccccttctag gcattttttct ttccaggtga agttctgtc aatcttttt    5280
cctcccagag ggagtcctgc acaatttatt gttcatatat tggggacagg tttccatggc   5340
aaaactcaat ctgattcttt tttacttttt ttttttttt tgagacagag tctcgctctg   5400
ttacccaggt tggaatgcag tgccatgatc tcggctcact gcaacctccg cctcccaggt   5460
tcaagcaatt ctccggcctc agcctcctga gtggttggga ttacaggcac ctgccaccat   5520
gcctggctat ttttgtattt ttagtagaga tgaggtttca ccgtgttggt caggctggtc   5580
tagaactcct gatctcaagc aatccactca cctcggtctc ccaaagtgtt gggattaaag   5640
gcgtgagcca ccgcccctgg ccctttctta ctttttaaat caagaactga aaacgacttt   5700
atttactctt cttgggacat ggccacgccc atggaagtcc ccaaagtagg ctggacaggc   5760
cacagcagca cccggagcag tggtggcagc tcctgttgag ctgccctcca gaagccagtt   5820
ctgatgcgcg gcctcgccgg gggcctgaga acccctgttt cctgtgaggc tgggccaggg   5880
acaggataac aagggaggca gaaaagagtg ctggcgggga gccaggaggc ctgggttcca   5940
gccccggccc tgccgcttgc ctgctaggag cccttgagaa agtcagttcc cctgcctgaa   6000
cctcagtctc ctcaccttca gatggagatg ccggcccaga gggtaccaga ggcctttcct   6060
ggcttgcaaa caggatgcca gtccacaaag ccacagggtg agggtgcttc ccagttctct   6120
gtgcttcgga acagcgtgct gctccggggg accttggaaa ggtgactggg ctcttctggc   6180
ggtttggggt gggggttgta gtttgtgctc ccggatgttt gcccacgtgg gtggagcctg   6240
```

```
cctgtctgtt gccccttaga gggaagttgg cagtaggatg ggttgggggg ccgtggatgt   6300
tgggaggccc taaagctgag cccagactct caggcttggg aaggaccttc ccgatcagcc   6360
ttctgtccat ggcttgaatt cctgtcttgt ggcatcagga aagacttatg tcttttaggg   6420
tccaaccaag aaagcagaaa aacactcagg tgttgcagac agagggcctt catacaggga   6480
gttagtcaca caggttatgg gagagccgag aagccgaaga gggtgtgatg agttaaccca   6540
gagattaaca actgcgagaa accaccaccg ccccaggatg gagaagccag ggaggtggtg   6600
gggttagcag atcctgggat cggggtcacc cagtaccagc caggggcttg tggcagagag   6660
ctggagcaca gaggagacat ggctgctgcc gctgagctca cgaaggaaga cagggaaggg   6720
gagggatacc cagcttctct catcacatgt gccccatctt cagtctcccc cagtgcctcg   6780
ctttggcaga actcgctgaa aaacgcagcc tgcaggtatc agcccccacc ctgccctgaa   6840
cacagagagg aacatatttg aggtcagagg cccaggactg gcccagtgac tgtgtttaaa   6900
tgcttcgggc actggggagc tcactctcta actcttaact gtagaggtgg tggcaacagc   6960
ctgttttgct ggcggctgag catgagcatt tggttcagaa taaggaagaa acattggttt   7020
cctgtgactc cctacagaaa gatgaggggt ttgtcttggg agcagaagcc cccgtgtgtg   7080
ttgctttgtg ctgtcatgtc tgccaggaag gcccttcccg ccctcccatc gcttgagacc   7140
caattctccc agaaaacctt ccggcacctc catgtcgagg gatagtaccg tcatgtccgt   7200
ccacagcacc tgcgcttcct tctctattta gcagaatgta gcgaacatta tgttcaacgt   7260
ggacttctct gtttgttctg cctcattcat aggggggcatg gagcttggag aacctgacgt   7320
tgcctaccca gagctggctc taggttaaag agatgctcac taaggcacct atagtgtgcc   7380
aggtctgcca aatgtttggc atgcattatc tagtttaatg ctcccaacaa ctccggaggt   7440
tggtatgatt agcccatgcc tgctcagctg gagaatctga ggctcaaaag gagggtgtcc   7500
aaggccactt ggctagtaag ggcagagcta ggattcgaac acagcctctt aaaggccgcg   7560
ttccttagcc acggggccac gtggtcttgc cacagtgcag ctgggcccag ggtgggattg   7620
tgtgaagtcc ctcactggga atgtttccag ctcagctcct ggtgcctcct ccctgtcct   7680 ctgtccaaga ccacatgtca gcccttgaa ggcgaggcag ccattcccac agccacttct   7740
ctattctgac atgaccaaga agcctggctg ggacagcagg tctgaccaca gattgacaga   7800 tgttccaca tgtggaagtg aggttttgagc ctcgatgtgc tgtttctgtg gttcccttt   7860 cacgctttcc ttgggagatg tgtccagaca tggtctcatt gccctaatag gtttccatgt   7920
ctgttgtgca cagtctttag actgtttaac aatcctgttc actggtagag cactgcccag   7980
cttgcacaca gcactttctt atgcattggc tcagtggctc ttcccaacaa tcctgggact   8040
tgggttcatt tactgatgg aggctcagag aggctaagta acaacagtga caaccattag   8100
ttgccttttg cagatctgtc agcatgcctt gctcaaagag agacagaaac tgcccagtgc   8160
acagtgtctc acttgatctt cacaatagcc ctgcaaggta gatattatta caacctctca   8220
ttggaagtag ggaaactgag gctcagagag aataattgac ttacccaagg tcacacagcg   8280
tcaaatccac acctagaacc catctcttgg tcttgactcc tggttcagtg ttccaagcaa   8340
ctgttgagaa catccatcaa acttaaaaat atatatgact atatttcaac aaatctgata   8400
catcattgaa tatagataca ccactctttt atataccca ggaaatagaa atgctgtcag   8460
ctacagtaag acacagtatt tctcatcaca tagaattttt ttattttaga ctaattaaaa   8520
gagctctttc atatctgtat gcatcatata tatataagca ttatatatgc atatatataa   8580
tgcatcatat atgcatcata tataagcata tatatgcata tatataatgc atcatatata   8640
```

```
tgcatcatat atatgcttat atatgatgca tatataagca tatatatgca tatataagca    8700
tatatgcata tatatatgta tctctctcag ttgtctgtac atagaaggaa aatttatctg    8760
aaaataaact tatatgacat gaaatggatt tatgtgaaaa taaacttctt catattcaaa    8820
atctaactga gtaactgggc gtggtggctc atgcctgtgt ccagcacttt gggaggtcaa    8880
ggcaggtgga tcacttgagg ccaggagttt gagaccagct tgggcaacat ggcgaaactc    8940
tgtctctaca aaaatacaa aagttagcca ggtgtggtgg cagaggctgt agccccagct     9000
acttgggagg ctggggcagg agagttgctt gaacccggga ggcggaggtt gcagtgagcc    9060
aagattgtgc cactgcactc cagtctgggt gacagagtga gactctgtct taagaaaaaa    9120
aaaaaaaaag acaaactctg agtgagcagt agaagcccag ctctttccca taagattgtt    9180
ctccgcacca gcaaatgctg gcgatgaaga tttctccctc tctcttcaaa aatatgttag    9240
agaggaaaag cgtgtttaca tataacaaag tacataaatt ataagtacac ttgatgaatt    9300
tttatccacg ttaatattca tctagactca ccagtgcgtt ggagctggct cacattagca    9360
ttgttaaaca ctcaggaatt ttgcaaactg gttttttaaat tgttggtcac ttaaaatcag   9420
ctgcgggcca ggcgcagtgg ctcacacctg taattccaac actttgggag gccaaggcag    9480
gaggactgct tgagcccagg agcttgagac cagcctgggc aacatagggA gaccctgtct    9540
ctacaaaaat atatatattt ttaaattagc cagatgtggt ggtgtgtgcc tgttaagttc    9600
cagttacttg ggaggattgc ttgagcccag gagattgagg ctgcagtagg ctatgatgga    9660
gctgctgcac tccagcctgt gtgacagagc gagacgccgt ctcaaaaaac aaaaacaaaa    9720
accaaaccct agctgcaatg ggagtatttt acatcatgga aattggcaaa tgctacataa    9780
tccagggctg ttttttttccc ttcagaggtc tggtttactg gcccaccact gagtgtagct   9840
actacccaga tggggagagc ttcccagcat cctagaagcc tcctttgtgg ctgtcccagc    9900
cccctttccac caagggaaca actactggat gcggcatttc ctagaggtgg ctgagggcca   9960
ctggcgctgg gctcctgcga ggggtttgcc attgtgcggg gctggcccac tttcgacgcc   10020
catgggagga atgctgctaa acacgtccga tttaccacct cctccatccc gtacccacag   10080
ccatttggtt cctagaggtt aaaagaacac tcctctattg tctccagggt ttccttccaa    10140
gccgcagaat cccattgtcg atgtgacggt gtaagcgggc tgtgaccact ccctggagag    10200
ggcctcctgc caacaattac tgtaagcaca accccctattt cagagacact aaaatgtgaa   10260
aaatcaagcc tcttagagtc accaaaatac agtatattgc cttttgaaga tctttactga    10320
agcagtttcc tctgagaagc agcttgtctc catcattaag ccccggaaag cagatgagac    10380
tgcagttcct ccgggctagc tgtctcagtg gtcacttcgc ccccagacag gtagcttctg    10440
cccacttctc tcatggggca gccaagtgtt actacctctg gccccggcct ggaataagag    10500
gaccagcagg ccgtgggaaa cctcagctct aataccaggc tgcttctgga cagtcctttc    10560
tgggtgtgga taaagaccag gcttgtgccc tctgggacc gttcaaagca gtcttcaggg     10620
tcggacctca gactcatccc tgtgatgatt gtttcaggtc ctagcgagtt actttcccaa    10680
cctgtgagct tctgcaactg tgtttttttg tttttgtta ttgttgtttg tttgttttaa     10740
tatttttttc ttttctttt tttttgagac agagtcttgc tctgttgccc aggctggagt     10800
gcagtggtgc gatctcggct cactgcaacc tccacctcct gggttcaagc gattcttctg    10860
cctcagcctc gcgagtagct gggattacag acgtgtgcca ccacaccagc taatctttgt    10920
atttttagta gagacagggt ttcgccatgt tgcccagact agtctcaaac tcctgacctc    10980
```

```
aagtgatcca cccacctcga cctcccaaag tgttgggact acaggggtga gccactgtgc    11040
ctggccatgc aactgtgttt taatcacctt tgtgttccca aggccctgac atggaacaag    11100
cacccagtaa gtatttgaat gaatgagcaa atgaaaggcc aggaagggag agcctttatt    11160
ttgaagcctg cccgccgggc tgccctggg  aaagccactt tctgcaaaag tcacaggagc    11220
aaatgagaca aagatgcaaa attgctctgc ctgagctgtg agggcttaac tgtgaatgtc    11280
tttaggtgac cttcttggag acctcaagac caccccctg  tgacttggtt caggctgccc    11340
tgctgtgatg cctgctgggg ccaaggcctg gatccctggg tggggtgggg tggggtgggg    11400
cggggcgggg aggggcgggg cggggcgggg caggagtggc agcaggaagg atccggctga    11460
gacttgccct ggggggccag ggaaggaggg tggcaggagg cagaatccac aaatgaagta    11520
gatctggagc caggcagatc agcccttaga tataatctca aaggggttg  ggagaatgga    11580 aggattttgt tgaggatgga gtgagagggt tggagggttg ggtatgttcc tgagcatatt    11640
tccctgtcta tggggccatt cagagagaag cccacgtgct ccaggccagt ggtggagcct    11700
tcaacgtgga gctggaagac ctgggctcga gtcccacctc tgccatgtcc catcctccct    11760
catgactccc agtagttacc gccttctctg ggcctcagtt tccccaactg gaaattaaag    11820
aaaattaccc tgttcctgca tcagatggtt ggttgtggat atcactgaaa tctcctcacg    11880
tggtattgag ccgctgctct tggccagaca cagagcaatt tacatgaaat gattttcgaa    11940
gtctggtccg gggaccagca gtgtcagcat cacttgggaa ctttgtcaga aatgcaaatt    12000
atcgggctcc accccaacta ctctagaccc aaaaacaatt tttattttta tttttattta    12060
ctttttagga tggagtcttg ctctgtcacc caggctggac tgcagtggtg caatctcagc    12120
tcactgaaac ctctgcctcc tgggttcaag cgattctcct gcctcagcct cctgaatagc    12180
tgggattaca ggcatgcacc acgacgccca gctaaatttt tttattttta gaagaggcag    12240
ggtttcacca tgttggccag gtggtctcgc actcctaacc tcaggtgatc cacctgtctc    12300
ggcctccaaa agtgctggga ttacaggcgt gagccacagc gccctgcccc aaggacaatt    12360
tttaaatgat ataattcata tcccataaaa ttaaccctt  aaagtgtgca gtgtggtggc    12420
ttttagtatt atccaccagg tcatacaacc tattatcact aattccagaa tattttcatt    12480
gctctcaaaa gaaaccttgt accatttagc agtgactccc cactcccctg tccctcagcc    12540
cctgcaatca caaacctact tttcatctct atggatttgc ctattctgga cacttctat   12600 aaatggaatc atagaatatg tggtcttttc tttcacttag cataatgtct tcaaggttca    12660
tccatattgt aatatgtatt agtacatgtt gtactgatgg aacatgtatg ttgtagcatg    12720 tttcacccctt ttaaaaaatc ttcttttttaa attaaaaaca ttttaaaat acattcaaag    12780 attttttag agtcgtttta gtttcacagc aaaattggga ggcaggtatg gagatttccc    12840
tatgttccct gccccacaa  catacgcagc ctcccatcat taacatcccc caccagaatg    12900
gaacaatttt aacaaccgat gaactgacat tgacacatca ttatcactgc aaatccatag    12960
tttactttgg ggttcactgt taatgtagta cattctatgg gtttggacaa gcgtataatg    13020
acacgtatct gtcatgatgg tatcatacaa agtattttca ctgccataaa aatcctctgt    13080
gtgccaccta tttcttcctc ccatcccct  aatcccggc  aaccactgat ctttctacca    13140
tctccacagt tttgccttt  ccagaatgtc attctcttag tccattttct gctgctataa    13200
caaaatacca cagactgggt aatttataaa gaaagagac  ttactaggct cgtggttggg    13260
gaaatccaag gttgagggt  tgcatctggt gagggcttc  ttgctgtgtc ataacacggc    13320
agagggcaag cgagctcacg gaacagagag aggaactcag actgaactca tctgtttatc    13380
```

```
aggagcccac tcctgcgata actaacccc tcccctaata atggtattaa tccattcaag    13440
agagcagagc tctcatggcc taatcacctc ttttttgttt gtttgttttt gttttcagac    13500
agggtctcac tctgttgctt aggctggagt gcagtggcac aaccatagct cattgcagcc    13560
ttgacctcgc aggctcaagt gatcctccta cctcaggctc ccaagtagtt gaaactatag    13620
gcatgtacca ccatgcttgg ctaattttga aattttttta gagatgaggg cttgctatgt    13680
ttcctaggct agtcttgaac tcctggactc aagtgatcct tctgcctcag cctcccaaag    13740
tgctgggatt acaggtgtga ggcattgcgc ctggccctaa tcacatccta aaggtcttgt    13800
ctctccacgc tgttacaatg gcaacgaaat ttcaacataa gttttggaaa agacattcaa    13860
gccatagcat tccacctctg gcccaccaaa actcttgtct tccttgcata caaaataaca    13920
ttcatcccat tccaatagcc ccaaagtttt aactcattcc agcaccgact caaaagactg    13980
aagtccagag tctcatctaa atcagatatg gatgagactc aaagcatgac tcatgctgtg    14040
gcaaattcct tccagttgtg agtctgcaaa atcaaaacaa gttatctact tccaaaatac    14100
aatagtggga caggcatagg atagatgttc ccattccgaa agggagcaac aggaaaggag    14160
aaaggagtaa caggcccaa agaagtgcaa acccaaaag ggaaaacaag attaagtctt     14220
aaagctggag aacaatctcc tttgactcca cgaccagcca cctgggcaca ctgggcagcc    14280
ctgcctctac ggcttgctg aggctcagcc acacaatttt cacaggttgg gatctcatgc     14340
ctgcagcttt cccaggctgc catcactcac tggcagctca acagttctgt ggtctggaga    14400
gtggccccac ttccacggct gcagtaggca ttgccctagt gaggactctg tgcagtgcct    14460
ctgatcccac acttccactc ggcatttacc taataggct ttctgtcatg gcttgccc       14520 tgtggcaggt ttctgcctgg gccccttttt aaatctagtt gaaggtagcc atgcccccac     14580
agctcttgca ttctgtgagc ttgcagacct aacaccatgt ggatgctgct aaagtttaaa    14640
gcttgtacct cctggagcag caggttgagc tgcacctggg accacttaag ccacagccag    14700
ggaagtcaag aggtgctgca ctggaatgat gggggcagag tcctgagatg gctctgggca    14760
gtgagcctgt ggaggatgtc ccaggcatgt tccctgaaac cattctgctc tcctagagct    14820
ctgggcccgt aataagagaa acagcccgga agagctctga aatgtctttg gagtcttttcc   14880 tccaaaggaa taacacctgg ctttcttcta tctagcctga tcttttaagt aaatggttgc    14940
ttggccacac ccttagtatt ctttttccgaa tgttattgct tttcactctt taggaggcca   15000
ggctgtgagt tttccttgc ttctctttta attataaatt ctgtctttaa gtcattcctt     15060 tcctttgca tctcactgta tgtggttaaa aggagccatg cagcaacctg aatgctctgc    15120
tgcttagctg tttcttccat cagatatccc cgttcattgc tcttcagtcc tgcactctat    15180 aaagcccta gacataaaca cagttcagcc aaagtctttg ctactttgta acaaagatgg    15240
cctttcctct tagtttccaa taccttgttc ctcatttctg tctgagacct cattagaatg    15300
gcctttactg ttcatatttc tacgacatt ctggtcatga ccacttaaat aatcttcaag     15360
aagatttagg ctgtccttag ttctagggcc ttcttttgag ccctcagcaa aattgctctt    15420
aatgctccat tcacaggaat ctaggctttt tctagcctgc tcctacaaac tcttccagct    15480
tctatccatt acccagttcc aaagcagctt ctacatgttc aagtatttgt catggcaaca    15540
gctcctcttc tgtgcaccaa ttttctgttg ctataacaca ataccacagg ctgggtaatt    15600
ttacgtatat atagaatata tatatagaat atatagaaaa aatatatatg tatgtatttt    15660
atataataat actgagcatt gactcatggt tctacaggct gggaagtcca aggttgagga    15720
```

```
actgcatctg gtgaggacct tcttgctgtg ccataacatg gcagaagggc caagagaaag    15780
agaacagaaa tcaggctgaa ctcattcttt ttatcaggag cctacttcct agataactaa    15840
ccaactgtca caataacagc attaatccat tcatgagggc agagctctca taacctaatc    15900 acctttttaaa ggtcttgcct ctcaacagtt actatggcaa ctaaacttca acatcagttt    15960
tttgagggga cttctcaaaca atagcagtca tatattggaa tcacacagta tgtagccttt    16020
tctgattggc ttctttcact tagtaatatg gatttaagtt tcctccattc ttttcatggc    16080
ttgatagctc atttcttttt agtgctgaat aatagttcat tgtctggatg taccacagtt    16140
aatccattta cctgctgaag gacatcctgg tttcttcttt tggcagcatg aaaaaagctg    16200
ctataaacat ctgtgtgcag attttttgtgt gaacataagt tttcaactct tttctgtaaa    16260
taccatggag tgtgattgct caatcatatg gtaaaagtat gtttagcttt atagaatgac    16320
aatttacctt tcaaagtgac tgtactatgt gctaagtggg tgtactattt tacatttacg    16380
tttacaacaa tgaaggaaag ttcctgttgc tccatatcct cctcagtgtt tggtgctgtt    16440
tgtattctgt attttggcca ttctaataga tatgtagtat cccgttattt tagttttcat    16500
tcccttgata acatgtgatg tagagtatct tttcttatgc ttatttgaca tctgtatatc    16560
ttttttggtg aggtgtctat taaggtacat ggcccatttt ttaattgggt tgttttttt    16620 cttattgaga gctttaagag ttcttttgtat attttggaca actgtctctt atcaaacatg    16680
tcttttgcaa atattttctc ccagtttgtt gcatgtctgg ttattccctt gacattggct    16740
ttcacaaaac agaagtttaa aaaatttttt taatgaattc cagctcattc attgtttatt    16800
tcagcaataa tgctttcggt gttataccctg acaagtcatc accataccta aggtcatcta    16860 gacttttttcc tatgttgtct tctcaagagt tttacagttt tgcattttta atttagattt    16920
atgaggtact ttgagttaac ttttgtggaa tgtataatgt ctgtgtctaa attcagtttt    16980
tttggtatat ggatgtccag ttattcatat ttttttaaaag atggattttt gcatgatatt    17040
ttgaaaagac tgtctttgct ctattgcatt gtctttgctt ctttgtcaaa gattagttga    17100
ctacatttat gtgggcctat gttgggctct ctattctgtt tattaatcta cttgtttatt    17160
cttttgccaa taccacactg tcttgattag tatagcttta agtctgaag attactatag    17220 ctttaagtct tgaagactac tatagctagt aagtcttgaa gtcaggtagt gtctgtcctc    17280
caactttgtt cttcctcagt attgtgttga ttattttgat cttcccctct tcatataaac    17340
tttagaatca tttttcaata tccacaaaat aacatgctgg gattttgatt gggattgcac    17400
tgaatctata gatcaggttg gggaaaactt atatcatgac aattttgaat cttcctatct    17460
gtgaatatgg aatatctctt tatttatatta gttcttcttt gattttgttc atcagagttt    17520
tgtagctttc ctcatataaa tcttatatat atttacttag atttataccct aagtactttc    17580 ttttattggg tgctaacgta aatggtattg tgttttaaat ttcaaatttc acttgcccat    17640
tgctggtata taggaaagtg acagacttgt acaacaacct tatatcctac aatcttacta    17700
taatcaccta ttagttccag agattttgt gttgatttat ttggattttt ctacatagat    17760
aatcatgtca tctacaaagg cagttttatt tcttccttcc caatcagtat aacttttatt    17820
tcattttctt gccttattga gttagcttgg acttccagta tgatgttgaa aaggagtggt    17880
gagaggaaac atccttgact tgttcctgat tttagtggga aagcttctag tttctcacca    17940
taagtatggt gtttgctgta agtttttttgt agatttttttc atcaaaataga ggaagttctc    18000 ctcaattcct agtttactga gagttgttat atgaatgggg gttgaatttt gcgaaattat    18060 tttttcttcat ctattgatat aatcatgggg ttttttctttt ttagcttgtt catgtgatgg    18120
```

```
ttatattaat ttattttcaa atcttgaacc agccttatat acccaggata aatctcactt    18180
gataatgagg tataattctt tttatacatg gttggatttg atttgctagt aatttgttga    18240
agatttttgc atctgtgttt atgagatata ttggtctgta gttttgtttt ttggtaatgt    18300 tttttatct ggttttgtta gtgctggact catagggtga gttagaaagt atttgctctg    18360
cttctatcct ctgaaagtga ttgtagagaa ttggtataat ttcttcctta aatgtttggt    18420
tgaacttacc agtgaactct tctctgcctg gtgccttctg ttttggaagg ttattaacta    18480
ttgattcaat agatataggc ctattcagat tgtctatttc ttcttttatg agttttggca    18540
aattgtgtct ttcacagagt tggtccattt cacccagatt atcaaatttc tgggcataga    18600
gttcatagta ttcctttctt atcctttcaa tgtccatagg atctgtagtg atgtcccttc    18660
tttaatttct gatattagta atttgtgttc cctctctttt tttcttagtc tggctataga    18720
cttattgatt taattgatct tttcaaagaa tcagcttttg atttcattga ttatttaatt    18780 ttctttttc aatttcattg atttctgccc taattttac tattctttt tttcttctac      18840 ttactttggc cttcttttcc tagtctgtta aggtggaaac ttagattatt gattttagat    18900
ttttcttctt tcctaatata tgcatttgat gctataatct tccctcaaac cactgctttg    18960
gcttatctta cacattttaa taagttgtgt tttaattttc atcaggtaaa aatattaaaa    19020 ttcttttga gatttcttct ttgacccatg tattatttag aagtgttttg tttaatctcc     19080
acatgttttg gaattttcta gttatctttc tgttattgat ttcttttaat tccattgttg    19140
tctgcgagca gaagttgtat gatttctact ccttttaatt tgttaaggtg ggttttatgg    19200
cccaaaatgt ggtcaaattc tttctgtttt atggcccaat aatattccat tgtatagata    19260
tacaacattt tgtttatcta ctcatgagtt ggtggacatt ggggttgttt tcattttttg    19320
ttaattccat tgtacactga acatacaatt cagtggtatt ttgtatgctc acaatgttgt    19380
gcagccatca cctctatcta actccaaaac atttcatcaa ctcaaaggag atcttgaatc    19440
cattaagcag ccactcctca tgtccctgct ctcaacccct ggcaaccact aatctgcttt    19500
ctgtctccat gaatatagct attttggata cttcatttaa atggaatcat acaatatgtg    19560
atcttttgta tctgacttct tttacttttc ataatgtttt caatgttcat ccatgttgat    19620
agcattcctt tttagggctg aatactgttg tgttgcatgg atatactatg ttgtgtttat    19680
ccattcatct actgatggac gtttgagttg tttccacttt tgctgtgtga atagtgctgc    19740
tatgtatttg tactcattgt acacattgtg tacaaacatt tgttcgaata cctgttttca    19800
attcttttgg agaattattt tcaattctag gagcagaact gctgggttat atggtatcat    19860
tgtgaggaac tgccaagctg tttcccaaag tggctgaacc attttacatc cccaccagca    19920
acatatgaga gttctaattt ctccacattc tcaccagtgc ttgttttcct ttcctttcct    19980
ttcctttcct ttcctttcct ttcctttcct ttcctttcct ctctctctct ttctgtcttt    20040
taaattatag ccattctagt ggatatgaaa gagtatctca ttgtggtttt gatttggatt    20100
tttcaaatga ctaatgatgt tgagcatctt ttcatgtgct tcttggccat tgtatatctt    20160
ctttgaaaaa atgtctgttc aagcattttg accattttta aattgggtta ttttgtcttt    20220
ctgttgctga attgcaagag ttttttttat atgtcctgga ttctagatgc ttatcagata    20280
aatgatttac aaacattttc tcccattatt cattatttgc tgtcattcca ttttcctttt    20340
tttttttttt ctttcttaga cagggtctta ctctgtcacc caggctggag tgcagtggtg    20400
caatcttggc tcactgccac ctccacctcc ccagctcaag cagtcctccc acctcagcct    20460
```

```
ccccagtagc tgggactaca ggtgcacacc accatgctct gctaattttt atatttcttg    20520
tagagatgaa gtttcactat gctgcccagg ctggtctcga actcctgagc tcaagtgatc    20580
ctcctgcctc agcctctaaa agtgttggaa ttacaggcat gagccactgt gcccagcctc    20640 atttttatttt cttgatagtg tcttttttttt tttttgaga caaggtctca ctctgtcacc    20700
caggctggag tacagtgaca tgattatagc tcactgtaac cttgaactct gggctcaag    20760 caatcctcct gactcagcct ctcaagcagc tagtacaaca ggtgtgtgcc accacgtctg    20820 gctaacttt acattttttt gtagaggtgg agtcttgctg tgttgcccag ctggatcttt    20880
gatagtgttt tgttttgttt tttttagatg gagtttcact tttgttgccc aggctgaagt    20940
gcaatgtgca attgcgcgat ctcggctcac agcaacctcc atctcccagg ttcaagtgat    21000
tcttctgcct cagcctccca agtagctgtg attacattta tgcaccacca cgcctagcta    21060
attttgcatt tttagtagag atggggtttc accatgttgg ccaggctagt caggtgatcc    21120
gcctgcctca gcctcccaaa gtgctaggat tataggcgtg agccactgtg cctgggtgcc    21180
tggccttgat agtgtttttt gattaactat ctactttttat tttgatgaaa tccaagttac    21240
ccatctatgt atatactgag ctgaccctga gacatggcaa aatgtgtgaa gatggtactt    21300
gagtgagtga gtttgggca atgttgtttc tagtgaattc tttctccttg gtggtttcct    21360
ctggcctgtg gatatacttt attcagcaaa agatgccagg gctgagggga tatggcctct    21420
ggtctgccac ccagagggta aacttggcaa gaccccagcc aggctccccc tcctctgctg    21480
ttcctaaaca tgcattcatg gacaagggt ctctggagca aaggagagtg actccttccc    21540
tctcccgcaa ccttgcccac ttaccttgta gccagccact ccctcctctt tctgtaactg    21600
ggcattggtc cagctgccag gcccaggacc tctcccattt agccagatgt agttccaaaa    21660
acaactgcag cagtatttgg atacattttc cagcctgaac tagtggtgtt cctgtccata    21720
gctgggatcc aggtttgttg cctctgggtg gggctacagc tccttacctc ctggaaggtt    21780
gtggaagtgt ggtttccttt ttctcctttc tcttgtggaa cataagcatc tttccaagtc    21840
cttctggcca gatgatgatg gtgtgagcct gtccgtctcc catcagtgct gagggggcctc    21900 agatgctgcc tcttacctat aacccagatg ctcccaggtg tgtttatttc ctagagctgc    21960
tgtgacacag agccacaaac tgggaggctc agaacaacag gcattgttcc ttgcacagtt    22020
ctggaggctg gaagtccaaa atcaaggtgt tggcagggct ggttcctacg ggaggctctg    22080
aggaagaatc tgttccaggc gctctcctgg ctcctggtgg ttgctggcaa tccttggagc    22140
cccttgactt gtagatgcat cactccagtc tctgccttca tcttcacatg gcgttctccc    22200
tttccctctg tctctgtgtc ttcttctcct catcttattg tcatattgga ttaagggcct    22260
accctgcatc agtatggcct cgtcttagct aatttcatct gcagttaccc tatttccaaa    22320
ggtcacattc tcaggttcta agaagtacat gaattttgag caggataatg tatggcccag    22380
tgcaccaggc aatgccaagg gcatcactag gtaggaggct ggagatgact ccatttctgt    22440
gagctcctcc ttggctcctc tgtgtctttg cttctaacag cctgtgcctg ccactctctc    22500
tcgagggctc cccttgagct attagagggg ctttgtgtgc acaaaattca gacacacaca    22560
cacacacacg cacatgcaca tgcacacaca catgcacaca tgcacacaca cacacatata    22620
cacacacaca cagagccaga gtgcctggat attcgtgacc cctggagctg tcttaccatg    22680
gtgatgactg acaggtgggc agggcacggt ggctcacacc tgtaattcca gcactttggg    22740
aggccaaggc aggtggacca cctgaggtta ggagttcaag accagcctaa ccaacatggt    22800
gaaaccttgt ctctactaaa aatagaaaaa aattagttgg gcatggtggc gcatgactgt    22860
```

```
aacccagcta cttgggaggc tgaggcagga gaatcacttc aacctgggag gcggaggttg    22920
caatgaaccg agatcacgcc attgcactca agcttgggca acaagagtga aactccatct    22980
caaaaaaaaa aaaaaaaaaa aaaaaaagga atgactgaca ggtgcacatg cagaagcata    23040
gaagcccaga tccctggcct gcagttgggc acaaactctg aggtgtaact tatactccgg    23100 agcccccccac aggtcagttt caactggcct caccctccat gtctagctcc ccctactctg    23160
acactggctt gtcctgggag tacttcctta agaaatcact ttcatgtgaa ttctcttctc    23220
aaagtctgct tctgggcagc ccaagctgaa acagatcccc atacctggag cctgctgcag    23280
ccaggactga tatgcaggaa cccagcccag ggagccacaa agggatccac ctccccggat    23340
ccaggggttc atgattcatg ggcgatggtg ctctgtaaat gggaaggccc tctgtgaaca    23400
ctggggtgtt tgccacgcat tgtgctcaat tgtccctct atgggcgggc cttccccaac    23460
cacaccatcc aagatattct aatcttgtcc tttcaggctg ctgatcaact agttcaggag    23520
tcactgtgga catgtcacac ttcttcctcc atgagatgga gatgaccaaa tctattcata    23580
gttctgtgtg ccaacctatg aaccagacct gagcccctta cccctctgac agtcggcttc    23640
aggaaatcgc catgaggcta caggtgtgtg ttgaggggtg ggtagagaca caacataagt    23700
gggtggcgtg gggtctggca cacttcttca tgtaacccac ttgtacctgc tggacctgcc    23760
agtctcaatc ccaaatatca ctgtagcatt tctcttttt ttatattatg acaaatactt    23820
atttatttat ttatttattt atttatttat ttatttttta atttattttt aagttccagg    23880
gtacatgtgc agaatgtgca ggtttgttac gtaggtaaat gtgtgccatg gtggcttgct    23940
gcacctatca acccatcatc taagcattaa gcccagcatg cattagctat ttatcctgat    24000
gctctccctc cccacgcacc tcctgaaagg ccccagtgtg tgttgttccc ccaccgtgtc    24060
cttgtgttct cattgttcag ctcccactta tgagtgaaaa cacgtggtgt ttggttttct    24120
gttcctgcat tagtttgctg agaataatgg ctcccagttc catccatgtc cctgcaaagg    24180 acataaatatc gttcctttt atggttgtat agtattccat ggtgtatgtg taccacattt    24240
tctttatcca gtctatcatt gatgggtatt tggattgatt tcatgtcttt gctattgtga    24300
atagtgcatt gtagcatttc cattgtacag tgggttactg ctgtgcctgc ctcacattag    24360
gatttggtgg atctggtcat agccagctca cagagggaaa ctcagccagc atagttgctt    24420
gatgtctcat ggtcaggctc tgagtctctg tagggttcag tagcatgcca gcaattgttt    24480
ttcaaaagga gagtagttct ccactgcaga aaattttaga ggtctgtact gggactcttc    24540
tactggggtt tgttaaaggc tccacccaag ttctttatct agcaccataa atcttctcag    24600
tctcatggct agcagagcag ctcacactgc agcttggacc tatgcagcgt tctcttttgc    24660
tttgtctcag aactgaaagc tttctgaatt gcctaataaa taggtcagag tagcattccc    24720
aagtgtggta tatgctgctt tgaaattcaa ggagaacaaa gaaggtgggc ataaaacaac    24780
agaaggacag tttctcgcag ctggggagat cagaagtctg aaaccaagat gttggcaggg    24840
ctgacacggg caatacacga ggcccgtgta ttgcctcttc ctgcttctct tggctccaga    24900
cattccttgg cttgtggctg catcactcca atctgcgtct gtggtcacat ggcctcctcc    24960
tcttccctat gtgcctctgt tctgtatgtc tcttataagg acatttgcca ttacatttag    25020
gacctgcctg catcatccaa gattacctcc ccatcttgag atccttaact gaattacatc    25080
tgcaaagatc tgttttccaa ataaggtaat atccccatag gttctggaaa ttaggacatg    25140
gacatatctt cgtggtgggg tgggggggtg cttttttcatc ctactgtatg gtagaggtgc    25200
```

```
aaatgcagca acttgtctttt ttttctgaga ggggatggct tggcatgcct cagatcacag    25260
gttccttaag atcttcatca atacggggga ccctgaattt tcagaggctt tatcttccac    25320
tctctggtgt gcatacattt ttgttttgtt ttgttttgag atggagtctc actctgtcac    25380
ccaggctgga gtgcagtggc acgatcttgg ctcactgaaa cctccaactc ctgggttcaa    25440
accattctcc tgcctcagcc tcccaagtag ctgggatgac aggtgcccgc caccatgcat    25500
ggctaatttt tgtattttta gtagagacag ggtttcacca tgttgaccag ctggcctcg    25560 aacgcctcac ctcaggtgat ccacccacct cagcctccca aagtgctggg attacaagcg    25620
taagccactg tgcccagcca tatattttat taaagcatct tgggttcttg ccattttttcc    25680 tccttaggtt tagagcagca ggagcatggg agcaactgtc cagtgaaggg ggtctgttga    25740
gaggctcacc cacagcatcc actgcagtgt ccttgatcat cttgacaccc cacgctacca    25800
cccaggtccg tcatgttaac attgtgtgag cattggctgc aaactgctca catctgcccc    25860
cttctctgga gaattgctct ctgccaaaca gtagacatct caccgtggag gttatgctcc    25920 tttggggtg tggcaagtct tgccaactga cttacctgag gacacaaaaa gtctgctatc    25980
tggaggggac aagtcagtgc tgtaattaat gctccaaagg ccctcatgag accagaatga    26040
ggctggcctc cagcccaggg atgtcataga ttaacttttct ttctctgctg tgtcctgctt    26100 ccctcttttcc acttcccctg aaagtcctcc ccacaaaaat ccccacctct tgatctgctt    26160
ctagggaaac ctgacctaag agattccttg ggtgtattag tctattctca cgctgctaat    26220
aaaggcatac tcgagactgg gtaatttata aaggaaagag gtttaattga ctcacagttc    26280
ccatggcagg ggaggcctca caatcatggt agaagagcaa ggaatgtctt acatggtggc    26340
aggcaagaga ggatgagagc taagttaaag gggaaactcc ttataaaatc tcgtgagatt    26400
tattcaatat cacaagaaca gtatgaggga aaccacctcc atgattcaat tagctcccac    26460
tgggtccctc ccacaacgta tgggaattat gggagctaca attcaagatg agatttgggt    26520
gaggatacag ccaaaacata tcattccctc cctagcccct cccaaatctt atgtcatcac    26580
atttcaaaat caatcatgcc attccaacag tccctcaaag tcttaactca tttcagcatg    26640
aactcaaaag ttcacagtcc aaagtctcat ctgaaacaag gtaaatccct tctgcctatg    26700
cacctgtaaa atcaaaagca agttagttac ttcctggata aaatgggggt acagggattg    26760
ggtaaataca gctgttccaa atgggagaaa ttggccaaaa caagggact acaggccca    26820 tgcaagtcca aaatccagtg gggcagtcaa atattaaagt tccaaaatga tctcctttga    26880
ctccatgtct cacatccagg tcacactgat gcaagaggtg ggttcccatg gtcttgggca    26940
gctctgcccc tgtggcttca tggggtagag cctccctcct ggctaatttc acaggctggc    27000
gttgagtatc tatggctttt ccagatgcac agtgcaacct gttggtgggt ctaccattct    27060
gaggtctgga ggatgatggc cctttctcac agctccacta ggcagcaccc cagtggggac    27120
tctatgtggg ggcttcaacc ccacatttct tttctgcact gccctagcag aggttctcca    27180
tgagggcctc accctgcag caaacttctg cctagacatc cagttacatc ctctgaaatc    27240
taagcagagg ttcccaaacc tcaattcttg acttctgtgc acccacaggc acaataccac    27300
atggaagctg ccaaggcttg gggcttccac ctctgaagcc acagcctgag ctgtaccttg    27360 gccccttta gatatgacta gagcaactgg gatgcagggc accaagtccc taggctgcac    27420
agagcagtgg ggctctggac cccagcccat gaagccattt tgtccttcta agcctctggg    27480
cctgtgatgg gaggggctgc cacaaagtct ctgttatgcc ctggagacat ttccccatt    27540 gtcttggcga ttaacatttg gctcctcatt acttatgcaa atttctgcag caggcttgaa    27600
```

```
tttctcctca gaatatggat ttttcttatc tattgcatca tcaggctgca acttttccaa   27660
acttttatgc tctgcttccc cattaaacat aagttccaat tccaaccat atctttgtga    27720 atgaataaaa ctgaatgctt ttaacagtac ccaagtcacc tcttgaacac tttgctgcct   27780
agaaatttct cccaccagat gccctaaatc atctctctca agttcaaaat gccaccagtc   27840
tctttggtaa aacatagcaa cagtcacctt tgctcttcct ttgtcttctg ccatgactgt   27900
gaggcctccc cagccatgtg aacagagag tcaattaaat gataccatga tggaggatgg    27960
agtgagggag tcctgaggct ggaccatgaa ggtgctctgc tgtccctgcc atgtaaactg   28020
ctctagtgcc tctctgctgt tggatatcag gaagaaagga tttaccaaat tggtagctgc   28080
ataccaaatt ccagagacag tgttgatctg ctgtagtcaa gatgccacaa ctggtacagt   28140
gggtgaaact ggactatgcc tggctatgtt tatgtagtcc acagtcagct cctctgagag   28200
accttccctg accatcttat ctaatgatgc cttccaactc ccagtcttcc tccatcatat   28260
tctcctgttt tattttttg tgtactgatt actgtctgta gccatgtgat ctatttattc    28320
gtttatggcc tttctcccca attagggtgt aggctccagg ggaataagga cattgtgtga   28380
cttgtttgca gctgcatccc aagcacccgc cactgtagta gatgcctaac caatgtgtgt   28440
tgaatgaata aaagagcagg ccaatgttct tttgctcaaa gtagagggga agaaatagg    28500 ttttctgtgg agattccaag gcagaggcca tttctggggg tcactggagt gggagaaggc   28560
aggtcaaggt gggttgtctt ccaggcagtg caaacccct ggcctctgcc agctgctcac    28620
tggccagtct gcttgttggg tctggcacag gcctcaagga acataacat ttttaataaa    28680 acctcagagt caataaaggc gaatggtcct gggtgcctct cctgccggcc ccagctgttg   28740
actttagaag tcaagagagt ggggcgttgc ccaattctca tgtagtacag ggagatataa   28800
gctggaaggg cctagcccat tttatatgaa aacaaaacaa aacaaaacaa aactcaccag   28860
gccctggaaa gagtccacca ccagccagaa tcaaaggtcc attcagagcg acagagctcc   28920
tcacattcgc cgctaatgaa aaccaaattt ctcatccctc tgagcatttc caggggctac   28980
aaatggaagg ggctgcagag tctttggcca ccgctcccac caccgaaggg gccccactgt   29040
gttaaaatag ttttatgata atataggcct tgtattttcc taatttcagg cgtcagtgat   29100
ttaggacgga gttgttttca tggaaaaaga aatagaacct gtttgtggcg gggcaagact   29160
gatgcctggg cagatattcc cactgtgggc atatttgggt aggggggtga gcctgccatg   29220
aagaggctca gacctagctc cggggaggcc tcgttcatga agttccccgc cttgggcggg   29280
gaagaatggg ctgggggttt ccagacagat tcagagacag tcacagtgac ttctgttttt   29340
tgatttcatg ctttgtgaaa tcttagaatc acaactcaga aaggtagagg catccctctc   29400
agacgcagag aaagggcctc tgttttttta aaaagacatt ttctcatttc ttttctttt    29460 tttcctcccc cttgatcaat ctttataagc aagtatgtgt agaaatgtca tatttttttt   29520
ttcttaaagt caacttgatt cttactttga gcctccaata cttttagttg gtaggaaact   29580
taatattttc agcgactgct ctgccttcgt caggatcagg tggaattctg tccttgtttc   29640
tcagttttgt tttgtttgt tttcagatgg aatctcactc tgttgtccag gctggagtgc    29700
agtggcacaa actcagctca ctgcaacctc tgcctcctgg attcaagtga ttctcctgcc   29760
tcagcctctt gagtagctgg gattacaggc atgtgccacc atgcctggct aattttttgta  29820 tttttagtag agatggggtt tcactatgtt ggccaggctg gtctcgaact cctgacctca   29880
ggtgatcctc ctgcctcagc ctcccaaagt gctgggatta caggcaggag ctaccgcacc   29940
```

```
caacctgttt ctcagttttt tttcatctgt aagatgggga gaatgataat acatacctca    30000
atgggctggg ttaaaaaatg gtgaaatatt tagaatagtg cctggcacag agtaagtatt    30060
aactattatt attattattt ttattattcc agagataaag agaaggcatc aaacctagta    30120
tgagggtatc agggaaggct acctggaaga ggtggtgttt cagctaatga cagatgaggt    30180
agtccttgca tgattttgaa ctcctctgct tggacattta tgtctagaat ttgatatgct    30240
atacctgaa caagtgtgct aattttagaa aactgtaaag aagaaaacag aaaacagcca     30300
taatcccatc tttgcattga tttcattctg gattaattt atctctattt ttaactatat     30360
taattgataa cctgtatacg cagtgtgtgt ctggctagaa aaatgtttat ttctaaaaag    30420
tatttatata tttataggaa ataaagatct gaatggggga gaaaagccta aaatattaa     30480
cagtggttat ctttggaggg ggggattatg gctcattttt ctcgtgtgtt tgttggtaat    30540
ccggactgtc tactttccct ctcatgatta tatattagtt tgtgtcattt aaaaatgtca    30600
tttagtctgg gcatggtggc tcatcctgta atcccgacac tttgggaggc caaggtggaa    30660
ggtttgcttg aggccaagag tttgaggcca gcctgggaaa cgtaacgagg ccctgcctct    30720
aaaaaaaaaa ttagccaggt gtggtggtgc acacctgtag ttctagctcc ttgagaggcc    30780
aaggcaggag ggaggatcac ttgagcccag gagttggagg ctgcaatgca ctccagtctg    30840
ggtgacagag tgagaccctg tctaaaaata aaaactaaaa atattactta aaatgtaata    30900
tatagaactc aggaaccgca gatggagagt ctcataatct ttatattttc agaccatgaa    30960
ggagagtggg gtagcttggc cggactctga gcgtcctgga cccacaagtc tgagaggaga    31020
ggctgcatgt ggcctctggt atggtcacat ggttctataa ggaaactgag gcaggacata    31080
aggcttcact tgtgaagtgg tggagaggga gggggcaatt gccaactggg tgataataaa    31140
gactattgtt aagaccttgc ccccagtggc acatgaaatg ccactaaccc tgagagattg    31200
agagacattc aaacctgagg tttggggcat ggtgccttc ctgtgacttt ggtgctaatg     31260
atgtctaaga tacctcttag ctcctcccct tgtcattctg cacaggcttc tcctttgcct    31320
ggactatttt agtagcctgt gaacaggtct ctggacctc atccccagtc cgcaccatga     31380
tggtgctccc atccaacaca tacatctccg cttggctccc ccgtgccact gacccctgac    31440
atggatcctc tcccacctcc catcaccatt gcgccacttg ccccaccatc ctcccagctc    31500
agcgacacct ggttctccag gccctttgcac atgggattcc ctcctgccac atctctgctt    31560
gatccattcc tactcatctt tccatctgat ctcggggggag agacattttc tctgaggagc    31620
ttggcttgtt tgccctgatc cacactgggc tggcacaacc tgcttcctg tctgtctgcc     31680
ctgtgagatc cctgaggcca tggctgtgac ttgttcacct tgttcttggt gtctggcacc    31740
tgagggtggg gtgggctct gtgtctggtg aatgagtgaa tgaattctgg ccaaggcctc     31800
aaagacaccc agcccaatga gctgagtggg gtggtgtggc ccaaatggtg tgtttggaca    31860
ccagagagcc cacattgctg ccagccgtca gggtgggcac aaaggagggt agtccaggcc    31920
ggctccaggg ctgccgcact ccccttccca tgataggtcc cctgggccag gcccagggca    31980
ggccctttct gtgggtgaat ataaatatat aaaacacaca gcgcactctt agctgcaaaa    32040
ctaaaaatag gaagcgcggg atccggctcc ccaggcttcc ccagccactg gaccacacag    32100
gtgtggctgc ggatgtcggg gcgatgtggc ccctcacccc tcccagctct ggagccctca    32160
tggggaggaa tgaggggcat tttggatttc tgccaggaac agttcattct ttcactctgg    32220
cctccctcct gccccgtcc catttgacag ctcatttcat ttacgacccc aaaatgaacc     32280
gacccactga ggtgtattct ctactcacgt ggccaggctg ggttgtttgg tgcagctgag    32340
```

```
agctgccctc tgggccatgc tgggggctg catttatgcg gggtgcagt ctggagcaga   32400
ggagaggccg gggctgagga gggaggcagg gctgggtctg catccagccc tgccctccc   32460
tacccacggc actggcccca ccccgcgcca tctcctcaag ccctcaccag gccctaacgt   32520
gggaatgtgt catctctggc ctgtagcctc actgccagga catccattgc tcagtgtaaa   32580
agccaaagcc atccccatgg ccacagccca acagtggcag ggctgctcct aggggccggc   32640
aaggcgggtc catctgggcc acttcacccc acaggaggcc acttctggga gccccaggc   32700
cacagccggc tctctgggtc catcattggg cccatctggg ccaacctcaa gctgtggggg   32760
ctgaagaaac tggagggact caaagtccag cccagatcaa caggactcct agagcctcca   32820
aagcggaatt ctggagtcca ggggctccca ggctgtggaa ctaaatggct tcctcaatct   32880
gaactggctt ctacatgacc taagctcttg ctggtggctc aggggacatg ggtgggctg   32940
ggcccagggt ccaggaggcc agggttgtaa aactatgaaa gtcaaccctg ccttcaagcc   33000
aggtacaccc tgtcccaaag cagacgatta tggggtgtgg ggtcctactc cacacctggc   33060
acacggccgg tgctcattca gcgtatgacc aaaaagggag actcagagag gacagggac   33120
ctcccactgc cacacggctc gggaagggaa aaccttcccc acatcaagac ctttagctgg   33180
cccttttcggg aatgagtcac ctgaggttgg gaagttcttc ttaatacctt acctgaattc   33240
ttgctgtaac caaggcagcc tctcctcacc cttgtccaaa ggggatgatg tccactctct   33300
ccacctgctg cccagggatg ccgcccccta ttgccacctg caggctgctg tggctactgc   33360
agcacttcct cccgcagccc tgggacctca ggcaagctga gacttctcgg gaccttgagt   33420
ttccccttgg caagctgggt gtgctggttc gtgcctgcta gggtgcaggt gatggagatt   33480
tgagtcagga actctggagg gcacagctcc tctccgatct gctgtggcac caaagtgtgc   33540
ctggtgagga gtgctaccat cccctacaaa gtgaccccaa ataaatagaa acagttttgg   33600
ccatgtagat gccgtttcag gaccaaccct ggcagaggct gcccagagca gaccaacaga   33660
gaagttctgt agccacggct gaggtcctgt ccagagatgg acctgctgtc ttttgggtaa   33720
aaggggatgc cgggctaggg aaatggaagc ttcttgttgg gagctgagtt tcaggcagac   33780
caaccaaact gagcagggca aagctttggg agtggttttt gaagtcggtg ggcatcactc   33840
aaaaataagg tctgttttgt aaaaatttcc cttcacaaat cccaactggc caggctctgg   33900
gctgtgtgtt ggtacaaatc ccaagtggac caggcctcct tgctggcaag gtgggagggg   33960
ggctgtcaag ccaggtcccc acaccatcac acccatgcta ccattgttgg gctgtggtcc   34020
cagttcagcc atgacaacc ccaggagac atggaccttg atgacactcc ttctttgcac   34080
cgcagttgtc tcatctgcaa aatgggggca ctgaagttgc cgcttactcc caatccccac   34140
tgctgctagc ttgccacaga tcttgaaaca cgagcctcag gggggggttc tcaccaaggc   34200
acttggactc tccctctgcc tctgcccct cccgaaatgt gaatctgagg aacaggcata   34260
ggaattcctc ccaacacggc tggaagact cacagcccgc tcatgattgg tggaagggtt   34320
gtggcacttt gaagacctat ttgatgctct cctggggtcc cagccataca ggagcaggcc   34380
tcaccggctg tcctgtggcc agggtggtct ctgcggccat tcctgaagaa gttggaagca   34440
aggagatgaa ggtgctgggt gtctctgttc ctgttcctcc tgggcaacag caggaggtct   34500
ccatcctctc ccccaccca ccccacctcc atgcatagcc ctagaaaccg ggcactggac   34560
tccttccaca catctcagag ttatattatt gtaacaaatc agtcaaaatt ccattttaca   34620
gttaaatagt acagaagaca gtttactgta caagcaagtt gtgcgttaaa aacaaacacc   34680
```

```
aagcaaacga tagtgcaaag cagtttccac ccagctccat cctctcgcca gctctgggat   34740
ggttttacat cagatgagtg cagcaggtgt cacacctcag catgacaata tgtcacaaaa   34800
gattggtacc cactactgac aggctcacag taacactata tcaaaacgtc ttcctttcct   34860
cgtgcttcct acatcagtgt gtttgcctag tacaacttta acgcagcctt gtaaataagg   34920
acctactttt accagcccag gctgtctgta cccactttgg gccttacaga ctcagtacgg   34980
ctgccgtcac ttttttgtcag gggatggggg atgggtagg aagagcaatt tatttactat   35040
ccctgcctct ccaggatcag gaagggttag taatctggga tgagactaca aagtgctggg   35100
cactgggaac ccaaaggtgc ctcccacgct gacctgggac cagctataac cagagaacag   35160
gagggaagaa actacaagga caatggattc atagctgctt cctaagaagg catggagagg   35220 cccctgggt gcagggagtc agcaactatt ttgaggagat ggagactgtt tttccagtga   35280
ggacaggcca agagaaaccg cagcaggagg gaatggaata ggatcaccag aaggactgcc   35340
taacctgcca gtgtgtctct ggtgtatggt tctggccgtt gtgacaggtt gggtggggac   35400
agtgctctca cagagacaac caatgaagag catttttgtag gcagatttc tgcatccaca   35460 gaggccgagg cagaaagtta aaataccgca tgctgctagc ctttatgagt tcccttacgc   35520
cttttctaag cctttctagg gccagagaac tctgatgtga gaatccatgc agcctggccc   35580
ttgggcaagc gcccacttc ccattttgca aaattcaggg gcaagacttc acctcggaac   35640
gcagtgcagc tgagctgcgg ctggagagcc ctttacagtg cttctgtcct gccacgcaca   35700
gccagtactc cccacctctc acatcctgcc cacctccgcc cagcctcctg gacagatgtc   35760
ctagagccac agaggagaga tgcccagcgt ctcatcagcg tttccctcgt cctcccaggg   35820
gagcctgtgg tgcaggctgg tgggatgctg cctgatgggg agtgtagccc cttgagaaag   35880
tattgagacc ctaataaccc cacaccctca ggaggcagct gggggtccgc gggggggaga   35940 ggggcgggg atgttgctta taatcacaga gctatcataa tcacggaact atacctgtaa   36000
gagaccttgt gtttgaaaac gttagattaa gcttctttt ctaaaatcag ttttaaaaac   36060
tgttttgttt tttttttgtt ttttttgttt ttttttttt ttgctcagga ctatttgctt   36120
tcagagcaca aaacaggtta cagacaggtg tgtgccagga gtcgcaagat ttggctggat   36180
cctcccagga ggcttggggg atggggcaca gcttggctgg acccagggggg gacagggaca   36240 ttgatgtctg acccaaaatg atccctcacc tcaatgcctt ctgctaggac ctatctatct   36300
ggccctcctg ttctctccac aaatggaatt atgagaccac ctaggggaaa ggggacctcc   36360 tatccccct cccccgccct gccaagagaa cagagagtgg atgcgttgag ctggtaaagt   36420
gcatggagga gccggtctgt aggtgctttc ctgggtttaa gaacctgatg ccatagactc   36480
atcttctctg gggcctggga cccgtgcggc tggggaaaag ccaacagtta ggaacgggagg   36540 ggaagctggg ctgggggggac tggcttggat gtgttctcaa accatctctg ccagcagcgt   36600
gctgggtcct gccccatctg tacaatgagg ggaaccccgc tcgagggtgg tggggtggg   36660 ggacactttc cagttctgac tcaaatctgt gtaaatgcag agggggctgg acccagggga   36720 tgcagggggct ccaacgaagg tgcagggggtc gggaggtttc ccagggcctg aggcttatcc   36780
tgtgggccaa tgctgcctct ctctggaaga gagatggcct ctgtcccagg agacatgggt   36840
cccatgcagc actgggcata gctggagaca gtgaggtcct tccggggggg tggcaggagg   36900
ctgattcccc acagaagtat gggatgagac ggccaggatc tgggccgggg gcagtatccc   36960 gggccgggggt gggggtggta acctatgcct ctgtacaagg atgtggctgc acagatgcag   37020
ccagaggctc ccaccagctg ggaccaccct gggaccgaga ccaccctgga gcgcaggtcc   37080
```

```
cattcccgcc cggagcctcg gagccggccc atcactggtc ttgaaggttg ttagggtccc   37140
cgcctccagc gggaggagtc caccagggcg gtcagtaggg ccgccacacg gcctcatcca   37200
tgcggcctgg cgtgctcagg gccgtgggtg agttgctgtg gctgccgtcg gcctccacgc   37260
catcactctg gccgcccagg ctggggttca tgaggttgcc ggcggcgaca gaggcagcgc   37320
tgctggtgca agaggccagc atgcgggtag gtgagcggtc gcccccactg ctgctgccgg   37380
ccaccatgga gaactggtag gagccagagg atgtcccgta gtagaggtgg taggggacg    37440 ggttggcctg gaagggcccg ctctggttct gcggggcccc cgggtagggt ggcgggaggt   37500
aggtatggtg gaagcggctg gtggccggca tgcccgccac gctgaggctg ctgatgctcg   37560
tgcccgaggg cgtggcgctg taggggaagg cagctgacat ggccccggga taatgcatcc   37620
tggggtctgg gaagcggctc tccgtgaggg ttggcagcgt ggggaaggag cggtcaaact   37680
ggcgggggtc ggagaatggg ttcagttccg aggtgcctgg aggacagcag ggaagaggtc   37740
agttccagct cgagacaacc ccaggagggc ttcctgaaga atgaccttgg gctctggttc   37800
ccaaggccca tctgggggac ccctagttct agacctggct ctcctcttcc tgccctaggc   37860
tgcccggggc ctcccccgcc aggactccga acacagacct gccgggaagc tggttggagc   37920
gtgccccggg ccaagagggg ccatgggagc cccccacag cagcaacaga acagaggagg    37980
gggtctattc ttcttttaa atcctccttc ccagcctcgc agaggagagg cctaggatgc    38040
ggtggtgggg ctgagggcag agtcagctca ggcctcccag cagccctgcc caggcaggtt   38100
cctctcccca ccggcccatg ttaacagctg ggaaggccgt ggatgtgtaa agggctccaa   38160
tgaccgtgtg agactgggag ttggaacccg cttttgaaga caagaaaatg gaggcagaga   38220
gagagcaaga ctgagtctct gtggcagaga aaggactggt tctcatcaca aggcctctgc   38280
tggggacaca cgtgcctctc ctgcccaggt gcagcacgcg gaggttctgt gcgctcacac   38340
ctgggttgtg ggcactgagt tcacaggagc tctggcctcc acctcaccct gggcctgtgt   38400
ctctggagcc gactcgtggc cacacagtga ctggatgcca ccctaacctg ccttggcagc   38460
aaagtgagac agcagtcaga caaacttggg gacccagacc ccaacctggt cacagtgtcc   38520
agcccagact ctgcccctgc tcccccagga atgtggcttc tcaatgggct ccaaggcaag   38580
ggtgttccat cctctgtccc caacttttgt catcacagac ccccaaaaacc tcagcattca   38640 aaggggctca gggattgagt ctaacaccct tgatggggaa actgaggccc agacagggtg   38700
aggcacttcc ctcagggtca cacagcacat tggacctggc acacaatcct agggcctctg   38760
gtcctgagcc ccaacacgta cttgagaggg agctgtcccg tctttgaggc agcacaggat   38820
caaggcttac tgtgtggctt ctggagccgg acagttatcc tggtttggac acttactagc   38880
tttgtgtcct tgggcaagtc acttaacctc tctgcgcatc agtttcccca tataaaacat   38940
gagacgataa cagttcatca ggattcagtt aattcacatc gagtacttag aatggcactg   39000
ggcacagagc agggtccat gaggctttgc aaggccactg tggctgtggt gtctcttact    39060
ctgggtaccc aggagaactg gctcattcag ggccctgcca agttgaggcc ctggtgcagg   39120
gcctcccttc tactctggca gccggggag gtggatgagc cccagcagt ggtccagagg     39180 tgcagtctgt ccagcccagc aaccctctg tgtcacccac caaaggataa gggccggtgc    39240
tagccggagt gggctctgcc tgccacgccg aggcttggct gaggacggag agctatgagc   39300
ctgaggtgtg tgtgacttcg gctgggactt ggaacttctc ggggctttgg ggtcttccca   39360
agtcagctgg ggtatgtttc cctcagcagc gtactctggc cctgggcgtg gatccgaacg   39420
```

```
gagtgatgct cctggcttaa ggtaagaaga tgtggggaca gcagtctggg tggcggggc    39480
cttctgggac atctgggatg ttccctagta ggtcacttgg ctgtcccggc cccttgaggc   39540
cgagagcctc cgaggcacct ggctgccagt tttcatctgg ggagcccctc ggggggagag   39600
gtcctgttgc aggtgctggg cacgtcagca cagctgagat gggtggggtg gaagtgggtg   39660
ctggccgcct gatgggaacc ccattctcaa gacgaaggaa acaaatgggg accgcaggat   39720
acaacggcag gactgtgccc ctcagagctc acgcgggctg cagggcgctg ggctgggcct   39780
ccctggacct gccaccatcc cctccagcct ctttcctcag ggccaccacc cctcctccgg   39840
ggtggtgggg gaagtacctg ccctcagcac tccctcagac cccccagcag cttccttgga   39900
gctcctgtac ccccaccctg cggcctcgca gccccaggaa acccgagctg cccggggcac   39960
tgtcgagtgg ccaatcccaa cagtggaaag aaatgtttat tttcttctcc agattgtccg   40020
ggctgctgca tggtggctga atgagccctt tcagctgtga aagcccccca ttgtgggcgg   40080
ctgcggctgg gggctggggc tggggtatgg gaggtgctgg ggtctctgca ctgcttgcca   40140
gtgaccaata ttggagggtc aaagcactta acaggcaccg agggaagtgg tggtgggtg    40200
tcccaagggg gatccccagg agggagtccg agggcagagg gaggagggcc tgtgagagtg   40260
acttcccaag cctaggtctg ccagcaaccc ctctttgtca gggacctcct tctccccact   40320
tcacagatga gaaaactgag gctgagttta agtgacttgt ctaagatcat acagccaatg   40380
cctggcagag cctgaattcc tagcctggtc cagctgactg cagagttcat gctcgccctg   40440
tcctggtcat ccgaggccct ttctctcacc caaagggggat gggcctgagg atggagatgc   40500
ctggctgcct gtgcccagt gctgtggggg ctagcgagg gactgggcca ggcctcagga    40560
gggagcaggc agagaagcag aagtcagcca ctgccccaca caggctgggc tcctttcctc   40620
ccagcccagg atgaagcag cagctgtgcc tgccgtgggg ccaggcattg attcccaagc    40680
tgtgcccacc cagcagtgga tgggcagatg tgggctctcc ttccatgggg gctggtggac   40740
aggaagccac tgttcacccc acctcctgga ttctggctcc cccgctgagc cccgatcccc   40800
tggcctggct ctgtccatgg cagagaaagg ctggctctca ggctactgca cctcgacaga   40860
tgctggccca tgggtagcag aagcagaggc agctacgcgg caggggtggg cgtgagcaca   40920
gcgtgcaggg ctccttccgc tacctcttga gagcagacct ccaactcctg ggctcgagag   40980
ctgagagtct caaatgcact agctcctggg ctcagagagg ctgggcctgg ggcttctccc   41040
aaccttggcg tctcagcagg accaaggcca aaagtcctga gcccaggcca aaggggagg    41100
ggtcctctct tcacactgaa ggcctgcatc cagcccctgg ctgcagcact atgcctggaa   41160
caatgtcagt agagagaccc agtcggcccc cacctcagcg tggcaccgga aaaggggggtg  41220
gggcaggcag accggttggc agccctgttc caggcccctt tatctgtccc ctcagaagta   41280
cagaaagttc ttgggagcag gtactgtgga gactgtggac ctggtcacag atgggctgtg   41340
tgacccgagg gtggctctga acctcttagg cctctcaatt cattcatctg ccaagggggtt  41400
ctaaccaggc tctgggggaat tgagaaagaa tgggcacagt ccgtgacggc agccagctgc   41460
ctgcctctgt ccaccccggcc accaagcacc cttggcaccc cacttagccc aagggccggc  41520
tgtgcacaca gcctcccatg tccccagctc actgactgag agaacagagg agagatgcag   41580
ccggcagccg tttagtgagc ggctactatg cgccaggcac ctcgatactc cagaagacct   41640
gcctgaggcc tggctgcaac tgtgcttgct gtatccgtct aggcagtgga gatggagacc   41700
ccagctcggt cttcccttcc acctcagctc ctcctgtttg ggaggatgct ctgggcaggg   41760
tgggagacct ttcccaggaa tgctatgtgc ctctctaggg ttggaatgtc acttaacagt   41820
```

```
gtgcaaagtt tgtgtgagta cagtaatgtc atttgaatgt catcccagcc ctgggtggag   41880
gcatccgccc caatccactt tcagatgaaa aatcgcaggc tgtggggcag gggtggggaa   41940
actgtacatg gcaggggcga gtctgtcacg gctccttgga caagtcatgc cccaatttta   42000
ataggggcac tatggggtta accccatttc cccaggcaca gtgaactcct ggtatgcaga   42060
tccctggggc caggcaccag gcatgtgtca gtaatgtcag tgtttgctga gtgaacgaat   42120
gatggctagc acacagaaag cccacaggaa ccgtctgcag gtgccaatga gcaccagcag   42180
ctcctctaca aaacaagggg gtgcagtgac tgatcttcgg acaggctttt ggtctggggc   42240
agattggacc acatcgaggc cctccacccc cacctcaccc cgctgcagcc cctccctccg   42300
tgccgtacct tggattgggg tctggggctg gctgctgaag tggcttgtgg tgctgagtga   42360
gcctcggggc tgggtgtgc tcggtgtcac ccgcatgcgc agccgttcca ggtccccaaa   42420
gcggtcaggg aacggcttgg tctggtcctc cagcttctgc cggtgccctg cagagcacag   42480
gaagcccatc agccgttgct tccccagagt ctcagtggag acagaaatgc ctcactctgc   42540
tgggaagttc ttcctgaggt ctgaccttag gcctctgctg ggagaaccct gaggtcaccg   42600
ccagcctctt cacagaggtt ttcaaaagac tttctgaaca gagaatggtc gttatgtgcc   42660
accccacata tctaaacctc tacaacacac ggtgatccaa acctctacaa cacgcggtga   42720
tctaaacctc tacaacacgc ggtgatctaa acctctacaa cacgcggtga tctaaacctc   42780
tacaacacac tgtgatgtaa acctctacaa cacgcggtga tctaaacctc tacaacacac   42840
ggtgatccaa acctctacaa cacacggtga tctaaacctc tacaacacac ggtgatctaa   42900
acctctacaa cacactgtga tgtaaacctc tacaacacgc ggtgatctaa acctctacaa   42960
cacactgtga tgtaaacctc tacaacacgc ggtgatctaa acctcaacca cacgcggtga   43020
tctaaacctc tacaacacgc ggtgatctaa acctctacaa cacgcggtga tccgaacctc   43080
aaccacacgc ggtgatccga acctctacga cacggtga tccgaacctc tacgacacgc   43140
ggtgatccga acctctacga cacgcggtga tccaaacctc tatgacacgc ggtgatccga   43200
acctctacga cacgcggtga tccgaagctc tacgacacgc ggtgatccga acctctacga   43260
cacgcggtga tctgaacctc tatgacacgc ggtgatctga acctctacga cacgcggtga   43320
tccaaacctc tacgacatgt ggtgatccaa acctctacga cacacggtga tccaaacctc   43380
tacaacacac tgtttggcag aagaggaaac tgagggccag gtgcagtggc ttacgcctat   43440
aatctcagca ctttgggaga ctgagatggg aggatcagtt gaacccagga gtttgagatc   43500
agcctgggca actatcgaga ccccgtctg tacaaaaatt aaaaaaaaaa aagaaaaaag   43560
aaaaacttag ccaggtgggg tggcacaagc ctgtagtccc agctactggg atgactgagg   43620
caggaggatc acttgagccc aggaggtgga ggctgcagtg agctgattgt accactgcat   43680
cccagtctgg gcaacggaac aaggaccccta gatctaaaaa aaggaaactg aggcaacaga   43740
catgagaaag tggctcatgc ccccaaggga ggcagggaga taacccagga gcactgccac   43800
cctctgcctc ccagcatccc agcctgcctt gcacactgtc tcccatgtct acaagaacaa   43860
tgggaggtgg ccccaggagg ggactgcagg cttttccagc cctaagtcac tctgggatcc   43920
ccagaacatg ccttcttctc tctgggcctc aggcagaaaa ataactccac caggatgctg   43980
ggcagaggtg tagggggctt gcatgaggga ctagacagcc atctctgcct ggaagctggg   44040
gtcaggggac gagatgtcac acctggagaa aactgccagc attttccact ccctatctgc   44100
cagagcccac acaggaagaa tcccagcctc acatccgagg actcagaggt gctgggaggg   44160
```

```
tcaaggtggc caggctccca ccctcctgcg gcctgctgag gccgagggac acttctggag    44220
tgatatcaag cttgcaggga cctcccccgc cacacacact tttttaatta ctaattttac    44280
atttcacaag caacacgtga atatttacaa aaataaaagc attacagata aggctctgtc    44340
caccgctcta agctcctctc cagagtccce accgtgacca gtttctttcc agacattttt    44400
catcttccat gaatggaaaa cgcaaagtag gcttctcatg gaactctctt gaacagcctc    44460
agtccgggtg tgtcattctg taacttgctt tcttagtagc acaccttgga gctcaaactc    44520
agtttcccta tctgcaaaat ggggacagta atccagcccc acagaaatga cggagttccc    44580
ataaaaccct ggggatcctc cctgctacgg aagggattca acaagcatgg cgagaatgac    44640
gctgctctcc ctcttcctg ctggccactg gaggcacagt tcactccgca gtcctctcca    44700
cccacatttc agtccttctc aagcttcccc tttagttccc ttacatgcaa cactcccggg    44760
aacgtccctg ttcgcacccc ctagtggctg cagcttctcc agggctgacc cgaggaaagg    44820
acggctccct tggaggactg tgcactccag ggttcggctg atcaaccta acacggtcac    44880 ggccattcta cctcacgtga cttggtggga ggctgccagt caggcaggt ggccaggccc    44940 tcttttacaa gtaagagaac tgcaactgcg gagaggcgag aagcttgtt ggaggccaca    45000 cgccgaacaa ggggtgggat ttcctggacc tgggaccctt tagaaaagat ggaggctagg    45060
catggtggct acgcctgtaa tcccagcgct ttgggaagcc gaggcgggcg gatcacctga    45120
gtgaggtcag gagtttgaaa ccagcctgac caatatggtg aaaccccgtc tctactaaaa    45180
gtacaaaaat tagccgggcg tggtggcggg cgcctatgat cccaactact gggaggctg    45240 aggcaggaga atcgcttgaa cccgggaggc ggaggttgca gtgagccaag atcacaccac    45300
tgcactccag cctaggtgac agagcaagat tccatctcaa aaaaaaaaa aaaaaaaat    45360 gtgggagggga gtaaggggga ggagaaggtt tgcctaaggc ctgggtcta gaatgacatg    45420 tgcgttttct agtttggcag agggagaaga ggcaagatgt aggtgggagg taaaacagaa    45480
ctcactgcgc ttcttggggc ctgaacaagt gattgctggg gactcgaaaa gtgggaaaag    45540
cctgtcgacc actgtagggc atgagggac agagcccgag gcctcgcatg ggcctgattt    45600
ctgattttca gaatgggaac gcaatggatt ctggtacttg taggccccca agctccctac    45660
gcatccctgt tggaagctca acaggtatc tgggagcctc agaaagaaag caggggggcct    45720 gggagccaca ggggctcagc cagtcaccaa gaaccaggga gccccacctt ctcctccaat    45780
gaggccccag accaggaatc catgggacac ttggtggcag gaataagacc atttggtctc    45840
tggccaggcc cccactgctg cctcccaggg cccttggcaa caaggggaa aacatgggct    45900 ggggggcgagt ttagctggag ctggggctgc aaactcagat gcccatgggg atgggcaag    45960 tcacgtgaac gaggcaagtg ggatgggtgg gcctggagc ggatggggag gagatgcctt    46020
gtggaaagca cctgactgct accctgagga gggcaggccc agtacggcca gagcttccaa    46080
ttccagaccg agtcctcagc cctaacaggc cttggaggaa atgttgtcct tgctcctgag    46140
gccactggaa atgcaggga gatgtggatg agctggggga caagtgagca gaagaatctt    46200
aacaggcatg aagcctgccg ggtggacgtg gggaccacag actgatccga caacagcctg    46260
agtgcaaagg atctgggtgt tttagtcagc cacaagcttg aagggagcca ataggctgg    46320 tgcaaaacct caggccttgt tactttcgtc acaggagaat aaagtcccct gtttctgagt    46380
cacaccatgt acaaagagtg tttacagtta ctcctgcggc ctggcggaag agggcggggt    46440
tgacagccag cctgggttcg aggacgggtc ctgtcacttg cagtctggtg gcctcactca    46500
agtcacactc ctttccccca cccgagctg cggtgtcccc atcacactgt ctttgtgggt    46560
```

```
tgaggtgctg gcctaaggtg tggacacttt ccagtcacgt gggtcaccac catcatgacc    46620
atcgctttta tctctgctca tgcccaaagg aagcagaact atcatcccca tgctggagac    46680
cggggtgtgg aggccaggat gctgaagtcg tgtgaggaac acagagcctg agcagcaagg    46740
caggattcac acccggatcc cccgactcca agcccagggc tctttcctg acactttccc    46800 ttttgttccc attgtttaga cggggccacc gaggcttcac catgagaccg acgctgagcg    46860
cctgttccgg gacccaggct gtgggtcagg taatctgacc ccggaaccca cgctcccacc    46920
acatgctccc ttgccctccg tagggcagac ttcccggagg aggggagtcc aacagcactt    46980
cggaaatagc ttccttgtta ctgtggaacg ctggagccac tgccagggag gggagagggg    47040
agccaaggcg gccccacgtg gccagggcgc cagagagtct cagagccaca gggccagggc    47100
tctcacactg ggaataggac agaagttcca gtgcctgagg aaagaagatg gtcttcagaa    47160
aaagcctctt tcattcggtt acccagagca agagctgcgt ggggagctct ggctctaacc    47220
cactccgtca ccttgggccc agtcctgcta cgcctcagtt tccctctgc acagtctgct    47280 cactgaggcc ccttcctttt gaaagtccct gatttaaggt agcaaagatc agccgctggt    47340
cagaggggcc ccagaaagaa aagaaggcag ggctgctggc cccagggccc acccactacc    47400
acttcttcct gctgctgctg ttcccagtat ttcttgaata ttctctgccc cccactcttc    47460
agagcctcag ctcaggacag cctctgccag caatgctttc tgtcctgtga agcccagtcc    47520
aggagcccct cctccaggaa gcccccttc tcccacagta gatccccatc acacctctgc    47580
aggctagggc tgtcctttaa agcagtcgcc agcaggagtg gaaatcatca aaacggcagc    47640
agatgcttgc tgggtgcttc ctccacggca gcgtctaagc agctgacaag caccatcttg    47700
tttcgcctgg cagcatcccc ttgagtaatg tctgccacca tcctatcata tgggtgaaaa    47760
aactgaggct ctggacagcc agtgagctca aggtcaagca gaagacacac agccacctgc    47820
tctccctaga gcctgtgaaa acacatctat tgtggcggaa gagggcgggg ttcacagcca    47880
gcctgggttc gatacatcaa tagatgtatc gggactccac aatagatgtt agggcccgt    47940 ccagccccag gccagagct gctatctgca ggcccaggag gataggactt gggagaggaa    48000
gatgagaagg tctcagtgga ctccaccagg ggcccttccc tgctctgaag ctcagggttg    48060
agagtgcaat ttccaatcat accctgctct agaccaccaa gtcactctct gcctctgggc    48120
cacagtttcc acatctgtaa agtggttatc atactgtcta accctgagg gtgccgatga    48180 gctggaggac aggccacatg ctttaaaag cagaggactg agatggctgg ggaaagcccc    48240
gcgttggccc tcagggcctg tcctggctgc tgtcagcctc cagctgctgg gctcagatca    48300
gacagctcct ccagcatggc ctggattagt gtctatgacc ctcacttatg ggagggcaga    48360
tcccagcctg cccctcccaa gggcccagtg gccccaagct cataccaggc agctctcacc    48420
caccagtggt cactgtcttg ggcaagccac tcttgccttc tgggcctcag ctgtcttatc    48480
tgcaaaatgg ggatcacacc tctaaccccc gagggtcagg aaaggtttca agaattacac    48540
agcccaccag gccttggcct ttgaggaagg tgttctgggt tccattctg acttggccat    48600 ctgctcctag gcaaacagct cctctctgat gcgtctgtgc agtgggggtg acccacctca    48660
caggcatatg ataaaggcca aagtgggagc aggaatgctg ggcccagcc agtctgggga    48720 ctcaccaggg tcacgcagtg tgggagctag aggaccaggg ctggattctg ggttggcagc    48780
tcctttacca ctgtccccag ggaatccttc cccaccacca gctggccag cctgggtcc    48840 tacccccgcc aggtacctga tgcttctggg ggaaccaaga gaccatcagg gttacccct    48900
```

```
tgcctccatg caggcccaac acaagcccct gtcataggag tggcaaccat tttagcaggc    48960
atccatgatg tgccgggcac tgtgcaaggg gggccatgca tgtcgtctcc aagggtcata    49020
tccctctgac aggctgtgac tatcacccccc gttttacaga tggaaaagtg gaggcacacg    49080
gtcaaggtca cacggtgtgt ggcacccctg agattcaaac ctggaaaggt cacacatgga    49140
gctcagctgc taaggtcatc gcttcccaag acctccatga gagaagagct gggtcacctg    49200
gccgtaaggt ccagctggca agaggccagc tcagtgttca gcctcttggg aaaagcagag    49260
tcgggcaggg ccacaggaac agcatcgtct gctggggaca gtgtgggctc caatgaccag    49320
gcccgtcacc catctgaagc cactcggcag ccttcttggc cgcctggtgc ggctgtgacc    49380
cagacacagc agccactgtc tacccagcag cagggtgggg cgccgggccc gaggccggct    49440
ctgcggcctg tcaggagatt tacacccgac tcttaacagc ctcgcggaat cgcaggcggg    49500
tgccgggcct ggggtggtct gctgtgaatc ggcccctgt gagcagatga aagccgggtc    49560
ggtggctggg cagggaaacg ggctggccgg gggccagcgg gcaggaggc gagcggttcc    49620
ctcccagggc tgcaagtggg gcttccagag gcctggggtt gattaggaga acccaggagg    49680
tctgtggtta accccttccc tcctgctggg cagactccgc tagccctgcc cctagcgcag    49740
gagacactcc tggggggttgt ggggatcttg ggagccaggg acctggagca gctgcctctc    49800
ctcagcccag gaagaaaacta cagaaactct aaggccttca aaggcccaac tgcgggctca    49860
gggtcacttc tcctgcccac gccaaaccct cggcagccac actctgctgg ctgctcactt    49920
caggcccctg ctcaaaggtc acctcttcag gaggcctccc cgccccatcc cttgttccat    49980
cccttgcacg ctccactcct tctcccagct ttgttttct tcataggact tcctactacc    50040
cgaaatgaca ttaatgaatc atttgcttat tcatcaacga tttatggagc agctgtgaag    50100
ggctcctgcc cacattctca gggtctagct ataccagggc ctggcaaacc agagcaaga    50160
actctgccct tgtagagcat aaacaacagg gggccgggtg cggtggctca cgcctgtagt    50220
cccagcactt tgggaggctg aggtgggcgg atcacttgag gtcgggagtt caagactagc    50280
ctggccaaca tggtgaaacc ctgtctctat taaaaataca aaaattagct gggtgtggtg    50340
gcgtgtgcct gtaatcccag ctcctaggga ggctgaggca agagaatctc ctgaacctgg    50400
gaggcggagg ttgctgtgag ccgagatctt gccactgcac tccagcctgg gcaacagagc    50460
aagactccat ctcaaaaaac aaaacaaaac aaaatgggag aaatgaataa caaatgaaac    50520
aaactatcgg actagatagc accttagaag gtggtagtgg taagtgctcg gggtaacctt    50580
aaagccagga aggaaagggg ggagaggtga ggaaggctgt gtgtgtgcca cttgaaacag    50640
gcgggctgct gagaagtgca gaggctttag ggtgtgaagg agtgtgccat gcatctgggg    50700
gtgtccgggg aggagtgttc cagatagaaa aagagcagt gcaaaggccc ccgaggcagg    50760
agtgtccctg gcaagttcaa agaccagcca ggataccagg gtggccagag caggatgtgg    50820
gagggagggc agggggtaac gggcacaggc tagggggggcg tgaggccctt tcccccaccg    50880
tggtccatgc cagacttgcc aggtgtcacc gcccctcctg ctgggatcct ggacctggct    50940
cagcaacctg cttcttaacc agccccccagt gactctgagg gacaccagca ctgagaacct    51000
cagaaaccga ggccacacag gcaggaagcc accaagccag ccttcaaacc cagctggcca    51060
cctggctgca ggccgggcac gctctgcagg gcaccagagg gaacgaccc ggccacagaa    51120
cccacagccg gcctcaggga tctacagatt cccagtcctt ggctcccagg accagcccct    51180
actcccactt caccccacag cgggctcaga tttcagaggg tcgaggtgg caaaacagga    51240
aaaaagccgg gaaaggaagt ccaggagcac aaaaggcctg taacaacctg tgaaggttgt    51300
```

| | | | | | |
|---|---|---|---|---|---|
| gggggcactt | cctggggcca | ggccccggta | aactcagtca | accttcacag | cgactcccct | 51360 |
| aggcagacac | caataccatc | catttgacag | ctgagcacac | tgaggtgaaa | aggcccttcc | 51420 |
| aagtggccct | cacttcccgc | agccccggg | tcggagcccc | cagggtgtgc | tgacagtcac | 51480 |
| cttgggcaaa | aggttttgcg | ccctggcctc | tatcctctcc | tggggttgcc | caagagatca | 51540 |
| gttactgggg | actttgcaca | gggcctgacg | caagggaggg | ggttgctcag | tgaccaggag | 51600 |
| ccgctgagct | ggtcccttca | ctcttacaga | tggggacgct | gaggacccga | aaggccaagg | 51660 |
| atttgtccag | ggccaaagac | aaaggagtgg | ggctgcaacc | cagggtatgg | gggggaccct | 51720 |
| gatctcaggg | ccaggatatg | ccagggacag | gaacaggcag | gtcctaagga | tgggggacct | 51780 |
| agtagactgc | cccccgactc | catctctgct | ctgttctgta | aataaaacca | ctgatccagc | 51840 |
| cgctgccggg | gcccagagag | ggaggtcacc | tgtctcaggt | ggtgcagcaa | gcctggcttc | 51900 |
| tgacgccgtg | ggtctccagg | cccagcctct | gtccctccct | cttgttgcct | cgtcctgagc | 51960 |
| cacgcattta | ccttccagct | caccccagaa | ggggccatct | caggtctggg | agacccaggc | 52020 |
| agggaagagc | aggcagggga | ttctgctgga | atctcccaca | ggcagggctg | agtctccatg | 52080 |
| ctcatccagg | ggtcccagca | gggcagagtg | ggcggctctg | gggtgggctg | ggctgagcat | 52140 |
| ggagggctct | cagaggggcc | aaccttgccc | ggtcccttgg | atcttcccac | caagcgtcaa | 52200 |
| gaccccgtcc | cgtgcctccc | tctttctgga | gtggctcccc | tctttctgga | gtggcttctg | 52260 |
| agtgccgcat | ccccacccag | agcccaactg | aggctcctgt | ccatgctgac | cctgcccctg | 52320 |
| gagacatagg | gcagggctgc | cacctccttc | aatggagact | tgatacctgc | acctctatta | 52380 |
| ccaaggcagc | cacccagctg | ctgcccatga | gagagctcac | cgttgactaa | tggtggtggt | 52440 |
| gggagtgcag | gaaggggct | gggtactgag | gacgacaaaa | cgctgcggac | ccagtgactc | 52500 |
| atgggacccc | tctgtgctac | ggccacgtgc | tgtccacatg | tcgcccctga | tctccaggtc | 52560 |
| cgcagggtgg | gtggcatcat | cacacttcat | ggaggaggga | gctgaggccc | agagaggtca | 52620 |
| gtgacttgcc | ctaggtcaca | ctgcagataa | cagccctggc | taaagtgacg | gatcccttgc | 52680 |
| taacccccac | cgctaagtgc | tttctataga | ttaagccact | gtttcctcgc | aatagcatca | 52740 |
| tgaggtagct | gcttgtgcga | atatcatttt | tcagttcagg | aaactgaggc | acggagatga | 52800 |
| ctagcccaag | gacccacagc | caggaaggct | ggcttggaaa | ctgctctcta | caccatggtg | 52860 |
| gtctatggct | catgagggct | tcccagccat | caccaccttg | agactcctgg | agtcactgat | 52920 |
| ccagttctca | gatgacaaaa | ctgaggccac | aaagaagaca | tgacttgcct | agggtcatga | 52980 |
| agcccaaggc | caagggcatg | ggctggtcta | tgtctgatct | cagcaggagg | gaaccagcag | 53040 |
| gagtgtggcc | agggcaagtg | ctggctggga | gctgacggtg | caggcctgag | gatgcgtgcc | 53100 |
| ggggctcagg | gctggcagag | gtgaccctga | gagccctgga | gggaaactct | tccagggctg | 53160 |
| ctggactcag | ctccaagcct | ttcccaagtg | gccagatgct | gggatgggcc | caggaattgg | 53220 |
| atgatgggt | gtcaggccca | gctgactccc | aagaagggag | gggccagccc | agggctaggc | 53280 |
| ctcctgcccc | aggcctcctg | ccccaggcct | gctcagccta | gaatcttgcc | tctgggaaga | 53340 |
| ctgaagcctg | gggcgccttc | ctgctccttg | cacagcatta | ggtcctattc | aggtacccaa | 53400 |
| ctccctcagg | cctggattct | ctcctcactg | gaacttgggt | gaccccctctg | gctctgctgt | 53460 |
| catcaagatc | ccattcaata | gtgactgcta | aaaggtcttc | taaactacaa | agggtcacat | 53520 |
| ttctgagaaa | gagaggggtg | ggccaacctt | cagtgcacca | agctgaaaat | gccttgggga | 53580 |
| ggtgggatgg | agctcaggaa | gctggctggc | tctatttcat | tcattcattc | attcattcag | 53640 |

```
tcagtcagtc agtcagtcat tcattcattc tgtggacaca gagcctcagc ctaccctccc    53700
acttccccag ccttaatctg accttcagca agcagagaga attaaacaca aactcgcttt    53760
gatggaccag aactccctgc tcatagggtc tgggtgcccg gactctgggt gacctgagca    53820
agtcacatgc taagattcaa agactcagtt tccaaggaag aggcctggcc tcacagccag    53880
accagcccct gacttttgat cactcctgcc ctccatgcat ccctcagcca cccgcagaga    53940
agctgggggc agagtaaagc aagcctggct caacctccac ccagaaacac acaagcaccc    54000
gacaaatgcc atatctgaaa gctttctcca tccttttcct ttccttgact ccctcagtag    54060
tctccatgga cagtcatctc cactcccagc ctcctcgctg gcctcccacg gtctcaggct    54120
aagcccagag ggtttagggg tttgccagca ggcacgcagt gtgtgggggc acagagccaa    54180
ggactgcaac cccccgagga gggctccatc tgtctgacct agctgctgtc cttcccgcac    54240
tggaccctcc tcccccgcgc aggggctcag ggggctcggt ggcacttacg tctgggctcc    54300
cggggtccgt ccacggtcac cttgatggct cggtggtagg tcgccacttg ggtgggttg    54360
gtgaacacag tgatggtcag ggtgaaactc ttccctgggg agagtgggga atagaggcag    54420
gtggttggca cctggagctt ccacaatacc ctgctctccc acctgtatct accccctggaa   54480
gcccctaact gtcaagaagg ggcactctgt cctctttgaa catgggcaga agatagggct    54540
ctgggtgaag ttcaagctct tgggcttggc attcaaggcc cctgggggtc tgacgccaac    54600
tttgtcaacc ccccgcccca tgccgtgacc acctggctc atgttcccct cttcttggcc     54660
tttctgctgt ctcttctatt cagagaccca cacgattttg tggtggggag caggatgggt    54720
atattctatt ttctgaaagt aattggtgat ctttgtagaa aaattcaaga acatacaaaa    54780
tataaataaa gaagaaaaga cacccccccc ccacggttcc actagctgga gatagacacc    54840
gttaccattt ggtgttttcc ctttcagctc ttttgtatg ggtttgtata tttacacagt      54900
cgcagtggta ctaaaataca gattttcata ctgttttttt tttcatttaa cctcacatca    54960
gaagcacttt cccacgtcat taaaacttcca taaacttcgt ttttaatggc tgcaaaatat   55020
ttcaactcaa ggaagcctcc tcatctttta tttatctacc tccttactct cgggtattta    55080
catcgttgct aatttcttat tgatgtgtgc agctggagct gaaaaaggac tgatttggga    55140
gctgcagaca tttcttctgt agacacaact gttatttcca gaatgttcta tttttagata    55200
gacatttggc tccaaagtct ccattcaaaa ttcctgagag gggaaaaaac ttttaaaata    55260
ctactttttt tttttttac catttaaaat aaaatgaaag tgaccttctg tttataaaaa      55320
tctttgtctg catctctgct tatttcctta gaagagattc caagaagcgg tgagtgattt    55380
cacggcagca gagggttggg acatattacg ggcgcggatc cctcttggag tgagatgact    55440
ctccggagag atttagtcgt caccctcgcg tgtgaggctg cgtcacaccc cagggatgtg    55500
tctatcaaga tggaagatct tttacacgct cttgattttg tttgcctttt tttctattac    55560
tagtgagaat gaaacttttt atatgattat tatccatcat aatccaacac aaattactgc    55620
ttcatgttct tttactttcc tgtgaaggtt ttagtgcctt ttaaaaattg ctatatatta    55680
agcttgttaa tactttccat gctgtatttg tggccatcag tttccccggg cacaggcctg    55740
cacattttgc cttcacacgc tgggtggttt ttcatttta cttctatttc tcgttcttct     55800
atcgttttat gttcagacgg gtttctccgt gtagaaagca gtttatgaag atttactttc    55860
gacagtcttc tctctacttt ctacagtgaa ttctctgatg tgtctggag tttgggggtc     55920
tgggtaagag tcctcctctc accctattct ctattacgat ccacagcctc atgctttatg    55980
agattggtgg ccggggagcgg gggagatttg cggatccccc aagccagact ttatcccct    56040
```

```
atccctgcct ctggatccca cgtacaggcc tgggaactcc ctgtgggtag gggccaatgg  56100
tctcgcactc tcacctgtac cccagggctg gcacaggatg gtcaaggaga gaggctgccc  56160
aagcgcatcc ctctggtgtc cccctgacac gcctccaaag tgagcaggta ggtttcaaca  56220
gccccacgtt gcaggtggga gatgaagctc agggtgagga ccagtatctc acagttctct  56280
ttgcatggcc gggtacttgt tagtcaactg atcaagtgaa aattctagcc ccagaggcag  56340
gagaatccgg aacaaaatta aaccagccag gctgccagga gccatgccac aggacccaag  56400
gccctctgag acaccagggg gaatttaaag ctcaagaccc actgagtgtc actccagctg  56460
ggaaatgagg ggcttctctg gaagcctttt cctaagccag tcggctgagg cagggataga  56520
aattctgact gcacttgccc ccggagcccc aggtcagaac agacctggtc tcccactctc  56580
aggtcacagg ggccactttg tatgatttct ggaagcagaa gtgcagatgg tctagggaag  56640
tgccaggcag atgcctcggg ctccctgccc gaccctcct actgcctttc ctcactctga  56700
ggtcatttct ctgctggacc tctttctcct ccaaccagcc cagcactctc ctggggtccc  56760
tgagcctctg accctgccag cattgtccag caccttcttg gttatgacgg ggagtttagg  56820
cagacagccc agagccctag gggccagact ggagacacgg aggactaatg ggtcccagtg  56880
ccctgccaca gggcccgggg cccacagcag catttgaaag cttactaaaa ccctccttca  56940
ggtcgcccac cttctcagtc aggccttccc tggtcacttt atctgaagta ggcatttta  57000 attttaatta atttttttga dacaaggtct tgctctgtca cccaggttgg agtgcagtgg  57060
catgatcata gctcactgca gcctggacct cccgggctca agtgatcctc ctgtctcagc  57120
ctcctgagta gctgggacaa caggtgagcg ccaccatgcc cggctatttc ttttttttccc  57180 ttccttcttt tccttccctc ccttccttcc ttcctttcct ttcttttctt tcttttcctttt  57240 cttctttttt ttttttttc aagctttac tatgtgccca ggctggtctt gaactcctgg  57300
gctcaagtga tcctcctgcc ttggcctccc aaagtgttgg gattacagtc gtaaaccact  57360
acacctggaa ggcatttta acttggctcc gtagagttga atgagcctga gaactagggt  57420
aggaaaaaat tacaattgta ttgtccctaa cctctaactg aaatttagca tcactctcaa  57480
gtacgagcgt aggcaacaaa ccacagaggt attatcagcc gtacctgtga ccttgtcacc  57540
aacagacgtc acagatactt acatatcaca ttacagttgc tgcagattgc tctaaatatc  57600
ttttatgctc atcacaactt caaaaccatg gttgtcatta ggcccaatgc tagatcttat  57660
ttaatacatt gaataaagca gcacatttac cacaattttt aaagtatttt gctatgtttt  57720
aatagaaatg gtttctattg taatactttg tatttgattt tataccttaa aaatatcatt  57780
gttctgagaa aggtgtgcgg gcttcaccag ctatcagagg ggcccacagg gcaaaaaaaa  57840 aaaaaaaaa aaaaaaagcg ctaagcagct caacctgaag tatcacaggc cctaccactc  57900
cctttctcta ttccctgcac ctgctggaat tttctcacaa tgcatatgct tttaataatc  57960
catctactca ttttgtctcc ttctactaga ttataacctc cccaggggcc caagtttttg  58020
tcttgttcat gcagtgtctc cagcccctag gacggcatcc ggcacagagt aggtgctcaa  58080
caacatttgt taaataaatt aagggcagag ataatggctc ccatttttgca cacaggtact  58140 aacgtcccgc tcctgagaag tgagaagccc ccacccatac caggtagcaa accacatgcc  58200 accctgagg tcaccagcac tcctcggccg cttccaccag cttccacgcc tgtcaccacc  58260
cctcccaggt acaaaggaga ggagtgtggg gcctaagagg aggagtgaga gggaggggca  58320
ggagtcctgg acctcgggag acagggagcc tggggagcag gggtgggaga aagctgtctc  58380
```

```
cctgagtgcc cctcagctac cccggccctg cccagctctc tctctgcctg gcagtggcaa     58440
acccatccat ccctctctct cagcctctag atataactct gtgcaggagt cccaggcaaa     58500
cctgcaatcc atcaggagcc caggaagtgt aaacccaggc tctctgaggg ctggccctgg     58560
ttgcagggga gaagtcttgg tctgggaaat gggtttcctt tagggctcca gaaactcctc     58620
caggacccat catcaaccag ccggggtggc agcagggcct caggcaagtc cttgagcatt     58680
ctctgcctgg gttcctatgt gtataaggtc cccgccccac ccacaggagc tgcatgggtg     58740
gggggagggg acgtgtctca gtctcagggg acctcggggt tttctcagct tcagccaaga     58800
agccattcat ctctccccca accagcggtt cccctcagcc tgcaccggca cactgcaccc     58860
cgaatctctg tcgacacaca gttgcttttt aaccagttga tcacagctcg agagctcatg     58920
tgcttttcat tttcacttag gccagtggcc gcctgctaga ggggcatttt tgggatttgt     58980
ggtggcgtgt ggtcaacata tgttggggt ggcactgcca gcgttagggg tggggtgcgt      59040
gtatgtggtg ggggatgcca gcacccaacg ctgcccaggg tggtgaagat tcaattcttc     59100
ctgggaggga aaaacttgct tataaaagtt ctctggctgg tcgcagtggc tcatgcctgt     59160
aatcccaaca ctttgagagg ctgaggcagg aggatcgctt gagtccagga gttcaagacc     59220
agcctgagca acacagtgaa caacaccccc atctctacaa caaataattt taaaaaatca     59280
gctgagcatg gtggcgcatg cctatagtcc cagctattga ggtgggagga ctgcttgaga     59340
ccaggaggtt gagactgcag tgatcgcacc actgcaccct ggcctgggcg acagagcgag     59400
accttgtccc aaaaaaaagt aaagaaaaa aaattatct gagtcatgaa cctaactcag       59460
ttttacataa aacaagggtt ttttttgtac ttttaatatc tactgaattt tccagaagga     59520
aagacagttc tttttttttt tttaattttg ttcagcgctt tgccaacagg tgttgacaac     59580
ttcagaaagt catggtattg gcagcaaggc caggttcaga ttgagccctg ccaccctgcc     59640
tgttccctct gctgtgggct tctgcatgga gggcattcgt ccacctcatg gagtcctgtg     59700
gccccaacgt ttacatattc aaatcagtgt tttattataa attactttcc ctttttttct     59760
ccatcatagc tatggaataa catagttgc aactgcatgt aaataggtag gtttcattat      59820
ttatacattt caacgtagaa tagtaaggct tgatataaaa tatgtattgt aagaaaggct     59880
cctcgtgtct ggcagggcag ggacctcagc cctaatcact gcaggagaca gcaatgacct     59940
ggttttcctc ccttccttt cttggttcac accttcagcc ctgttgttaa gagctctgtg      60000
gtgttactgg gtgcgtgtct ttcatggaaa gccatcttcc tggaattcag acagaatgta     60060
gaactaaaaa ttgaggcaac aagcagaggt ttccatcaga cttcttagtt ctggcagaag     60120
tcaagagacc caggcaaggg ttctgggtcc caaccccag tcttaactcc caaagtgtcc      60180
catctcctaa agtggcccag attgtcactg tcaaccactg actgttctct caggtgggaa     60240
tttcccagtc agcaggatgg gcactgcaga tgtgtgtctg catgccagcg gacccggcac     60300
cctccttcct ccctgccaac cgcctccacc tctcccactc agcagttcac accttctggg     60360
tttcccccac cccgcccaa accacacagt aatcagagaa tcagtggctg tcaccgctca      60420
aagggacctc aaagtcctcc tccagtccca ggcatttgaa gtaacaaaat ctctaacatg     60480
tatccagctc tcaatatgcg ccagctgata cacttgtgtc aatttcccta accttcccaa     60540
aatctcatga ggtaggtacc attatcatcc ccatctcaca gatgaggaaa ctgaggcaca     60600
gagtggttaa gtcatttgcc caatgtcatc cagcaagtca ttagcagagc tgggactcaa     60660
acgcagggtg gctgatacta gaatgcaggc tctcaaagac ctcgagcctc tgaaggctga     60720
acgccttagc cacagttcct cagacatcgg aactcctcct cagatcactt cctgcctccc     60780
```

```
aggaccactg agactggtta tggacctctg agaggagatg gatgagagaa tggtttataa    60840
actcagcctc ttgcatctcc cagagccaca gtcccagcct cggccattcc tgctacaagg    60900
acaagctccc aaccaacgcc ttggaaaccc atttccctcc ctgcaggcct ggggagggggg   60960 gctcaaggtc tgtgggcatg aaaaccccta aaaaaatcat tctcagtgtg cagaatggcc    61020
agacaaggtc tcggtaactc agaaaatcgt cgtctcttct cttttctctcg cttcccagga   61080 gagagagtgg gaagggagaa tcaagttcct gatgccttgc tgggctccca gatcgacagc    61140
accttctgcc cgcctcgcaa caggcagcag ctatagtgct cctgacacat acctgggcta    61200
gcagacctgg ccactgcccc gcagtcagca gagctcatca gccttgtctg ccaccgacca    61260
aggaccagtg actgtcctct cagggttggg attaagtcgc aaagggtttg agagattggg    61320
gatgacaaaa gggacttgga gactaattag gagcagcaat gaaagcttaa ttcataaaag    61380
caaacatttt ccatccatca acctgcaacc agttaagggc accgtttgaa agaaatctgt    61440
gtgtggggaa gggagccaac aggaacagga aatgtttgaa agaatgtaaa ctatttcagt    61500
ttcataaaaa gtaacaagta aacagttatt acatgcaaat aatgtcctgg ttttaattaa    61560
tgctgaaaag tcaaaatatg ctgacatttt gtatgtatac atcgaacggc tggaaaggaa    61620
aaaatggtgc ccagatgcct gtttcagagc ggggctggca gctcagaggg aactagaacc    61680
ttgagaaggt cctgtttatt ggtgatgaaa agcacggttc tgcttcagcc acttcagcct    61740
gctgtggagt tggggagcag agggaaccca gcttacttct taacaaagct agaggcgggc    61800
ctggtgcttg ggaagggcga ctcccacttc agccacttct cgtaggcagg ctggtcttaa    61860
agggccagtg gaccctcagg cctccgttcc acaggggcag ggtttccagg actttcccat    61920
ccaggagtta agtgatgatg ggtttcaggt cccagaagcc tcccattcaa cagccccccca  61980 ccccgtccc gccttccttc tgctgctcaa ggtcggtcag acaggcaggg tggcacaccc     62040
gccttgactc tggggcagga gatggcagcc ttcgagctgt gctttccaac attcagctgc    62100
gttagcttcc gttctagacc acctagggct caaaggcgct gggaaactgg gtctgggaga    62160
ccacagctgg agagacagcc tcagagtgtg ggggatattc tgcccccctat ggagagagtg   62220 gctggggtgc ttgggcccca cagatcaggg acttgtcctg caaccgcctt gctgaaagac    62280
ctataagctc ccttttttgag cttgttaatc caccatctcc tgccagcatt ttttgtgaga   62340
ccaggtgtgc ttaaccggga aagaggggggt ggcatgaacg gtttcaggag ttggtaaacc   62400
ctagaaactg ggagaaaatt gtcttttttct ggcaagagac cataactttc ctcacctcct   62460
caaagcgatc tgtaatatcc tacaggatta caaattgctg tttttagaca gagctgcatc    62520
tggagacctg ttttttcggga ttctaaggcc cctctttcaa cctccttccc tgctgcccct   62580
gccattgcca atgctgaaat ggcgaggcct cccttccact tacctcgccc actgcggccc    62640
acgaagcgaa ggtcgttgaa cctggccacc tggttcttca tgacggccga ggcattgcgc    62700
agctcagcgg agtagttctc gtcattgcct gccatcacag tcaccaccgt accatccggc    62760
acgtccccca atgccaccac ctgaagacac ggggcggggg gatgcagggg gacagcttag    62820
aaaggaagag ggtgaccagg gaaggaggg gaggggctgg gctgggcagc tcccccaggt    62880
cccaggcaca ctgagtattt ctccaatgca gggtggagaa gaggcttaaa aacaataaag    62940
accttccccc aaatatcacg aaaacaagaa gatggaatct cgagcttcca caccaaaatc    63000
ctagatcaac tgcttacata aactgtgtcc caagaaatca tcctttcaat gaaatctaag    63060
ccagagctgt gaatcagctc agtcactatg atgtggggtg cagttcccct gttgtcttcg    63120
```

| | |
|---|---|
| gctgcagcga aagaggaatc aacatgctcc tagcaacgaa gtctccaaat gagaaagagt | 63180 |
| aacaacaata ataacaacag ggctgctacc cccactcaat ttatgcaaga gctgtttagg | 63240 |
| gcatgaaatt tggccctgaa atgtggacca ggcccagttt attggcctct gcagagccta | 63300 |
| aattcgttat gcagagaaaa tgcagaatgc aaaactcact ggtgttttga aaaaggccac | 63360 |
| cagaaaaccc ctttaaagtg agagtggggc ttttgataat ggaaggatgc acctgccggg | 63420 |
| aattgcagga tgggggtggc gatgtccccc taaacaccat ctcccccaaa tcccccaccc | 63480 |
| ccaggagcac ggagaggcgg atgccttttg aaaagaatc agactttaaa cagagtcaca | 63540 |
| actatttaaa cgtggccgcc gcgtgcaggg actggggatc catatggtaa aaatttcaag | 63600 |
| gagaaaatgt ttgggatctg attaagaaga ccagatttcc tgtcaacatc ctgtcttctt | 63660 |
| ttaatttcaa agactccttt taagctccaa gtgacagtaa aacctccgat ctgacgatta | 63720 |
| aagtcacacg ggcctcccgc ccctcccggc gagatttccc ccactggtat tttaagatgt | 63780 |
| cacccgggag acctcaaaga gccactcttc cttttttttcc catttagagt cgtcttaatg | 63840 |
| ggagcaggga cggcctcagc ttccagccac ctcgggcagc accaccccca gccgccggcc | 63900 |
| cttcctgccc tgcccttttc tcacggcagc tgtgagaggt ttaggggaaa accgaggcgt | 63960 |
| tttcgtttca tctcgctgcc cccttaaaaa aatgaaaatg aaacagtcgc ctactccctg | 64020 |
| gcataaagaa aaaggtcctc taaatggctg ggggctgcca gggttagggg tcccccaatc | 64080 |
| tcaactcgcg attcgggacg cataatatcc ccgagcaaac gtctggagag cagtgccccg | 64140 |
| atcccggcct agcgccgtcc ggtaaaattt cggaagcccg agggtgtgag caggaagctt | 64200 |
| ttgcgaagcg gcgcgggagg aggggtgctg gaggcggagg gtaggccctt tcaccgttcg | 64260 |
| caccccaccc gcggtgtcct tgccctgtc ccgggatcct cttctccgtt acccgcaggg | 64320 |
| ctgtatctga gcgatccggg ttaggggggc gcaaaacccc atccgcccat ttccgcacca | 64380 |
| acgtctctac gcaaggcgcc ccaaaaccca ggtggagcgg ggcaacccg ttaaaagtca | 64440 |
| ttcctgcagg gcgcatccaa aacgaacgc cgaggtcccg gagccgagcg cgcagccaga | 64500 |
| ctgaaccggg tgcccgggtg tcgccgcggc gtctcgggca cctcccatcc ccactgctcc | 64560 |
| cgaggctctg gctcccgcag ctcagacgcc cggagcccca gggccggcgc cctcccgccc | 64620 |
| cgggtcccgc actcaccttg aaggcgacgg gcagcgtctt gttgcagcgc cagtgcgagg | 64680 |
| gcagcacgga gcagaggaag ttggggctgt cggtgcgcac gagctcgcct gcgtggtccg | 64740 |
| ccagcacgtc caccatcgag cgcacctcgg gccgggcgcg ccctccgggc cccacggccg | 64800 |
| cctgcgcgct cagcgcgccg ctgttctcgc ccatcttgcc gccgccgccg ccgcagggga | 64860 |
| aggccgggga gggaggtgtg aagcggcggc tggtgcttgg gtctacggga atacgcataa | 64920 |
| cagcggccgt cagggcgccg ggcaggcgga gacggcgcgg cttccccgg gggcggccgg | 64980 |
| cgcgggcgcc tcctcggccg ccgctgccgc gagaagcggg aaagcagaag cggcggggcc | 65040 |
| cgggcctcag ggcgcagggg gcggcgcccg gccactactc gccagggccc gcccgctgcg | 65100 |
| aggcctcgct ggcccgacgg ccgcccgcag cctgcccggc tagtcccgca tcctcggcgc | 65160 |
| gcggcccccgc gtgcggccgc ccctcgtggc tgtcccggct gcctgggccg cggcggggcc | 65220 |
| cgcgcggggc tgtgccgctg ccgccgcctc ccgccccgaa gctcgcccgc ggccgccccg | 65280 |
| actccgcggc cgcagcccca gaacaaatcc tccagaatca gtggcggggg ccgcggccgc | 65340 |
| ccgcgcgggg ttagtacccc cggggcccgc ggggcgggc tggcggagcg acgcgtcgca | 65400 |
| cagccaatcg gcgcgagcccc catcgcgggc acctcggtgg cgttcgcggg gaggaacggg | 65460 |
| gcctgccgga ggccgcccaa cggggagggg cggaaggcgc caccccgcgg aggaggcccc | 65520 |

```
agtgccacag cccagggccc ccgagagctc tgggagcccg gggcaaatgc tagaaatttg   65580
cttagaacgt ccgggtccca cggaaggcgc ccttgccgcc ctctctcggg tcgtagctcc   65640
ctgacgctgg ggcgcaaccc cttcgctcct cctccccgct ggccgcggcc gggcttcccc   65700
agctcttgct gcttcgggcc tgtgacttct gcaaccccgg gctgggggcc gcggggtctc   65760
agggccggtg acgccgcact gggagccgcc ccaaagaggt tactcacctc cctcgtcccg   65820
cacattattc tgacccaaga gcctccaccc cacacgggat tttgcgcgtc gtccacgccc   65880
ggccggcggc ctttgctgct cccagccctg cgcggctttg gtcccagcct cggtggcccc   65940
tgtgccaaac cggggacagg cggaagggag tctcctaggg accctaagta gcctggggcc   66000
aacaacccct ttcctctctg ctctcccctc aaaacaagtt tcaggatctt gcaggcctcg   66060
cggcgtcgtt cttcgttgtg gcggcctgtg gctctttgaa aaacacgacg aggcctgcaa   66120
aatgcgtttt tctttttttc ctttacgcat gtaaccacgg tcctgcatcg tgaaacggta   66180
cgcgcgtcgg tggcaaaaga aaaacagcag tggctgcaaa gctaagggcc ctcgctttca   66240
gaggagagaa ttttctttct ccatgcgggt ggaaagtggc ctctgcgggt ccaaccccac   66300
ttcttcttgg gcccgtgcgc tccggctgcg ccgcagggac cgcggacagc ttcgccaagg   66360
cactgcctgc ccgcccggct ccgggtcccc gctcccactc ccagccgcgt ggcccaacct   66420
ctcctgggct tcactgcaaa tcacccctc ctctcccgcc tcctaagtct gtcgagcaga   66480 cctagggcc ggctacagtt gggagggcaa cgggaaagat caagccacaa tcattccgaa   66540
ttatcgcccc agacacctcc ctagactctg ggaacgaac gcgtgctgag cctccccgcc   66600
gctttggaga cggggctaga ttttcgttgc ctccggctct cgacaggtgc aaaacaatga   66660
attccaagcc tcggaagcaa agaagcttag gatccgacgg tggccgcaag atctcatcat   66720
ggatctgacc cctgctcagc gcgcgccatt tcgtcgttgc caaacgaaat caagcccgc   66780 gtgcgctcca ggggcgaagg actctggact caccccgacc accggagag ctggccccta   66840 cccacctcgg gacctcacag cacgcccctca ggccgtgtcg aaaggaagga cggcaaaggt   66900
cccttactga acctttaag agagcctgcg cctggcagtt gtcgattgcg gacccaggcc   66960
cgcgcgccct cggacgcgct ggcacgagca gcagaactag aggaaagcga gtgatccagc   67020
ctgggcgctc ccacctccgg gaacgtctcc gagaaggcgc agcgcgtcgt ggccaggtag   67080
ggccctggcc gggggcgggc aacacgtgct gccctcgagc aggttgcggg accatgaccc   67140
gctgtttcag gtggtggtaa attccatttg tcgaatggtt tcggtttgca ccgtgccctt   67200
tgcttgttcc tccgcctgat ttctccctct ccgcttacga tgggttcaca gacaagtttc   67260
cagagaatga gggactcttg tgggccctgg cacctggcgc agggcccggc acggctccgg   67320
ctctccgtag ggcgctggct ccccgtgggc accagatcca agggaccagg gcggcggggg   67380
gagggggggc gggtgcaggc ccttgggtcc ccagaccaag gtcgcggggc cgcctggcag   67440
gcacagtggc gggagccgcc gctagttggc gcccgcgccc tgccagccgc ggaggtgcgg   67500
gcccggccgg gctacagatg cgcgccagct gcggcccgg gtgcaggcgc ggcgaccgcc   67560
cccgaggagc tgccctttcc ttgccatcca tgccggcagg tctcagacaa accgatggct   67620
ttgtgtcaaa ccaaggccgc cttcctcacc tctgataaga tggacgcctt ctgtcttcgc   67680
gttttcaggc acccggggaa gacccacaga acaggctagc ttgttcccaa tttccacctg   67740
cttcctcccc atcccggacc gacaaaaatt gtcgtctgtt tgatgggagg gagaactccg   67800
actcccccac ctggggcatg cagacaccct cgcccttccc cagttggcat ggaccgtcgt   67860
```

```
cttttctccc tcttccatca gatcgatgga caaacaggcc agtttctccc cagtggcccc    67920
caccctaagag caccctaagt tgtccacagc agggctagga agcagaaggt caggacactc   67980
ccctacccta ccttgactta gagctgggta aacccagaac ccatcccgg gcaaatagag    68040
ccagctcctt tgccccagga aggggattcg tctccctctg gcatttagga gtgctctcta   68100
agtgcgttct tggcagtgag ggtgccgcct tcccagggca ggtgtgattc atgtggactc   68160
tgtggcgcct gggcagggat ccccaggtat accagacaag gggcaggtgt gccctgggaa   68220
accgcctaag aggtccatgg gctatggaag gagctggggt ccacagtccc tctgcctgag   68280
cgtgtctttt tccctcaccc acagcgctct agggaaagtt gcctaaacct ctctgagcct   68340
catttctttc atttgtaaag tggggcactc atagtggccc ttcatagaat tgtgtgtaaa   68400
gtgcttagca caggcctggc acatggaggg tgctccagcc tccgggagcc atcactgtca   68460
tgaaaaaata agacctctca atccttgctg ggggcctttg acccacccct cctctctctg   68520
ggcctcacac ttccatctgt gaaatgtcca gttctcatat tcaaagctta ctaggactcc   68580
aagccagtcc atgctgtcct gatccctcaa ttcgcccaca ggctgcctgg gggaggtaag   68640
gactggctgt gacctacctc cacgtggagt cagctcatag cggggtttcc agcaaccatc   68700
acagggcggc cagagctggg tctcgatgat tgcctgtctg accattcctc tcagaacctc   68760
actttcgccc ccagccggcc gccctcctgt gggcagaccc tttcctgagt agcaactggg   68820
cctcagcgga cactgccagg gaccccgttt ccttcccagg aggcctctgt tccccatatc   68880
ccgaatcaca caggagccta gtccagcgaa gagagcagag gactctcttc tagaactgaa   68940
aatttctccc agcctggccc taaatcccct gtccagaggg accgtggtg aaacctatct    69000
cctgcccagt gccctagaac tcaaagggga cattcatgcc cctcactgag cctcaatttc   69060
ctcttctgtc aatggaggtc attctaacca ctccatttca cggggagggg attaaggatt   69120
ccctctagga ggggaggggc atcattgtga ttgatgatcg attgtttgaa gaaacagaaa   69180
gaaaatgctg ctgagtaaac taggactcat ctgcatcctg atttcagata atgatctctg   69240
aatatataag cgagaaatgt taatgaaaaa tggcaatata tctgggttga ggggttgtct   69300
cctgtaggcc gggggtccag ctccagagag tccagctctg gggtcatcta tcctgggcag   69360
cctctctgga aggattcaga atgtgtggga gcacaaatgt gcttctcaaa ttacagagat   69420
ctttcttcct ttttggaaag ttccagactt ggagggagg gagaaggagc aagggagagc    69480
agggtggtga gggtgttagg acccagatgc tgcctgtgcg gtctgagact tttgcctggt   69540
gtccacgctc ccctgagcct tggtccccga gggtaaaatg ggaagaacag taacagctgg   69600
gggtgctgag gctttacctt gtgccaggcg ccgcacatgg gcattgctca tggtattcaa   69660
tccccacggc gtcatatgtg gtaggtgtta tgcccatgta agcaaagagg aacgttgtcc   69720
gaggtcagcc aggctagaga gggccagacc cgggttaaaa gtctgctctg gttcaaaatg   69780
tgggcatga acgcatcacc tggccaagca tgtcagcact ctcctcctag tggctgagta    69840
atgggaagag ctagcatcta gatacagagg aaagagctat tgtgatgggg agagggagct   69900
gggtttggta atcctgcta agcagccctg ggcttggaaa tcagtaaact cttcaaatct    69960
gcagggagtc aggaaggact tgccaggtc attcggagg gtcctgtgat agtcaaggtg     70020
caccaccac ctgctctcct ttggcctcag aaccagtctg cgaggaggca ggactggcag    70080
tagtccccag tttacagatg ggaacactga ggcccagaaa ggggaaggg cgtgatcagg    70140
atctggaatg agctccagca aggccaggag caagcacctc gaggcaaaac gcagttgac    70200
aggacctttg ccttgcagga gactgcagcc cagtcctggg cctcatacac tagcaccctg   70260
```

```
atgccacatt cagtgcctct cgcccagggg aagtgctaat cagacgtgtt tccctctggg    70320
cctcagtgtt tgcatctgaa tgcggggtg cactttcaag gccctctac atgccatgcg      70380 ggttccatag gaccccaggg tttggttgtg acccgaggcc cctcctcccc acccacctcc    70440
tctccacctc ccgcggggcg ccagctccct tgcgtccaca tgacctcgga tccttccacg    70500
cccatcccca ccctgttctg caggtgggtg gtcagagggt gctctgcttt gaggatggga    70560
gagagaaagg gaggcaagga cggagaaaag agacttcttt tgcgggagcg cagagcagaa    70620
aaaccgtctc catcggttac cagggaaggg gtttctggtt tcagatccca tcacttggtg    70680
gggccttcct accaccctcc ctgctactcg ctcttgtcat ctgtaaatca gggaaatact    70740
tctggaagac agttatctgg tctgtgactt tgatcattgg tctatgacta ataattgccc    70800 taatttttg aacacctgcc gcatgctggg agttttccgc caattgtcgc tcaccctcag    70860
gtgcctctga agggcagaga ttttattctt tccatttcac agatggggaa acccaagctc    70920
cgaaagtaaa gagcttttcc tctgtgggcc tcagaatctg agaagttcaa acaggttctc    70980
aggagccctt ccagcacccc actcctcgat cagggagggg ctgtctgcac tctgaccgct    71040
gctctcagcg cagagctctc catccaaagc agcaggtgcg tgcagagcta cctgccagca    71100
gagccatcaa acacggactc ttctactggg agccatggag tggtgagaga cctgggca     71160 gcttggagcc aagggggctt ctgggaaaca tgtgccttc ccccagggtg gggttcagct     71220
ctggcgggca gggagagaaa gggctcttct gagtggctgt tgctttacac acattttgc    71280 ttcacagtat tcttagggag tagcgacagt tatcactccc atttttacagg aaagaaaact  71340 gaggcttaga gagctcaagt aacttgtcca agttggcacc actgggaaac cacagggta    71400 ggattccaac gaggcagcct ggccccagag cccatgttgc tgcccactac actctactct   71460
tgtggactaa aaccagatgc tcagagttac agtcatggaa tagaattaga atcctggcag   71520
aagaactgtg gcaggattc ggaattttac aatgtcagac tcgaaagggc tctgagatat    71580
caaatccaaa tcccccatttc tcaaatgaca gaactgaggc ctaggaagga agagtctcac  71640
tcaaggtcac agccagtgcc agggacagag tctgcacccc ctgcctctcc agctacctcc   71700
cgctgactcc gcaccttcct ctctcgcagg ccctcctctc cccactgccc acccagcagc   71760
ttctgggccc agccaggccc attagggatt ttccacctcc ccaaaaaggt cctgatgact   71820
gtcagtcctt gtgaagcctt aattaatctc agaggccgat ggctcggagg agactggggg   71880
ctttggcctt acgcagatga agattgcggc tctatttcat gtggtggtga aagaacgcct   71940
cagacattcc tgccagcaat aaaagccaca tggctttcca gcatcgccct tggaaaagaa   72000 aaaaagtgc agcccttgc ggaaataaat caactatgtg ctgtacgcat ggcatgagat     72060
acaaatgggc atacggaggt gggcaacagt cggtcttta tgccgcctct gatgtccact    72120
gacagtggca gggccagcgg tcatggtccc agctgcaatc ctggggagag ggagtgaccc   72180
ccagtgtggt gggggaagcc tcagcttctc cacctgaact ggatttgagc caccctagat   72240
atcccagagg cagggccggc tttctggcct gtgacccatg cagtcgcaca gggccctggt   72300
ctcagaaggg tcctgagctt gttttaatgc cctgccacca ctgccttgaa cttctgaata   72360
cttgctcaac aaaggtcctg cgttttcatt ttgtactggg ccccccaaat tatatagcca   72420
gtcctgacca caaatccacc cctcatcacc aattgtcacg tctctcctgg cccctgccat   72480
gtacccaatc ccggggagta gggtttcttg agtgcctact agccagtttg cttatatcac   72540
ctgagatgaa cttcagaatg actttgtgaa ttgggcagat gtggaaaatt gaggctcaga   72600
```

```
gaggcttcca tatggcaagg aagcctagac ttgaactcag gtctccctga ctccaaagtg    72660
agtgctctta gcagctctac attctgcatt atttcatctt caccatgccc aggggggatg    72720
ggatacacac agttaggctg ctctattccc agataacaga aggcataact gaggccagag    72780
aagtgaaggt tctcaagtca gtgtcaaacc gagggcctgg gcaacagtgg acctgggcct    72840
ggatccatag ggctggggat ggagtctcag ttttatagtt gtttgtgcca cttgtaaatt    72900
tattagctct ttccatgcag gtcactgcct tgagtctggt ctggaatgtg gctggagccc    72960
taccctgtcc ccctccccca cagctctcca ttctaaacat ctggaagtcc ttccttgtgt    73020
cttcttccac tctttcacgc tgcagttttc ctctgccacc ctcactggtt gggaagcagt    73080
tggatctggc accttgataa actcaaaaga gtccaaattc ttgatgaaag ttggggctga    73140
acagagccca tagattgcca tgtcctataa ccaggcctgg gcctaaggct catagagcca    73200
actgctagat ccagggcagc catttccttg ttccttgctg ggtaaccttg agcaagtccc    73260
ttccctctct ggccctcaga ctccccttca gggagataaa tgcattggac cacacctgag    73320
ccccaggagg cctctctgtc ttcaacattc tagaattcca tattaatcta caacaggtct    73380
gttcatttcc gcatctaata gctggggaaa ccgaggccca ggaaggatca gagatttgcc    73440
caccgtcaca gaaggtgctt attgacaagt ggacttgact ctgaggctcc tgtcagctgg    73500
cccggttgcc tctgcacaaa ctttcggagg atctggcctc agcatcagct cagcttgccc    73560
ttgtcccgcc gcctttagcc caggtggtct gtcaggcacc ctcagtgtcc aggcctggaa    73620
atcacagcta agagtccttg gcaggcaata aagttcctct tctatggctt gaatgtctcc    73680
caaaagtcat acattaaaac ttcaccccca ttgtgatggt attaagaggc agtgggggc    73740 ctttcgggaa gtgattaagt ggtgaaggct ctgccctcat gaatggatta ggccctcttt    73800
gcccttctga cttcaggaca caatgttctg tgtcctccgg aggacacagc cagaagacac    73860
tgccttggaa acagggagtc caggacctca ccagatgcgg aacctgccag agccttgatc    73920
ttggacttcc cagtctccag aaccatgtgt agtaagtttc tatttctcta tttataaatt    73980
atcccgtctc aggtattttg ttacagcgac acagagtgaa ctaagacact ctctttagac    74040
aaaagtgggc caggggatgg cagcaaccct tttctcccca atcgcatttg gctgtgtca    74100 gtgtttccgt aataaaggcc cctttccag gggttataat ttggctggaa aatgaggagg    74160
aaagaccaga ctccaggact ggaggggcac atgaagtagg aggctaggat gggaaaagtc    74220
tccactggac cctgggcacg cagagtgcac acacacacgc acacacatct ataccctaca    74280
tgtgtgcact cacacacagc acccacgctc atgggcacag tctctcacac attcactggc    74340
agctcacacc cacatggaca agccctcatg gaggacagca ttgttacagt gcagccacag    74400
gtgcaaacag ttaagtgcag gtgtgtgcaa agatgctcct aggagatgcc tctgtctgca    74460
tcatcatgca tggacctatt ggtatagatg cgcagataga tgcacagata ggccccatta    74520
tatgagtggt gtggacacac acatgggcag aaacccacat cacagctgtg taaacagcag    74580
accattgtgt ggacaaatct ttacacacag aggcaggcat ggaatcaggg ctcagagctt    74640
tggatttgtt ctacagagca gctctgggag gagtcgaacc ctggctctgg aagtttctgc    74700
ttctcctcaa ttcagaggca tggactttct gggtggtttg ccccctggg gcttccaaac    74760 cattccccag catctgagtt taacccgctc cctcattgtt cgatggggac aaggagagcc    74820
tgtcttcctg gtcagagaa aggcagtggg aggggagaag tgggagggtt gcagctaggg    74880
tgccccacgg cagcatgggt ggaagggcag ggcactagcc taggggccca gagacctgag    74940
tttgggttta ggttgagatg ccctaggcca acacatggcc tctctgggct tcatcctgag    75000
```

```
ccccctctgt tagggccatg tgacaccccc aggggcctca gcatgggaa  gagcactgaa   75060 accatgtcac atgatgaact attaaagcaa ctggagactt tgccctggag gagagcaggc   75120 ttgggggta  agagctcctc tggcagatct atgaagagct cccaggtggc agggaccata   75180
tggatgctgg gggctccata ccaggaatag aaatattgag agctggcttg aataggac    75240 acgtcccctc agaggtagag atcaagttga gaccaggata ttgtgcaggg agttcgagtg   75300
ttagatgggg caggggccgg accagatact agtgtctcaa acgctcagct catagcaaac   75360
acgtattgaa caaatgagag agcgactgca gagctccatt tctgagccaa tcatccgtga   75420
ttcagagcat accagctctg ggttcccacc ttgccatctg catgaccttg ccctctcca    75480 aacctcagtt tcctcatcta tgaaatgggg agaacaaatt atttccaaga gctccagcaa   75540
gtcacatccc ctattgttgg tctttcaggt catcccagaa tttctgctct tataaataga   75600
aaatgacatt gaaggtgaaa agcagacaga caagcaagag aatagttaat acaaaaatca   75660
tagctaggcg tggtaacttg tgtctgtaat ctcagctact tggaagggtg aggtgggggg   75720
atctacttga ggcctagagt tcaagactag cctgggcaac aaagtgagac tctgtatcta   75780
ccaaaaaaaa aaaaaaaaat caggagagtg gtccccacca cttgccacct gtgatgagta   75840
gggagaggga tgcagtcagg gaagggacac tggtgggagc cctaaggtcc cattagtgct   75900
ttgtttttta aagccaggtg gtaggtagat agatgtctgc tttattcttc ttcctttaaac  75960 aatacttata ttttatacat tcttctgtac atgtatttta catgtttaaa aatattttaa   76020
aggaaagcaa aagataaaat atagaaaaag ttccctgcc  ccaaacctct gaaaaatgg    76080 acaatatgct caaatgtgca taatatcgta caattattca tgatgcagca aagctgcact   76140
gtttcatccg gatggtcctg tgtaccatca cactctcagt tgaatctctg caggcccttg   76200
cagctgtcct catcatggca accccacct  aggtaagcac ttctaggtaa cagccctgc    76260 tgagcacgct ccccaagcac tcctcatggc cgaccagtag cccttcaggt atgtgtcagt   76320
gggcccactt tacaggcaag gaagtccctt gcacctacat aggaaggggc agagctggga   76380
tttgaaccag ctctgtcaat gccaaagttg tgcagcaacc tcacccgagg agccaggccc   76440
cttgattata gtaactagcg ttatgtacac tcacacatgc tgttgaatcc ccggagccac   76500
ttttgtatta ggtacattta tcatcatccc cattgtaaca gtaggacaac ggaggcatag   76560
caaggtcagg aacgtgttca agttcacacc ctaggtgagt atcagagctg agccttgaac   76620
ctcagcagcc tgatcccaga ttgtgtttcc tggcctggct gtgtgggag  ctcagacttc   76680 atggaaacaa aagacagaac ggtggctcca gggtccacag cggatcccaa gggaccagag   76740
gccagcaggg gggttggctg gggttggagg atgctgccta ggagatctgc tcccagagtg   76800
atgctagccc tgtgtgatga cctgagtccc cgcctcctta cagggtcatg gctgctggga   76860
aggtgctgag gctgtgggta cagccaaacg gagctagagc aggctttgga ctccctgcct   76920
ggcaagtcca ggtgacaggc tcagacactg ggcactctgt catttgctgt tggcataagt   76980
ttccactggc aggaatgtga catttatcac ctgagtgggc ttccagaagc ccactgaatg   77040
tcctcagacc tggggtgggg ggccctctca ctgcctcacc tctgagcctt aatcaaatcc   77100
agggtggctg gatgatctga aggccctttt agctcacgga ggcctgggct tgcccctgcc   77160
cccatccgtg tcctcagggg aaaaggttcc cagtcctgcc cttagcagct ctgagcttag   77220 atgaggggggg gagatgagat ggaaaggaaa aggagaagta agaaacagac agaggaaaag   77280
gagttggcac tagattgaag cagtcaacac acacttatta ggcacctagg gctatttag    77340
```

```
gtgctgggga tacaagcaat ggaccagaaa gccatggagc tccttggggg ctttgattcc   77400
agcagggcag acagaagaca gacaaggagg caaataaata agcacgccaa tatttgatag   77460
tgtcttggga cactcaagaa aacagatggg ggtaaagtca gagagagtga ctgggtggat   77520
ggggagagag gggctcttgg caatacttta gacaggtgg tcaggaagg tctgtcggag    77580 caggtgacat gcgagctgag accagagggt tgagagggac ccaggaaggg agaaggggc    77640 tggtaggagg gcccactgca cagtggaact ggctttaccc acctgcctc tccccactcc   77700 tctgcactgc tagtatcccc agttcctaaa actcttactg cccttctct ctgttgcttc   77760 tcccacaaca gccctgagag ccagatgggg tgagcctaag tagcctgacc tgcagtgcag   77820
gaaactgagg ctagagtggg gagggtcagc atcagcggtg ccctaatgcc aggacctgac   77880
ccgggctccc gcctcccagc ctggtgctcc tcggagcctg cccattgcct ggcatgttat   77940
tcaaccaccc cagtccaggc aggctgcagc cactgtggag ccagcccgtg ggcaccgctc   78000
ctgagaggtc acaggctgga aatgtgggca gctgggtagg gtctaggagg gggcagcggc   78060
tcaggactgg gcgggggtcc ggagcggaag gcgcccagcc ctgattggaa caaggtggca   78120
gcaccgggag ccgagccggg tgtcattgat cttgcccggt gttccagcca ccaggcggga   78180
ccagcgccgg gcagactgcc ggttttccca ggtgtgggga cccctgagg gaatgacttt   78240 tcatgtggtt gtggggcagg catgccaccc agcacgtggg ggaggccagg gctttgggag   78300
catgctggca gcagggtgga ggggggtgtc tggagactca gaatcccaca gccagcaaat   78360
gtgaggctcc tggagacagg gtcatggact tgaggctctg agaccctgag gatgttagaa   78420
tcttcatcgc agtagctccc actgatggtg tgctcacggt gccaggcacg gttctgagaa   78480
ctcacacagc ttaactcttc atccttgctc catcctaaga gggggttctg tgatcatccc   78540
cacttacagt tggggaaact gaggctcggc aaggttaagt agcctgccaa acacacagct   78600
accaggtttt tgtcttagga aataagagcc ctggaacagt tggccagtgc ggagaggacc   78660
cccgaagatc tctgaggcta gtccccttgt gtcggaaaaa caggtctgga gagggatgt    78720 gacgtgctgg ggcccagggg agtccaaagt caggactcat tcttccccca ggtcatcgtg   78780
ggacctccgc tggtccctga atgtcaggcc ccctgagggc agggtcctca gccaggacct   78840
aggctcccag atgttaccaa ccttaactga cagttttctg ctagcacaca ggaagttctt   78900
ttgaacatct aacctgaatc cctcgtttgc agggaaagcc tcttccttct catcttgcag   78960
tactctaaga agagtttggc ctttgatgtt agggaagatc accagttccc tggtgttgtg   79020
ggaggtgaga ctgtgcccct ctctgccata aaatatctct ttactgtcca tcgctgggcc   79080
taaacattag cgacttagcc cttggggcct tacagagttt cttattaaaa tgtgagtact   79140
cctggaatgg gtgtcagctt agcaggacag ggtggtactt caggggcagg gcttgggggc   79200
cgttgagggg caggagagag ctgattctcc ccttctagcc aggcttgatg gggtctacat   79260
gacctgccac cctccacctc tctgacctca tctgcttcca ctctgcccct ccctcaccct   79320
gctccagcca ccctgccttc aaatatgccc atcatactcc caccacaggg cctttgtctg   79380
tgctgccctt tacctggaaa acccttccca ttctgtctgc ctggctcagc tacccacttc   79440
attcaggtcc ctgctgcctc ctccaagagg ccttctctgg tctcctgtgg taggcagaat   79500
aatggccaca gagatgtcca catcctaatc cccaaacctg tggctatgtt accttatatg   79560
gcaaaaggga cttcgcagat gtgatgaagg ataaagactt tcagtgggga gattatcctg   79620
gattccccag gtgggcccca tatgatcaca aggatcctca cacatggaat agggaggcag   79680
aaaaggacag tcggagggag atgggggtgtg gaaactgatt agggaacctg agagatggca   79740
```

```
gcgtgggaaa aacatggctc aaagctgtgg gctttgaagg tggaggaagg ggctatgagc   79800
catggaaagc agacagcctt taggagctgg acaagacaag gaaacaaatt ctccaccaga   79860
gcctccagca aggaacacag ccctgccctg accttgatct tggccaaggg agactcatag   79920
agaatttctg atccctggaa ctgtaagatt ataaatgcat gtttttttta aggcactaaa   79980
agtgggttaa tttatgatgg caggcatagg aaacgaatat gtctcccttc cttgattgac   80040
agttcctcag cacatttatt agtgcctgat acacaatagc ttgacttatg aattgtctct   80100
tttctctcac agaaggtcag ctgcaggagg gcagggattt tttgcttgct tggtgttaca   80160
ttcgcagata gagttgtcac atttaacaaa tggaaatata aaacacccag ttaaattgaa   80220
tttcagataa ataatgaact ccttttttagt ataaagttgc cccaaatatt gcaattattt   80280
atcgtttatc tgaaattaaa ataatttagg agtcttgtat tttatctggc gaattcatcc   80340
ccaacacata aaccattcc tgggtatgta ttaggatctc aataaatgtc tgttgaatga   80400
gtgaaataga taagcaaatg aattcacatt aacttctagc ttaaaaaccc tctttggctc   80460
ccagaatgcc tacagggtaa agtgtaaatc atagcaaatg ataaaagcag acagtttcat   80520
agccgcttca atatgccaga cccgggctga gtgctttaca cttattaact cactcggttc   80580
ttgcaataac ccaatgaggt ggttagccca ttttccagat gaggaaactg aggcccagga   80640
ggcttagtaa cttgttcaaa gtcacataac cattgagcag cagagccagg caattccagg   80700
cctttgaaaa cttggctcat ggaatgttct aatgttatct ccctacccat tccctgaac   80760 actgtggatc ctctctctct aacagccccc ggttccttttt cagggtatgt gcttccgcat   80820
tctctgactg ctgaactcct cctcatacat caaagccctg tcctacttttt ctctctttgt   80880 gagaccatct ctaaaactcc caggaggact tggccccctc tctttcccct ccccaccatg   80940
gccccttgtc tgaatgcgtt gtaaggactt gctattgtgt cctttacgtt ccctgactgt   81000
gacctccctg agaacggaga tgggccccctt tcagctcttt ggcatggggc ttcaaactga   81060
gtctggcttt aggggggttc ccagaagcat ttgagaatga atgaatgaat gaatgaatga   81120
gtgagtgaat gaatggctga gtgaatgaac gaatgctgtt tgtttccact ctgggcctca   81180
gtttcagagt ctataaaagg ggaagaacaa tcctgaaccg ccccccattc cttaaaacaa   81240
aacacatttt tttctgatta taaaaataat acacattcat taaagaaaaa ttggaaaata   81300
ataaaattat gaagaagaaa attaaaacca tccataatcc tgccacccag aacaatggtt   81360
cccactgggt gttcagcctt ctgctcttct tactgtatgt atagatttat tatcttcttc   81420
tcttccccgc cctccctccc ttctctcctt cctttttttt ttgagtgttg ggaacataca   81480
gtatggggtc ctttaaacct gcttttgaaa tcccccaaca tgtgtgtatg tgtgttctcc   81540
tgttttctta aagcctccct gatggcaggg gacaagtggc tgctagacaa gcctggtagg   81600
ggccagggtg tggaaagccc attccccccc tactcatgga ccaccatagt tcccttgtga   81660
tgggctgttt aggggggtttc cagatttctg tcagggaaca ccctgcgtgg atgtcttagc   81720
tgcatccctg gttccttcct taggacagat tctgggactg gggttgctga gaccagtata   81780
gacactgaga ggctccggac accgccccac atcctcccca cagctgctct ccagccccac   81840
tcccactggc agcctggact tctcagcttg cagaaagcc gggggcagta ttccacctcc   81900
tccagagaaa agccttgtct cacccaagg cctcactgat tccatccaac gctgaaaata   81960
cccatttact cagctatttc tccacgttat ggtctaaggc ccagatgctt agttccaacc   82020
aaaatagcca cagaggtcac tgtggtctga gggtcctctg gacctcaggc ctgtgtagac   82080
```

```
atcatacttg gtaataatta acccacggag ctcaccacgt gccagaccct ctgcgtctct    82140
gtgtgtcctc acggtaaccc tgaagctagg gatggctgtc tcccatctta caggtgagaa    82200
cactgagggt gctccagaga gctgtgggcc ctaggccttg tcacctgggg gtgcaaaggc    82260
gctgccccag tagtccggct gcctgctacc tggctgcctg ctacccaatg gggcaaagtc    82320
ccagcactac cccgaaacaa ggacaagctt tggcctagaa gctgggcagc caggtcctgt    82380
gcctgttttt tctccatatg tgccctgggc agctcaccct ctccgtctgt gaaatgggag    82440
agcagggagt cagagacagc ctcctaggcc tgtggcggct ctgagcacag tgggtgcaga    82500
tactcagtgc tgagtcaaag agagagagaa ccctgccaga tgggccagct caccacaagc    82560
agccaagccc ggtctttgag gggttggagt gggcaggcct ttgaccaagg ctgagctagg    82620
agggacctga cggccccaga tggaggctgg cccaccctgc cccagcagat gggaggctat    82680 ttttttaaccc cacaggaaga agaggacaga aatgattgca gggggttaac ctaggcccct    82740
ggggacgctc cctgtttgca tcctcctttc cccacaaccc agagagctat gtgggcttca    82800
cctggagttc cctgaatcct tctggagctc cccgcagatc acagccggag ctggcagggc    82860
ctgagtggcc cctgtctgcc aggcgaggga cccagagccc agagaagttt gaccaggact    82920
ggcttcctct gccctctctg ctgtgtgctt ccaccaggtg aggctgcctc ctccgcttct    82980
acctttcttc ctggggtgac ctggggaggc cccaccttct cccgggccag tttccccatc    83040
tgtcagacaa tgggacccctc cagacatcac tgaggcttct cccagctggg aaacctcctt    83100
ctgagctggg gcctgactc tgtcacatca gtcctggatt cctggaggcc tcagccctcc    83160
agaagcatcc acccagtgga caggagctcg tggcaggtgt ctggggaccc ccaggaagag    83220
gaaggatttc ctggccagag ataagaagag cagcgtgggt aggggttaag catcctcccc    83280
ctgcagcctc cctcagacca cgccaccagg tgggcccttgg tccccccaaa aggagttcct    83340
gaaaagtctg tgtctgttgc agcaggtgcg gcctgtgaag tgtgtgtatg cttgtgtgag    83400
ggtggtgtgt gttcacatgc acatggtggg ggtgggcaca caaggcggga ggcctaacat    83460
ggtggcaggg acagactttg gttgctgagc tgggacagcc tgtgacagag gccccagcac    83520
acccgcaggt cttaccagaa accctcagat ggtgctggtc tgacctgaag gtgggcacat    83580
gcagggaagg ggtacatgca ggacaggggt gcatgtgggg gagggccatg tacagggcag    83640
gggtgcatgt ggaggagggg tacatgcagg atgggtgcat gtcggggagg gtcatgtgca    83700
ggacggggtg catgtggggg gtgcgtgcaa gacagaggtg catgggagag aagggtttgt    83760
acatggcagg ggtgcattgg gggtgcatgc agggcaggtg tgcatgtggg ggaggggcat    83820
atccaggaca agggtacatg tggggaggcc acagggctca aatgctgtca gggcctctgg    83880
gaagctggga ccccagtgaa tgcttgaggg gagccaactc tgcctgacct cctcttatga    83940
ttgtctattt aaacaatact gtaaattaat cacattaatc gaacccacct ccctgcctcc    84000
tgctgcttgc ccctgtgata caaataatat gagcacaatg aaaaatcttg gaaaatacag    84060
aaaacacata aaaaatgtta aagcctgaag tcttataacc acagtgaaca ctgcgagtgt    84120
ctttgagggg atgggggtct gcaggtcttc ttgatacaat cacattcatt cccacatact    84180
ggagcatttc ccacgggcgg ctgtggagct gagcacttca ggtttgtctt agtgaattct    84240
ctaacagcct gagagggagg tactgttatt ctccccattg tatggctgaa gaaacagcaa    84300
aaaggaggtt aaatatcccc ctcagggtgt aagaagcaga gccaagattt gaatccaagt    84360
ctggctaaat ggaaagtgca aatcgtccag cgtccagggc tgcactccag ccatgccccg    84420 cccccgtga gcagaccact catttattca ttcctccagg agcatttact gagcacctcc    84480
```

```
tgtgactcag accctgccca gcacccacac caaggacttg gcggatgtga acgagacaga    84540
gagaggcccc aacctgactc cccaagcggc cacaaactga gtcccaacct tgaccacagc    84600
ttgatttcta gtccaagttg tcactgaccc ccactggcct tcatcactga ctgaactgtg    84660
acctggcctc ctgcactctg cagtggcctc tgtgagcttt tcattcccg tgatgtgtgt    84720 gaaagccaag gccagcagcc cacctcaccc agcctatcat ccacgcggcc tgggccaggg    84780
aggccgtcag gagcccaccc accacctctg gcctgccact ctgggccagg cctctctgga    84840 gcggggttt ggccttggcc cttggcaccc tgcttggcag aagggtgggc cttggctcag    84900
agcatggggc cacccagga ggggtcagca tagctgagct cagggtacct gtgggcgggg    84960
cttccatgtc ccagggtcct cacactgcag cctcctcttt ttgcctgggc cctggaaccc    85020
caggagaccc caggagccgt tgctccctcc tctcacttgc agaaactcaa cagggcagct    85080
catctgagct cccccgatgc ctgcactgta tttctggggg tcctgcatgt ctctccaatc    85140
ctcaggcagg gccagttacc tactttatag gacccagtgc aaaagaaaaa tacaggaccc    85200
cttttcaaaa tgcaggaaca aaagttttc ctttcttctg tggactctca acccacggtg    85260
gtgtttttta tttgctgttc aatgtcacac gtacttggac ctggggagac ttgtgcagaa    85320
agtgcagacc ctcacagatg ctcaggggcc accccaaaac ttggtgtgca gattccaacc    85380
cctttctcct ccccatgcct gcctcagtgg agggcggcag tgcaggtagt gggctgctga    85440
gaacccatcc ctggaggcag caggaggcag actggacccg ggccccaagt ccccaggcat    85500
gctgcactag cccatcaggc ttcatttaca acacactaat tcagagcgaa aatgatccag    85560
catttcaata tggcaactgc tgagcgttaa attcaagcac aggaggtggg ggggccaggt    85620
agccctggaa catagcagtc tcacaggtgg ctgggcgtgg ggtggatctc tgttcttgga    85680
gtagagggat gtggagtacc tccctctgct tggagtatct gggtacctg gacaagcaca    85740 ggggggcatg aacagggcca tgcctgtgtg cctgccctc gctcagaaga gggcacctga    85800
cgggaatacc agggcatatc tgcaccatgc ccgggcagta ggcctgggca tgaccctgga    85860
tcaggcagac ctgtagtagg tggaagggcc ccaggagagc tgaggagcct agggagagg    85920 aacccagagg tccctgccaa agtgcttgat gtgctgccgt aagaagggca gcataggccg    85980
ggcgtggtgg ctcacgcctg taatcctagc accttgggag gctgaggtgg gtggatcacg    86040
aggtcaggag attgagaccc tcctggataa catggggaaa ccctgtctct actaaaaata    86100
caaaaattag ccggttgtgg tggtgcgtgc ctgtaatccc agctactcgg aaggctgagg    86160
tagaagaatt gcttgaacca gggagttgga ggttgcagtg agccaagatc atgccactgc    86220
actccagtct ggcaacagag agagactcca tctcaaaaaa aaaaaaaaa aaataaggca    86280 gcatgggtgc ctgctgagag agagagaaag aagctctttc cctgcatgtg ttgccatggg    86340
attctggccc agctccctgg ggtgctctct gagctcagct ttggccctgt ccctctctct    86400
ctgtgcctca atttctctaa ctatgcactg agcaaggaga agaccaccac acctcaagta    86460
ccttctgcat gggccataca ctgagttttta tgaatctccc ctctcttgtt ccacaaatga    86520
ttactgcccc atttctcaga cgaggaaact gaagcccaga ggaggcaatg actcacccag    86580
taagaaggtg gtggagctgg ttctgcctgg cttcccttca ccccttgagt cgctccagcc    86640
tctctaggtt tgggtggagg acgtgggaac caagctcgtg ggggcaccac cagctcttgc    86700
cagaaatggg gccaagagaa gaccaaggat gctccttgac ctgaggaaac gtccattaat    86760
tcatagctac tgtgctttgg cgagccacgc aggctctgga tgcaggctgc ctgggtgggt    86820
```

```
gacctgagca gatgccttaa tctctctggg gttcagtttt ctcatctgta aaataggcct    86880
cataagagct tttgtcttat agggttgtga ggattaaatg agctaaggta tatcacttga    86940
gcctgggagg cagagacttt agtgagcaag attatgccac tgcactccag cctggaagac    87000
agagccagaa cctgtctcaa atacatatat aaacaaaatg agcaaggta tggaaaacac     87060 ttagacagtg gctgacatag agttaagagc tatgtaaatg tttactgcta atggaactat    87120
ttaaaagttg agtcataatt tatattttct agactgtcaa ttacgaattg attcatttca    87180
atgttgtgct tttcccttt gtatttagga tccagcaaat tttcctttga aatctcaata     87240
caatttccta ggtccttgag aagataattt ccccgccccc acagtgctta tagcccatgg    87300
tggatccaat agctctctct agagcagctt ttccaaaagt ggactttgca cacaccagcc    87360
ccttccagat gcatcatctc accccaagag ataactcaat aaacagttga gcatacacta    87420
ttttagatct ccatggccca acaaggtagc cattagcata tcaaagactc tgacaagtcc    87480
tgcagcaaaa caccattgaa cattgtttga acaaccaat cccaatcttg tttgaccaca     87540
gagttccatt atttctgctc aacagctgat aacatctgaa cacacgttgg gagatgccac    87600
cctcatttcc tgctttctag gaaatggcaa ggggagtcag agctgtgagg aacaccctct    87660
cgcagggatg agtggctcca cctctacaga aatcatctcc agtcatgtgc accatcgcta    87720
ggccattcct cctgttctca ccttccttgt ctgattcagc ccccacagcg gcctggagag    87780
gtcactagca tcaatgtctc catcatacag atgaggaaat tgaggttcac aaaggttaag    87840
tgggcacata gccagtaagt ggcagatccg gtagacaaac ccacagcttc tgattctaaa    87900
ccccacattc gttcttctgt atgttgactg gaaaagtaaa aatagatcct attctaacag    87960
gatcaatctt cccccatcat aggcttttaa aaaactcagg tatttttttt ttccggtagc    88020
attgaatgct ttaaaaactt aaaattttta ctatctttct tttgattact aaagcagtac    88080
gtgcttgtta tgtataaaac ttttcaaaca ttttgagttg aaaaatgaaa aaaaggcagg    88140
gcgcggtggc tcaagcctgc aatcccatca ctttgggagg ctgaggcggg cggatcacga    88200
ggtcaggaga tcgagaccat cctggctaac acagtgaaac cccgtctcta ctaaaaatac    88260
aaaaattagc caggcgtagt ggcgggcacc tgtagtccca gctactcgag aggctgaggc    88320
aggagaatgg cgtgaaccca ggaggcggag cttgcagtga gtgcgattgc gccactgcac    88380
gccagcctgg gcgacagagc cagactccgt ctgaaaaaaa aaaaaaaaag aaaagaaaag    88440 aaagaaaaa tgaaaaaaaa aaaaaaacag atctgcatag ccctacaaag tagccattag    88500
cttttaaatg aaaatactta aatgctatct aaatgaaaat agttaaaatg aaataagata    88560
aaaaattcag ttcctcagtt acagtagcca cgtttcaagc gctcgggatt cacgtgcccc    88620
tggtggctac tgtgttgggc agcacagaca tgggacatta ctatcatcac agagaatcct    88680
acgggacggt gccgttctag attcttctta gacatatcct aacacctata caggttgatt    88740
atccctaatt caaaaatcta aaatctgaaa tgctccaaaa tccaaaactt ttttagggcc    88800
aacatggtac tcaaaggaaa tgctcattgg agaatttgg attttggact gaagtataat     88860
ccaactattc cgaaatctga caaaatcaga agtcctaaat ttgaatgctt ctggtcccag    88920
ccatcttggg taaggatgt tcaacctgta atgactgtta atgtgtggtt ttttttttg       88980 gagaccaggt cttgctctgt cgcccaagct agagtgcagt ggcacgatca tagttcactg    89040
cagccttcac ctcttgagct caagttatcc tcctgcctca gcctcccaaa gtgttgggat    89100
tacaggcggg agccgccatg ccccagccta ttgatattct tgttgaggtt ctcagacata    89160
tctgcatggc ctcacacatg gaggaaagag acccacagag gcaaaaacaa gacatgggt     89220
```

```
aaaaatagac tggaaggaaa cacaccgaat gatagtggtt ttttctgggt gttgagatta   89280
ccgagcttat ttttaaattt cttagatcct tcaggtgttc tacaacgtaa aatgcagaca   89340
gggtggggac gttggttgga gtcatgtttt ccctaatgtt cttactggtt ctaaatctt    89400 caagctatgc tctcacccaa ggcttcactt attattattt taacactgtg gattcataaa   89460
gaatggaagc ccacacaagt ccagggaagg aaggaaaggc agacagaggc ttattttcag   89520
gcctgggcag ttgcacaggg tcccttgctt agaagggcct catgcttggt ttcgtgttct   89580
gtggtcgctg tcctgaaatt cttactgatt tttgaacaag ggatcctgta ttttcatttt   89640
gcactgtgcc ctgaaaatca tgccgccgtc actagccctg ggattctccc caggacaggt   89700
ttcccttcag ctgctctaag ccttcgccct tgtccttgtc caaccacgga cgtggccatc   89760
cacggagccc tctacgtgcc tcagagcaag tgtgcttcgg ctgctcaggt gtgtgtctag   89820
agactgataa aaacagggct cgtgagtggg tgcgggaggc ccctgtggtc tctgttcaca   89880
cacgtaccta ccctcaaggc catgtctaca ctggcctatt tcagagaacc gccctgtgca   89940
tcatgggatg cttttgcccca catcacggcc cagcttggtt cagtcctgga gccctgtgtc   90000
ctgaagccat gaccaacccc aggcctggcc caccttcttc ctcagtctcc tctccctcaa   90060
gccctccaca ggacccataa accttccatc tccatgtaat ccttttgtgt gatccttctt   90120 ccatacccttt gcccatgctg ttcactctgc ttgtaccagc aaggttcctt cctccccaga   90180
tctgcccttt ctagacccat ctcagattcc acccttcta gaaagacttc aggaagtatt    90240
tgagaagggc ctgaagatgc tgtggttgca tagaggagga tatgaatcac ctcgcttaga   90300
ggtatcgggg agggctccat ggaggtggtg ccctcaggcc aaggaagaga agatatcttc   90360
cgggcagaag ggagagtttg acgggctggt ttgatgtcag acagaccaca ggatgactca   90420
aggtcctctt tcctcttctt aaacattagt tgcagcaagt cccaccatct gcctgagtct   90480
gttttcatct ccacaatgga ggtggtgatg cccagcacac ggagctgtga tgaggattta   90540
atggggaatc cagagcattt atggaagtgc caggaggcca agattctgca taggtaggaa   90600
ggacctaagc cagagggggtg tgggtggcca aggagagagag cctaccttag tagggcttgg   90660
taggctaagg tctgggctga atctcgaggc tctggagctt agaacagcat ctgcaactcc   90720
ctggctgtcg gggttcaggc aaggactgcc tcctctctga gtgtcagttt ccccatctat   90780
aaatggaaag ctgggacact gaaaaacact gggggggagg gtggttcctg aggcagtctc   90840
tctccacaca tcacaggaat gtggcgcccc agggagaagg catctttgtc cattgtgttc   90900
acttctgcat ctccagtgcc cagaacagtg cttgcatgca gtagatgctc aataaatgtt   90960
cattgaatga atcagcagca accaattcgc ccacctcaca tcctaagtcc gctggggacg   91020
taggcccacc tctccaggga aactgtctgc agattgggac cacacctcag gtcacaagca   91080
tttcctgagc acctactgta tgcatggctc tgcgcagccc ggggcagacc cttgctccac   91140
agcccgacag ggcagagcca aggaggcagg tgacagacac agtgatttgg gaagaagaac   91200
agagagcagg gtggccagca gggccttgcc tgggtgggag caggccgttc ccaggctgga   91260
gctcaggctg atgggagccc cagcttgcct gttcctggga gggtgggact gcctcttcct   91320 cttctttct ctgaaaacaa aaattgtttt cccttaaatt tacaagtatt aaagtttgg    91380 aaaatacaca ataatcaaaa gaatataaaa taaaggttac ctgccatcat ggcggaccac   91440
acagtattaa ctactatgga cttttcagtg tttccctcta gtcttttttc tgaggtggct   91500
ttgctctcag aggtggcttt ctctccccct gggaagggat atagctgctc tgtaggagat   91560
```

```
gtgggggcac caggctctct ccatgggctc tttatcactt ctgacttgga ggtcctttct    91620
ccaccccccc tggacctagc acctcttccc gagacacagg ggtgcgaaga gctgggggag    91680
gtacgtcagc aggcctcccc tcctgcccct gcttacccca cggaggtggg gtgggacaga    91740
actcaggctt gaggaaggag cactggaggc caagccacag gtgctggtcc tcagccctgg    91800
tgcccaggca agttgggttt gggaataggg gcatgaccaa aatggacccc tcctttcctc    91860
cccacccctt tccactccat ccgcctttcc ctttgcgttc tccaagcgtt ccgtccccca    91920
gatgccctct gtttcctctg ctccagcctt ttaactcctc tcaacaaagg ccaaggaatc    91980
aggcagactg tggacactca ggtgtgcatg atgggaaggg acctgcattt acaaaagctc    92040 cccccacag ggactgcatg tgctggtgga atctcagtca ccatgtccca cgttgaagga    92100
tgtttggagg gggctgactt tggtcaccct tcaaatcata agttatatgc gtctgccctt    92160
tccgcccaca cgtaagtctg aaccttttgc caaaaacact tttcccagac tcgaagaaa    92220 accccaaaga ggaacctaaa ccttcacgct gcctgcaccg attggaccgg agtgctcagg    92280
ctcgcgccaa caagtgtttc aaagaagaag ccagacagtg aagggggaag tgagggagaa    92340
gctgaaaaac tctcaggctg accaatcgtc agcccattca ttcgttcatc catccatcca    92400
tccatccatc catccatcca tccatccatc cattcttctt ttctttcctc tatccattca    92460
gtgagaaggg ctgaatatca cctgtgagcc tgcccctgct cccaagaaca cccttgggac    92520
acctgtgggg tgagtagtga ggggcagcaa tggcagagca ccccaccgc ctggagggga    92580 gaaagggaag ggctgggaag gctccccaag ggggcggcca tgaagctggg ccttgagaag    92640
acaggccagg gtttctcacc ttccacatcc tgcttagagt cagacagaag gcttttgcag    92700
aggaggagga acattaaata gtagtaattt ctggcattcc atgagggctt gtctgtgccg    92760
ggccctgtgc tgtgcacgtg atacacacta cctcattaaa cctacccaac atgccttgag    92820
ggggtgctat tcattttctc cattttacag gtaagaaaat gaaacacaga gaggtgaggc    92880
acctctccca acgccacaca gcgaggaagt ggcagagcct ggctgcagct gaggcttata    92940
gccgcatttt acattgcttt ctctccgaag agtgccttcc tttatccctg ggagccattg    93000
acaaggggtc tgacagtccc tctagtcttg tgcctgctca gccctctcta gccctgaaaa    93060
aaccagggct tggcgctgga gaaagagcag gagggtgaga tgtggaaaca tctgttgagt    93120
ggcaggggat cacgctggcg cagaggggcc cgagccgatc aggaggccgg cctgtgccag    93180
gccagtgctc cctgtgtacc aggtgccaca tgcggggctc agggtagggc cacagttgct    93240
cctcccaacc acccttggag gtcagtgtta ctagcccatt ttacagagga ggaaactgag    93300
accttaagag gtgaattaac atgtcaggtc acccagctac catgcagttt aagcctagat    93360
tgttctgact cctaaactgt gtgcaaggcg gatgattgga ccccagggag gcaaggaaag    93420
tcagttttcc tgctgctgaa ttcaatgttt tacaagacca cacacctctt tagacctcag    93480
tttcgtcatg tatgaaatga ggaggggaac tctctgcctc cgggctctga tatgctcctg    93540
gactgattca ctgttccttg ttcttgtgac ttctcaaagc aagaccagag tcccactccc    93600
agccctaggc ccgagattcc catccccact gtgtccaggg gcttcaggag gtgctatttt    93660
agggcagatg gcaaaggcct gggctgtaga tccactgagg gctaaaggca atctttcttc    93720
cctccacccc tccccttcctt ccttccttct ctttacttcc actaagcaag gtagggaact    93780
actcgctgag tctcagggca ggcccacgga ctgaagctca ggaggacagg gctccccagt    93840
ggctgcaggt gtcccagcac tgactcctag cagaggggg gtttgggttc agtctggaag    93900
attgggtgag attccccaac tacggggggt gggggcacac tctgggtggc agatttgagg    93960
```

-continued

```
aagagtctgc agataaggca tccccaggag atggcaataa gagctggtgt tggggctgcc    94020
ccactgaacc cagagcccag gcctgtttcc cacccatgg  aggagtccgg actggctcag    94080
tggcaaggcc ggggtcagag gctgccactc tcctcctgcc tctcacagcc cgctggaagg    94140
tcaggttttc aggctctgct tatccgtctc ccggcctcct ccctccaggt aaccgaggga    94200
gcctccgctt tgatgcggcc acctccaggc ccaggcgtca atgagccctc tatatgacca    94260
gtggggctgc tgggggcctc cagcccgcca gagtgggtgc ggtgaggcct ggacacacag    94320
tcccgctgtg tggggtcggc tcatgcctgc ctagaccctg tgggcagtgg ggggctccta    94380
ggaatgcttt tccagcctgg ggggcacttt ggacaggcag ggtggtctgg ggagacgggt    94440
gtgtgcaggg cagcctcaga agccgccatc aaagggacct agcagacgtg gcgccaggca    94500
agcgccatag tgggcacgga agggctggcg gtcagtctgt tcctctccca gggatggcgg    94560 ggaggggag  gccccatgga cacatgtgct cagggtgacc agccatcagg ggttgcctgg    94620
gatgaagggg tttcctggga cgtggagctt tcagtgctaa aacagagagt ccctgttat    94680 tggaacttcc tggaccttcg gaaaggatac agtgactgac ctctctggtc tgggcagcct    94740
cctccctgtc cggtgacctc tgagtcagac catctcggcc agacctgccc agggccattt    94800
tgtccacccc ctgcctccac acaggcctgc ctcatacca  agagtccact ttccatttct    94860
cccaggcatc ttcaggggag gagctgccgg ccaactccaa ccactgctag ggggacctcg    94920
gccagaccca caccacgctc ccagccctcc ctgtggctcc cgagccagct catactttcc    94980
tgcttccaca ccttttgccca ggacgttcct tctgcctgga acatcctttc cctgtctttg    95040
ttacctcttt acccttaggg acccagtttc caagtcactc ctccagagga cttgttctct    95100
ctttcccaag gctgggctag taccccctctt tgaactcaca gccctggttc ttctcccaaa    95160
aaacctttgt cacgccccag gcaattttc  tgttgaccca tctttttcta caccagatgg    95220
tgagctctta ggatggagat c                                              95241
```

<210> SEQ ID NO 54
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
tcctcttacc tatccctact tccccytccc aaagaagcct tagtagtgtt g            51

<210> SEQ ID NO 55
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
agtgagcaaa ctgaggcaca gagatrttac atcacctgta caagggtaca c            51

<210> SEQ ID NO 56
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
ctttccagag actggcttcc tacagkacag gcggggtcac aggatgtgtt c          51

<210> SEQ ID NO 57
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
tttaatttta gccattcttc tgcctmattt cttaaaatta gagaattaag g          51

<210> SEQ ID NO 58
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
ttttcctgct tccagacatg aatcakgtca ctattcaatg ggatgcagta a          51

<210> SEQ ID NO 59
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
attgggatat ttaacagatc attccraact gggtaggttt ttgcagaatt t          51

<210> SEQ ID NO 60
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
ttatctagaa ataaaaaagc atacawttga taattcacca aattgtggag c          51

<210> SEQ ID NO 61
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
aactctaact ctttatatag gaagtygttc aatgttgtca gttatgactg t          51

<210> SEQ ID NO 62
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide -continued

<400> SEQUENCE: 62
ttagcttctc ctgataaact aattgyctca cattgtcact gcaaatcgac a                51

<210> SEQ ID NO 63
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
acacctaaac ttgggagaac attgtycccc agtgctgggg taggagagtc t                51

<210> SEQ ID NO 64
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
ccagtttctc cctcgctgtt tttatrgctt tcaaaagcag aagtaggagg c                51

<210> SEQ ID NO 65
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
cataagcctc gttatcccat gtgtcraaga agataggttc tgaaatgtgg a                51

<210> SEQ ID NO 66
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
tgcccttccc attttccttc agaagragag attcttctat gacctcattg g                51

<210> SEQ ID NO 67
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
ttaaagaaac ttttcgcga gggacrgttc aactgaaact tcgaaagcat c                51

<210> SEQ ID NO 68
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
ggtttctgga ggacttctag gaaaaygagg gaagagcagg aaaaggcgac a           51

<210> SEQ ID NO 69
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
aacactgata tcaagatact ggattstatt atgagaaatt atcaaaatcc t           51

<210> SEQ ID NO 70
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
gcctggctcc aggccaaaag gaagcmcagg aaagctccca gcaggaacat c           51

<210> SEQ ID NO 71
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
ctcactatgc tcgatctttc ctacawcaac ttaaatgtgg ttggtaacga t           51

<210> SEQ ID NO 72
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
acttgctcat tctcccttac acataytcaa cctaaccaag aataaaatct c           51

<210> SEQ ID NO 73
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
gcatacttag actactacct cgatgrtatt attgacttat ttaattgttt g           51

<210> SEQ ID NO 74
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
tgttctcaaa gtgattttgg dacaaycagc ctaaagtatt tagatctgag c          51

<210> SEQ ID NO 75
<211> LENGTH: 51
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 75
ttgagggtaa aattcagtaa ggttgracct ctggtgagtt ctgataaaaa t          51

<210> SEQ ID NO 76
<211> LENGTH: 51
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 76
tttccaatgt ggacactgaa gagacwaatt cttatccttt ttaacataat c          51

<210> SEQ ID NO 77
<211> LENGTH: 51
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 77
agtgaagttg gcttctgctc aaatgycaga acttctgtag aaagttatga a          51

<210> SEQ ID NO 78
<211> LENGTH: 51
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 78
ggtttgtctg gtgggttaac catacrgagg tgactattcc ttacctggcc a          51

<210> SEQ ID NO 79
<211> LENGTH: 51
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 79
aatgaaaaat tagaacaaca gaaacrtggt aagccacttc tatttcttta g          51

<210> SEQ ID NO 80
<211> LENGTH: 51
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 80
aatcaaatgg cttgaatatc acagaygggg cattcctcaa cctaaaaaac c          51

<210> SEQ ID NO 81
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
gtctggattt atcccttaat aggctsaagc acatcccaaa tgaagcattc c          51

<210> SEQ ID NO 82
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
tgtgtgagtg gccggccccc agctcyacct ccacccactc cacttcatgg g          51

<210> SEQ ID NO 83
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
agctgaggtc cagggcctcc agtcgyggta gctccgtgaa tgagtgctcg t          51

<210> SEQ ID NO 84
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
agcaatagaa ccgatgtctt agcatkttct aaactaagat ttcgttgcat t          51

<210> SEQ ID NO 85
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
agagttttca agtgaggcag ttggakagtt cttttaaaca actcgtctgt t          51

<210> SEQ ID NO 86
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
gagatcagtt agaaaattaa atgcartatt tagttctcgt aaggccatca g          51

```
<210> SEQ ID NO 87
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87 aaattttta attcacaggt acaccrgaat ggatttcttc ccgcatttag a          51
```